US012491267B2

(12) United States Patent
Gannon et al.

(10) Patent No.: US 12,491,267 B2
(45) Date of Patent: Dec. 9, 2025

(54) GENE THERAPY FOR NEURODEGENERATIVE DISORDERS

(71) Applicant: The Brigham and Women's Hospital, Inc., Boston, MA (US)

(72) Inventors: Kimberley S. Gannon, Boston, MA (US); Martin Goulet, Boston, MA (US); Neil R. Hackett, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 722 days.

(21) Appl. No.: 17/779,980

(22) PCT Filed: Nov. 25, 2020

(86) PCT No.: PCT/US2020/062394
§ 371 (c)(1),
(2) Date: May 25, 2022

(87) PCT Pub. No.: WO2021/108686
PCT Pub. Date: Jun. 3, 2021

(65) Prior Publication Data
US 2023/0068087 A1 Mar. 2, 2023

Related U.S. Application Data

(60) Provisional application No. 63/004,422, filed on Apr. 2, 2020, provisional application No. 62/942,059, filed on Nov. 29, 2019.

(51) Int. Cl.
*C12N 15/11* (2006.01)
*A61K 48/00* (2006.01)
(Continued)

(52) U.S. Cl.
CPC ...... *A61K 48/0066* (2013.01); *C07K 14/4711* (2013.01); *C12N 15/86* (2013.01);
(Continued)

(58) Field of Classification Search
None
See application file for complete search history.

(56) References Cited

U.S. PATENT DOCUMENTS 5,328,470 A 7/1994 Nabel et al.
5,658,776 A 8/1997 Flotte et al.
(Continued)

FOREIGN PATENT DOCUMENTS

CN 103282374 A 9/2013
CN 103816540 A 5/2014
(Continued)

OTHER PUBLICATIONS

Wang Z, Day N, Trifillis P, Kiledjian M. An mRNA stability complex functions with poly(A)-binding protein to stabilize mRNA in vitro. Mol Cell Biol. Jul. 1999;19(7):4552-60. doi: 10.1128/MCB.19.7.4552. PMID: 10373504; PMCID: PMC84253. (Year: 1999).*
(Continued)

*Primary Examiner* — Evelyn Y Pyla
*Assistant Examiner* — Jagamya Vijayaraghavan
(74) *Attorney, Agent, or Firm* — Fish & Richardson P.C.

(57) ABSTRACT

The disclosure relates to nucleic acid expression cassettes for the treatment of neurodegenerative disorders. Methods of treating neurodegenerative disorders such as Alzheimer's disease, frontotemporal dementia, frontotemporal lobar degeneration, Pick's disease, Lewy body dementia, memory loss, cognitive impairment, and mild cognitive impairment are also provided.

29 Claims, 4 Drawing Sheets

Specification includes a Sequence Listing.

(51) Int. Cl.
*C07K 14/47* (2006.01)
*C12N 15/86* (2006.01)

(52) U.S. Cl.
CPC .............. *C12N 2750/14143* (2013.01); *C12N 2830/50* (2013.01); *C12N 2840/10* (2013.01)

(56) References Cited

U.S. PATENT DOCUMENTS

| | | | | |
|---|---|---|---|---|
| 6,020,143 | A * | 2/2000 | St. George-Hyslop | A01K 67/0278 435/7.1 |
| 6,180,613 | B1 | 1/2001 | Kaplitt et al. | |
| 6,395,960 | B1 | 5/2002 | St. George-Hyslop | |
| 6,503,888 | B1 | 1/2003 | Kaplitt et al. | |
| 6,686,449 | B2 | 2/2004 | Carter et al. | |
| 6,783,955 | B2 | 8/2004 | Arvizu | |
| 6,979,537 | B2 | 12/2005 | McCarthy et al. | |
| 7,271,313 | B2 | 9/2007 | Shen | |
| 7,498,316 | B2 | 3/2009 | Xu et al. | |
| 7,709,616 | B2 | 5/2010 | Bentwich et al. | |
| 8,129,334 | B2 | 3/2012 | Dewji et al. | |
| 9,512,191 | B2 | 12/2016 | Dewji et al. | |
| 9,956,271 | B2 | 5/2018 | Guild et al. | |
| 10,221,223 | B2 | 3/2019 | Dewji et al. | |
| 2002/0015939 | A1 | 2/2002 | McCarthy et al. | |
| 2002/0082211 | A1 | 6/2002 | Arvizu et al. | |
| 2003/0065141 | A1 | 4/2003 | Carter et al. | |
| 2005/0288243 | A1 | 12/2005 | Xu et al. | |
| 2007/0134761 | A1 * | 6/2007 | Chatellard | C12N 15/63 435/320.1 |
| 2009/0305946 | A1 | 12/2009 | Dewji et al. | |
| 2011/0201052 | A1 | 8/2011 | Raitano et al. | |
| 2017/0073384 | A1 | 3/2017 | Dewji et al. | |
| 2018/0094280 | A1 | 4/2018 | Kutner et al. | |
| 2018/0169148 | A1 | 6/2018 | Adair et al. | |
| 2019/0134155 | A1 | 5/2019 | Kaetzel et al. | |
| 2021/0108186 | A1 | 4/2021 | Shen et al. | |
| 2022/0235374 | A1 | 7/2022 | Shen et al. | |
| 2023/0136245 | A1 | 5/2023 | Gannon et al. | |

FOREIGN PATENT DOCUMENTS

| | | | | |
|---|---|---|---|---|
| CN | 106604988 A | | 4/2017 | |
| CN | 107614008 A | | 1/2018 | |
| EP | 0826042 B1 | | 8/2008 | |
| EP | 2010663 | | 1/2009 | |
| JP | H11504214 A | | 4/1999 | |
| JP | 2013509890 | | 3/2013 | |
| JP | 2013107890 | | 6/2013 | |
| JP | 2016523835 | | 8/2016 | |
| JP | 2018510615 A | | 4/2018 | |
| JP | 2021525245 A | | 9/2021 | |
| WO | WO 1995/00655 | | 1/1995 | |
| WO | WO 1995/11984 | | 5/1995 | |
| WO | WO 1995/27071 | | 10/1995 | |
| WO | WO 2000/003248 A1 | | 1/2000 | |
| WO | WO 2001/051671 | | 7/2001 | |
| WO | WO 2005/003350 A2 | | 1/2005 | |
| WO | WO-2005037226 A2 | * | 4/2005 | C07K 14/62 |
| WO | WO 2005/116250 A2 | | 12/2005 | |
| WO | WO 2009/042727 | | 4/2009 | |
| WO | WO 2015/006743 A1 | | 1/2015 | |
| WO | WO 2016/209654 A1 | | 12/2016 | |
| WO | WO 2017/191274 | | 11/2017 | |
| WO | WO-2017205767 A1 | * | 11/2017 | A61K 31/7105 |
| WO | WO-2018045022 A1 | * | 3/2018 | A61K 35/35 |
| WO | WO 2018/140532 | | 8/2018 | |
| WO | WO-2018175443 A1 | * | 9/2018 | A61K 47/6425 |
| WO | WO 2018/222890 | | 12/2018 | |
| WO | WO 2019/028306 | | 2/2019 | |
| WO | WO 2019/226832 | | 11/2019 | |
| WO | WO 2021/155296 | | 8/2021 | |

OTHER PUBLICATIONS

Olafsdóttir G, Svansson V, Ingvarsson S, Marti E, Torsteinsdóttir S. In vitro analysis of expression vectors for DNA vaccination of horses: the effect of a Kozak sequence. Acta Vet Scand. Nov. 4, 2008;50(1):44. doi: 10.1186/1751-0147-50-44. PMID: 18983656; PMCID: PMC2600637. (Year: 2008).*

Pesole G, Liuni S, Grillo G, et al; UTRdb and UTRsite: specialized databases of sequences and functional elements of 5' and 3' untranslated regions of eukaryotic mRNAs. Update 2002. Nucleic Acids Res. Jan. 1, 2002;30(1):335-40. doi: 10.1093/nar/30.1.335. PMID: 11752330; PMCID: PMC99102. (Year: 2002).*

Bäck S, Dossat A, Parkkinen I, Koivula P, Airavaara M, Richie CT, Chen YH, Wang Y, Harvey BK. Neuronal Activation Stimulates Cytomegalovirus Promoter-Driven Transgene Expression. Mol Ther Methods Clin Dev. Jul. 3, 2019;14:180-188. doi: 10.1016/j.omtm.2019.06.006. PMID: 31380464; PMCID: PMC6661544. (Year: 2019).*

Emery DW. The use of chromatin insulators to improve the expression and safety of integrating gene transfer vectors. Hum Gene Ther. Jun. 2011;22(6):761-74. doi: 10.1089/hum.2010.233. Epub Mar. 25, 2011. PMID: 21247248; PMCID: PMC3107579. (Year: 2011).*

Leppek K, Das R, Barna M. Functional 5' UTR mRNA structures in eukaryotic translation regulation and how to find them. Nat Rev Mol Cell Biol. Mar. 2018;19(3):158-174. doi: 10.1038/nrm.2017.103. Epub Nov. 22, 2017. Erratum in: Nat Rev Mol Cell Biol. Oct. 2018;19(10):673. doi: 10.1038/s41580-018-0055-5. (Year: 2018).*

Naso MF, Tomkowicz B, Perry WL 3rd, Strohl WR. Adeno-Associated Virus (AAV) as a Vector for Gene Therapy. BioDrugs. Aug. 2017;31(4):317-334. doi: 10.1007/s40259-017-0234-5. PMID: 28669112; PMCID: PMC5548848. (Year: 2017).*

Kim, Seon-Young, et al. "Human β-Globin Second Intron Highly Enhances Expression of Foreign Genes from Murine Cytomegalovirus Immediate-Early Promoter." (2005): 544-550. (Year: 2005).*

Diss G, Lehner B. The genetic landscape of a physical interaction. Elife. Apr. 11, 2018;7:e32472. doi: 10.7554/eLife.32472. PMID: 29638215; PMCID: PMC5896888. (Year: 2018).*

Dryja TP, McGee TL, Hahn LB, Cowley GS, Olsson JE, Reichel E, Sandberg MA, Berson EL. Mutations within the rhodopsin gene in patients with autosomal dominant retinitis pigmentosa. N Engl J Med. Nov. 8, 1990;323(19):1302-7. doi: 10.1056/NEJM199011083231903. PMID: 2215617. (Year: 1990).*

JP Office Action in Japanese Appln. No. 2021-569550, mailed on May 28, 2024, 8 pages (with English translation).

CN Office Action in Chinese Appln. No. 201980049127.3, mailed on Oct. 30, 2023, 26 pages (with English translation).

EP Partial European Search Report in European Appln. No. 20893982.7, mailed on Nov. 15, 2023, 14 pages.

NCBI sequence NM_000021.3, "*Homo sapiens* presenilin 1 (PSEN1), transcript variant 1, mRNA," dated Dec. 18, 2017, 7 pages.

NCBI reference sequence : NM_007318.2, "*Homo sapiens* presenilin 1 (PSEN1), transcript variant 2, mRNA," dated Jun. 18, 2017, 7 pages.

Wang et al., "Visualization of Alzheimer's disease related α-/β-/γ-secretase ternary complex by bimolecular fluorescence complementation based fluorescence resonance energy transfer," Frontiers in Molecular Neuroscience, Nov. 2018, 11:431, 9 pages.

Castle et al., "Controlling AAV tropism in the nervous system with natural and engineered capsids," Gene Therapy for Neurological Disorders: Methods and Protocols, Jan. 2016, 133-49.

CN Office Action in Chinese Appln. No. 201980049127.3, mailed on Jul. 16, 2024, 14 pages (with English translation).

Haery et al., Adeno-associated virus technologies and methods for targeted neuronal manipulation. Frontiers in Neuroanatomy, Nov. 2019, 13:493120, 16 pages.

IL Office Action in Israeli Appln. No. 278813, mailed on Jul. 21, 2024, 4 pages (English translation).

AU Office Action in Australian Appln. No. 2019272848, mailed on Oct. 29, 2024, 5 pages.

(56) References Cited

OTHER PUBLICATIONS

CN Office Action in Chinese Appln. No. 201980049127.3, mailed on Dec. 18, 2024, 16 pages (with English translation).
CN Office Action in Chinese Appln. No. 202080052274.9, mailed on Sep. 26, 2024, 7 pages (with English translation).
Wang et al., "An mRNA stability complex functions with poly (A)-binding protein to stabilize mRNA in vitro," Molecular and Cellular Biology, Jul. 1999, 19(7):4552-60.
Honda et al., "The modeling of Alzheimer's disease by the overexpression of mutant Presenilin 1 in human embryonic stem cells," Biochemical and Biophysical Research Communications, Jan. 2016, 469(3):587-92.
Sun et al., "Analysis of 138 pathogenic mutations in presenilin-1 on the in vitro production of Aβ42 and Aβ40 peptides by γ-secretase," Proceedings of the National Academy of Sciences, Jan. 2017, 114(4):E476-85.
Tenchov et al., "Lipid nanoparticles—from liposomes to mRNA vaccine delivery, a landscape of research diversity and advancement," ACS Nano, Jun. 2021, 15(11):16982-7015.
Yang et al., "Influence of solubilization and AD-mutations on stability and structure of human presenilins," Scientific Reports, Dec. 2017, 7(1):17970, 12 pages.
CN Office Action in Chinese Appln. No. 201980049127.3, mailed on Apr. 25, 2024, 9 pages (with English translation).
D'Argenio et al., "New insights into the molecular bases of familial Alzheimer's disease," Journal of Personalized Medicine, Apr. 2020, 10(2):26, 14 pages.
Deaton et al., "Presenilin 1 regulates membrane homeostatic pathways that are dysregulated in Alzheimer's disease," Journal of Alzheimer's Disease, Jan. 2020, 77(3):961, 25 pages.
EP Extended European Search Report in European Appln. No. 20893982.7, mailed on May 2, 2024, 14 pages.
Götz et al., "Rodent models for Alzheimer disease," Nature Reviews Neuroscience, Oct. 2018, 19(10):583-98.
Hudry et al., "Therapeutic AAV gene transfer to the nervous system: a clinical reality," Neuron, Mar. 2019, 101(5):839, 26 pages.
John et al., "Synaptic basis of Alzheimer's disease: Focus on synaptic amyloid beta, P-tau and mitochondria," Ageing Research Reviews, Jan. 2021, 65:101208, 35 pages.
Yang et al., "Presenilin-1 (PSEN1) mutations: clinical phenotypes beyond Alzheimer's disease," International Journal of Molecular Sciences, May 2023, 24(9):8417, 21 pages.
CN Office Action in Chinese Appln. No. 202080052274.9, mailed on Mar. 12, 2024, 9 pages (with English translation).
EP Extended European Search Report in European Appln. No. 21747911.2, mailed on Mar. 14, 2024, 11 pages.
GenBank Accession No. NM_000021.4, "*Homo sapiens* presenilin 1 (PSEN1), transcript variant 1, mRNA," Nov. 20, 2018, 7 pages.
JP Office Action in Japanese Appln. No. 2020-565341, mailed on Jan. 9, 2024, 14 pages (with English translation).
Millington-Ward et al., "Suppression and replacement gene therapy for autosomal dominant disease in a murine model of dominant retinitis pigmentosa," Molecular Therapy, Apr. 2011, 19(4):642-9.
Montenegro et al., "Human Presenilin-1 delivered by AAV9 rescues impaired γ-secretase activity, memory deficits, and neurodegeneration in Psen mutant mice," Proceedings of the National Academy of Sciences, Oct. 2023, 120(42):e2306714120, 8 pages.
Pelletier et al., "RNA based gene therapy for dominantly inherited diseases," Current Gene Therapy, Feb. 2006, 6(1):131-46.
Pimenova et al., "Novel presenilin 1 and 2 double knock-out cell line for in vitro validation of PSEN1 and PSEN2 mutations," Neurobiology of Disease, Feb. 2020, 138, 24 pages.
Sierant et al., "Specific silencing of L392V PSEN1 mutant allele by RNA interference," International Journal of Alzheimer's Disease, Jan. 2011, vol. 2011, 14 pages.
Trochet et al., "Therapy for dominant inherited diseases by allele-specific RNA interference: successes and pitfalls," Current Gene Therapy, Oct. 2015, 15(5):503, 27 pages.
Uniprot Accession No. P49768.1, "Presenilin-1," Oct. 1, 1996, 55 pages.
Uniprot Accession No. P49810.1, "Presenilin-2," Oct. 1, 1996, 14 pages.
Bryan et al., "Implications of protein fold switching," Current Opinion in Structural Biology, 2013, 2(23):314-6.
Bulcha et al., "Viral vector platforms within the gene therapy landscape," Signal Transduction and Targeted Therapy, Feb. 2021, 6(1):53, 24 pages.
Chávez-Gutiérrez et al., "Mechanisms of neurodegeneration—Insights from familial Alzheimer's disease," Seminars in Cell & Developmental Biology, Sep. 2020, (105):75-85.
Cruz et al., "Protein function prediction," Functional Genomics: Methods and Protocols, 3rd edition, Aug. 2018, 55, 22 pages.
Hur, "γ-Secretase in Alzheimer's disease," Experimental & Molecular Medicine, Apr. 2022, 54(4):433, 14 pages.
Ingusci et al., "Gene therapy tools for brain diseases," Frontiers in Pharmacology, Jul. 2019, 10:724, 19 pages.
Kabir et al, "Exploring the role of PSEN mutations in the pathogenesis of Alzheimer's disease," Neurotoxicity Research, Dec. 2020, 38:833-49.
Kotterman et al., "Engineering adeno-associated viruses for clinical gene therapy," Nature Reviews Genetics, Jul. 2014, 15(7):445, 18 pages.
Lenzi et al., Gene Transfer Research: The Evolution of Clinical Science, NCBI Bookshelf, A Service of the National Library of Medicine, National Institute of Health, Oversight and Review of Clinical Gene Transfer Protocols: Assessing the Role of the Recombinant DNA Advisory Committee, National Academies Press, Mar. 2014, 16 pages.
Maqbool et al., "The substrate-binding protein in bacterial ABC transporters: dissecting roles in the evolution of substrate specificity," Biochemical Society Transactions, Oct. 2015, 43(5):1011-7.
Shim et al., "Nonviral delivery systems for cancer gene therapy: strategies and challenges," Current Gene Therapy, Feb. 2018, 18(1):3-20.
Stepanichev, "Gene editing and Alzheimer's disease: is there light at the end of the tunnel?," Frontiers in Genome Editing, Jun. 2020, 2:4, 10 pages.
Sudhakar et al., Gene therapy for neurodegenerative diseases, Neurotherapeutics, Jan. 2019, 16(1):166-75.
Acosta-Baena et al., "Pre-dementia clinical stages in presenilin 1 E280A familial early-onset Alzheimer's disease: a retrospective cohort study," The Lancet Neurology, Mar. 1, 2011, 10(3):213-20.
Amtul et al., "A presenilin 1 mutation associated with familial frontotemporal dementia inhibits γ-secretase cleavage of APP and notch," Neurobiology of Disease, Mar. 1, 2002, 9(2):269-73.
Asokan et al., "The AAV vector toolkit: poised at the clinical crossroads," Molecular Therapy, Apr. 1, 2012, 20(4):699-708.
Ausubel et al., "Current Protocols in Molecular Biology, Sections 9.10-9.14," Greene Publishing Associates, 1989, 51 pages.
Beglopoulos et al., "Reduced β-amyloid production and increased inflammatory responses in presenilin conditional knock-out mice," Journal of Biological Chemistry, Nov. 5, 2004, 279(45):46907-14.
Bentahir et al., "Presenilin clinical mutations can affect γ-secretase activity by different mechanisms," Journal of Neurochemistry, Feb. 2006, 96(3):732-42.
Bessis et al., "Immune responses to gene therapy vectors: influence on vector function and effector mechanisms," Gene Therapy, Oct. 2004, 11(1):S10-7.
Bird et al., "Wide range in age of onset for chromosome 1-related familial Alzheimer's disease," Annals of Neurology, Dec. 1996, 40(6):932-936.
Bose et al., "Role of nucleolin in human parainfluenza virus type 3 infection of human lung epithelial cells," Journal of Virology, Aug. 1, 2004, 78(15):8146-58.
Brouwers et al., "Molecular genetics of Alzheimer's disease: an update," Annals of Medicine, Jan. 1, 2008, 40(8):562-83.
Brunkan et al., "Two domains within the first putative transmembrane domain of presenilin 1 differentially influence presenilinase and γ-secretase activity," Journal of Neurochemistry, Sep. 2005, 94(5):1315-28.
Cai et al., "Mutations in presenilin 2 and its implications in Alzheimer's disease and other dementia-associated disorders," Clinical Interventions in Aging, Jul. 2015, 10:1163-1172.

(56) References Cited

OTHER PUBLICATIONS

Chen et al., "Enhancing the Utility of Adeno-Associated Virus Gene Transfer through Inducible Tissue-Specific Expression," Human Gene Therapy Methods, Aug. 2013, 24(4):270-278.
Chen et al., "Gene therapy for brain tumors: regression of experimental gliomas by adenovirus-mediated gene transfer in vivo," Proceedings of the National Academy of Sciences, Apr. 12, 1994, 91(8):3054-7.
Chen et al., "Presenilin 1 mutations activate γ42-secretase but reciprocally inhibit ε-secretase cleavage of amyloid precursor protein (APP) and S3-cleavage of notch," Journal of Biological Chemistry, Sep. 27, 2002, 277(39):36521-6.
Colin et al., "Engineered lentiviral vector targeting astrocytes in vivo," Glia, Apr. 2009, 57(6):667-79.
Cressant et al., "Improved behavior and neuropathology in the mouse model of Sanfilippo type IIIB disease after adeno-associated virus-mediated gene transfer in the striatum," Journal of Neuroscience, Nov. 10, 2004, 24(45):10229-39.
Crook et al., "A variant of Alzheimer's disease with spastic paraparesis and unusual plaques due to deletion of exon 9 of presenilin 1," Nature Medicine, Apr. 1998, 4(4):452-5.
Dana et al., "Molecular mechanisms and biological functions of siRNA," International Journal of Biomedical Science, Jun. 2017, 13(2):48-57.
De Jonghe et al., "Aberrant splicing in the presenilin-1 intron 4 mutation causes presenile Alzheimer's disease by increased Aβ42 secretion," Human Molecular Genetics, Aug. 1, 1999, 8(8):1529-40.
De Strooper, "Loss-of-function presenilin mutations in Alzheimer disease: Talking Point on the role of presenilin mutations in Alzheimer disease," EMBO Reports, Feb. 2007, 8(2):141-6.
Deyle et al., "Adeno-associated virus vector integration," Current Opinion in Molecular Therapeutics, Aug. 2009, 11(4):442, 11 pages.
Dittgen et al., "Lentivirus-based genetic manipulations of cortical neurons and their optical and electrophysiological monitoring in vivo," Proceedings of the National Academy of Sciences, Dec. 28, 2004, 101(52):18206-11.
Doll et al., "Comparison of promoter strengths on gene delivery into mammalian brain cells using AAV vectors," Gene Therapy, May 1, 1996, 3(5):437-47.
Dong et al., "Poly (d, 1-lactide-co-glycolide)/montmorillonite nanoparticles for oral delivery of anticancer drugs," Biomaterials, Oct. 1, 2005, 26(30):6068-76.
Duff et al., "Increased amyloid-β42 (43) in brains of mice expressing mutant presenilin 1," Nature, Oct. 1996, 383(6602):710-3.
Elbashir et al., "Duplexes of 21±nucleotide RNAs mediate RNA interference in cultured mammalian cells," Nature, May 2001, 411:494-498.
EP Extended Search Report in European Appln. No. 19808081.4, dated Feb. 21, 2022, 7 pages.
EP Extended Search Report in European Appln. No. 20813435.3. dated Jun. 12, 2023, 6 pages.
EP Supplementary European Search Report in European Appln. No. 19808081.4, dated Mar. 11, 2022, 8 pages.
Felsenstein et al., "O1-11-03: Endogenous cholesterol metabolites as potential Alzheimer's therapeutics," Alzheimer's & Dementia, Jul. 2012, 8(4S Part 3):P104-5.
Feng et al., "Forebrain degeneration and ventricle enlargement caused by double knockout of Alzheimer's presenilin-1 and presenilin-2," Proceedings of the National Academy of Sciences, May 25, 2004, 101(21):8162-7.
Flotte et al., "Gene expression from adeno-associated virus vectors in airway epithelial cells," Am J Respir Cell Mol Biol, Sep. 1, 1992, 7(3):349-56.
Foley et al., "Intra-arterial delivery of AAV vectors to the mouse brain after mannitol mediated blood brain barrier disruption," Journal of Controlled Release, Dec. 28, 2014, 196:71-8.
GenBank Accession No. AAW01891, "Sequence 12 from patent U.S. Pat. No. 6,783,955," dated Dec. 14, 2004, 1 page.
GenBank Accession No. AFD46703, "Sequence 2 from patent U.S. Pat. No. 8,129,334," Mar. 14, 2012, 1 page.
GenBank Accession No. NM_000021.3, "*Homo sapiens* presenilin 1 (PSEN1), transcript variant 1, mRNA," dated Aug. 7, 2008, 5 pages.
GenBank Accession No. NM 000447.2, "*Homo sapiens* presenilin 2 (Alzheimer disease 4) (PSEN2), transcript variant 1, mRNA," dated Aug. 17, 2007, 4 pages.
GenBank Accession No. NM 007318.2, "*Homo sapiens* presenilin 1 (PSEN1), transcript variant 2, mRNA," dated Aug. 7, 2008, 5 pages.
GenBank Accession No. NM 012486.2, "*Homo sapiens* presenilin 2 (PSEN2), transcript variant 2, mRNA," dated Aug. 17, 2007, 6 pages.
GenBank Accession No. NP 000438.2, "presenilin-2 isoform 1 [*Homo sapiens*]," May 14, 2018, 4 pages.
Gholizadeh et al., "Reduced phenotypic severity following adeno-associated virus-mediated Fmr1 gene delivery in fragile X mice," Neuropsychopharmacology, Dec. 2014, 39(13):3100-11.
Gonçalves et al., "Adeno-associated virus: from defective virus to effective vector," Virology Journal, Dec. 2005, 2(1):1-7.
Gray et al., "Optimizing promoters for recombinant adeno-associated virus-mediated gene expression in the peripheral and central nervous system using self-complementary vectors," Human Gene Therapy, Sep. 2011, 22:1143-1153.
Haberman et al., "Inducible long-term gene expression in brain with adeno-associated virus gene transfer," Gene Therapy, Dec. 1998, 5(12):1604-11.
Handler et al., "Presenilin-1 regulates neuronal differentiation during neurogenesis," Development, Jun. 15, 2000, 127(12):2593-606.
Heilig et al., "A presenilin-1 mutation identified in familial Alzheimer disease with cotton wool plaques causes a nearly complete loss of γ-secretase activity," Journal of Biological Chemistry, Jul. 16, 2010, 285(29):22350-9.
Heilig et al., "Trans-dominant negative effects of pathogenic PSEN1 mutations on γ-secretase activity and Aβ production," Journal of Neuroscience, Jul. 10, 2013, 33(28):11606-17.
Henikoff et al., "Amino acid substitution matrices from protein blocks," Proceedings of the National Academy of Sciences, Nov. 15, 1992, 89(22):10915-9.
Hermonat et al., "Use of adeno-associated virus as a mammalian DNA cloning vector: transduction of neomycin resistance into mammalian tissue culture cells," Proceedings of the National Academy of Sciences, Oct. 1, 1984, 81(20):6466-70.
Herreman et al., "γ-Secretase activity requires the presenilin-dependent trafficking of nicastrin through the Golgi apparatus but not its complex glycosylation," Journal of Cell Science, Mar. 15, 2003, 116(6):1127-36.
Herskowitz, "Functional inactivation of genes by dominant negative mutations," Nature, Sep. 1987, 329(6136):219-22.
Hester et al., "AAV as a gene transfer vector for the treatment of neurological disorders: novel treatment thoughts for ALS," Current Gene Therapy, Oct. 1, 2009, 9(5):428-33.
Hiltunen et al., "Identification of a novel 4.6-kb genomic deletion in presenilin-1 gene which results in exclusion of exon 9 in a Finnish carly onset Alzheimer's disease family: an Alu core sequence-stimulated recombination?," European Journal of Human Genetics, Apr. 2000, 8(4):259-66.
Hitoshi Niwa et al., "Efficient selection for high-expression transfectants with a novel eukaryotic vector," Gene, Dec. 15, 1991, 108(2):193-9.
Hsu et al., "Discovery and validation of autosomal dominant Alzheimer's disease mutations," Alzheimer's Research & Therapy, Dec. 2018, 10(1):1-8.
Iwata et al., "Global brain delivery of neprilysin gene by intravascular administration of AAV vector in mice," Scientific Reports, Mar. 18, 2013, 3(1):1-8.
Jackson et al., "AAV9 supports wide-scale transduction of the CNS and TDP-43 disease modeling in adult rats," Molecular Therapy-Methods & Clinical Development, Jan. 1, 2015, 2:15036, 8 pages.
JP Japanese Office Action in Japanese Appln. No. 2020-565341, Apr. 4, 2023, 11 pages (with English translation).
Kang et al., "An evolutionarily conserved role of presenilin in neuronal protection in the aging *Drosophila* brain," Genetics, Jul. 1, 2017, 206(3):1479-93.

(56) References Cited

OTHER PUBLICATIONS

Karabinos et al., "Essential roles for four cytoplasmic intermediate filament proteins in Caenorhabditis elegans development," Proceedings of the National Academy of Sciences of the United States of America, Jul. 2001, 98(14):7863-7868.
Kelleher et al., "Presenilin-1 mutations and Alzheimer's disease," Proceedings of the National Academy of Sciences, Jan. 24, 2017, 114(4):629-31.
Kim et al., "Presenilins are required for maintenance of neural stem cells in the developing brain," Molecular Neurodegeneration, Dec. 2008, 3(1):1-3.
Kim et al., "Viral transduction of the neonatal brain delivers controllable genetic mosaicism for visualising and manipulating neuronal circuits in vivo," European Journal of Neuroscience, Apr. 2013, 37(8):1203-20.
Klein et al., "Dose and promoter effects of adeno-associated viral vector for green fluorescent protein expression in the rat brain," Experimental Neurology, Jul. 1, 2002, 176(1):66-74.
Kosik et al., "Homozygosity of the autosomal dominant Alzheimer disease presenilin 1 E280A mutation," Neurology, Jan. 13, 2015, 84(2):206-8.
Kumar-Singh et al., "Mean age-of-onset of familial alzheimer disease caused by presenilin mutations correlates with both increased Aβ42 and decreased Aβ40," Human Mutation, Jul. 2006, 27(7):686-95.
Lalli et al., "Origin of the PSEN1 E280A mutation causing early-onset Alzheimer's disease," Alzheimer's & Dementia, Oct. 2014, 10:S277-83.
Langer et al., "New methods of drug delivery," Science, Sep. 28, 1990, 249(4976):1527-33.
Lanoiselée et al., "APP, PSEN1, and PSEN2 mutations in early onset Alzheimer disease: A genetic screening study of familial and sporadic cases," PLOS Medicine, Mar. 2017, 14(3):e102270, 16 pages.
Lee et al., "Presenilins regulate synaptic plasticity and mitochondrial calcium homeostasis in the hippocampal mossy fiber pathway," Molecular Neurodegeneration, Dec. 2017, 12(1):1-5.
Lebkowski et al., "Adeno-associated virus: a vector system for efficient introduction and integration of DNA into a variety of mammalian cell types,". Molecular and Cellular Biology, Oct. 1, 1988, 8(10):3988-96.
Lee et al., "Synaptic function of nicastrin in hippocampal neurons," Proceedings of the National Academy of Sciences, Jun. 17, 2014, 111(24):8973-8.
Lei et al., "Structure-function analysis of human glucose-6-phosphatase, the enzyme deficient in glycogen storage disease type 1a," Journal of Biological Chemistry, May 19, 1995, 270(20):11882-6.
Lemere et al., "The E280A presenilin 1 Alzheimer mutation produces increased Aβ42 deposition and severe cerebellar pathology," Nature Medicine, Oct. 1996, 2(10):1146-50.
Levitan et al., "Assessment of normal and mutant human presenilin function in Caenorhabditis elegans," Proceedings of the National Academy of Sciences, Dec. 10, 1996, 93(25):14940-4.
Levy-Lahad et al., "Candidate gene for the chromosome 1 familial Alzheimer's disease locus," Science, Aug. 18, 1995, 269(5226):973-7.
Ling et al., "Enhanced transgene expression from recombinant single-stranded D-sequence-substituted adeno-associated virus vectors in human cell lines in vitro and in murine hepatocytes in vivo," Journal of Virology, Jan. 2015, 89(2):952-61.
Liu et al., "Systematic comparison of 2A peptides for cloning multi-genes in a polycistronic vector," Scientific Reports, May 19, 2017, 7(1):1-9.
Löbenberg et al., "Improved body distribution of 14C-labelled AZT bound to nanoparticles in rats determined by radioluminography," Journal of Drug Targeting, Jan. 1, 1998, 5(3):171-9.
Lopera et al., "Clinical features of early-onset Alzheimer disease in large kindred with an E280A presenilin-1 mutation," Jama, Mar. 12, 1997, 277(10):793-9.
Marambaud et al., "A presenilin-1/γulates disassembly of adherens junctions," The EMBO Journal, Apr. 15, 2002, 21(8):1948-56.
Matsushita et al., "Adeno-associated virus vectors can be efficiently produced without helper virus," Gene Therapy, Jul. 1998, 5:938-945.
Mauro et al., "A critical analysis of codon optimization in human therapeutics," Trends in Molecular Medicine, Nov. 1, 2014, 20(11):604-13.
Mayford et al., "Control of memory formation through regulated expression of a CaMKII transgene," Science, Dec. 6, 1996, 274(5293):1678-83.
McLaughlin et al., "Adeno-associated virus general transduction vectors: analysis of proviral structures," Journal of Virology, Jun. 1, 1988, 62(6):1963-73.
McLean et al., "Widespread neuron-specific transgene expression in brain and spinal cord following synapsin promoter-driven AAV9 neonatal intracerebroventricular injection," Neuroscience Letters, Jul. 25, 2014, 576:73-8.
Mingozzi et al., "Therapeutic in vivo gene transfer for genetic disease using AAV: progress and challenges," Nature Reviews Genetics, May 2011, 12(5):341-55.
Moehlmann et al., "Presenilin-1 mutations of leucine 166 equally affect the generation of the Notch and APP intracellular domains independent of their effect on Aβ42 production," Proceedings of the National Academy of Sciences, Jun. 11, 2002, 99(12):8025-30.
Mucke et al., "High-level neuronal expression of Aβ-42 in wild-type human amyloid protein precursor transgenic mice: synaptotoxicity without plaque formation," Journal of Neuroscience, Jun. 1, 2000, 20(11):4050-8.
Muzyczka, "Use of adeno-associated virus as a general transduction vector for mammalian cells," Viral Expression Vectors, 1992, vol. 1992:97-129.
Palmisano et al., "Characterization of membrane-shed microvesicles from cytokine-stimulated β-cells using proteomics strategies," Molecular & Cellular Proteomics, Aug. 1, 2012, 11(8):230-43.
Parra et al., "Memory binding and white matter integrity in familial Alzheimer's disease," Brain, May 1, 2015, 138(5):1355-69.
PCT International Preliminary Report on Patentability in International Appln. No. PCT/US2019/033616, dated Nov. 24, 2020, 12 pages.
PCT International Preliminary Report on Patentability in International Appln. No. PCT/US2020/034040, dated Nov. 16, 2021, 7 pages.
PCT International Preliminary Report on Patentability in International Appln. No. PCT/US2020/062394, mailed on May 17, 2022, 7 pages.
PCT International Preliminary Report on Patentability in International Appln. No. PCT/US2021/015911, mailed on Jul. 28, 2022, 9 pages.
PCT International Search Report and Written Opinion in International Appln. No. PCT/US2019/033616, dated Oct. 28, 2019, 18 pages.
PCT International Search Report and Written Opinion in International Appln. No. PCT/US2020/034040, dated Sep. 17, 2020, 10 pages.
PCT International Search Report and Written Opinion in International Appln. No. PCT/US2021/015911, mailed on Jun. 30, 2021, 14 pages.
Podlisny et al., "Presenilin proteins undergo heterogeneous endoproteolysis between Thr291and Ala299and occur as stable N-and C-terminal fragments in normal and Alzheimer brain tissue," Neurobiology of Disease, Jan. 1, 1997, 3(4):325-37.
Qi et al., "Distinct mechanisms by mutant presenilin 1 and 2 leading to increased intracellular levels of amyloid β-protein 42 in Chinese hamster ovary cells," Biochemistry, Feb. 4, 2003, 42(4):1042-52.
Qian et al., "Mutant human presenilin 1 protects presenilin 1 null mouse against embryonic lethality and elevates Aβ1-42/43 expression," Neuron, Mar. 1, 1998, 20(3):611-7.
Reiman et al., "Brain imaging and fluid biomarker analysis in young adults at genetic risk for autosomal dominant Alzheimer's disease in the presenilin 1 E280A kindred: a case-control study," The Lancet Neurology, Dec. 1, 2012, 11(12):1048-56.

(56) References Cited

OTHER PUBLICATIONS

Rios-Romenets et al., "The value of pre-screening in the Alzheimer's Prevention Initiative (API) Autosomal Dominant Alzheimer's Disease trial," The Journal of Prevention of Alzheimer's Disease, Jan. 2018, 5(1):49-54.
Robinson et al., "Lipid nanoparticle-delivered chemically modified mRNA restores chloride secretion in cystic fibrosis," Molecular Therapy, Aug. 1, 2018, 26(8):2034-46.
Rogaev et al., "Familial Alzheimer's disease in kindreds with missense mutations in a gene on chromosome 1 related to the Alzheimer's disease type 3 gene," Nature, Aug. 1995, 376(6543):775-8.
Ryan et al., "Correlating familial Alzheimer's disease gene mutations with clinical phenotype," Biomarkers in Medicine, Feb. 2010, 4(1):99-112.
Ryman et al., "Symptom onset in autosomal dominant Alzheimer disease: a systematic review and meta-analysis," Neurology, Jul. 15, 2014, 83(3):253-60.
Saito et al., "Potent amyloidogenicity and pathogenicity of Aβ43," Nature Neuroscience, Aug. 2011, 14(8):1023-32.
Sakuma et al., "Mucoadhesion of polystyrene nanoparticles having surface hydrophilic polymeric chains in the gastrointestinal tract," International Journal of Pharmaceutics, Jan. 25, 1999, 177(2):161-72.
Samulski et al., "Helper-free stocks of recombinant adeno-associated viruses: normal integration does not require viral gene expression," Journal of Virology, Sep. 1, 1989, 63(9):3822-8.
Saura et al., "Conditional inactivation of presenilin 1 prevents amyloid accumulation and temporarily rescues contextual and spatial working memory impairments in amyloid precursor protein transgenic mice," Journal of Neuroscience, Jul. 20, 2005, 25(29):6755-64.
Saura et al., "Loss of presenilin function causes impairments of memory and synaptic plasticity followed by age-dependent neurodegeneration," Neuron, Apr. 8, 2004, 42(1):23-36.
Schroeter et al., "A presenilin dimer at the core of the γ-secretase enzyme: insights from parallel analysis of Notch 1 and APP proteolysis," Proceedings of the National Academy of Sciences, Oct. 28, 2003, 100(22):13075-80.
PCT International Search Report and Written Opinion in International Appln. No. PCT/US2020/062394, mailed on Apr. 28, 2021, 15 pages.
Sepulveda-Falla et al., "Deposition of hyperphosphorylated tau in cerebellum of PS1 E280A Alzheimer's disease," Brain Pathology, Jul. 2011, 21(4):452-63.
Sepulveda-Falla et al., "Familial Alzheimer's disease-associated presenilin-1 alters cerebellar activity and calcium homeostasis," The Journal of Clinical Investigation, Apr. 1, 2014, 124(4):1552-67.
Shen et al., "Skeletal and CNS defects in Presenilin-1-deficient mice," Cell, May 16, 1997, 89(4):629-39.
Shen et al., "The presenilin hypothesis of Alzheimer's disease: evidence for a loss-of-function pathogenic mechanism," Proceedings of the National Academy of Sciences, Jan. 9, 2007, 104(2):403-9.
Perez-Pinera et al., "RNA-guided gene activation by CRISPR-Cas9-based transcription factors," Oct. 2013, Nature Methods, 2013, 10(10):973-976. doi: 10.1038/nmeth.2600.
Sherrington et al., "Cloning of a gene bearing missense mutations in early-onset familial Alzheimer's disease," Nature, Jun. 1995, 375(6534):754-60.
Siman et al., "Presenilin-1 P264L knock-in mutation: differential effects on Aβ production, amyloid deposition, and neuronal vulnerability," Journal of Neuroscience, Dec. 1, 2000, 20(23):8717-26.
Song et al., "Proteolytic release and nuclear translocation of Notch-1 are induced by presenilin-1 and impaired by pathogenic presenilin-1 mutations," Proceedings of the National Academy of Sciences, Jun. 8, 1999, 96(12):6959-63.
Steiner et al., "A pathogenic presenilin-1 deletion causes abberrant Aβ42 production in the absence of congophilic amyloid plaques," Journal of Biological Chemistry, Mar. 9, 2001, 276(10):7233-9.
Sun et al., "Analysis of 138 pathogenic mutations in presenilin-1 on the in vitro production of Aβ42 and AB40 peptides by γ-secretase," Proceedings of the National Academy of Sciences, Jan. 24, 2017, 114(4):E476-85.
Sun et al., "Hippocampal spatial memory impairments caused by the familial Alzheimer's disease-linked presenilin 1 M146V mutation," Neurodegenerative Diseases, Aug. 2005, 2(1):6-15.
Szymczak et al., "Correction of multi-gene deficiency in vivo using a single'self-cleaving'2A peptide-based retroviral vector," Nature Biotechnology, May 2004, 22(5):589-94.
Tabuchi et al., "Conditional forebrain inactivation of nicastrin causes progressive memory impairment and age-related neurodegeneration," Journal of Neuroscience, Jun. 3, 2009, 29(22):7290-301.
Théry et al., "Isolation and characterization of exosomes from cell culture supernatants and biological fluids," Current Protocols in Cell Biology, Mar. 2006, 30(1):3-22.
Trichas et al., "Use of the viral 2A peptide for bicistronic expression in transgenic mice," BMC Biology, Dec. 2008, 6(1):1-3.
Tysoe et al., "A presenilin-1 truncating mutation is present in two cases with autopsy-confirmed early-onset Alzheimer disease," The American Journal of Human Genetics, Jan. 1, 1998, 62(1):70-6.
Virovic et al., "Novel delivery methods for treatment of viral hepatitis: an update," Expert Opinion on Drug Delivery, Jul. 1, 2005, 2(4):707-17.
Waldenström et al., "Cardiomyocyte microvesicles contain DNA/RNA and convey biological messages to target cells, " PloS one, Apr. 10, 2012, 7(4):e34653, 7 pages.
Walker et al., "Presenilin 2 familial Alzheimer's disease mutations result in partial loss of function and dramatic changes in Aβ 42/40 ratios," Journal of Neurochemistry, Jan. 2005, 92(2):294-301.
Sen et al., "Improved adeno-associated virus (AAV) serotype 1 and 5 vectors for gene therapy," Scientific Reports, May 2013, 3:1832, DOI: 10.1038/srep01832, 1-6.
Sherrington et al., "Alzheimer's disease associated with mutations in presenilin 2 is rare and variably penetrant," Jul. 1996, 5(7):985-988.
Wang et al., "Wild-type presenilin 1 protects against Alzheimer disease mutation-induced amyloid pathology," Journal of Biological Chemistry, Jun. 2006, 281(22):15330-6.
Watanabe et al., "Dominant negative mechanism of Presenilin-1 mutations in FAD," Proceedings of the National Academy of Sciences, Nov. 28, 2017, 114(48):12635-7.
Watanabe et al., "Familial frontotemporal dementia-associated presenilin-1 c. 548G> T mutation causes decreased mRNA expression and reduced presenilin function in knock-in mice," Journal of Neuroscience, Apr. 11, 2012, 32(15):5085-96.
Watanabe et al., "Indirect regulation of presenilins in CREB-mediated transcription," Journal of Biological Chemistry, May 15, 2009, 284(20):13705-13.
Watanabe et al., "Partial loss of presenilin impairs age-dependent neuronal survival in the cerebral cortex," Journal of Neuroscience, Nov. 26, 2014, 34(48):15912-22.
Wiley et al., "Familial Alzheimer's disease mutations inhibit γ-secretase-mediated liberation of β-amyloid precursor protein carboxy-terminal fragment," Journal of Neurochemistry, Sep. 2005, 94(5):1189-201.
Wines-Samuelson et al., "Characterization of age-dependent and progressive cortical neuronal degeneration in presenilin conditional mutant mice," PLoS One, Apr. 15, 2010, 5(4):e10195.
Wines-Samuelson et al., "Presenilins in the developing, adult, and aging cerebral cortex," The Neuroscientist, Oct. 2005, 11(5):441-51.
Wines-Samuelson et al., "Role of presenilin-1 in cortical lamination and survival of Cajal-Retzius neurons," Developmental Biology, Jan. 15, 2005, 277(2):332-46.
Wu et al., "Presenilins regulate calcium homeostasis and presynaptic function via ryanodine receptors in hippocampal neurons," Proceedings of the National Academy of Sciences, Sep. 10, 2013, 110(37):15091-6.
Xia et al., "Loss of Aβ43 production caused by presenilin-1 mutations in the knockin mouse brain," Neuron, Apr. 20, 2016, 90(2):417-22.

(56) References Cited

OTHER PUBLICATIONS

Xia et al., "Presenilin-1 knockin mice reveal loss-of-function mechanism for familial Alzheimer's disease," Neuron, Mar. 4, 2015, 85(5):967-81.
Wang et al., "Rescue and replication of adeno-associated virus type 2 as well as vector DNA sequences from recombinant plasmids containing deletions in the viral inverted terminal repeats: Selective encapsidation of viral genomes in progeny virions," Journal of Virology, Mar. 1996, 70(3):1668-1677.
Xia, "Relationship between presenilinase and gamma-secretase," Drug News & Perspectives, Mar. 1, 2003, 16(2):69-74.
Wang et al., "Rescue and replication signals of the adeno-associated virus 2 genome," Journal of Molecular Biology, Jul. 1995, 250(5):573-580.
Yu et al., "APP processing and synaptic plasticity in presenilin-1 conditional knockout mice," Neuron, Sep. 13, 2001, 31(5):713-26.
Zhang et al., "Inactivation of presenilins causes pre-synaptic impairment prior to post-synaptic dysfunction," Journal of Neurochemistry, Dec. 2010, 115(5):1215-21.
Zhang et al., "Mutation of the conserved N-terminal cysteine (Cys92) of human presenilin 1 causes increased Aβ42 secretion in mammalian cells but impaired Notch/lin-I2 signalling in C. elegans," Neuroreport, Sep. 28, 2000, 11(14):3227-30.
Zhang et al., "Presenilins are essential for regulating neurotransmitter release," Nature, Jul. 2009, 460(7255):632-6.
Zhao et al., "Mechanisms of recognition of amyloid-β (Aβ) monomer, oligomer, and fibril by homologous antibodies," Journal of Biological Chemistry, Nov. 3, 2017, 292(44):18325-43.
Zhou et al., "Dominant negative effect of the loss-of-function γ-secretase mutants on the wild-type enzyme through heterooligomerization," Proceedings of the National Academy of Sciences, Nov. 28, 2017, 114(48):12731-6.
Zimmermann et al., "Electrolyte-and pH-stabilities of aqueous solid lipid nanoparticle (SLNTM) dispersions in artificial gastrointestinal media," European Journal of Pharmaceutics and Biopharmaceutics, Sep. 1, 2001, 52(2):203-10.
Xia et al., "Presenilin-1 knockin mice reveal loss-of-function mechanism for familial Alzheimer's disease," Neuron, Mar. 2015, 85(5):967-981.
Xiao et al., "Production of high-titer recombinant adeno-associated virus vectors in the absence of helper adenovirus," Journal of Virology, Mar. 1998, 72(3):2224-2232.
CA Office Action in Canadian Appln. No. 3,100,946, mailed on Feb. 5, 2025, 5 pages.
JP Office Action in Japanese Appln. No. 2021-569550, mailed on Jan. 14, 2025, 3 pages (with English translation).
Kou et al., "Catalytic immunoglobulin gene delivery in a mouse model of Alzheimer's disease: prophylactic and therapeutic applications," Molecular Neurobiology, Feb. 2015, 51:43, 29 pages.
AU Office Action in Australian Appln. No. 2020285638, mailed on May 1, 2025, 4 pages.
Borel et al., "Recombinant AAV as a platform for translating the therapeutic potential of RNA interference," Molecular Therapy, Apr. 2014, 22(4):692-701.
EP Office Action in European Appln. No. 19808081.4, mailed on Apr. 23, 2025, 6 pages.
Kilikevicius et al., "Reexamining assumptions about miRNA-guided gene silencing," Nucleic Acids Research, Jan. 2022, 50(2):617-34.
O'Reilly et al., "RNA interference-mediated suppression and replacement of human rhodopsin in vivo," The American Journal of Human Genetics, Jul. 2007, 81(1):127-35.
Riolo et al., "miRNA targets: from prediction tools to experimental validation," Methods and Protocols, Dec. 2020, 4(1):1, 20 pages.
Seok et al., "MicroRNA target recognition: insights from transcriptome-wide non-canonical interactions," Molecules and Cells, May 2016, 39(5):375-81.
SG Office Action in Singaporean Appln. No. 11202205560S, mailed on Jun. 5, 2025, 12 pages.

* cited by examiner

GENE THERAPY FOR NEURODEGENERATIVE DISORDERS

CROSS-REFERENCE TO RELATED APPLICATIONS

This application is a 35 USC § 371 National Stage application of International Application No. PCT/US2020/062394 filed Nov. 25, 2020, now pending; which claims the benefit under 35 USC § 119(e) to U.S. Application Ser. No. 63/004,422 filed Apr. 2, 2020 and to U.S. Application Ser. No. 62/942,059 filed Nov. 29, 2019. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, named APRES1110-2_ST25.txt, was created on May 3, 2022 and is 105 kB in size. The file can be accessed using Microsoft Word on a computer that uses Windows OS.

BACKGROUND OF THE INVENTION

Technical Field

The present disclosure relates generally to gene therapy for neurodegenerative disorders, and more specifically to polynucleotides and expression cassettes for delivery of therapeutic genes. In particular embodiments, a therapeutic gene is presenilin-1.

Background Information

Alzheimer's disease (AD), also referred to as Alzheimer's, is a chronic neurodegenerative disease that is the cause of a majority of neurodegenerative dementia. Symptoms include difficulty with memory, problems with language, disorientation, mood swings, loss of motivation, and other behavioral problems such as withdrawal from family and society. Bodily functions are gradually lost, ultimately leading to death. Although the disease can last for more than ten years, the average life expectancy is three to nine years following diagnosis.

The disease is accompanied by a variety of neuropathologic features principal among which are the presence in the brain of amyloid plaques and the neurofibrillary degeneration of neurons. The etiology of this disease is complex, although in about 10% of AD cases it appears to be familial, being inherited as an autosomal dominant trait. Among these inherited forms of AD, there are at least four different genes, some of whose mutants confer inherited susceptibility to this disease. The σ4 (Cys112Arg) allelic polymorphism of the Apolipoprotein E (ApoE) gene has been associated with AD in a significant proportion of cases with onset late in life. A very small proportion of familial cases with onset before age 65 years have been associated with mutations in the β-amyloid precursor protein (APP) gene on chromosome 21. A third locus associated with a larger proportion of cases with early onset AD has recently been mapped to chromosome 14q24.3. The majority (70-80%) of heritable, early-onset AD maps to chromosome 14 and appears to result from one of more than 20 different amino-acid substitutions within the protein presenilin-1 (PS1). A similar, although less common, AD-risk locus on chromosome 1 encodes a protein, presenilin-2 (PS-2, highly homologous to PS-1).

SUMMARY OF THE INVENTION

The present disclosure relates to polynucleotides and nucleic acid expression cassettes encoding presenilin-1 (PSEN-1) for the treatment of neurodegenerative disorders.

In some embodiments, the disclosure provides an isolated cDNA or a hybrid genomic/cDNA that encodes the naturally occurring human presenilin-1 amino acid sequence set forth in either SEQ ID NO: 12 (isoform X1) or SEQ ID NO:14 (isoform X2), wherein as compared to the cDNA corresponding to the naturally occurring PSEN-1 X1 isoform coding sequence (SEQ ID NO:15) or PSEN-1 X2 isoform coding sequence (SEQ ID NO: 13), the isolated cDNA or hybrid genomic/cDNA comprises codon optimization changes in at least 25% of the tolerant codons. In some aspects of these embodiments, no intolerant codons are altered in the PSEN-1 coding sequence in the isolated cDNA or hybrid genomic/cDNA. In some aspects of these embodiments, the isolated cDNA or hybrid genomic/cDNA comprises codon optimization changes in at least 40%, at least 50%, at least 60%, at least 70%, at least 80%, at least 85%, at least 90%, at least 95%, at least 97%, at least 98%, at least 99% or all of the tolerant codons in the PSEN-1 coding sequence.

In some embodiments, the disclosure provides an isolated cDNA or hybrid genomic/cDNA that encodes the naturally occurring human presenilin-1 amino acid sequence set forth in either SEQ ID NO: 12 (isoform X1) or SEQ ID NO:14 (isoform X2), wherein the isolated cDNA or hybrid genomic/cDNA comprises 20 or less CpG dinucleotides. This is a reduction as compared to SEQ ID NO:1 or SEQ ID NO:13, each of which has 23 CpG dinucleotides in the PSEN1 open reading frame. It will be understood that in these embodiments, the replacement of any CpG dinucleotide present in SEQ ID NO:1 or SEQ ID NO:13 must be achieved by replacing either the cytosine or the guanine (or both) with another nucleotide that, due to the redundancy of the genetic code, does not alter the amino acid encoded by the codon containing the replaced nucleotide. In other words, any nucleotide substitution utilized to remove a CpG dinucleotide must preserve the amino acid sequence encoded by SEQ ID NO:1 or SEQ ID NO:13. In some aspects of these embodiments, the isolated cDNA or hybrid genomic/cDNA comprises less than 15, less than 12, less than 10, less than 9, less than 8, less than 7, less than 6, less than 5, less than 4, less than 3, one, or none of the CpG dinucleotides present in SEQ ID NO:1 or SEQ ID NO:13. In some aspects of these embodiments, all intolerant codons present in SEQ ID NO:1 or SEQ ID NO:13 are preserved in the isolated cDNA or artificial gene that has a reduced number of CpG dinucleotides.

In some embodiments, the isolated cDNA or hybrid genomic/cDNA comprises codon optimization changes in at least 25% of the tolerant codons present in SEQ ID NO:1 or SEQ ID NO:13 and comprises 20 or less CpG dinucleotides. In some aspects of these embodiments, the isolated cDNA or hybrid genomic/cDNA comprises codon optimization changes in at least 40%, at least 50%, at least 60%, at least 70%, at least 80%, at least 85%, at least 90%, at least 95%, at least 97%, at least 98%, at least 99% or all of the tolerant codons in the PSEN-1 coding sequence. In some aspects of these embodiments, the isolated cDNA or hybrid genomic/cDNA comprises less than 15, less than 12, less than 10, less than 9, less than 8, less than 7, less than 6, less than 5, less than 4, less than 3, one, or no CpG dinucleotides. In some aspects of these embodiments, all intolerant codons present in SEQ ID NO:1 or SEQ ID NO:13 are preserved in the isolated cDNA or artificial gene that has a reduced number of CpG dinucleotides.

In some embodiments, the disclosure provides a hybrid genomic/cDNA that comprises: 1) at least a portion or all of naturally occurring PSEN-1 exon 3 with two alternate splice donor sites as used to produce the cDNAs in SEQ ID NO:1 and SEQ ID NO: 13; 2) at least a portion of naturally occurring PSEN-1 intron 3, wherein the portion of intron 3 comprises a splice acceptor site; and 3) a nucleotide sequence capable of encoding upon expression both SEQ ID NO: 12 (isoform X1) and SEQ ID NO:14 (isoform X2) due to the use of the alternate splice donor sites, wherein the hybrid genomic/cDNA: a) includes less than 70% of naturally occurring PSEN-1 intron 3; b) includes less than 70% of naturally occurring PSEN-1 intron 4; c) lacks at least one of naturally occurring PSEN-1 introns 5, 6, 7, 8, or 9; and/or d) is less than 4.4 kb in length. In some aspects of these embodiments, the portion of the hybrid genomic/cDNA that encodes the naturally occurring human presenilin-1 amino acid sequence set forth in either SEQ ID NO: 12 (isoform X1) or SEQ ID NO:14 (isoform X2), comprises codon optimization changes in at least 25% of the tolerant codons wherein as compared to the cDNA corresponding to the naturally occurring PSEN-1 X1 isoform coding sequence (SEQ ID NO:15), or the PSEN-1 X2 isoform sequence (SEQ ID NO:13). In some aspects of these embodiments, the hybrid genomic/cDNA that encodes the naturally occurring human presenilin-1 amino acid sequence set forth in either SEQ ID NO: 12 (isoform X1) or SEQ ID NO:14 (isoform X2), comprises less than 50 CpG dinucleotides throughout the nucleotide sequence. In some embodiments, the hybrid genomic/cDNA comprises less than 20 CpG dinucleotides in the PSEN-1 coding sequence. In some embodiments, the hybrid genomic/cDNA comprises codon optimization changes in at least 30% of the tolerant codons in SEQ ID NO:15 or SEQ ID NO:13; less than 50 CpG dinucleotides throughout the nucleotide sequence; less than 20 CpG dinucleotides in the PSEN-1 coding sequence; and no changes in any intolerant codons in SEQ ID NO:1 or SEQ ID NO:13. In some more specific versions of any of the aspects set forth in this paragraph, the hybrid genomic/cDNA comprises less than 40, less than 30, less than 20, less than 15, less than 12, less than 10, less than 9, less than 8, less than 7, less than 6, less than 5, less than 4, less than 3, one, or no CpG dinucleotides throughout the nucleotide sequence. In some more specific versions of any of the aspects set forth in this paragraph, the hybrid genomic/cDNA comprises less than 15, less than 12, less than 10, less than 9, less than 8, less than 7, less than 6, less than 5, less than 4, less than 3, one, or no CpG dinucleotides in the PSEN-1 coding region. In some more specific versions of any of the aspects set forth in this paragraph, the hybrid genomic/cDNA comprises codon optimization changes in at least 40%, at least 50%, at least 60%, at least 70%, at least 80%, at least 85%, at least 90%, at least 95%, at least 97%, at least 98%, at least 99% or all of the tolerant codons in the PSEN-1 coding sequence in SEQ ID NO:15 or SEQ ID NO:13.

Described herein, in some embodiments, are isolated polynucleotides set forth in SEQ ID NO:6, SEQ ID NO:7, or SEQ ID NO:8; or polynucleotides having at least 95% identity to SEQ ID NO:6, SEQ ID NO:7, or SEQ ID NO:8. In some embodiments, the isolated cDNA or hybrid genomic/cDNA is SEQ ID NO:6 (a cDNA), SEQ ID NO:7 (a cDNA), or SEQ ID NO:8 (a hybrid genomic/cDNA); or a polynucleotide having at least 95% identity to SEQ ID NO:6, SEQ ID NO:7, or SEQ ID NO:8 and encoding the same amino acid sequence as SEQ ID NO:6, SEQ ID NO:7, or SEQ ID NO:8, respectively. In some embodiments, the polynucleotide having at least 95% identity to SEQ ID NO:6, SEQ ID NO:7, or SEQ ID NO:8 and encoding the same amino acid sequence as SEQ ID NO:6, SEQ ID NO:7, or SEQ ID NO:8, respectively, maintains the intolerant codons present therein and either (1) maintains all optimized codons present therein; or (2) replaces one or more optimized codons therein with other codons that encode the same amino acid and are also optimized.

Described herein, in some embodiments, are isolated polynucleotides set forth in SEQ ID NO:36, SEQ ID NO:37, SEQ ID NO:38, or SEQ ID NO:39; or polynucleotides having at least 95% identity to SEQ ID NO:36, SEQ ID NO:37, SEQ ID NO:38, or SEQ ID NO:39 and encoding the same amino acid sequence as encoded by each of SEQ ID NO:36, SEQ ID NO:37, SEQ ID NO:38, and SEQ ID NO:39. In some aspects of these embodiments, the polynucleotide having at least 95% identity to SEQ ID NO:36, SEQ ID NO:37, SEQ ID NO:38, or SEQ ID NO:39 encodes the same amino acid sequence as SEQ ID NO:36, SEQ ID NO:37, SEQ ID NO:38, and SEQ ID NO:39, maintains the intolerant codons present therein and either (1) maintains all optimized codons present therein; or (2) replaces one or more optimized codons therein with other codons that encode the same amino acid and are also optimized. In some aspects of these embodiments, the isolated polynucleotide is SEQ ID NO:36. In some aspects of these embodiments, the isolated polynucleotide is SEQ ID NO:37. In alternate aspects of these embodiment, the isolated polynucleotide is SEQ ID NO:38. In alternate aspects of these embodiment, the isolated polynucleotide is SEQ ID NO:39.

In certain embodiments, the disclosure provides nucleic acid expression cassettes comprising any of the cDNA or hybrid genomic/cDNA polynucleotides encoding presenilin 1 set forth above.

In certain embodiments, nucleic acid expression cassette comprises sequences encoding a 5' AAV inverted terminal repeat sequence (ITR), a promoter with an optional enhancer, a polynucleotide encoding presenilin 1 and a 3' AAV ITR. In certain embodiments, a nucleic acid expression cassette comprises a full-length AAV 5' inverted terminal repeat (ITR) and a full-length 3' ITR. In certain embodiments, a nucleic acid expression cassette comprises a shortened version of the 5' ITR, termed ΔITR, has been described in which the D-sequence and terminal resolution site (trs) are deleted (X. S. Wang, et al., *J Mol Biol* 250:573-580, 1995; X. S. Wang, et al., *J Virol* 70:1668-1677, 1996); C. Ling et al., *J Virol*. January 2015, 89 (2) 952-961; DOI: 10.1128/JVI 02581-14). In certain embodiments, the ITRs are selected from a source which differs from the AAV source of the capsid. For example, AAV2 ITRs may be selected for use with an AAV capsid having a particular efficiency for a selected cellular receptor, target tissue or viral target. In certain embodiments, the AAV capsid is from AAV9. In one embodiment, the ITR sequences from AAV2, or the deleted version thereof (ΔITR), however, ITRs from other AAV sources maybe selected. Where the source of the ITRs is from one AAV serotype and the AAV capsid is from another AAV serotype, the resulting vector may be termed pseudotyped. In certain embodiments, the ITRs and capsids are from AAV9. In certain embodiments, the ITRs are from single stranded or self-complementary AAV vectors. In certain embodiments, the ITRs may be part of the expression cassette, while in alternate embodiments, the ITRs may be part of the vector into which the expression cassette is cloned.

In some embodiments, the one or more regulatory elements comprise a Kozak translation initiation signal such as a polynucleotide set forth in SEQ ID NO:5, or a nucleotide sequence having at least an 80% sequence identity to SEQ ID NO: 5.

In some embodiments, the one or more regulatory elements comprise a chromatin insulator sequence, such as the polynucleotide set forth in SEQ ID NO:4, or a nucleotide sequence having at least a 95% sequence identity to SEQ ID NO: 4.

In some embodiments, the one or more regulatory elements comprise promoter. In some aspects of these embodiments, the promoter is a neuron-specific promoter. A neuron-specific promoter can comprise (i) a polynucleotide set forth in SEQ ID NO:2; (ii) a polynucleotide set forth in SEQ ID NO:3; (iii) a functional fragment of SEQ ID NO:2 or SEQ ID NO:3; or (iv) polynucleotide with at least 95% identity to (i), (ii), or (iii). In alternate aspects of these embodiments, the promoter is selected from CAG (SEQ ID NO: 23), CBA (SEQ ID NO: 24), UBC (SEQ ID NO: 25), PGK (SEQ ID NO: 26), PKC, EF1a (SEQ ID NO: 27), GUSB, CMV (SEQ ID NO: 28), NSE (SEQ ID NO: 29), PDGF, desmin, MCK, MeCP2 (SEQ ID NO: 30), GFAP (SEQ ID NO: 31), CaMKII or MBP.

In some embodiments, the one or more regulatory elements comprise at least one mRNA stability element. The at least one mRNA stability element can comprise (i) a polynucleotide set forth in SEQ ID NO:9, SEQ ID NO:10, SEQ ID NO:11; (ii) a functional variant of SEQ ID NO:9, SEQ ID NO:10, SEQ ID NO:11; or (iii) a polynucleotide with at least 95% sequence identity to (i) or (ii). In some aspects of these embodiments, the nucleic acid expression cassette comprises a mRNA stability element located 5' of the open reading frame of the polynucleotide encoding PSEN1; and a mRNA stability element located 3' of the polyadenylation signal. In certain embodiments, the nucleic acid expression cassette comprises one or more polyadenylation enhancer elements, such as, for example Human growth hormone (hGH) polyadenylation signal sequences, rabbit beta-globin (rBG) polyadenylation signal sequences, SV40 polyadenylation signal sequences or bovine growth hormone (BGH) polyadenylation signal sequences.

In some embodiments, the one or more regulatory elements comprise one, two or three micro RNA ("miRNA" or "miR") binding sites to suppress expression of the encoded PSEN-1 in dorsal root ganglia. MicroRNAs are 19-25 nucleotide noncoding RNAs that bind to miRNA binding sites and down-regulate gene expression either by reducing nucleic acid molecule stability or by inhibiting translation. In some aspects of these embodiments, each miRNA binding site is independently selected from a binding site for any of the following miRNAs: miRNA-1914, miR1181, miR3918, miR939, miR324, miR650, MiR29C, or miR2277. In some aspects of these embodiments, the miRNA binding site(s) are located 3' to the coding sequence of the viral genome.

Other embodiments provide vectors comprising the nucleic acid expression cassettes provided herein. A vector can be a viral vector, such as an adeno-associated virus (AAV) vector, a retroviral vector, a lentiviral vector, or an adenoviral vector. An AAV vector can be AAV1, AAV2, AAV3, AAV4, AAV5, AAV6, AAV7, AAV8, AAV9, AAVDJ, AAVrh10, AAV11, AAV12, AAV13, AAV14, AAV15, AAV16, AAV2/1, AAV2/5, AAV2/6, AAV2/7, AAV2/8, AAV2/9, AAV2/rh10, AAV2/11, or AAV2/12.

A vector as described herein can be a pseudotyped vector. Pseudotyping provides a mechanism for modulating a vector's target cell population. Pseudotyped vectors comprise the genome of one vector, e.g., the genome of one AAV serotype, in the capsid of a second vector, e.g., a second AAV serotype. A lentiviral vector may be pseudotyped with envelope glycoproteins derived from Rhabdovirus vesicular stomatitis virus (VSV) serotypes (Indiana and Chandipura strains), rabies virus (e.g., various Evelyn-Rokitnicki-Abelseth ERA strains and challenge virus standard (CVS)), Lyssavirus Mokola virus, a rabies-related virus, vesicular stomatitis virus (VSV), Mokola virus (MV), lymphocytic choriomeningitis virus (LCMV), rabies virus glycoprotein (RV-G), glycoprotein B type (FuG-B), a variant of FuG-B (FuG-B2) or Moloney murine leukemia virus (MuLV). A virus may be pseudotyped for transduction of one or more neurons or groups of cells.

Other embodiments provide nucleic acid expression cassettes comprising: (i) any of the cDNA or hybrid genomic/cDNA polynucleotides encoding presenilin 1 set forth above; (ii) a Kozak translation initiation signal; (iii) a neuron-specific promoter; (iv) a chromatin insulator sequence; (v) at least one mRNA stability element; or (v) any combination thereof. In some aspects of these embodiments, the nucleic acid expression cassettes comprises each of: (i) any of the cDNA or hybrid genomic/cDNA polynucleotides encoding presenilin 1 set forth above; (ii) a Kozak translation initiation signal; (iii) a neuron-specific promoter; (iv) a chromatin insulator sequence; and (v) at least one mRNA stability element. In more specific aspects of these embodiments, the Kozak translation initiation signal comprises a polynucleotide set forth in SEQ ID NO:5; the chromatin insulator sequence comprises a polynucleotide set forth in SEQ ID NO:4; the at least one mRNA stability element comprises a polynucleotide set forth in SEQ ID NO:9, SEQ ID NO:10, SEQ ID NO:11, or any combination thereof; and the neuron-specific promoter comprises a polynucleotide set forth in SEQ ID NO:2 or SEQ ID NO:3.

Described herein are methods of treating a neurodegenerative disease, disorder, or condition comprising administering to a subject in need thereof a nucleic acid expression cassette or vector. In some embodiments, the neurodegenerative disease, disorder, or condition is Alzheimer's disease, posterior cortical atrophy (PCA), logopenic progressive aphasia (lvPPA), hippocampal sparing AD, frontotemporal dementia, frontotemporal lobar degeneration, Pick's disease, Lewy body dementia, aphasic variants of AD, behavioral-comportmental ("frontal") variant of AD, a dysexecutive variant, memory loss, cognitive impairment, or mild cognitive impairment.

Described herein are methods of producing presenilin 1 protein including transforming a host cell with an optimized polynucleotide set forth in SEQ ID NO:6, SEQ ID NO:7, SEQ ID NO:8, SEQ ID NO:36, SEQ ID NO:37, SEQ ID NO:38, or SEQ ID NO:39; or by a polynucleotide having at least 95% identity to SEQ ID NO:6, SEQ ID NO:7, SEQ ID NO:8, SEQ ID NO:36, SEQ ID NO:37, SEQ ID NO:38, or SEQ ID NO:39, and encoding the same polypeptide encoded by each of the foregoing, or with a vector encoding presenilin 1 optimized polynucleotide; and culturing the cell under conditions and for a time that allow expression of the presenilin 1 protein. In some aspects, the expression level of the presenilin 1 protein encoded by the optimized polynucleotide in the host cell is greater than a level of expression of presenilin 1 protein encoded by a wild-type polynucleotide in a host cell, thereby producing presenilin 1 protein.

It is to be understood that one, some, or all of the properties of the various embodiments described herein may be combined to form other embodiments of the present invention.

DETAILED DESCRIPTION

Figure 1:
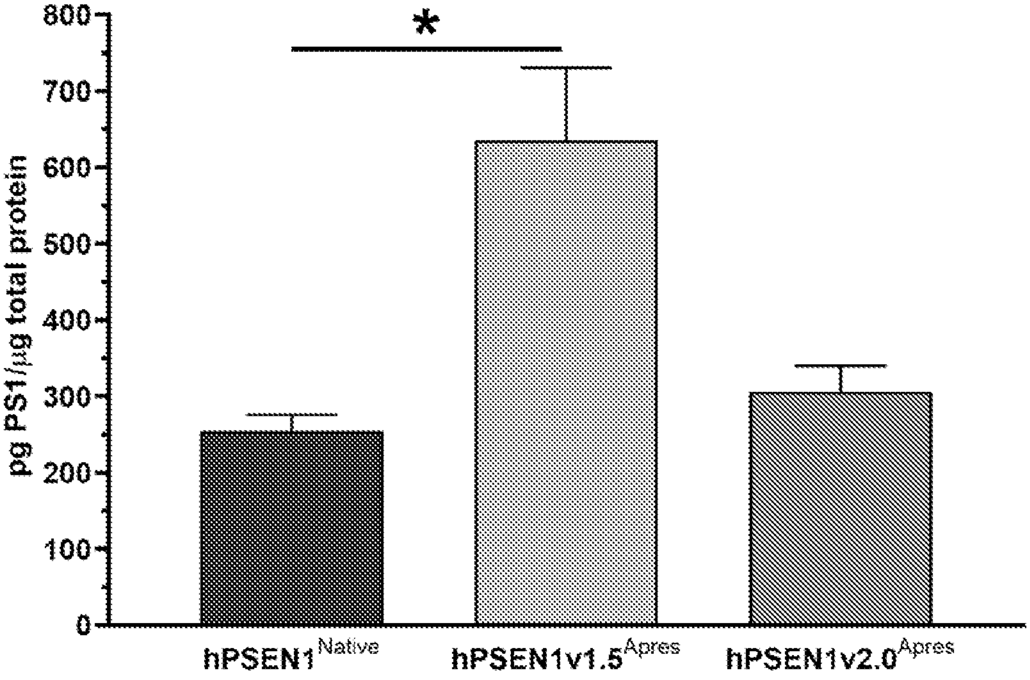
FIG. 1 is a bar graph showing the amount of presenilin-1 protein expressed from HEK293 cells harboring constructs comprising various codon-optimized versions of a presenilin-1 coding sequence under control of a CMV promoter, as well as from a wild-type presenilin-1 coding sequence. The asterisk "*" indicates a statistically significant difference ($p<0.05$, One way ANOVA followed by Tukey's multiple comparison test).

The present invention is based on the seminal discovery that optimized polynucleotides and expression cassettes encoding optimized therapeutic genes such as presenilin-1 can be used to increase expression levels of the therapeutic gene, as compared to a wild-type sequence, to deliver gene therapy for use in the treatment of neurodegenerative disorders.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

All publications, patents, and patent applications mentioned in this specification are herein incorporated by reference to the same extent as if each individual publication, patent, or patent application was specifically and individually indicated to be incorporated by reference.

Definitions

Unless specifically defined otherwise, all technical and scientific terms used herein shall be taken to have the same meaning as commonly understood by one of ordinary skill in the art (e.g., in cell culture, molecular genetics, and biochemistry). Although any methods and materials similar or equivalent to those described herein can be used in the practice or testing of the invention, it will be understood that modifications and variations are encompassed within the spirit and scope of the instant disclosure. The preferred methods and materials are now described.

As used herein, the term "about" in the context of a numerical value or range means ±10% of the numerical value or range recited or claimed, unless the context requires a more limited range. Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising." It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

By an "AAV vector" is meant a vector derived from an adeno-associated virus serotype, including without limitation, AAV-1, AAV-2, AAV-3, AAV-4, AAV-5, AAV6, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. ITRs don't need to be the wild-type nucleotide sequences, and may be altered, e.g., by the insertion, deletion or substitution of nucleotides, so long as the sequences provide for functional rescue, replication and packaging.

The control elements are selected to be functional in a mammalian cell. The resulting construct which contains the operatively linked components is bounded (5' and 3') with functional AAV ITR sequences. By "adeno-associated virus inverted terminal repeats" or "AAV ITRs" is mean the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. As used herein, an "AAV ITR" does not necessarily comprise the wild-type nucleotide sequence, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV6, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Additionally, AAV ITRs may be derived from any of several AAV serotypes, including without limitation, AAV-1, AAV-2, AAV-3, AAV-4, AAV 5, AAV6, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

The term "wild-type" and "native" are used herein interchangeably and refer to a form of a substance (e.g., a polynucleotide, a nucleotide sequence, a protein, etc.) that is found in nature. The term "wild-type presenilin-1 coding sequence" as used herein means the polynucleotide sequence set forth in SEQ ID NO:15.

The term "hybrid genomic/cDNA" as used herein means a non-naturally occurring nucleotide sequence that encodes a protein (e.g., a human presenilin-1), wherein the coding sequence for the protein is interrupted by one or more non-coding intronic sequences.

The term "intolerant codon" as used herein means a codon present in a reference nucleotide sequence that is not changed in a corresponding subject nucleotide sequence encoding the same amino acids sequence. Intolerant codon in SEQ ID NO: 15 are underlined.

The term "tolerant codon" as used herein means a codon present in a reference nucleotide sequence that is not an intolerant codon. A tolerant codon may be changed to a different codon encoding the same amino acid in a corresponding subject nucleotide sequence encoding the same amino acid sequence.

The term "optimized codon" means a codon set forth in Table 2 or Table 3. A codon in a subject nucleotide sequence is said to be "optimized" when the corresponding codon in a reference sequence is replaced with a different codon coding for the same amino acid and selected from a codon set forth in Table 1 or Table 2.

The term "codon optimization change" means the replacement of a tolerant codon in a reference sequence with a codon encoding the same amino acid selected from Table 2. For some amino acids, there exists more than one optimized codon (see Table 2). For the purpose of clarity, the term "codon optimization changes" includes replacing an optimized codon present in a reference sequence with a different optimized codon coding for the same amino acid set forth in Table 1.

The exons and introns of the PSEN1 gene can be identified with reference to GenBank reference sequence number NG_007386 as follows: Exon 1 consist of nucleotides 5037 to 5113; intron 1 consist of nucleotides 5,114 to 16,324; exon 2 consist of nucleotides 16,325 to 16,406; intron 2 consist of nucleotides 16,407 to 16,496; exon 3 consist of nucleotides 16,497 to 16,636; intron 3 consist of nucleotides 16,637 to 39,326; exon 4 consist of nucleotides 39,327 to 39,577; intron 4 consist of nucleotides 39,578 to 42,095; exon 5 consist of nucleotides 42,096 to 42,237; intron 5 consist of nucleotides 42,238 to 55,382; exon 6 consist of nucleotides 55,383 to 55,450; intron 6 consist of nucleotides 55,451 to 61,173; exon 7 consist of nucleotides 61,174 to 61,394; intron 7 consist of nucleotides 61,395 to 66,560; exon 8 consist of nucleotides 66,561 to 66,659; intron 8 consist of nucleotides 66,660 to 74,915; exon 9 consist of nucleotides 74,916 to 75,002; intron 9 consist of nucleotides 75,003 to 80,298; exon 10 consist of nucleotides 80,299 to 80,472; intron 10 consist of nucleotides 80,473 to 85,655; exon 11 consist of nucleotides 85,656 to 85,776; intron 11 consist of nucleotides 85,775 to 87,663; exon 12 consist of nucleotides 87,664 to 92,222.

The term "CpG dinucleotide" means any occurrence of the nucleotide sequence CG in a reference nucleotide sequence.

"Self-complementary AAV" refers to a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

As used herein, "operably linked," "operable linkage," "operatively linked," or grammatical equivalents thereof refer to juxtaposition of genetic elements, e.g., a polynucleotide encoding a protein or RNA, a promoter, an enhancer, a polyadenylation sequence, etc., wherein the elements are in a relationship permitting them to operate in the expected manner. For example, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

As used in this specification and the appended claims, the term "or" is generally employed in its sense including "and/or" unless the content clearly dictates otherwise.

"Percent (%) identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

As used herein, the term "polynucleotide or gene expression" refers to the process by which a nucleic acid sequence or a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "polynucleotide or gene product." If the polynucleotide is derived from genomic DNA, expression may include splicing of the mRNA in a eukaryotic cell. The terms "polynucleotide or gene expression" and "expression" can be used interchangeably, unless context clearly indicates otherwise.

As used herein, the term "presenilin-1" denotes a protein encoded by the PSEN1 gene. Presenilin 1 is one of the four core proteins in the presenilin complex, which mediate the regulated proteolytic events of several proteins in the cell, including gamma secretase. Gamma-secretase is considered to play a strong role in generation of beta amyloid, accumulation of which is related to the onset of Alzheimer's disease, from the beta-amyloid precursor protein. There are two forms of presenilin-1 encoded by the PSEN1 gene based on alternate splicing. The predominant form in humans is the 467 amino acid isoform X1. The alternate form is the 463 amino acid isoform X2. Presenilin-1, presenilin 2 (PSEN2), and amyloid precursor protein (APP) are mostly associated with autosomal dominant forms of early onset Alzheimer's disease.

The term "promoter" as used herein is defined as a DNA sequence recognized by the synthetic machinery of the cell, or introduced synthetic machinery, required to initiate the specific transcription of a polynucleotide sequence. A "constitutive" promoter is a nucleotide sequence which, when operably linked with a polynucleotide which encodes or specifies a gene product, causes the gene product to be produced in a cell under most or all physiological conditions of the cell. An "inducible" promoter is a nucleotide sequence which, when operably linked with a polynucleotide which encodes or specifies a gene product, causes the gene product to be produced in a cell substantially only when an inducer which corresponds to the promoter is present in the cell. A "tissue-specific" promoter is a nucleotide sequence which, when operably linked with a polynucleotide encodes or specified by a gene, causes the gene product to be produced in a cell substantially only if the cell is a cell of the tissue type corresponding to the promoter. Alternatively, heterologous control sequences can be employed. Useful heterologous control sequences generally include those derived from sequences encoding mammalian or viral genes. Examples include, but are not limited to, the phosphoglycerate kinase (PGK) promoter, CAG, neuronal promoters, promoter of Dopamine-1 receptor and Dopamine-2 receptor, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), Rous sarcoma virus (RSV) promoter, synthetic promoters, hybrid promoters, and the like. In addition, sequences derived from non-viral genes, such as the murine metallothionein gene, will also find use herein. Such promoter sequences are commercially available from, e.g., Stratagene (San Diego, Calif.). For purposes of the present invention, both heterologous promoters and other control elements, such as CNS-specific and inducible promoters, enhancers and the like, will be of particular use. Examples of heterologous promoters include the CMV promoter. Examples of CNS specific promoters include those isolated from the genes of myelin basic protein (MBP), glial fibrillary acid protein (GFAP), and neuron specific enolase (NSE).

As used herein, the term "regulatory element" refers to a genetic element or polynucleotide that either alone or together with one or more additional regulatory elements influences or modulates expression of a polynucleotide or gene. A regulatory element can facilitate polynucleotide or gene expression, increase polynucleotide or gene expression, decrease polynucleotide or gene expression and/or confer selective polynucleotide or gene expression in a particular cell type or tissue. A regulatory element can influence or modulate polynucleotide or gene expression temporally and/or spatially. As used herein, the term "regulate polynucleotide or gene expression," "influence polynucleotide or gene expression," or "modulate polynucleotide or gene expression" refers to increasing polynucleotide or gene expression, decreasing polynucleotide or gene expression, and/or conferring selective polynucleotide or gene expression. "Regulating polynucleotide or gene expression," "influencing polynucleotide or gene expression," or "modulating polynucleotide or gene expression" can refer to temporal and/or spatial regulation.

A "transgene" is used herein to conveniently refer to a polynucleotide or a nucleic acid that is intended or has been introduced into a cell or organism. Transgenes include any nucleic acid, such as a gene that encodes a polypeptide or protein.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.1, 2.2, 2.7, 3, 4, 5, 5.5, 5.75, 5.8, 5.85, 5.9, 5.95, 5.99, and 6. This applies regardless of the breadth of the range.

The present disclosure provides compositions and methods for treating subjects with Alzheimer's disease and other neurodegenerative diseases, disorders and conditions. In particular, aspect, the present disclosure contemplates gene therapy by providing a polynucleotide encoding a presenilin-1 (PSEN1) gene to a subject in need of treatment. Alzheimer's disease (AD) is the most common form of neurodegenerative disease of the brain. Pathological hallmarks of AD include intraneuronal accumulation of paired helical filaments composed of abnormal tau proteins and extracellular deposits of β-amyloid peptide (Aβ) in neuritic plaques. Clinically, AD can be categorized into two phenotypes based on the ages of onset: early-onset AD (EOAD; <65 years) and late-onset AD (LOAD; >65 years), of which LOAD is the more common form worldwide. The proportion of EOAD in all AD cases is between 5% and 10%. Presenilin 1 (PSEN1), presenilin 2 (PSEN2), and amyloid precursor protein (APP) are mostly associated with autosomal dominant forms of EOAD. Apart from genetic factors, mutations are environmentally related. Genetic-environmental interactions may be caused by variation in the age of onset, neuropathological patterns, and disease duration.

PSEN1 and PSEN2 encode transmembrane proteins PS1 and PS2, respectively, that constitute the catalytic core of γ-secretase, the founding member of an emerging class of unconventional, Intramembrane-Cleaving Proteases (I-CLiPs). Active γ-secretase is a multiprotein complex composed of PS1 or PS2 together with nicastrin (NCT), the anterior pharynx-defective protein 1 (APH1), and the presenilin enhancer 2 (PEN2). Experimental evidence such as the binding of transition-state analogue γ-secretase inhibitors to PS1, as well as the abolishment of γ-secretase activity when PS1 lacks the aspartate residues critical for proteolysis have confirmed that presenilins harbor the active site of the enzymatic complex.

PS1 and PS2 play fundamental roles in cell signaling as part of the γ-secretase complex. The latter cleaves numerous type-I membrane proteins in their transmembrane domain releasing their corresponding intracellular domains, which are capable of influencing gene expression. The amyloid precursor protein (APP) is processed by the successive actions of β-secretase (BACE1) and γ-secretase, generating amyloid-beta peptides (Aβ) of different lengths, ranging from 37 to 46 amino acids. Cleavage of the APP C-terminal fragments (APP-CTFs) by γ-secretase also releases the APP intracellular domain (AICD), which has been recently involved in the regulation of brain ApoE expression, a major genetic determinant of AD, and in cholesterol metabolism. In addition, PS1 has been shown to interact with a growing list of proteins that modulate γ-secretase activity.

Nucleic Acid Compositions

Accordingly, the present disclosure provides an isolated cDNA or a hybrid genomic/cDNA that encodes the naturally occurring human presenilin-1 and characterized by one or more of: codon optimization only at some or all tolerant codons, reduction of CpG dinucleotides, or the presence of donor/acceptor splice sites to enable expression of both PSEN-1 isoforms; nucleic acid expression cassettes comprising the foregoing and additional regulatory elements; vectors comprising such expression cassettes; compositions comprising those vectors; and methods for gene therapy of neurodegenerative disorders such as Alzheimer's disease that utilize any of the foregoing. Without being bound by theory, it is believed that the nucleic acid expression cassettes disclosed herein will result in increased and improved PSEN-1 expression as compared to native or mutated forms of PSEN-1 in patients in need thereof, e.g. Alzheimer's disease patients. Thus, PSEN-1 protein expression can be increased at a lower dose of the expression cassette or the vector comprising that expression cassette.

An embodiment provides nucleic acid expression cassettes comprising any of the cDNA or hybrid genomic/cDNA polynucleotides encoding presenilin 1 set forth above; and one or more regulatory elements operably linked to the polynucleotide encoding presenilin 1.

Any genetic element that modulates or influences polynucleotide or gene expression can be a regulatory element, including, for example, promoters, enhancers, chromatin insulators, translation initiation sequences such as strong and weak Kozak signal sequences and internal ribosomal entry sites, mRNA stability sequences, sequences that influence mRNA processing such as splicing and cleavage, sequences that influence mRNA export from the nucleus and/or mRNA retention, posttranslational response elements, non-coding sequences such as introns, poly A sequences, repressors, silencers, terminators, and others. Regulatory elements can function to modulate polynucleotide or gene expression at the transcriptional level, at the posttranscriptional level, at the translational level, or any combination thereof. Regulatory elements can increase the rate at which RNA transcripts are produced, increase the stability of RNA produced, increase the rate of protein synthesis from RNA transcripts, prevent RNA degradation and/or increase RNA stability to facilitate protein synthesis, for example.

An expression cassette as used herein may suitably comprise a promoter and poly A sequence. In certain preferred embodiments, an expression cassette may comprise a promoter, poly A sequence and mRNA stability element. A particularly preferred expression cassette may include a CAG promoter, Kozak, codon optimized PSEN1 (tolerant only), mRNA stability element and poly A. A specifically preferred expression cassette may include SEQ ID NO:23, SEQ ID NO:5, SEQ ID NO:6, SED ID NO:9, and SEQ ID NO:34. In certain embodiments, preferred vectors may comprise AAV surrounded by ITRs and packaged into an AAV9 or AAVrh10 capsid.

The nucleic acid expression cassettes described herein can comprise regulatory elements that regulate or modulate polynucleotide or gene expression at any step, including the transcriptional, posttranscriptional, and translational levels, for example. A regulatory element can regulate or modulate polynucleotide or gene expression at more than one level or function in more than one way to regulate or modulate polynucleotide or gene expression. Thus, a regulatory element can have any function, or any combination of the functions described above. For example, a regulatory element can function as an mRNA stabilizing element and modulate, i.e., increase or decrease, translation. As yet another example, a regulatory element can modulate transcription initiation and modulate mRNA stability. A regulatory element can also have a predominant function by which it modulates polynucleotide or gene expression and have one or more additional functions that increase or decrease polynucleotide or gene expression. A regulatory element can comprise a sequence that is located within or overlaps with other regulatory elements that have the same or different functions in modulating polynucleotide or gene expression or that modulate polynucleotide or gene expression at the same or different steps.

Regulatory elements can be derived from coding or non-coding DNA sequences. Regulatory elements derived from non-coding DNA can be associated with genes, e.g., may be found in a gene, such as upstream sequences, introns, 3' and 5' untranslated regions (UTRs), and/or downstream regions. As used herein, the term "upstream" when referring to nucleic acid means 5' relative to another sequence and the term "downstream" means 3' relative to another sequence. The term "upstream" can be used interchangeably with the term "5'" when referring to location of sequences relative to each other, unless context clearly indicates otherwise. The term "downstream" can be used interchangeably with the term "3'" when referring to location of sequences relative to each other, unless context clearly indicates otherwise.

In some embodiments, regulatory elements derived from non-coding DNA sequences are not associated with a gene, e.g., may not be found in a gene. The genomic region from which a regulatory element is derived can be distinct from the genomic region from which an operably linked polynucleotide is derived. In some embodiments, a regulatory element is derived from a distal genomic region or location with respect to the genomic region or location from which the operably linked polynucleotide (such as a cDNA derived from an endogenous gene or an endogenous version of a heterologous gene, for example) is derived. In some embodiments, a regulatory element comprises intron sequences. Intron sequences can include sequences derived from any gene. In some embodiments, the intron sequences are derived from the genomic region from which an operatively linked polynucleotide is derived. For example, the nucleic acid expression cassettes described herein can include introns from an endogenous gene that corresponds to a polynucleotide or that gave rise to a polynucleotide in the form of a cDNA. As another example, the nucleic acid expression cassettes described herein can include introns from an endogenous gene that does not correspond to or gave rise to a polynucleotide.

In some embodiments, the one or more regulatory elements comprise a Kozak translation initiation signal such as a polynucleotide set forth in SEQ ID NO:5. In some embodiments, the one or more regulatory elements comprise a chromatin insulator sequence, such as the polynucleotide set forth in SEQ ID NO:4.

Kozak Sequences: A 5' UTR generally includes sequences that are recognized by the ribosome that allow the ribosome to bind and initiate translation. Exemplary sequences for translation initiation include Kozak initiation signal sequences. As used herein, the terms "Kozak initiation signal sequence," "Kozak consensus sequence," and "Kozak sequence" can be used interchangeably, unless context clearly indicates otherwise. A person of skill in the art will appreciate that a Kozak initiation signal sequence can be located in part in the 5' UTR and include the AUG translation initiation codon itself and the nucleotide immediately following or downstream of the AUG start codon, as described below.

Translation initiation of an mRNA typically occurs at an ATG codon that is recognized by a ribosome. The ATG codon at which translation begins may not be the first ATG start codon present in an mRNA sequence. A motif called a Kozak sequence can direct translation initiation to an ATG codon. The Kozak consensus sequence is defined as 5'-(gcc) gccRcc<u>AUG</u>G-3, where the underlined AUG indicates the translation start codon; uppercase letters indicate conserved bases; "R" indicates the presence of a purine, with adenine more frequent; lowercase letters indicate the most common base at a position that can vary; and the sequence (gcc) is of uncertain significance. In addition to these features, other positions and features can contribute to translation initiation. Strong and weak Kozak consensus sequences have been described, with a strong Kozak consensus sequence including the features above that are considered optimal for translation initiation and a weak Kozak consensus sequence including features that deviate or differ from a strong Kozak consensus sequence. The amount of protein synthesized from an mRNA can depend on the strength of the Kozak sequence. For example, a CCACC (SEQ ID NO: 5) sequence immediately upstream of an AUG translation initiation codon can increase the rate of translation initiation compared to a sequence that differs from CCACC.

In some embodiments, the nucleic acid expression cassettes provided herein comprise a Kozak translation initiation signal. The Kozak translation initiation signal can be located immediately upstream or 5' of a translation initiation AUG codon. Any Kozak consensus sequence that is a strong Kozak sequence can be used. In some embodiments, the Kozak translation initiation signal comprises a sequence set forth in SEQ ID NO:5.

Promoters: Promoters are a major cis-acting element within the vector genome design that can dictate the overall strength of expression as well as cell-specificity. Accordingly, in certain embodiments, the promoter is a neuron-specific promoter. A neuron-specific promoter can provide selective expression of a polynucleotide or therapeutic gene in neuronal cells. Selective expression that is restricted or limited to a particular cell type can prevent or reduce off-target effects that are often undesirable and can result in side effects, for example. As used herein, "selective expression" refers to expression that is at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, and any number or range in between, higher in neurons as compared to non-neuronal cells. In some embodiments, there is no expression in non-neuronal cells.

In some embodiments, a neuron-specific promoter of the nucleic acid expression cassettes described herein provides for expression that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, and any number or range in between, higher as compared to expression provided by a promoter that can drive expression in any cell type. In some embodiments, a neuron-specific promoter of the nucleic acid expression cassettes described herein provides for expression that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, and any number or range in between, higher as compared to expression provided by a promoter that can drive expression in one or more non-neuronal cell types.

Any neuron-specific promoter can be used in the nucleic acid expression cassettes provided herein. Exemplary promoters include a somatostatin (SST; SEQ ID NO: 2) gene promoter, a neuropeptide Y (NPY; SEQ ID NO: 3) promoter, an alpha-calcium/calmodulin kinase 2A promoter, a synapsin I promoter (e.g., nucleotides 273-684 of SEQ ID NO:46), a neuron-specific enolase (NSE) (e.g., SEQ ID NO:29), a dopaminergic receptor 1 (Drd1a) promoter, a tubulin alpha I promoter, a GFAP promoter (e.g., SEQ ID NO:31) and known variations thereof (e.g., gfaABC(1)D) and others. Hybrid promoters can also be used. A hybrid promoter is a promoter that includes promoter sequences derived from more than one gene. Promoters can be from any species, including human, rhesus macaque, mouse, rat, and chicken, for example. A neuron-specific promoter can comprise (i) a polynucleotide set forth in SEQ ID NO:2; (ii) a polynucleotide set forth in SEQ ID NO:3; (iii) a functional fragment of SEQ ID NO:2 or SEQ ID NO:3; or (iv) polynucleotide with at least 95% identity to (i), (ii), or (iii). In alternate aspects of these embodiments, the promoter comprises CAG, CBA, UBC, PKC, EF1a, GUSB, CMV, NSE, PDGF, desmin, MCK, MeCP2, GFAP, CaMKII or MBP.

Constitutive promoters such as the human elongation factor 1α-subunit (EF1α) (e.g., SEQ ID NO:27 or nucleotides 237-1415 of SEQ ID NO:44), immediate-early cytomegalovirus (CMV) (e.g., SEQ ID NO:28), chicken β-actin (CBA) (e.g., SEQ ID NO:24 or nucleotides 237-890 of SEQ ID NO:43) and its derivative CAG (SEQ ID NO:23 or SEQ ID NO:40), the β glucuronidase (GUSB), ubiquitin C (UBC) (e.g., SEQ ID NO:25 or nucleotides 237-1323 of SEQ ID NO:42 or), phosphoglycerate kinase 1 (PGK) (e.g., SEQ ID NO:26), or even the native PSEN-1 promoter (e.g., nucleotides 237-1200 of SEQ ID NO:41) can be used to promote expression in most tissues. Generally, CBA and CAG promote the larger expression among the constitutive promoters; however, their size of ~1.7 kbs in comparison to CMV (~0.8 kbs) or EF1α (~1.2 kbs) limits its use in vectors with packaging constraints such as AAV. The GUSB or UBC promoters can provide ubiquitous gene expression with a smaller size of 378 bps and 403 bps, respectively, but they are considerably weaker than the CMV or CBA promoter. Thus, modifications to constitutive promoters in order to reduce the size without affecting its expression have been pursued and examples such as the CBh (~800 bps) and the miniCBA (~800 bps) can promote expression comparable and even higher in selected tissues.

When expression is restricted to certain cell types within an organ, e.g. brain, central nervous system etc., promoters can be used to mediate this specificity. For example, within the nervous system promoters have been used to restrict expression to neurons, astrocytes, or oligodendrocytes. In neurons, the neuron-specific enolase (NSE) promoter drives stronger expression than ubiquitous promoters; however, its size of 2.2 kbs limits its use in smaller vectors. Additionally, the platelet-derived growth factor B-chain (PDGF-β), the synapsin (Syn), and the methyl-CpG binding protein 2 (MeCP2) (e.g., SEQ ID NO:30) promoters can drive neuron-specific expression at lower levels than NSE, but their sizes of 1.4 kbs, 470 bps and 229 bps, respectively, make them more suitable for vectors with limitations in size. In astrocytes, the 680 bps-long shortened version [gfaABC(1)D] of the glial fibrillary acidic protein (GFAP, 2.2 kbs) promoter can confer higher levels of expression with the same astrocyte-specificity as the GFAP promoter. Targeting oligodendrocytes can also be accomplished by the selection of the myelin basic protein (MBP) promoter, whose expression is restricted to this glial cell (Gray S J, et al., Optimizing promoters for recombinant adeno-associated virus-mediated gene expression in the peripheral and central nervous system using self-complementary vectors. *Hum Gene Ther.* 2011; 22:1143-1153).

Tissue specific promoters provide the advantage of limiting the expression to the desired cell or tissue. However, low levels of expression and/or large size may limit their use. To compensate for weak strength, the level of expression can be increased by adding enhancer elements such as from CMV.

MicroRNA binding sites: In some embodiments, the one or more regulatory elements comprise one, two or three micro RNA ("miRNA" or "miR") binding sites to suppress expression of the encoded PSEN-1 in dorsal root ganglia. MicroRNAs are 19-25 nucleotide noncoding RNAs that bind to miRNA binding sites and down-regulate gene expression either by reducing nucleic acid molecule stability or by inhibiting translation. In some aspects of these embodiments, each miRNA binding site is independently selected from a binding site for any of the following miRNAs: miRNA-1914, miR1181, miR3918, miR939, miR324, miR650, MiR29C, or miR2277. In some aspects of these embodiments, the miRNA binding site(s) are located 3' to the mRNA stability element.

Endogenous miRNAs can 'de-target' or inhibit transgene expression when their exact complementary target sequences are engineered into an expression cassette. The level of repression, in vitro, correlates with the number of target sequences within the expression cassette In an in vivo study, when an engineered lentiviral vector containing 4 copies of the neuronal-specific miR-124 target sequence was injected into mouse brain, PGK-driven transgene expression was de-targeted from neurons to only astrocytes (Colin A. et al., Engineered lentiviral vector targeting astrocytes in vivo. *Glia.* 2009 Apr. 15; 57(6):667-79). Endogenous miRNAs are a useful tool in obtaining transgene cell specificity because their respective binding sites are small, can be combined, and are robust in their ability to restrict expression.

mRNA Stability Element: Exemplary mRNA stability elements include a MALAT1 mRNA stability element, C-rich stability elements of HBA1, HBA2, lipoxygenase, alpha(I)-collagen, and tyrosine hydroxylase 3' UTRs, for example, AU-rich elements (AREs) of 3' UTRs, and others.

An mRNA stability element can be, for example, an expression and nuclear retention element. An mRNA stability element can prevent or decrease degradation of mRNA. For example, degradation of mRNA can be decreased by about 5%, about 10%, about 20%, about 30%, about 40%, about 50%, about 60%, about 70%, about 80%, about 90%, about 95%, about 99%, and any number or range in between, when an mRNA stability element is included as compared to a nucleic acid expression cassette that does not include an mRNA stability element. In an embodiment, there is no degradation of mRNA. Any sequence that prevents or decreases degradation of the mRNA can be an mRNA stability element. An mRNA stability element can be placed into any location in a nucleic acid expression cassette. For example, an mRNA stability element can be placed 3' to the open reading frame of a polynucleotide and before or 5' of a polyadenylation site. As another example, an mRNA stability element can be placed 3' to the open reading frame of a polynucleotide and 3' to a polyadenylation site. As yet another example, an mRNA stability element can be placed 5' to an open reading frame of a polynucleotide.

In some embodiments, an mRNA stability element comprises (i) a polynucleotide set forth in SEQ ID NO:9; (ii) a functional variant thereof; or (iii) a polynucleotide with at least 95% sequence identity to (i) or (ii). In some embodiments, an mRNA stability element comprises a polynucleotide with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO:9.

Accordingly, in certain embodiments, the at least one mRNA stability element comprises (i) a polynucleotide set forth in SEQ ID NO:9, SEQ ID NO:10, SEQ ID NO:11; (ii) a functional variant of SEQ ID NO:9, SEQ ID NO:10, SEQ ID NO:11; or (iii) a polynucleotide with at least 95% sequence identity to (i) or (ii).

In some embodiments, the nucleic acid expression cassettes embodied herein include an mRNA stability element comprising (i) a polynucleotide set forth in SEQ ID NO:10; (ii) a functional variant thereof; or (iii) a polynucleotide with at least 95% sequence identity to (i) or (ii). In some embodiments, the mRNA stability element comprises a polynucleotide with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO:10. In some embodiments, the mRNA stability element comprises (i) a polynucleotide set forth in SEQ ID NO:10; (ii) a functional variant thereof; or (iii) a polynucleotide with at least 95% sequence identity to (i) or (ii) is located 5' of an open reading frame of a polynucleotide encoding PSEN1 or other therapeutic gene.

In some embodiments, the nucleic acid expression cassettes described herein include an mRNA stability element comprising (i) a polynucleotide set forth in SEQ ID NO:11; (ii) a functional variant thereof; or (iii) a polynucleotide with at least 95% sequence identity to (i) or (ii). In some embodiments, the mRNA stability element comprises a polynucleotide with at least 80%, with at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO:11.

In some embodiments, the mRNA stability element comprises a polynucleotide with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO:10. In some embodiments, the mRNA stability element comprising (i) a polynucleotide set forth in SEQ ID NO:10; (ii) a functional variant thereof; or (iii) a polynucleotide with at least 95% sequence identity to (i) or (ii) is located 5' of an open reading frame of a polynucleotide encoding PSEN1 or other therapeutic gene.

In some embodiments, the nucleic acid expression cassettes described herein include an mRNA stability element comprising (i) a polynucleotide set forth in SEQ ID NO:11; (ii) a functional variant thereof; or (iii) a polynucleotide with at least 95% sequence identity to (i) or (ii). In some embodiments, the mRNA stability element comprises a polynucleotide with at least 80%, with at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO:11. In some embodiments, the mRNA stability element comprising (i) a polynucleotide set forth in SEQ ID NO:11; (ii) a functional variant thereof; or (iii) a polynucleotide with at least 95% sequence identity to (i) or (ii) is located 5' of an open reading frame of a PSEN1 nucleotide sequence.

In some aspects of these embodiments, the nucleic acid expression cassette comprises a mRNA stability element located 5' of the open reading frame of the polynucleotide encoding PSEN1; and a mRNA stability element located 3' of the polyadenylation signal.

Polyadenylation Signal: In certain embodiments, the nucleic acid expression cassette also comprises one or more polyadenylation enhancer elements, such as, for example, human growth hormone (hGH; SEQ ID NO: 33; nucleotides 3330-3806 of SEQ ID NO:41) polyadenylation signal sequences, rabbit beta-globin (rBG; SEQ ID NO: 34 or 35; nucleotides 2139-2367 of SEQ ID NO:47) polyadenylation signal sequences, SV40 polyadenylation signal sequences or bovine growth hormone (BGH) polyadenylation signal sequences. The polyadenylation of a transcript is critical for nuclear export, translation, and mRNA stability. Therefore, the efficiency of transcript polyadenylation is important for transgene expression. The poly(A) tail contains binding sites for poly(A) binding proteins (PABPs). These proteins cooperate with other factors to affect the export, stability, decay, and translation of an mRNA. PABPs bound to the poly(A) tail may also interact with proteins, such as translation initiation factors, that are bound to the 5' cap of the mRNA. This interaction causes circularization of the transcript, which subsequently promotes translation initiation. Furthermore, it allows for efficient translation by causing recycling of ribosomes. While the presence of a poly(A) tail usually aids in triggering translation, the absence or removal of one often leads to exonuclease-mediated degradation of the mRNA. Polyadenylation itself is regulated by sequences within the 3'-UTR of the transcript. These sequences include cytoplasmic polyadenylation elements (CPEs), which are uridine-rich sequences that contribute to both polyadenylation activation and repression. CPE-binding protein (CPEB) binds to CPEs in conjunction with a variety of other proteins in order to elicit different responses.

Chromatin Insulator Sequence: In certain embodiments, a nucleic acid expression cassette can further comprise a chromatin insulator sequence. Packaging of genes into chromatin can render genes inaccessible to the transcription machinery of the cell, resulting in little or no gene expression. Chromatin insulators can protect a sequence from being packed into transcriptionally inactive chromatin. Including a chromatin insulator sequence in a nucleic acid expression cassette can keep a polynucleotide in an accessible state and allow transcription to occur. Any chromatin insulator can be used in the nucleic acid expression cassettes provided herein. Exemplary chromatin insulator sequences include a CTCF insulator, a gypsy insulator, and a β-globin locus. Chromatin insulator sequences from any species can be used, including mammals and non-mammals and vertebrates and non-vertebrates. As an example, a chromatin insulator sequence from human beta globin locus HS4 can be used. Other examples of chromatin insulator sequences include sequences form chicken and Drosophila. A chromatin insulator sequence can comprise a polynucleotide set forth in SEQ ID NO:4, a functional variant of SEQ ID NO:4, or a polynucleotide with at least 95% identity to SEQ ID NO:4. A chromatin insulator sequence can comprise at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO:4 as long as the function of the reference sequence and the ability to protect a sequence with which it is associated from being packed into transcriptionally inactive chromatin is maintained.

Transcription Termination Region: A transcription termination region of a recombinant construct or expression cassette is a downstream regulatory region including a stop codon and a transcription terminator sequence. Transcription termination regions that can be used can be homologous to the transcriptional initiation region, can be homologous to the polynucleotide encoding a polypeptide of interest, or can be heterologous (i.e., derived from another source). A transcription termination region or can be naturally occurring, or wholly or partially synthetic. 3' non-coding sequences encoding transcription termination regions may be provided in a recombinant construct or expression construct and may be from the 3' region of the gene from which the initiation region was obtained or from a different gene. A large number of termination regions are known and function satisfactorily in a variety of hosts when utilized in both the same and different genera and species from which they were derived. Termination regions may also be derived from various genes native to the preferred hosts. The termination region is usually selected more for convenience rather than for any particular property.

Regulatory elements and polynucleotides of the nucleic acid expression cassettes provided herein can be combined in any fashion. In some embodiments, a nucleic acid expression cassette comprises a polynucleotide encoding presenilin 1, wherein the polynucleotide comprises any one of (I) a polynucleotide set forth in SEQ ID NO:6, SEQ ID NO:7, SEQ ID NO:8, SEQ ID NO:36, SEQ ID NO:37, SEQ ID NO:38, or SEQ ID NO:39; or (III) a polynucleotide having at least 95% identity to (I) or (II). In some embodiments, the polynucleotide comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO:6, SEQ ID NO:7, SEQ ID NO:8, SEQ ID NO:36, SEQ ID NO:37, SEQ ID NO:38, or SEQ ID NO:39. In some embodiments, the nucleic acid expression cassette further comprises one or more regulatory elements operably linked to the polynucleotide encoding presenilin 1. In some embodiments, the one or more regulatory elements comprise a neuron-specific promoter.

In some embodiments, the nucleic acid expression cassette further comprises (i) a Kozak translation initiation signal; (ii) a chromatin insulator sequence; (iii) at least one mRNA stability element; or (iv) any combination thereof, wherein the one or more regulatory elements comprise a neuron-specific promoter. In some embodiments, the Kozak translation initiation signal comprises a polynucleotide set forth in SEQ ID NO:5; the chromatin insulator sequence comprises a polynucleotide set forth in SEQ ID NO:4; the at least one mRNA stability element comprises a polynucleotide set forth in SEQ ID NO:9, SEQ ID NO:10, SEQ ID NO:11, or any combination thereof; the neuron-specific promoter comprises a polynucleotide set forth in SEQ ID NO:2 or SEQ ID NO:3.

In some embodiments, the mRNA stability element comprising SEQ ID NO:9 is located 3' of an open reading frame of the polynucleotide encoding PSEN1 and 5' of a polyadenylation signal, the mRNA stability element comprising SEQ ID NO:10 is located 5' of an open reading frame of the polynucleotide encoding PSEN1, and the mRNA stability element comprising SEQ ID NO:11 is located 3' of an open reading frame of the polynucleotide encoding PSEN1.

In some embodiments, the nucleic acid expression cassettes provided herein comprise: (a) one or more regulatory elements operably linked to a polynucleotide encoding presenilin 1, wherein the polynucleotide comprises any one of (I) a polynucleotide set forth in SEQ ID NO:6, SEQ ID NO:7, SEQ ID NO:8, SEQ ID NO:36, SEQ ID NO:37, SEQ ID NO:38, or SEQ ID NO:39; (II) a polynucleotide having at least 95% identity to (I); and wherein the one or more regulatory elements comprise a neuron-specific promoter comprising a polynucleotide set forth in SEQ ID NO:2 or SEQ ID NO:3; (b) a Kozak translation initiation signal comprising a polynucleotide set forth in SEQ ID NO:5; (c) a chromatin insulator sequence comprising a polynucleotide set forth in SEQ ID NO:4; and (d) at least one mRNA stability element comprising a polynucleotide set forth in SEQ ID NO:9, SEQ ID NO:10, SEQ ID NO:11, or any combination thereof.

Other embodiments provide nucleic acid expression cassettes comprising: (i) any of the cDNA or hybrid genomic/cDNA polynucleotides encoding presenilin 1 set forth above; (ii) a Kozak translation initiation signal; (iii) a neuron-specific promoter; (iv) a chromatin insulator sequence; (v) at least one mRNA stability element; or (v) any combination thereof. The Kozak translation initiation signal can comprise a polynucleotide set forth in SEQ ID NO:5; the chromatin insulator sequence can comprise a polynucleotide set forth in SEQ ID NO:4; the at least one mRNA stability element can comprise a polynucleotide set forth in SEQ ID NO:9, SEQ ID NO:10, SEQ ID NO:11, or any combination thereof; and the neuron-specific promoter can comprise a polynucleotide set forth in SEQ ID NO:2 or SEQ ID NO:3.

Codon-Optimization

Codon optimization can be utilized to enhance protein expression for heterologous gene expression. Codon optimization is a method of gene optimization, where in the synthetic gene sequence is modified to match the "codon usage pattern" for a particular organism. For example, in order to optimize expression of a particular amino acid sequence in a specific organism, one would select the "most frequently used codons" (from a list of degenerate codons for an amino acid), by that organism. See, Table 2 for a list of preferred codons used. Upon codon optimization, the encoded amino acid sequence remains the same but with the DNA sequence encoding the amino acid sequence is different, optimized for that organism. Accordingly, the disclosure provides a codon-optimized presenilin-1 (PSEN1)-encoding polynucleotide suitable for use in the compositions and methods described herein. The codon-optimized PSEN1 can include a full length hybrid genomic/cDNA (e.g. SEQ ID NO: 8), comprising one or more optimized codons set forth in Table 2. In certain embodiments, the PSEN-1 polynucleotide comprising SEQ ID NO: 1, comprises one or more optimized codons set forth in Table 2. In certain embodiments, a codon-optimized presenilin-1 (PSEN1)-encoding polynucleotide is set forth as SEQ ID NO: 6. In certain embodiments, a codon-optimized presenilin-1 (PSEN1)-encoding polynucleotide is set forth as SEQ ID NO: 36. In certain embodiments, a codon-optimized presenilin-1 (PSEN1)-encoding polynucleotide is set forth as SEQ ID NO: 37. In certain embodiments, a codon-optimized presenilin-1 (PSEN1)-encoding polynucleotide is set forth as SEQ ID NO: 38. In certain embodiments, a codon-optimized presenilin-1 (PSEN1)-encoding polynucleotide is set forth as SEQ ID NO: 39.

Vectors

A "vector" is a macromolecule or association of macromolecules that comprises or associates with a polynucleotide and which can be used to mediate delivery of the polynucleotide to a cell. Examples of vectors include plasmids, viral vectors, liposomes, and other gene delivery vehicles. A vector can comprise one or more elements for vector replication. A vector can be engineered to lack one or more elements for vector replication.

A vector can be an integrating or non-integrating vector, referring to the ability of the vector to integrate the nucleic acid expression cassette and/or polynucleotide into a genome of a cell. Either an integrating vector or a non-integrating vector can be used to deliver a nucleic acid expression cassette containing a polynucleotide. Examples of vectors include, but are not limited to, (a) non-viral vectors such as nucleic acid vectors including linear oligonucleotides and circular plasmids; artificial chromosomes such as human artificial chromosomes (HACs), yeast artificial chromosomes (YACs), and bacterial artificial chromosomes (BACs or PACs); episomal vectors; transposons (e.g., PiggyBac); and (b) viral vectors such as retroviral vectors, lentiviral vectors, adenoviral vectors, and AAV vectors. Viruses have several advantages for delivery of nucleic acids, including high infectivity and/or tropism for certain target cells or tissues. In some embodiments, a virus is used to deliver a nucleic acid molecule or nucleic acid expression cassette comprising one or more polynucleotide.

In some embodiments, the vector is a viral vector. In some embodiments, the viral vector is an adeno-associated virus (AAV) vector, a retroviral vector, a lentiviral vector, or an adenoviral vector. The vectors comprising the nucleic acid expression cassettes provided herein can be a viral vector, such as an adeno-associated virus (AAV) vector, a retroviral vector, a lentiviral vector, or an adenoviral vector.

In some embodiments, the AAV vector is AAV1, AAV2, AAV3, AAV4, AAV5, AAV6, AAV7, AAV8, AAV9, AAVDJ, AAVrh10, AAV11, AAV12, AAV13, AAV14, AAV15, AAV16, AAV2/1, AAV2/5, AAV2/6, AAV2/7, AAV2/8, AAV2/9, AAV2/rh10, AAV2/11, or AAV2/12, single-stranded AAV (ssAAV) vector or self-complementary AAV (scAAV) vector. In some embodiments, the AAV vector is a hybrid or chimeric AAV serotype.

In some embodiments, the AAV vector comprises: a) promoter selected from a CAG promoter, a presenilin-1 promoter, a ubiquitin C promoter, a CBA promoter, a synapsin-1 promoter, a PGK promoter, and an EF1α promoter, operatively linked to b) a presenilin-1 coding sequence selected from SEQ ID NO:6, SEQ ID NO:7, SEQ ID NO:8, SEQ ID NO:36, SEQ ID NO:37, SEQ ID NO:38, or SEQ ID NO:39, or a polynucleotide having at least 95% identity to any of the foregoing PSEN-1 coding sequences and encoding a wild-type PSEN-1 amino acids sequence; and c) a polyadenylation sequence selected from a human growth hormone polyadenylation sequence and a rabbit β-globin polyadenylation sequence. In some aspects of these embodiments, the AAV vector additionally comprises, in between the promoter and the PSEN-1 coding sequence, an intron selected from a human beta globin intron (either wild-type or synthetic) or a minute virus of mice intron.

In some embodiments, the AAV vector comprises:

a. nucleotides 1-141 of SEQ ID NO:41 thereto, nucleotides 237-1200 of SEQ ID NO:41 thereto, nucleotides 1221-1786 of SEQ ID NO:41 thereto, nucleotides 1899-3299 of SEQ ID NO:41 thereto, nucleotides 3330-3806 of SEQ ID NO:41 thereto and nucleotides 4553-4693 of SEQ ID NO:41 thereto;

b. Nucleotides 1-141 of SEQ ID NO:42 thereto, nucleotides 237-1323 of SEQ ID NO:42 thereto, nucleotides 1344-1909 of SEQ ID NO:42 thereto, nucleotides 1983-3416 of SEQ ID NO:42 thereto, nucleotides 3447-3923 of SEQ ID NO:42 thereto, and nucleotides 4554-4694 of SEQ ID NO:42 or a sequence having at least 95% identity thereto;

c. Nucleotides 1-141 of SEQ ID NO:43 thereto, nucleotides 237-890 of SEQ ID NO:43 thereto, nucleotides 911-1476 of SEQ ID NO:43 thereto, nucleotides 1550-2983 of SEQ ID NO:43 thereto, nucleotides 3014-3490 of SEQ ID NO:43 thereto, and nucleotides 4553-4694 thereto of SEQ ID NO:43;

d. Nucleotides 1-141 thereto, nucleotides 237-1415 thereto, nucleotides 1436-2001 thereto, nucleotides 2075-3508 or a sequence having at least 95% identity thereto, nucleotides 3539-4015 or a sequence having at least 95% identity thereto, and nucleotides 4500-4640 thereto of SEQ ID NO:44 thereto;

e. Nucleotides 1-141 of SEQ ID NO:45 thereto, nucleotides 237-664 of SEQ ID NO:45 thereto, nucleotides 684-1249 of SEQ ID NO:45 thereto, nucleotides 1323-2756 of SEQ ID NO:45 thereto, 2787-3263 of SEQ ID NO:45 thereto, and nucleotides 4533-4673 of SEQ ID NO:45 thereto;

f. Nucleotides 1-141 of SEQ ID NO:46 thereto, nucleotides 237-684 of SEQ ID NO:46 thereto, nucleotides 705-1270 of SEQ ID NO:46 thereto, nucleotides 1344-2777 of SEQ ID NO:46 thereto, nucleotides 2808-3284 of SEQ ID NO:46 thereto, and nucleotides 4554-4695 of SEQ ID NO:46 or a sequence having at least 95% identity thereto; or g. Nucleotides 1-105 of SEQ ID NO:47 thereto, nucleotides 113-766 of SEQ ID NO:47 thereto, nucleotides 776-867 of SEQ ID NO:47 thereto, nucleotides 881-2311 of SEQ ID NO:47 thereto, nucleotides 2319-2367 of SEQ ID NO:47 thereto, and nucleotides 2386-2526 of SEQ ID NO:47 or a sequence having at least 95% identity thereto.

In some embodiments, the AAV vector comprises: a) nucleotides 1-141, 237-1200, 1221-1786, 1899-3299, 3330-3806 and 4553-4693 of SEQ ID NO:41; b) nucleotides 1-141, 237-1323, 1344-1909, 1983-3416, 3447-3923, and 4554-4694 of SEQ ID NO:42; c) nucleotides 1-141, 237-890, 911-1476, 1550-2983, 3014-3490, and 4553-4694 of SEQ ID NO:43; d) nucleotides 1-141, 237-1415, 1436-2001, 2075-3508, 3539-4015, and 4500-4640 of SEQ ID NO:44; e) nucleotides 1-141, 237-664, 684-1249, 1323-2756, 2787-3263, and 4533-4673 of SEQ ID NO:45; e) nucleotides 1-141, 237-684, 705-1270, 1344-2777, 2808-3284, and 4554-4695 of SEQ ID NO:46; or f) nucleotides 1-105, 113-766, 776-867, 881-2311, 2319-2367, and 2386-2526 of SEQ ID NO:47.

In some embodiments, the AAV vector comprises a nucleotide sequence of any one of SEQ ID NOs:41-47, or a nucleotide sequence having 95% identity to any one of SEQ ID NOs:41-47.

It will be understood by one of skill in the art that in the above embodiments of AAV vectors wherein a sequence has less than 100% identity to a specified range of nucleotides, such sequence should provide a similar functionality (e.g., be a functional ITR pair; be a functional promoter that can drive expression of the PSEN-1 coding sequence; be a functional intron; encode the same amino acid sequence as wild-type PSEN-1; or be a functional polyadenylation sequence).

Techniques contemplated herein for gene therapy of somatic cells include delivery via a viral vector (e.g., retroviral, adenoviral, AAV, helper-dependent adenoviral systems, hybrid adenoviral systems, herpes simplex, pox virus, lentivirus, and Epstein-Barr virus), and non-viral systems, such as physical systems (naked DNA, DNA bombardment, electroporation, hydrodynamic, ultrasound, and magnetofection), and chemical systems (cationic lipids, different cationic polymers, and lipid polymers).

Viral gene therapy vectors or gene delivery vectors can have the ability to be reproducibly and/or stably propagated and purified to high titers; to mediate targeted delivery (e.g., to deliver the polynucleotide specifically to a tissue or organ of interest without widespread vector dissemination elsewhere or off-target delivery); and to mediate gene delivery and/or polynucleotide expression without inducing harmful side effects or off-target effects.

The term “AAV” is an abbreviation for adeno-associated virus, and may be used to refer to the virus itself or a derivative thereof. The term covers all serotypes, subtypes, and both naturally occurring and recombinant forms, except where required otherwise. The abbreviation “rAAV” refers to recombinant adeno-associated virus, also referred to as a recombinant AAV vector (or “rAAV vector”). The term “AAV” includes AAV1, AAV2, AAV3, AAV4, AAV5, AAV6, AAV7, AAV8, AAV9, AAV10, AAV11, AAV 12, rh10, and hybrids thereof, avian AAV, bovine AAV, canine AAV, equine AAV, primate AAV, non-primate AAV, and ovine AAV. The genomic sequences of various serotypes of AAV, as well as the sequences of the native terminal repeats (TRs), Rep proteins, and capsid subunits are known in the art. Such sequences may be found in the literature or in public databases such as GenBank. An “rAAV vector” as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). The term “rAAV vector” encompasses both rAAV vector particles and rAAV vector plasmids. An rAAV vector may either be single-stranded (ssAAV) or self-complementary (scAAV). An “AAV virus” or “AAV viral particle” or “rAAV vector particle” refers to a viral particle composed of at least one AAV capsid protein and an encapsidated polynucleotide rAAV vector. If the particle comprises a heterologous polynucleotide (i.e., a polynucleotide other than a wild-type AAV genome such as a polynucleotide or a nucleic acid expression cassette to be delivered to a mammalian cell), it is typically referred to as an “rAAV vector particle” or simply an “rAAV vector.” Thus, production of rAAV particle necessarily includes production of an rAAV vector, as such a vector is contained within an rAAV particle.

The cloning capacity of vectors or viral expression vectors can be a particular challenge for expression of large polynucleotides. For example, AAV vectors typically have a packaging capacity of ~4.8 kb, lentiviruses typically have a capacity of ~8 kb, adenoviruses typically have a capacity of ~7.5 kb, and alphaviruses typically have a capacity of −7.5 kb. Some viruses can have larger packaging capacities, for example herpesvirus can have a capacity of >30 kb and vaccinia a capacity of ~25 kb. Advantages of using AAV for gene therapy include low pathogenicity, very low frequency of integration into the host genome, and the ability to infect dividing and non-dividing cells.

Several serotypes of AAV, non-pathogenic parvovirus, have been engineered for the purposes of gene delivery, some of which are known to have tropism for certain tissues or cell types. Viruses used for various gene-therapy applications can be engineered to be replication-deficient or to have low toxicity and low pathogenicity in a subject or a host. Such virus-based vectors can be obtained by deleting all, or some, of the coding regions from the viral genome, and leaving intact those sequences (e.g., inverted terminal repeat sequences) that are necessary for functions such as packaging the vector genome into the virus capsid or the integration of vector nucleic acid (e.g., DNA) into the host chromatin. A nucleic acid expression cassette comprising a polynucleotide, for example, can be cloned into a viral backbone such as a modified or engineered viral backbone lacking viral genes, and used in conjunction with additional vectors (e.g., packaging vectors), which can, for example, when co-transfected, produce recombinant viral vector particles.

In some cases, an AAV vector or an AAV viral particle, or virion, used to deliver a nucleic acid expression cassette into a cell, cell type, or tissue, in vivo or in vitro, is replication-deficient. In some cases, an AAV virus is engineered or genetically modified so that it can replicate and generate virions only in the presence of helper factors.

In some embodiments, a nucleic acid expression cassette is designed for delivery by an AAV or a recombinant AAV (rAAV). In some embodiments, a nucleic acid expression cassette is delivered using a lentivirus or a lentiviral vector. In some embodiments, larger polynucleotide, i.e., genes that exceed the cloning capacity of AAV, are preferably delivered using a lentivirus or a lentiviral vector.

The nucleic acid expression cassette can be designed for delivery by an optimized therapeutic retroviral vector, e.g., a lentiviral vector. The retroviral vector can be a lentiviral vector comprising a left (5') LTR; sequences which aid packaging and/or nuclear import of the virus, at least one regulatory element, optionally a lentiviral Rev response element (RRE); optionally a promoter or active portion thereof; a polynucleotide operably linked to one or more regulatory elements; optionally an insulator; and a right (3') retroviral LTR. A lentiviral vector can also include a post-transcriptional regulatory element, such as the Woodchuck Hepatitis Virus Posttranscriptional Regulatory Element (WPRE). A lentiviral vector can be a self-inactivating (SIN) lentviral vector. Any suitable packaging system can be used with a lentiviral vector, including second, third, and fourth generation packaging systems, for example. A lentiviral vector can be pseudotyped. Any envelope glycoprotein can be used for pseudotyping, including, for example, a glycoprotein from vesicular stomatitis virus (VSV), rabies virus, Lyssavirus, Mokola virus, lymphocytic choriomeningitis virus (LCMV), Lassa fever virus (LFV), retroviruses, Moloney murine leukemia virus (MuLV), filoviruses, paramyxoviruses, measles virus, Nipah virus, orthomyxoviruses, and others. A lentiviral vector can be pseudotyped to alter tropism. Any cell type can be targeted by pseudotyping, including neuronal cells, for example.

Methods of Treatment

Methods of treating a neurodegenerative disease, disorder, or condition comprising administering to a subject in need thereof a nucleic acid expression cassette described herein. Any neurodegenerative disease, disorder, or condition can be treated with the nucleic acid expression cassettes provided herein. In some embodiments, the neurodegenerative disease, disorder, or condition is Alzheimer's disease, familial Alzheimer's disease, sporadic Alzheimer's disease, late-onset Alzheimer's disease, frontotemporal dementia, frontotemporal lobar degeneration, Pick's disease, Lewy body dementia, memory loss, cognitive impairment, or mild cognitive impairment. Other exemplary neurodegenerative diseases, disorders, or conditions include tauopathy, primary age-related tauopathy (PART), chronic traumatic encephalopathy (CTE), progressive supranuclear palsy (PSP), corticobasal degeneration (CBD), frontotemporal dementia and parkinsonism linked to chromosome 17 (FTDP-17), amyotrophic lateral sclerosis-parkinsonism-dementia (ALS-PDC, Lytico-bodig disease), ganglioglioma, gangliocytoma, meningioangiomatosis, postencephalitic parkinsonism, subacute sclerosing panencephalitis (SSPE), lead encephalopathy, tuberous sclerosis, pantothenate kinase-associated neurodegeneration, synucleinopathy, Parkinson's disease, multiple system atrophy (MSA), neuroaxonal dystrophies, Parkinson's-like disease, Parkinsonism, prion diseases, motor neuron diseases, dementia, transmissible spongiform encephalopathies, systemic atrophies primarily affecting the central nervous system, trinucleotide repeat disorders, proteopathies, amyloidosis, neuronal ceroid lipofuscinoses, amyotrophic lateral sclerosis (ALS), Huntington's disease, traumatic brain injury, stroke, autism spectrum disorder (ASD), depression, anxiety, post-traumatic stress disorder (PTSD), schizophrenia, Attention-Deficit/Hyperactivity Disorder (ADHD), bipolar disorder, Obsessive-Compulsive Disorder (OCD), personality disorder, pain, and others.

Familial Alzheimer's disease (FAD) or early-onset familial Alzheimer's disease (EOFAD) is an uncommon form of Alzheimer's disease that usually strikes earlier in life, defined as before the age of 65 (usually between 50 and 65 years of age). FAD is inherited by autosomal dominant mutation. Mutations in three different genes have been identified as responsible for the development of FAD, and other genes are being studied. As used here, "FAD" refers to an Alzheimer's disease caused by a mutation is any of those three genes, which code for presenilin 1 (PSEN-1), presenilin 2 (PSEN-2), and amyloid precursor protein (APP). "PSEN-1 mediated FAD" is meant to only refer to FAD caused by a mutation in the PSEN-1 gene.

As used herein, the terms "treat," "treatment," "therapy," "therapeutic," and the like refer to obtaining a desired pharmacologic and/or physiologic effect, including, but not limited to, alleviating, delaying or slowing the progression, reducing the effects or symptoms, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, covers any treatment of a disease in a mammal, particularly in a human, and includes: (a) inhibiting the disease, i.e., arresting its development; and (b) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. The methods of the present disclosure may be used with any mammal or other animal. In some cases, the treatment can result in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "subject" refers to any individual or patient on which the methods disclosed herein are performed. The term "subject" can be used interchangeably with the term "individual" or "patient." The subject can be a human, although the subject may be an animal, as will be appreciated by those in the art. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The vectors provided herein can be administered in an amount effective to treat the neurodegenerative disease, disorder, or condition, The term "effective amount" or "therapeutically effective amount" refers to that amount of a composition described herein that is sufficient to affect the intended application, including but not limited to disease treatment, as defined herein. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in a target cell. The specific dose will vary depending on the particular composition chosen, the dosing regimen to be followed, whether it is administered in combination with other compounds, timing of administration, the tissue to which it is administered, and the physical delivery system in which it is carried. Exemplary AAV vector doses that can be administered include about $10^3$ genome copies (GC)/kg, $10^4$ GC/kg, $10^5$ GC/kg, $10^6$ GC/kg, $10^7$ GC/kg, $10^8$ GC/kg, $10^9$ GC/kg, $10^{10}$ GC/kg, $10^{11}$ GC/kg, $10^{12}$ GC/kg, $10^{13}$ GC/kg, $10^{14}$ GC/kg, and any number or range in between, although higher or lower doses can be used.

Nucleic acid expression cassettes can be delivered by any suitable method or vectors. Exemplary methods include intracranial injection, stereotaxic injection, and intravenous injection. In some embodiments, nucleic acid expression cassettes are delivered as viral vectors.

The procedures described herein employ, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., (1989); Sambrook and Russell, *Molecular Cloning,* 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, NY (1992); Guthrie and Fink, *Guide to Yeast Genetics and Molecular Biology*, Academic Press, NY (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology,* 6th Edition, Blackwell Scientific Publications, Oxford (1988); Fire, et al., *RNA Interference Technology From Basic Science to Drug Development*, Cambridge University Press, Cambridge (2005); Schepers, *RNA Interference in Practice*, Wiley-VCH (2005); Engelke, *RNA Interference* (*RNAi*): *The Nuts & Bolts of siRNA Technology*, DNA Press (2003); Gott, *RNA Interference, Editing, and Modification: Methods and Protocols* (*Methods in Molecular Biology*), Human Press, Totowa, N.J. (2004); and Sohail, *Gene Silencing by RNA Interference: Technology and Application*, CRC (2004)).

The compositions and methods are more particularly described below and the Examples set forth herein are intended as illustrative only, as numerous modifications and variations therein will be apparent to those skilled in the art.

The terms used in the specification generally have their ordinary meanings in the art, within the context of the compositions and methods described herein, and in the specific context where each term is used. Some terms have been more specifically defined below to provide additional guidance to the practitioner regarding the description of the compositions and methods.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the invention are described in terms of Markush groups or other grouping of alternatives, those skilled in the art will recognize that the invention is also thereby described in terms of any individual member or subgroup of members of the Markush group or other group.

Presented below are examples describing therapeutic polynucleotides encoding presenilin 1, contemplated for the discussed applications. The following are provided for exemplification purposes only, to further illustrate the embodiments of the present invention, and are not intended to limit the scope of the invention described in broad terms above. While they are typical of those that might be used, other procedures, methodologies, or techniques known to those skilled in the art may alternatively be used.

EXAMPLES

Example 1

This example describes modification of the human presenilin 1 (PSEN1) cDNA by codon-optimization.

The native cDNA sequence of the human presenilin 1 gene (PSEN1; GenBank Accession No. NM_000021.4, SEQ ID NO:1) is shown below (SEQUENCES section). The coding sequences are underlined in SEQ ID NO: 1. The coding sequence present in SEQ ID NO: 1 is repeated as SEQ ID NO: 15 which is broken up into codons and the intolerant codons are underlined. The open reading frame encoding the protein itself corresponds to nucleotides (nt) 213 through 1616. Notable elements of the mRNA are the long 5' untranslated sequence (212 nt) and long 3' untranslated sequence (4012 nt). The start codon at nt 213 is preceded by a weak Kozak translation initiation signal of CTCCA, missing the A residue at the −3 position relative to the A residue of the AUG start codon defined as +1.

The native PSEN1 cDNA (SEQ ID NO:1) was modified by codon optimization. Several methods of codon optimization can be used in which the DNA sequence encoding the protein is changed in ways that do not affect protein sequence. Codon optimization identifies preferred codons based on statistical surveys of codon usage or abundance of cognate tRNA level in cells.

SEQ ID NO:6 is a codon optimized PSEN1 cDNA that was generated by modified codon optimization with the additional constraint of allowing only tolerant synonymous codon changes. Tolerability was determined by comparison of DNA sequences encoding the same protein in related species. For example, a codon choice that is the same in all related species implies that changing this codon would not be tolerated. Thus, only codons that tolerate change are modified to preferred synonymous codons.

SEQ ID NO:6 was generated based on the open reading frame of n=11 primate cDNAs (Table 1). The cDNAs sequences were obtained from GenBank and aligned using CLUSTAL OMEGA facility (ebi.ac.uk/Tools/msa/clustalo/). Of the 467 codons in the human cDNA for PSEN1, 267 were invariant among all 11 species. These were designated as codons that could not tolerate change and were preserved in SEQ ID NO:6.

TABLE 1

Open Reading Frames of Primate PSEN1 cDNAs.

| No. | GenBank Code | Order | Genus/Species | Common Name |
|---|---|---|---|---|
| 1 | NM_000021.4 | Ape | *Homo sapiens* | Human |
| 2 | XM_024231237.1 | Ape | *Pongo abelii* | Orang Utan |
| 3 | | Ape | *Nomascus leucogenys* | Gibbon |
| 4 | XM_007987195.1 | Old world | *Chlorocebus sabaeus* | African Green |
| 5 | XM_028850213.1 | Old world | *Macaca mulatto* | Rhesus |
| 6 | XM_011983100. | Old world | *Mandrillus leucophaeus* | Drill |
| 7 | | New World | *Aotus nancymaae* | Ma's night monkey |
| 8 | XM_003924504.2 | New World | *Saimiri boliviensis boliviensis* | Bolivian squirrel monkey |
| 9 | XM_021718361.1 | Tasiers | *Carlito syrichta* | Philippine tarsier |
| 10 | XM_012656183.1 | Prosimian | *Propithecus coquereli* | Coquerels sifaka |
| 11 | NM_001309945.1 | Prosimian | *Microcebus murinus* | Gray mouse lemur |

For the remaining codons where change is tolerated, synonymous codons were chosen in locations with bias of codon choice in human genes.

Step 1. Took human cDNA. Accept all 267 codons conserved across 11 primates. Changed tolerant codons according to rules in Table 2.

TABLE 2

Preferred Optimized Codons

| Amino acid | Most preferred codon | Preferred codon | Non-preferred | Highly non-preferred |
|---|---|---|---|---|
| A (Alanine) | GCC | GCT, GCA | | GCG |
| C (Cysteine) | | TGT, TGC | | |
| D (Aspartate) | | GAT, GAC | | |
| E (Glutamate) | | GAA, GAG | | |
| F (Phenylalanine) | | TTT, TTC | | |
| G (Glycine) | GGC | GGA, GGG | GGT | |
| H (Histidine) | CAC | | CAT | |
| I (Isoleucine) | ATC | ATT | ATA | |
| K (Lysine) | | AAA, AAG | | |
| L (Leucine) | CTG | CTC | TTG, CTT | TTA, CTA |
| M (Methionine) | | ATG | | |
| N (Asparagine) | | AAT, AAC | | |
| P (Proline) | CCT | CCC, CCA | | CCG |
| Q (Glutamine) | CAG | | CAA | |
| R (Arginine) | AGA, AGG | CGC, CGG | CGA | CGT |
| S (Serine) | AGC | TCT, TCC, TCA, AGT | | TCG |
| T (Threonine) | ACC | ACT, ACA | | ACG |
| V (Valine) | GTG | GTC | GTT, GTA | |
| W (Tryptophan) | | TGG | | |

TABLE 2-continued

| Preferred Optimized Codons | | | | |
|---|---|---|---|---|
| Amino acid | Most preferred codon | Preferred codon | Non-preferred | Highly non-preferred |
| Y (Tyrosine) | | TAT, TAC | | |
| STOP | TGA | TAA | TAG | |

Example 2

This example describes modification of the human presenilin 1 (PSEN1) cDNA by elimination of CpG dinucleotides.

In mammalian DNA, there is selective methylation of CpG dinucleotides. This affects the recruitment of chromatin proteins which in turn affects gene expression. In addition, there is an innate immune response to newly introduced DNA aimed at eliminating viral infection. This innate immune response is mediated by toll like receptor 9 (TLR9) which recognizes unmethylated CpG dinucleotides.

SEQ ID NO:7 uses the redundancy of the genetic code to completely eliminate CpG dinucleotides in the PSEN1 cDNA. The number of CpG dinucleotides was reduced from 24 in the native cDNA to zero. Elimination of CpG dinucleotides can reduce recognition of a viral vectors such as AAV, for example, and polynucleotides by antigen presenting cells and reduce immune responses to gene therapy, thereby prolonging polynucleotide expression and reducing the need for immunosuppressive therapies. However, it was not possible to both eliminate all CpG dinucleotides while also maintaining all intolerant codons. Thus, SEQ ID NO:7 includes changes to six intolerant codons as indicated by underlining in that sequence.

SEQ ID NO:36 uses the redundancy of the genetic code to eliminate as many CpG dinucleotides in the PSEN1 cDNA as possible without altering any intolerant codons. In this construct, the number of CpG dinucleotides was reduced from 24 in the native cDNA to five.

Example 3

This example describes modification of the human presenilin 1 (PSEN1) cDNA by inclusion of genomic sequences.

Previous gene therapy constructs have introduced exogenous or artificial introns into the expression cassette. For example, many AAV vectors used in clinical trials use the CAG promoter which includes an artificial hybrid intron of chicken beta actin and rabbit beta globin genes.

SEQ ID NO:8 is a hybrid genomic/cDNA PSEN1 gene sequence intended to direct pre-mRNA into the splicing apparatus and thereby enhance nuclear export and overall mRNA levels. SEQ ID NO:8 represents a shortened genomic version of PSEN1 that includes exons 2, intron 2, exon 3, intron 3, exon 4, intron 4 followed by the remainder of the protein coding gene in cDNA form. Introns 3 and 4 are too large to be inserted into an AAV gene transfer vector, for example, and are therefore internally shortened. Without being limited by theory, generally, splicing factors bind near the ends of introns and therefore internal deletions do not interfere with splicing.

Importantly, PSEN1 mRNA is found in two forms, one encoding the most abundant protein of length 467 amino acid and an alternate version (X2) encoding a 463 amino acid version of presenilin 1. There are two splice donors at the beginning of intron 3 separated by 12 nt. Alternate splicing at this location leads to different mRNAs encoding proteins that differ by a deletion of 4 amino acids. The significance of this alternative splicing is unknown but isoform X2 is seen across a wide range of primates (e.g., marmots: Gen Bank references XP_027787309.1 presenilin-1 isoform and XP_027787310.1 presenilin-1 isoform X2). This suggests some physiological significance.

SEQ ID NO:8 was designed with important features of intron 4 that allow for alternative splicing to produce isoforms X1 an X2 is enabled. Without being limited by theory, SEQ ID NO:8 will express both isoforms and therefore provide the full range of physiological effects that are provided by the native PSEN1 gene.

Example 4

This example describes identification of neuron-specific promoter sequences.

PSEN1 expression should be specifically restricted to neurons to prevent AP accumulation in neurons. Previously reported AAV gene therapy vectors with neuron-specific expression included the neuron-specific elastase and synapsin 1 promoters.

The availability of RNA-Seq data from multiple cell types allowed an unbiased search for highly expressed neuron-specific genes (see web.stanford.edu/group/barres_lab/brain_rnaseq.html). Genes with high neuronal to endothelial expression ratio were identified and sorted by decreasing neuron expression level. Genes were then manually inspected to exclude candidates with potentially confounding factors (e.g., maternal expression/multiple transcription start sites) that might limit utility. Two novel highly expressed neuron-specific promoter sequences, SEQ ID NO:2 and SEQ ID NO:3, were identified by this method.

SEQ ID NO:2 includes a 480 base pair (bp) fragment of the human somatostatin gene (SST) from −407 to +73 relative to transcription start site. The use of the SST promoter from rhesus macaque has been previously reported with a fragment of ~300 bp that drives neuron-specific expression of a reporter polynucleotide in the context of lentiviral gene transfer.

SEQ ID NO:3 includes a 1000 bp segment from −952 to +48 relative to the mRNA start of the human neuropeptide Y (NPY) promoter. This will provide a highly specific expression pattern in brain.

Example 5

This example describes regulatory elements to increase polynucleotide expression.

SEQ ID NO:4 from the human beta globin locus called HS4 can function as a chromatin insulator sequence. It has been used in the context of lentiviral gene transfer vectors to ensure ongoing expression of introduced polynucleotides.

SEQ ID NO:5 is a Kozak translation initiation signal. It can be used to replace the weak non-consensus Kozak signal in the native mRNA of the PSEN1 gene.

SEQ ID NO:4 and/or SEQ ID NO:5 can be used in nucleic acid expression cassettes in combination with any of the elements and features described herein. For example, SEQ ID NO:4 and/or SEQ ID NO:5 can be used in nucleic acid expression cassettes that include any one of the synthetic PSEN1 cDNA sequences set forth in SEQ ID NO:6, SEQ ID NO:7, or SEQ ID NO:8. The nucleic acid expression cassettes can further include any one of the neuron-specific promoters of SEQ ID NO:2 or SEQ ID NO:3. In addition, the nucleic acid expression cassettes can include any one of the sequences set forth in SEQ ID NO:9, SEQ ID NO:10, or SEQ ID NO:11 described below (Example 6) that enhance mRNA expression by providing mRNA stability or enhancing mRNA transcription and processing, or any combination of SEQ ID NO:9, SEQ ID NO:10, and SEQ ID NO:11.

Example 6

This example describes regulatory sequences that enhance polynucleotide expression by conferring stability to mRNA or enhancing transcription and processing of mRNA.

SEQ ID NO:9 is an expression and nuclear retention element that confers mRNA stability. Expression and nuclear retention elements stabilize mRNAs by making complex secondary structures with the terminal polyadenylated sequence of the mRNA, thereby inhibiting 3' to 5' degradation. Without being limited by theory, the insertion of this sequence beyond the open reading frame and before polyadenylation site will provide promoter mRNA stability.

SEQ ID NO:10 corresponds to the 3' non-coding sequence of the native PSEN1 cDNA. Without being limited by theory, 3' untranslated sequences may contain important elements that enhance mRNA transcription and processing, thereby enhancing polynucleotide or gene expression. SEQ ID NO:10 in part or in its entirety can be appended to the 5' end of any presenilin coding sequence to enhance expression level.

SEQ ID NO:11 corresponds to the 5' non-coding sequence of the native PSEN1 cDNA. Without being limited by theory, 5' untranslated sequences can contain important elements that enhance mRNA stability, thereby enhancing polynucleotide or gene expression. SEQ ID NO:11 in part or in its entirety can be appended to the 3' end of any presenilin encoding sequence to enhance expression level.

SEQ ID NO:9, SEQ ID NO:10, and SEQ ID NO:11 can be used in any combination in nucleic expression cassettes described herein. Nucleic acid expression cassettes that include SEQ ID NO:9, SEQ ID NO:10, SEQ ID NO:11 or any combination of SEQ ID NO:9, SEQ ID NO:10, and SEQ ID NO:11 can have any of the combination of elements and features described herein. For example, an expression cassette that includes SEQ ID NO:9, SEQ ID NO:10, SEQ ID NO:11 or any combination of SEQ ID NO:9, SEQ ID NO:10, and SEQ ID NO:11 can include any one of the synthetic PSEN1 cDNA sequences set forth in SEQ ID NO:6, SEQ ID NO:7, or SEQ ID NO:8. The nucleic acid expression cassettes can further include any one of the neuron-specific promoters of SEQ ID NO:2 or SEQ ID NO:3. Nucleic acid expression cassettes can also include further regulatory elements that increase polynucleotide expression, such as SEQ ID NO:4, SEQ ID NO: 5, or both.

Example 7

This example describes design of presenilin 1 (PSEN1) expression cassettes.

Any elements and features described herein, including sequences set forth in SEQ ID NOs:2-11, can be combined into presenilin 1 expression cassettes. For example, nucleic acid expression cassettes can include any one of the synthetic cDNA sequences set forth in SEQ ID NO:6, SEQ ID NO:7, or SEQ ID NO:8 that encode PSEN1. Expression of any one of the synthetic cDNAs can be driven by a neuron-specific promoter of SEQ ID NO:2 derived from the human somatostatin (SST) gene or SEQ ID NO:3 derived from the human neuropeptide Y (NPY) promoter.

A nucleic acid expression cassette that has any of the synthetic cDNA sequences and promoter sequences described above can further include any of the elements that increase polynucleotide expression, including, for example, a chromatin insulator sequence of SEQ ID NO:4, a Kozak consensus sequence of SEQ ID NO:5, an mRNA stability element of SEQ ID NO:9, a 3' non-coding sequence of SEQ ID NO:10 derived from the native PSEN1 cDNA, a 5' non-coding sequence of SEQ ID NO:11 derived from the native PSEN1 cDNA, or any combination of these elements. Selection of elements can be based on desired levels of expression, for example. For example, expression levels can vary with cell type or the brain region a neuron is found in, which can be used as a guide or criterion for inclusion or exclusion of regulatory elements that affect any step in gene expression, such as mRNA transcription, processing, stability, and/or translation, for example.

The nucleic acid expression cassettes can be included in a viral vector, for example. Any viral vector can be used, including adeno-associated virus (AAV) vectors, lentiviral vectors, retroviral vectors, and adenoviral vectors, for example.

Example 8

This example describes the synthesis of two different codon-optimized PSEN-1 constructs and the expression of presenilin 1 protein from each of the constructs, as well as from a construct comprising wild-type PSEN-1 coding sequence.

Constructs encoding codon-optimized human presenilin 1 were designed by making changes to the cDNA sequence encoding wild-type PSEN-1 only at codons that are variable across primate sequences. The wild-type PSEN-1 cDNA sequence contains 267 codons that are conserved across 11 primate sequences (see underlined codons in SEQ ID NO:15). These intolerant codons were left unchanged. The remaining 200 tolerant codons in the wild-type cDNA were considered for optimization.

For one construct (v2.0), conservative codons changes (34 codons in lower cases) were made to construct SEQ ID NO:38. Native wild-type PSEN-1 cDNA codons were conserved for codons translated into: phenylalanine, tyrosine, cysteine, histidine, asparagine, lysine, aspartic acid and glutamic acid because only two different codons of equal usage in primates encode these amino acids. For glutamine-encoding codons, CAG was preferred. For isoleucine-encoding codons, ATA codons were changed to ATC and either ATC or ATT were maintained if present in native sequence. Methionine (ATG) and tryptophan (TGG) encoding codons were unchanged. For proline-, threonine-, and alanine-encoding codons, every codon terminating with a guanine (G) was changed into a redundant codon terminating with a cytosine (C). For valine- and glycine-encoding codons, every codon terminating with a thymine (T) or adenine (A) was changed into a redundant codon terminating with a cytosine (C) or guanine (G), respectively. AGG, AGA, CGC, CGG, AGT, AGC, TCC, TCT, TCA, TTG, CTC and CTG codons were left unchanged. CGT codons were changed to CGC; CGA codons were changed to CGG; TCG codons were changed to TCC; TTA codons were changed to TTG; CTT codons were changed to CTC; and CTA codons were changed to CTG.

For another construct (v1.5) more codons changes (138 codons in lower cases) were made to construct SEQ ID NO:37 compared to native sequence. In this construct, native codons were conserved for codons translated into: tryptophan, cysteine and methionine. For glutamine-encoding codons, selected CAA codons were changed to CAG. For isoleucine-encoding codons, selected ATA and ATT codons were changed to ATC. For proline-encoding codons, selected codons were changed to CCC or CCT. For threonine-encoding codons, selected codons were changed to ACC or ACA. For alanine-encoding codons, selected codons were changed to GCC or GCT. Glycine-encoding codons not terminating with a cytosine (C) were changed into redundant codons terminating with a cytosine (C). For valine-encoding codons, GTG was preferred. AGC codons were left unchanged. For aspartic acid-encoding codons, selected codons were changed to GAT or GAC. For glutamic acid-encoding codons, GAA or GAG were preferred. For phenylalanine-encoding codons, TTT codons were changed to TTC. For histidine-encoding codons, CAT codons were changed to CAC. For lysine-encoding codons, selected AAA codons were changed to AAG. For leucine-encoding codons, most selected codons were changed to CTG. For asparagine-encoding codons, AAT codons were changed to AAC. For arginine-encoding codons, AGA was preferred, but AGG and CGG codons were also used. For serine-encoding codons, AGC was preferred. but TCC and TCT were also used on selected codons. For tyrosine-encoding codons, TAT codons were changed to TAC.

Each of the PSEN-2.0, PSEN-1.5 and wild-type PSEN-1 coding sequences were separately cloned into cloning vector pCMV6-XL5 (Origene, Rockville, MD). The resulting constructs (WT (pAT001), v1.5 (pAT010) and v2.0 (pAT012)) were transfected into HEK293 cells to determine the effect of codon optimization on presenilin 1 expression. The 293 cells were harvested 48 hours post-transfection, lysed using 300 μL of RIPA buffer (50 mM Base/Tris-HCl, 150 mM Sodium Chloride, 0.5% Sodium Deoxycholate, 0.1% Sodium Dodecyl Sulfate, 1% Nonidet P-40 substitute with added cOmplete™, Mini, EDTA-free Protease Inhibitor Cocktail, Sigma Aldrich), and the supernatant was collected. The total protein concentration of each sample was measured using the THERMO SCIENTIFIC™ PIERCE™ BCA™ Protein Assay according to the manufacturer's instructions.

ELISAs for detecting human presenilin 1 (PS1) protein in cell lysates were performed using the RayBio® Human Presenilin 1 ELISA Kit. Dilutional linearity (DL) and spike-in recovery (SR) was assessed using untransfected 293 cells to test the compatibility of cell lysates with this ELISA kit. Table 3 shows that cell lysates exhibit acceptable dilutional linearity (1:250-1:1000) and spike-in recovery.

TABLE 3

Dilutional linearity and spike-in recovery

| Sample ID | Expected concentration (pg/mL) | Interpolated Values (pg/mL) | | Accuracy (% RE) | Precision (% CV) | SR/DL % |
|---|---|---|---|---|---|---|
| Neat sample (cell lysate) | — | 67.18 | 63.88 | — | 3.56% | — |
| Control Spike (assay diluent) | 750 | 800.47 | 834.07 | 8.97% | 2.91% | |
| Sample Spike (cell lysate) | 750 | 808.80 | 1068.02 | 25.12% | 19.53% | 99% |
| 1:250 dilution (cell lysate) | 3000 | 2490.14 | 2654.88 | 14.25% | 4.53% | 83% |
| 1:500 dilution (cell lysate) | 1500 | 1305.48 | 1320.87 | 12.46% | 0.83% | 87% |
| 1:1000 dilution (cell lysate) | 750 | 747.87 | 766.82 | 0.98% | 1.77% | 100% |

ELISAs for detecting human presenilin 1 (PS1) protein in transfected 293 cell lysates were performed using the RayBio® Human Presenilin 1 ELISA Kit. Technical duplicates were run at a 1:1000 dilution according to the manufacturer's instructions. Table 4 and FIG. 1 shows that transfection with plasmid pAT010 resulted in a 2.5-fold increase in PS1 expression when compared with the native sequence.

TABLE 4

PSI expression in transfected 293 cell lysates

| Sample ID | Interpolated Values (pg/mL) | | Mean (pg/mL) | Precision (% CV) | Dilution | ug/mL total protein | pg PS1/ug total protein |
|---|---|---|---|---|---|---|---|
| WT pAT001 replicate 1 | 196.63 | 202.47 | 199.55 | 2% | 1000 | 854.3 | 233.59 |

TABLE 4-continued

PSI expression in transfected 293 cell lysates

| Sample ID | Interpolated Values (pg/mL) | | Mean (pg/mL) | Precision (% CV) | Dilution | ug/mL total protein | pg PS1/ug total protein |
|---|---|---|---|---|---|---|---|
| WT pAT001 replicate 2 | 225.13 | 227.79 | 226.46 | 1% | 1000 | 820.4 | 276.03 |
| V1.5 pAT010 replicate 1 | 486.76 | 499.90 | 493.33 | 2% | 1000 | 675.4 | 730.39 |
| V1.5 pAT010 replicate 2 | 418.15 | 413.65 | 415.90 | 1% | 1000 | 767.1 | 542.14 |
| V2.0 pAT012 replicate 1 | 209.48 | 240.41 | 224.95 | 10% | 1000 | 824.1 | 272.95 |
| V2.0 pAT012 replicate 2 | 215.98 | 223.97 | 219 98 | 3% | 1000 | 645.9 | 340.60 |

Example 9

This example describes another codon-optimized PSEN-1 coding sequence.

For construct v3.0 (SEQ ID NO:39) 140 tolerant codons (as indicated in lower case) were changed, as was the stop codon, compared to codons present in wild-type PSEN-1 coding sequence. Methionine (ATG) and tryptophan (TGG) encoding codons were unchanged. For glutamine (Q)-encoding codons, all tolerant codons were changed to CAG. For isoleucine (I)-encoding codons, all tolerant codons were changed to ATC. For proline (P)-encoding codons, all tolerant codons were changed to CCC. For threonine (T)-encoding codons, all tolerant codons were changed to ACC. For alanine (A)-encoding codons, all tolerant codons were changed to GCC. For glycine (G)-encoding codons, all tolerant codons were changed to GGC. For valine (V)-encoding codons, all tolerant codons were changed to GTG. For aspartic acid (D)-encoding codons, all tolerant codons were changed to GAC. For glutamic acid (E)-encoding codons, all tolerant codons were changed to GGC. For phenylalanine (F)-encoding codons, all tolerant codons were changed to TTC. For histidine (H)-encoding codons, all tolerant codons were changed to CAC. For lysine (K)-encoding codons, all tolerant codons were changed to AAG. For leucine (L)-encoding codons, all tolerant codons were changed to CTG. For asparagine (N)-encoding codons, all tolerant codons were changed to ACC. For arginine (R)-encoding codons, all tolerant codons were changed to AGA, except for codon 307 that was changed from AGG to CGG. For serine (S)-encoding codons, all tolerant codons were changed to AGC. For tyrosine (Y)-encoding codons, all tolerant codons were changed to TAC.

Example 10

This example describes the relative expression levels of PSEN1 driven by the CAG promoter from two different codon-optimized PSEN-1 coding sequence as compared to the wild-type PSEN1 coding sequence.

Plasmid pAAV-CAG-MCS (Vector Biolabs) was modified by replacing the ampicillin antibiotic resistance gene with a kanamycin resistance gene. The sequence of the CAG promoter therein is set forth in SEQ ID NO:40 and has 98% sequence identity to SEQ ID NO:23. We then inserted the PSEN-1 coding sequence of either SEQ ID NO:39 ("CAG-v3.0"; pAT029), SEQ ID NO:37 ("CAG-v1.5"; pAT024), or the wild-type PSEN-1 coding sequence (SEQ ID NO:15; "CAG-native"; pAT022) into the modified plasmid and used those plasmids to transfect HEK293 cells in order to determine the effect of codon optimization on presenilin 1 expression. The 293 cells were harvested 48 hours post-transfection, lysed using 300 μL of RIPA buffer (50 mM Base/Tris-HCl, 150 mM NaCl, 0.5% Sodium Deoxycholate, 0.1% Sodium Dodecyl Sulfate, 1% Nonidet P-40 substitute with added cOmplete™, Mini, EDTA-free Protease Inhibitor Cocktail, Sigma Aldrich), and the supernatant was collected. The total protein concentration of each sample was measured using the THERMO SCIENTIFIC™ PIERCE™ BCA™ Protein Assay according to the manufacturer's instructions.

Figure 2:
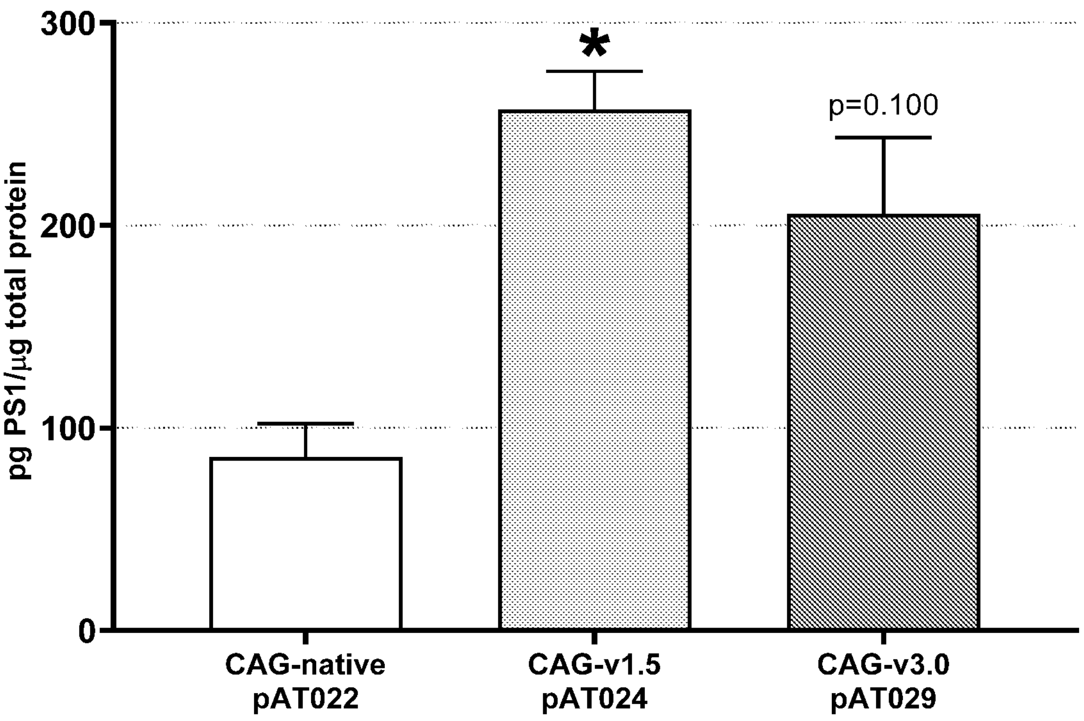
FIG. 2 is a bar graph showing the amount of presenilin-1 protein expressed from HEK293 cells harboring constructs comprising various codon-optimized versions of a presenilin-1 coding sequence whose expression is driven by a CAG promoter (CAG-v1.5 containing PSEN1 coding sequence of SEQ ID NO:37; CAG v3.0 containing PSEN1 coding sequence of SEQ ID NO:39)), as well as from a wild-type presenilin-1 coding sequence (SEQ ID NO:15) driven by a CAG promoter. The asterisk "*" indicates a statistically significant difference compared to wild-type presenilin 1 ($p<0.05$, One way ANOVA followed by Tukey's multiple comparison test).

ELISAs for detecting human presenilin 1 (PS1) protein in cell lysates were performed using the RayBio® Human Presenilin 1 ELISA Kit. Technical duplicates were run at a 1:40 dilution according to the manufacturer's instructions. Data was analyzed using the two-tailed t test. FIG. 2 shows that transfection with plasmid comprising codon-optimized SEQ ID NOs:37 or 39 resulted in increased in PS1 expression when compared with the wild-type coding sequence and that the level of PSEN-1 expression from the SEQ ID NO:37-containing plasmid showed a statistically significant increase over that from the wild-type coding sequence (as indicated by the asterisk $p<0.05$). PSEN-1 expression from the SEQ ID NO:39-containing plasmid showed a trend towards increased expression as compared to the wild-type coding sequence ($p=0.100$).

In summary, synthetic cDNA sequences based on codon optimization, exclusion of CpG dinucleotides, and inclusion of genomic sequences, neuron-specific promoter sequences, and other regulatory elements that enhance any step in gene expression, such as mRNA transcription, processing, stability, and/or translation, for example, can be combined according to desired expression levels in neurons. Combining multiple modes of enhancing polynucleotide expression by combining elements described above, some or all of which may have a relatively small effect on protein production depending on cell type, neuronal location, and other factors, can allow for a relatively large increase in expression from a nucleic acid expression cassette or vector molecule.

Example 11

This example describes the effect of a codon-optimized PSEN-1 nucleotide sequence on the gamma-secretase activity of FAD patient fibroblasts.

Primary dermal fibroblasts from patients with Familial Alzheimer's disease (FAD) carrying C410Y or G206A mutations in PSEN1 were electroporated with plasmids encoding a Notch1 fragment (Notch1ΔE) with either an empty noncoding plasmid(pAAV-CAG-MCS-KanR) or human codon-optimized presenilin-1 (hPSEN1v1.5) of SEQ ID NO:37.

As described in Example 10, the cDNA plasmid pAAV-CAG-MCS (Vector Biolabs) was modified to replace the ampicillin resistance gene with a kanamycin resistance gene and create the resulting plasmid pAAV-CAG-MCS-KanR. The resulting plasmid pAAV-CAG-MCS-KanR was used as a control or further modified to contain the codon-optimized human presenilin 1 coding sequence (SEQ ID NO:37) to evaluate functional gamma-secretase activity. The Notch1ΔE plasmid encodes the transmembrane domain and a portion of the intracellular domain of human Notch1 but lacks the entire extracellular domain of Notch 1. Inside cells, the Notch1ΔE is cleaved by gamma-secretase and can be detected by an antibody specific (Cell Signaling, #4147) for the cleaved fragment, MCD. The gamma-secretase activity can be inhibited with a known gamma-secretase inhibitor DAPT (Sigma-Aldrich, D5942).

To determine whether the codon-optimized construct is functional, NICD was measured following treatment with hPSEN1v1.5 (3 μg) compared to a non-coding plasmid in FAD patient fibroblasts containing one of two PSEN1 pathogenic mutations (C410Y or G206A). Some fibroblasts were exposed to DAPT inhibitor 24 hours after electroporation and were harvested 48 hours post-transfection, lysed using 100 μL of RIPA buffer (50 mM Base/Tris-HCl, 150 mM NaCl, 0.5% Sodium Deoxycholate, 0.1% Sodium Dodecyl Sulfate, 1% Nonidet P-40 substitute with added cOmplete™, Mini, EDTA-free Protease Inhibitor Cocktail, Sigma Aldrich), and the supernatant was collected. The total protein concentration of each sample was measured using the THERMO SCIENTIFIC™ PIERCE™ BCA™ Protein Assay according to the manufacturer's instructions.

Figure 3:
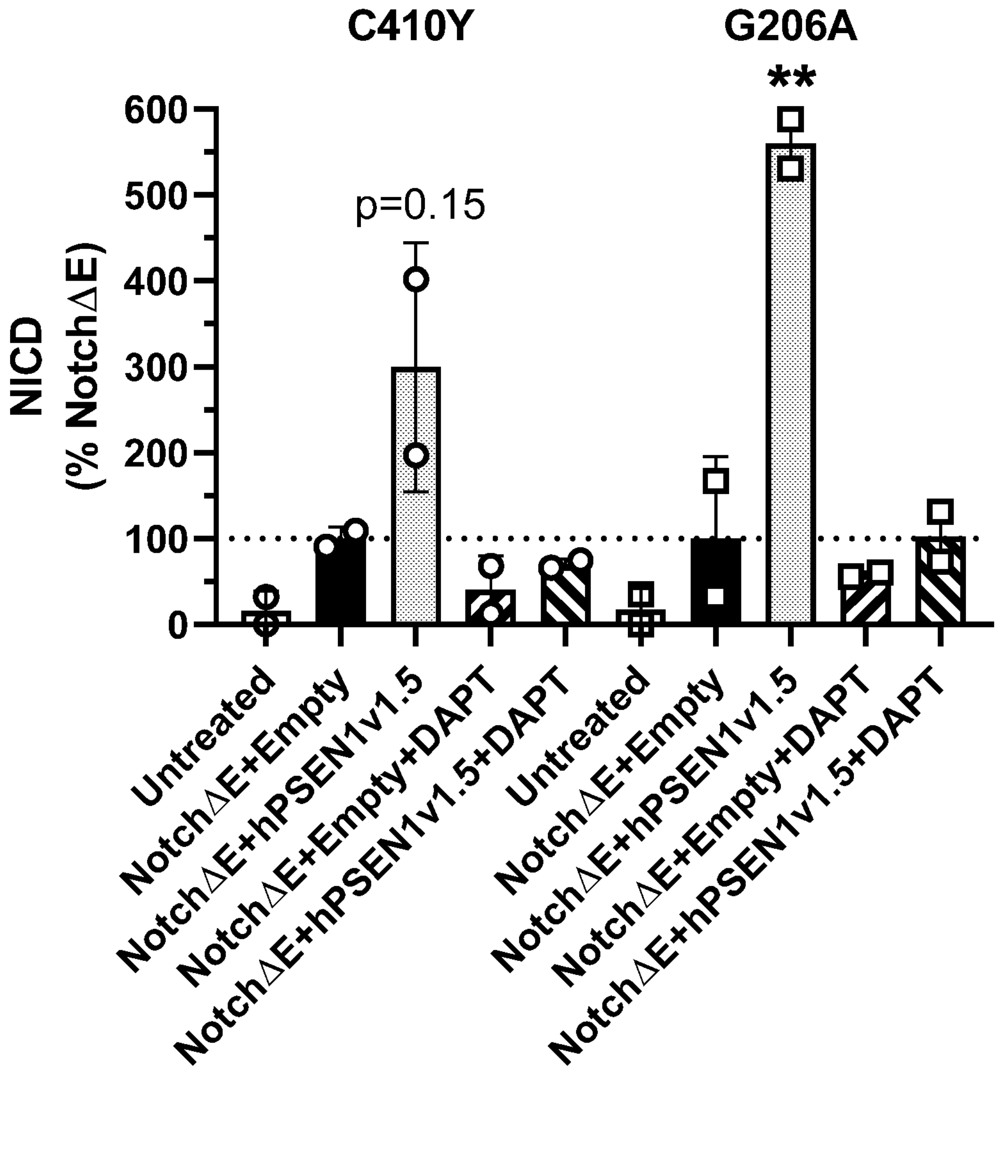
FIG. 3 is a bar graph showing gamma secretase activity as measured by cleavage of NotchΔE to NICD in fibroblasts from familial Alzheimer's disease (FAD) patients harboring either a C410Y or G206A mutation in PSEN1. Fibroblasts were transformed with an empty vector ("NotchΔE+Empty"), or a vector containing SEQ ID NO:37 encoding PSEN1 ("NotchΔE+hPSENv1.5") in the presence or absence of the gamma secretase inhibitor DAPT and the levels of NICD measured. The asterisks "**" indicates a statistically significant difference compare to empty vector ($p<0.01$, One way ANOVA followed by Tukey's multiple comparison test).

Total protein lysates from technical duplicates were electrotransferred to nitrocellulose membrane according to the manufacturer's instructions. Western blots for detecting cleaved Notch (NICD) in cell lysates were performed using recommended conditions. FIG. 3 shows that transfection with the plasmid containing SEQ ID NO:37 resulted in increased NICD when compared with the non-coding construct (Empty) in both C410Y and G206A PSEN1 mutant fibroblasts.

Example 12

This example describes the effect of a codon-optimized PSEN-1 nucleotide sequence on the AB40 levels in FAD patient fibroblasts.

Primary dermal fibroblasts from patients with Familial Alzheimer's disease (FAD) carrying the C410Y mutation in PSEN 1 were electroporated with a plasmid encoding the amyloid precursor protein (APP) C99 fragment and either a non-coding empty plasmid (pAAV-CAG-MCS-KanR) or a similar plasmid containing a codon-optimized human presenilin 1 coding sequence pAT028 (SEQ ID NO:37), each of which is described above, in order to evaluate functional gamma-secretase activity. Inside the cells, the C99 is sequentially cleaved by gamma-secretase to produce Aβ peptides of varying lengths, which are then released into the cell culture media.

Figure 4:
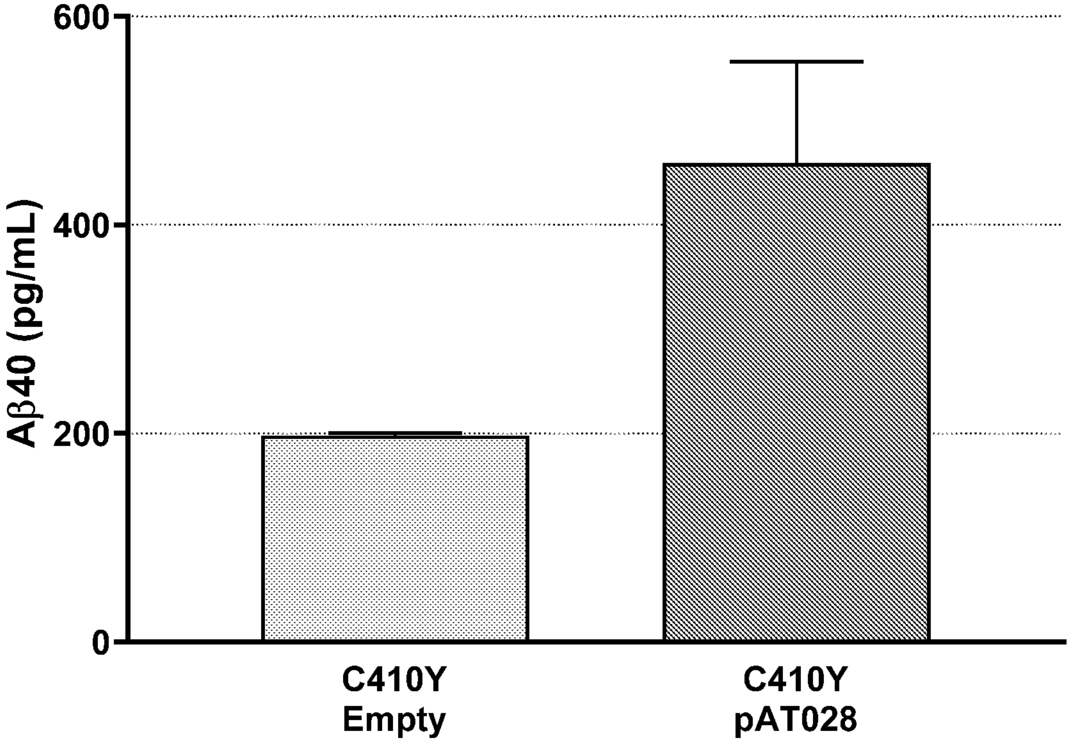
FIG. 4 is a bar graph showing the level of Aβ40 production in fibroblasts from familial Alzheimer's disease (FAD) patients harboring a C410Y mutation in PSEN1 (C410Y) following transformation with either an empty vector ("Empty"), or a vector containing SEQ ID NO:37 encoding PSEN1 ("pAT028").

To determine the functionality of the codon-optimized construct, Aβ40 was measured in the cell culture media following electroporation of the cells with the above plasmids. The cell culture media was collected 48 hours post-transfection and analyzed for Aβ40 via an MSD ELISA. Data was analyzed using the two-tailed t test. FIG. 4 shows that transfection with the SEQ ID NO:37-containing plasmid resulted in increased Aβ40 production when compared with the non-coding construct (Empty) in C410Y FAD fibroblasts, with a trend towards statistical significance (p=0.23).

Example 13

This example describes the synthesis of various AAV vectors comprising a partially codon optimized PSEN-1 coding sequence of the invention.

In order to prepare AAV viral vectors containing the PSEN-1 coding sequences of the invention, we removed the CAG promoter from the pAAV-CAG-MCS-KanR plasmid described above and replaced it with varying expression cassettes. Each expression cassette comprised a different promoter operatively linked to the PSEN-1 coding sequence of SEQ ID NO:37 and a polyadenylation sequence. In addition, the cassettes further comprised a human beta globin intron between the promoter and the PSEN-1 coding sequence; an HA-tag in between the human beta globin intron and the PSEN-1 coding sequence, which may be removed prior to use in subjects; and either human growth hormone or albumin genomic stuffer sequences following the polyadenylation sequence. The sequence of each of these expression cassettes and the AAV2 ITRs that flank them (which are already present in the modified pAAV-CAG-MCS-KanR plasmid) are set forth in SEQ ID Nos: 41-46.

For the production of a self-complementary AAV vector, the 5' AAV2 ITR in pAAV-CAG-MCS-KanR is modified prior to insertion of the expression cassette. The expression cassette for this construct comprised a CBA promoter, a minute virus of mice intron, an HA-tag, which may be removed prior to use in subjects, SEQ ID NO:37, and a rabbit β-globin polyadenylation sequence. The sequence of this expression cassette including the modified 5' and native 3' AAV2 ITRs from the modified pAAV-CAG-MCS-KanR plasmid into which it was inserted, is set forth in SEQ ID NO:47.

Each of the resulting vector genome plasmids containing the expression cassette were used to create recombinant AAV vectors using the triple plasmid transfection method (Xiao and Samulski, J Virol 72: 2224-2232, 1998). This method used an AAV serotype-specific rep and cap plasmid specific to the serotype of interest as well as the vector genome DNA plasmid, but eliminated the use of Ad infection by supplying the essential Ad genes on a third plasmid. Multiplasmids transient transfection of adherent HEK293 cells is a widely used method for rAAV production (Grimm et al., Hum Gene Ther 9: 2745-2760, 1998; Matsushita et al., Gene Ther 5: 938-945, 1998) and can be used to create these recombinant AAV vectors. The AAV particles may be formulated in phosphate buffered saline (PBS) or in 10 mM sodium phosphate, 180 mM NaCl with 0.001% of pluronic acid (F-68) at a pH of about 7.4.

Sequences

>NM_000021.4 *Homo sapiens* presenilin 1 (PSEN1), transcript variant 1, mRNA. Coding sequence underlined

SEQ ID NO: 1

GGAAACAAAACAGCGGCTGGTCTGGAAGGAACCTGAGCTACGAGCCGCGGCGG

-continued

CAGCGGGGCGGCGGGGAAGCGTATACCTAATCTGGGAGCCTGCAAGTGACAACA

GCCTTTGCGGTCCTTAGACAGCTTGGCCTGGAGGAGAACACATGAAAGAAAGAA

CCTCAAGAGGCTTTGTTTTCTGTGAAACAGTATTTCTATACAGTTGCTCCAATGAC

AGAGTTACCTGCACCGTTGTCCTACTTCCAGAATGCACAGATGTCTGAGGACAAC

CACCTGAGCAATACTGTACGTAGCCAGAATGACAATAGAGAACGGCAGGAGCAC

AACGACAGACGGAGCCTTGGCCACCCTGAGCCATTATCTAATGGACGACCCCAG

GGTAACTCCCGGCAGGTGGTGGAGCAAGATGAGGAAGAAGATGAGGAGCTGAC

ATTGAAATATGGCGCCAAGCATGTGATCATGCTCTTTGTCCCTGTGACTCTCTGC

ATGGTGGTGGTCGTGGCTACCATTAAGTCAGTCAGCTTTTATACCCGGAAGGATG

GGCAGCTAATCTATACCCCATTCACAGAAGATACCGAGACTGTGGGCCAGAGAG

CCCTGCACTCAATTCTGAATGCTGCCATCATGATCAGTGTCATTGTTGTCATGACT

ATCCTCCTGGTGGTTCTGTATAAATACAGGTGCTATAAGGTCATCCATGCCTGGC

TTATTATATCATCTCTATTGTTGCTGTTCTTTTTTTCATTCATTTACTTGGGGGAAG

TGTTTAAAACCTATAACGTTGCTGTGGACTACATTACTGTTGCACTCCTGATCTGG

AATTTTGGTGTGGTGGGAATGATTTCCATTCACTGGAAAGGTCCACTTCGACTCC

AGCAGGCATATCTCATTATGATTAGTGCCCTCATGGCCCTGGTGTTTATCAAGTA

CCTCCCTGAATGGACTGCGTGGCTCATCTTGGCTGTGATTTCAGTATATGATTTAG

TGGCTGTTTTGTGTCCGAAAGGTCCACTTCGTATGCTGGTTGAAACAGCTCAGGA

GAGAAATGAAACGCTTTTTCCAGCTCTCATTTACTCCTCAACAATGGTGTGGTTG

GTGAATATGGCAGAAGGAGACCCGGAAGCTCAAAGGAGAGTATCCAAAAATTCC

AAGTATAATGCAGAAAGCACAGAAAGGGAGTCACAAGACACTGTTGCAGAGAA

TGATGATGGCGGGTTCAGTGAGGAATGGGAAGCCCAGAGGGACAGTCATCTAGG

GCCTCATCGCTCTACACCTGAGTCACGAGCTGCTGTCCAGGAACTTTCCAGCAGT

ATCCTCGCTGGTGAAGACCCAGAGGAAAGGGGAGTAAAACTTGGATTGGGAGAT

TTCATTTTCTACAGTGTTCTGGTTGGTAAAGCCTCAGCAACAGCCAGTGGAGACT

GGAACACAACCATAGCCTGTTTCGTAGCCATATTAATTGGTTTGTGCCTTACATT

ATTACTCCTTGCCATTTTCAAGAAAGCATTGCCAGCTCTTCCAATCTCCATCACCT

TTGGGCTTGTTTTCTACTTTGCCACAGATTATCTTGTACAGCCTTTTATGGACCAA

TTAGCATTCCATCAATTTTATATCTAGCATATTTGCGGTTAGAATCCCATGGATGT

TTCTTCTTTGACTATAACAAAATCTGGGGAGGACAAAGGTGATTTTCCTGTGTCC

ACATCTAACAAAGTCAAGATTCCCGGCTGGACTTTTGCAGCTTCCTTCCAAGTCT

TCCTGACCACCTTGCACTATTGGACTTTGGAAGGAGGTGCCTATAGAAAACGATT

TTGAACATACTTCATCGCAGTGGACTGTGTCCCTCGGTGCAGAAACTACCAGATT

TGAGGGACGAGGTCAAGGAGATATGATAGGCCCGGAAGTTGCTGTGCCCCATCA

GCAGCTTGACGCGTGGTCACAGGACGATTTCACTGACACTGCGAACTCTCAGGA

CTACCGTTACCAAGAGGTTAGGTGAAGTGGTTTAAACCAAACGGAACTCTTCATC

TTAAACTACACGTTGAAAATCAACCCAATAATTCTGTATTAACTGAATTCTGAAC

TTTTCAGGAGGTACTGTGAGGAAGAGCAGGCACCAGCAGCAGAATGGGGAATGG

AGAGGTGGGCAGGGGTTCCAGCTTCCCTTTGATTTTTTGCTGCAGACTCATCCTTT

TTAAATGAGACTTGTTTTCCCCTCTCTTTGAGTCAAGTCAAATATGTAGATTGCCT

TTGGCAATTCTTCTTCTCAAGCACTGACACTCATTACCGTCTGTGATTGCCATTTC

-continued

TTCCCAAGGCCAGTCTGAACCTGAGGTTGCTTTATCCTAAAAGTTTTAACCTCAG

GTTCCAAATTCAGTAAATTTTGGAAACAGTACAGCTATTTCTCATCAATTCTCTAT

CATGTTGAAGTCAAATTTGGATTTTCCACCAAATTCTGAATTTGTAGACATACTTG

TACGCTCACTTGCCCCAGATGCCTCCTCTGTCCTCATTCTTCTCTCCCACACAAGC

AGTCTTTTTCTACAGCCAGTAAGGCAGCTCTGTCGTGGTAGCAGATGGTCCCATT

ATTCTAGGGTCTTACTCTTTGTATGATGAAAAGAATGTGTTATGAATCGGTGCTG

TCAGCCCTGCTGTCAGACCTTCTTCCACAGCAAATGAGATGTATGCCCAAAGACG

GTAGAATTAAAGAAGAGTAAAATGGCTGTTGAAGCACTTTCTGTCCTGGTATTTT

GTTTTTGCTTTTGCCACACAGTAGCTCAGAATTTGAACAAATAGCCAAAAGCTGG

TGGTTGATGAATTATGAACTAGTTGTATCAACACAAAGCAAGAGTTGGGGAAAG

CCATATTTAACTTGGTGAGCTGTGGGAGAACCTGGTGGCAGAAGGAGAACCAAC

TGCCAAGGGGAAAGAGAAGGGGCCTCCAGCAGCGAAGGGGATACAGTGAGCTA

ATGATGTCAAGGAGGAGTTTCAGGTTATTCTCGTCAGCTCCACAAATGGGTGCTT

TGTGGTCTCTGCCCGCGTTACCTTTCCTCTCAATGTACCTTTGTGTGAACTGGGCA

GTGGAGGTGCCTGCTGCAGTTACCATGGAGTTCAGGCTCTGGGCAGCTCAGTCAG

GCAAAACACACAAACAGCCATCAGCCTGTGTGGGCTCAGGGCACCTCTGGACAA

AGGCTTGTGGGGCATAACCTTCTTTACCACAGAGAGCCCTTAGCTATGCTGATCA

GACCGTAAGCGTTTATGAGAAACTTAGTTTCCTCCTGTGGCTGAGGAGGGGCCAG

CTTTTTCTTCTTTTGCCTGCTGTTTTCTCTCCCAATCTATGATATGATATGACCTGG

TTTGGGGCTGTCTTTGGTGTTTAGAATATTTGTTTTCTGTCCCAGGATATTTCTTAT

AAGAACCTAACTTCAAGAGTAGTGTGCGAGTACTGATCTGAATTTAAATTAAAAT

TGGCTTATATTAGGCAGTCACAGACAGGAAAAATAAGAGCTATGCAAAGAAAGG

GGGATTTAAAGTAGTAGGTTCTATCATCTCAATTCATTTTTTTCCATGAAATCCCT

TCTTCCAAGATTCATTCCCTCTCTCAGACATGTGCTAGCATGGGTATTATCATTGA

GAAAGCACAGCTACAGCAAAGCCACCTGAATAGCAATTTGTGATTGGAAGCATT

CTTGAGGGATCCCTAATCTAGAGTAATTTATTTGTGTAAGGATCCCAAATGTGTT

GCACCTTTCATGATACATTTCTTCTCTGAAGAGGGTACGTGGGGTGTGTGTATTTA

AATCCATCCTATGTATTACTGATTGTCCTGTGTAGAAAGATGGCAATTATTCTGTC

TCTTTCTCCAAGTTTGAGCCACATCTCAGCCACATTGTTAGACAGTGTACAGAGA

ACCTATCTTTCCTTTTTTTTTTTTTAAAGGACAGGATTTTGCTGTGTTGCCCAGGCT

AGACTTGAACTCCTGGGCTCAAGTAATCCACCTCAGCCTGAGTAGCTGAGACTAC

AGCCCATCTTATTTCTTTAAATCATTCATCTCAGGCAGAGAACTTTTCCCTCAAAC

ATTCTTTTTAGAATTAGTTCAGTCATTCCTAAAACATCCAAATGCTAGTCTTCCAC

CATGAAAAATAGATTGTCACTGGAAAGAACAGTAGCAATTTCCATAAGGATGTG

CCTTCACTCACACGGGACAGGCGGTGGTTATAGAGTCGGGCAAAACCAGCAGTA

GAGTATGACCAGCCAAGCCAATCTGCTTAATAAAAAGATGGAAGACAGTAAGGA

AGGAAAGTAGCCACTAAGAGTCTGAGTCTGACTGGGCTACAGAATAAAGGGTAT

TTATGGACAGAATGTCATTACATGCCTATGGGAATACCAATCATATTTGGAAGAT

TTGCAGATTTTTTTTCAGAGAGGAAAGACTCACCTTCCTGTTTTTGGTTCTCAGTA

GGTTCGTGTGTGTTCCTAGAATCACAGCTCTGACTCCAAATGACTCAATTTCTCA

-continued

ATTAGAAAAAGTAGAAGCTTTCTAAGCAACTTGGAAGAAAACAGTCATAAGTAA

GCAATTTGTTGATTTTACTACAGAAGCAACAACTGAAGAGGCAGTGTTTTTACTT

TCAGACTCCGGGATTCCCATTCTGTAGTCTCTCTGCTTTTAAAAACCCTCCTTTTG

CAATAGATGCCCAAACAGATGATGTTTATTACTTGTTATTTACGTGGCCTCAGAC

AGTGTATGTATTCTCGATATAACTTGTAGAGTGTGAAATATAAGTTTAACTACCA

AATAAGGTCTCCCAGGGTTAGATGACTGCGGGAAGCCTTTGATCCCAACCCCCA

AGGCTTTGTATATTTGATCATTTGTGATCTAACCCTGGAAGAAAAAGAGCTCAGA

AACCACTATGAAAAAATTTGTTCAGTGTTTTCTGTGTTCCCGTAGGTTCTGGAGTC

TGAGGATGCAAAGATGAATAAGATAAATTCTCAGAATGTAGTTATAATCTCTTGT

TTTCTGGTATATGCCATCTTTCTTTAACTTCTCTAAAATATTGGGTATTTGTCAAA

TAACCACTTTTAACAGTTACCATTACTGAGGGCTTATACATTGGTGTTATAAAAG

TGACTTGATTCAGAAATCAATCCATTCAGTAAAGTACTCCTTCTCTAAATTTGCTG

TTATGTCTATAAGGAACAGTTTGACCTGCCCTTCTCCTCACCTCCTCACCTGCCTT

CCAACATTGAATTTGGAAGGAGACGTGAAAATTGGACATTTGGTTTTGCCCTTGG

GCTGGAAACTATCATATAATCATAAGTTTGAGCCTAGAAGTGATCCTTGTGATCT

TCTCACCTCTTTAAATTCCCACAACACAAGAGATTAAAAACAGAGGTTTCAGCTC

TTCATAGTGCGTTGTGAAATGGCTGGCCAGAGTGTACCAACAAAGCTGTCATCGG

GCTCACAGCTCAGAGACATCTGCATGTGATCATCTGCATAGTCCTCTCCTCTAAC

GGGAAACACCTCAGATTTGCATATAAAAAAGCACCCTGGTGCTGAAATGAACCC

CTTTCTTGAACATCAAAGCTGTCTCCCACAGCCTTGGGCAGCAGGGTGCCTCTTA

GTGGATGTGCTGGGTCCACCCTGAGCCCTGACATGTGGTGGCAGCATTGCCAGTT

GGTCTGTGTGTCTGTGTAGCAGGGACGATTTCCCAGAAAGCAATTTTCCTTTTGA

AATACGTAATTGTTGAGACTAGGCAGTTTCAAAGTCAGCTGCATATAGTAGCAAG

TACAGGACTGTCTTGTTTTTGGTGTCCTTGGAGGTGCTGGGGTGAGGGTTTCAGT

GGGATCATTTACTCTCACATGTTGTCTGCCTTCTGCTTCTGTGGACACTGCTTTGT

ACTTAATTCAGACAGACTGTGAATACACCTTTTTTATAAATACCTTTCAAATTCTT

GGTAAGATATAATTTTGATAGCTGATTGCAGATTTTCTGTATTTGTCAGATTAATA

AAGACTGCATGAATCCA

>Human SST promoter

SEQ ID NO: 2 acactaaaatgttagagtatgatgacagatggagttgtctgggtacatttgtgtgcatttaagggtgatagtgtatttgctctttaagagctg agtgtttgagcctctgtttgtgtgtaattgagtgtgcatgtgtgggagtgaaattgtggaatgtgtatgctcatagcactgagtgaaaataaa agattgtataaatcgtggggcatgtggaattgtgtgtgcctgtgcgtgtgcagtatttttttttttttaagtaagccactttagatcttgtcacct cccctgtcttctgtgattgattttgcgaggctaatggtgcgtaaaagggctggtgagatctgggggcgcctcctagcctgacgtcagag agagagtttaaaacagagggagacggttgagagcacacaagccgctttaggagcgaggttcggagccatcgctgctgcctgctgatc cgcgcctagagtttgaccagcc >Human NPY promoter

SEQ ID NO: 3 ttttggccaggggatgtggcttggactggagagaaaggagataaggatgtaaacacatgtagggcatatcacccccctatttttattctct gaatccttaaccctcagaataagttcttattcttgagaatcaatgacattatcttaagctaaattaatcaagcctccacagtgttcttctctcaa tagtggtgtgggccttcctagaagtaatttttcccaaattcagtgatacattttaagttcagattttaattgatatgaatctgtgatacactctaa aataagattattttattgaaaagtggactgtaactttccctttatctaggaagagctctaagttagaagatgttttgcacttttaccgaaggctg tgtcttgtaagcacccccgagcaactctgagagccttgattttgtgtcctcagcatatgtttgtgtaatacagaaagagaagcagttgcca -continued agtgaaagggatgttggtctccaaaattatagtttgatcccacaaacacacaaacacatacatgcaaaggattgtttgcttcacggtttttg atatttaattcaatgctgttggaacagcacaaaaactaagtgtcagtttaacagaatcacttgtccttttagcattaaaataacatggaactta atgctttaatttcccaacatgcctttttatttagaaagattcagacttttatttcatttagaaataaaatgccattttatttagaaagatacaggag cattcattcacggaactttcagatctcagtccactgcataaaatcttgatcctgtaataatagtttctgtatcttgcatattcattcaacaggttt aacgcgatgagcaaattaatgttcatcgtttttaacatgtttcgtcttaatcagaacccacattctcaacgttaattgaacgtacataggacta tacaagggttagtaaataagacagaaactgttgctcatttaaccaccgtcactttgga

>HS4 CHROMATIN INSULATOR

SEQ ID NO: 4 cagcctaaagctttttccccgtatccccccaggtgtctgcaggctcaaagagcagcgagaagcgttcagaggaaagcgatcccgtgcc accttccccgtgcccgggctgtccccgcacgctgccggctcggggatgcggggggagcgccggaccggagcggagccccgggc ggctcgctgctgccccctagcgggggagggacgtaattacatccctgggggctttgggggggggctgtccccgtgagctc

>KOZAK CONSENSUS SEQUENCE

SEQ ID NO: 5 ccacc

>Human PSEN1 with all tolerant, non-preferred codons changed to highly preferred synonymous codon. Changed codons in lower case:

SEQ ID NO: 6

ATGACAGAGTTACCTGCAcctTTGTCCTACTTCCAGAATGCACAGATGTCTGAGGA

CAACCACCTGAGCAATACTGTACGTAGCCAGAATGACAATAGAGAACGGCAGGA

GCACAACGACAGACGGAGCctgGGCCACCCTGAGCCActgTCTAATGGAagaCCCCA

GGGTAACTCCCGGCAGGTGGTGGAGcagGATGAGGAAGAAGATGAGGAGCTGAC

ActgAAATATGGCGCCAAGcacGTGATCATGCTCTTTGTCCCTGTGACTCTCTGCATG

GTGGTGGTCGTGGCTACCATTAAGTCAGTCAGCTTTTATACCCGGAAGGATGGGC

AGCTAATCTATACCCCATTCACAGAAGATACCGAGACTGTGGGCCAGAGAGCCC

TGCACTCAATTCTGAATGCTGCCATCATGATCAGTGTCATTGTTGTCATGACTATC

CTCCTGGTGGTTCTGTATAAATACAGGTGCTATAAGGTCATCCATGCCTGGctgATT

ATATCATCTctgTTGctgCTGTTCTTTTTTTCATTCATTTACctgGGGGAAGTGTTTAAA

ACCTATAACGTTGCTGTGGACTACATTACTGTTGCACTCCTGATCTGGAATTTTggc

GTGGTGGGAATGATTTCCATTCACTGGAAAggcCCActgagaCTCCAGCAGGCATATC

TCATTATGATTAGTGCCCTCATGGCCCTGGTGTTTATCAAGTACCTCCCTGAATGG

ACTgccTGGCTCATCTTGGCTGTGATTTCAGTGTATGATTTAGTGGCTGTTctgTGTcc tAAAGGTCCActgCGTATGCTGgtgGAAACAGCTCAGGAGAGAAATGAAaccctgTTTC CAGCTCTCATTTACTCCTCAACAATGGTGTGGctgGTGAATATGGCAGAAGGAGAC cctGAAGCTCAAAGGAGAgtgTCCAAAAATTCCAAGTATAATGCAGAAAGCACAGA AAGGGAGTCAcagGACACTGTTGCAGAGAATGATGATGGCGGGTTCAGTGAGGAA TGGGAAGCCCAGAGGGACAGTcacctgGGGCCTcacCGCTCTACACCTGAGTCAagaG CTGCTGTCCAGGAActgTCCAGCAGTATCCTCGCTggcGAAGACCCAGAGGAAAGG GGAGTAAAACTTGGATTGGGAGATTTCATTTTCTACAGTGTTCTGGTTggcAAAGC CTCAGCAACAGCCAGTGGAGACTGGAACACAACCATAGCCTGTTTCGTAGCCatcT TAATTggcctgTGCCTTACActgctgCTCctgGCCATTTTCAAGAAAGCActgCCAGCTctgC CAATCTCCATCACCTTTGGGCTTGTTTTCTACTTTGCCACAGATTATctggtgCAGCC TTTTATGGACcagctgGCATTCcaccagTTTTATATCtaa >SYNTHETIC PSEN1 CDNA with all CpG dinucleotides removed, all tolerant codons changed to highly preferred synonymous codon, and some intolerant codon changed as a consequence of eliminating CpG dinucleotides. Changed codons in lower case; changed -continued intolerant codons in lower case and underlined.

SEQ ID NO: 7

ATGACAGAGTTACCTGCAccaTTGTCCTACTTCCAGAATGCACAGATGTCTGAGGA
CAACCACCTGAGCAATACTGTAagaAGCCAGAATGACAATAGAGAAagaCAGGAGC
ACaatGACAGAagaAGCCTTGGCCACCCTGAGCCATTATCTAATGGAagaCCCCAGGG
TAACTCCagaCAGGTGGTGGAGCAAGATGAGGAAGAAGATGAGGAGCTGACATTG
AAATATggtGCCAAGCATGTGATCATGCTCTTTGTCCCTGTGACTCTCTGCATGGTG
GTGgttGTGGCTACCATTAAGTCAGTCAGCTTTTATACCagaAAGGATGGGCAGCTA
ATCTATACCCCATTCACAGAAGATactGAGACTGTGGGCCAGAGAGCCCTGCACTC
AATTCTGAATGCTGCCATCATGATCAGTGTCATTGTTGTCATGACTATCCTCCTGG
TGGTTCTGTATAAATACAGGTGCTATAAGGTCATCCATGCCTGGCTTATTATATC
ATCTCTATTGTTGCTGTTCttcTTTTCATTCATTTACTTGGGGGAAGTGTTTAAAACC
TATaatGTTGCTGTGGACTACATTACTGTTGCACTCCTGATCTGGAATTTTGGTGTG
GTGGGAATGATTTCCATTCACTGGAAAGGTCCACTTagaCTCCAGCAGGCATATCT
CATTATGATTAGTGCCCTCATGGCCCTGGTGTTTATCAAGTACCTCCCTGAATGG
ACTgccTGGCTCATCTTGGCTGTGATTTCAGTATATGATTTAGTGGCTGTTTTGTGT
cccAAAGGTCCACTTagaATGCTGGTTGAAACAGCTCAGGAGAGAAATGAAaccCTT
TTTCCAGCTCTCATTTACTCCTCAACAATGGTGTGGTTGGTGAATATGGCAGAAG
GAGACccaGAAGCTCAAAGGAGAGTATCCAAAAATTCCAAGTATAATGCAGAAAG
CACAGAAAGGGAGTCACAAGACACTGTTGCAGAGAATGATGATggtGGGTTCAGT
GAGGAATGGGAAGCCCAGAGGGACAGTCATCTAGGGCCTCATaggTCTACACCTG
AGTCAagaGCTGCTGTCCAGGAACTTTCCAGCAGTATCctgGCTGGTGAAGACCCAG
AGGAAAGGGGAGTAAAACTTGGATTGGGAGATTTCATTTTCTACAGTGTTCTGGT
TGGTAAAGCCTCAGCAACAGCCAGTGGAGACTGGAACACAACCATAGCCTGTtttG
TAGCCATATTAATTGGTTTGTGCCTTACATTATTACTCCTTGCCATTTTCAAGAAA
GCATTGCCAGCTCTTCCAATCTCCATCACCTTTGGGCTTGTTTTCTACTTTGCCAC
AGATTATCTTGTACAGCCTTTTATGGACCAATTAGCATTCCATCAATTTTATATCT
AG

>GENOMIC/CDNA HYBRID PSEN1 GENE

SEQ ID NO: 8 cccAGATCTgacaacagcctttgcggtccttagacagcttggcctggaggagaacacatgaaagaaaggtttgtttctgcttaatg
taatctatgaaagtgtttttataacagtataattgtagtgcacaaagttctgtttttctttcccttttcagaacctcaagaggctttgttttctgtg
aaacagtatttctatacagttgccaccatgacagagttacctgcaccgttgtcctacttccagaatgcacagatgtctgaggacaaccac
ctgagcaatactgtacgtagccaggtacagtgtcagtctctgaaactgcctttgccagactggattcacttatcatctcccctcacctctga
gaaatgctgagggggctaggcaggctttctctacttttagaactcatagtgacgggtctgttgttaatcccaggtctaaccgttaccttga
ttctgctgagaatctgatttactgaaaatgtttttcttgtgcttatagaatgacaatagagaacggcaggagcacaacgacagacggagc
cttggccaccctgagccattatctaatggacgaccccagggtaactcccggcaggtggtggagcaagatgaggaagaagatgagga
gctgacattgaaatatggcgccaagcatgtgatcatgctctttgtccctgtgactctctgcatggtggtggtcgtggctaccattaagtcag
tcagcttttatacccggaaggatgggcagctgtacgtatgagttttgttttattattctcaaagccagtgtggcttttctttacagcatgtcatc
atcaccttgaaggcctctgcattgaaggggcatgacttgaattaagaaaaagaaaattctgtgttggaggtggtaatgtggttggtgatct
ccattaacactgacctagggcttttgtgtttgttttattgtagaatctataccccattcacagaagataccgagactgtgggccagagagcc
ctgcactcaattctgaatgctgccatcatgatcagtgtcattgttgtcatgactatcctcctggtggttctgtataaatacaggtgctataagg
tcatccatgcctggcttattatatcatctctattgttgctgttctttttttcattcatttacttgggggaagtgtttaaaacctataacgttgctgtg -continued gactacattactgttgcactcctgatctggaattttggtgtggtgggaatgatttccattcactggaaaggtccacttcgactccagcaggc atatctcattatgattagtgccctcatggccctggtgtttatcaagtacctccctgaatggactgcgtggctcatcttggctgtgatttcagta tatgatttagtggctgttttgtgtccgaaaggtccacttcgtatgctggttgaaacagctcaggagagaaatgaaacgctttttccagctctc atttactcctcaacaatggtgtggttggtgaatatggcagaaggagacccggaagctcaaaggagagtatccaaaaaattccaagtataa tgcagaaagcacagaaagggagtcacaagacactgttgcagagaatgatgatggcgggttcagtgaggaatgggaagcccagagg gacagtcatctagggcctcatcgctctacacctgagtcacgagctgctgtccaggaactttccagcagtatcctcgctggtgaagaccc agaggaaaggggagtaaaacttggattgggagatttcattttctacagtgttctggttggtaaagcctcagcaacagccagtggagact ggaacacaaccatagcctgtttcgtagccatattaattggtttgtgccttacattattactccttgccattttcaagaaagcattgccagctctt ccaatctccatcacctttgggcttgttttctactttgccacagattatcttgtacagccttttatggaccaattagcattccatcaattttatatct agcataGTCGACc

>MALAT1 MRNA STABILITY ELEMENT

SEQ ID NO: 9 tagggtcatgaaggtttttcttttcctgagaaaacaacacgtattgttttctcaggttttgctttttggcctttttctagcttaaaaaaaaaaaaa gcaaaagatgctggtggttggcactcctggtttccaggacggggttcaaatccctgcggcgtctttgctttgact

>3' FLANKING SEQUENCE FROM NATIVE PSEN1 RNA

SEQ ID NO: 10

GGAAACAAAACAGCGGCTGGTCTGGAAGGAACCTGAGCTACGAGCCGCGGCGG

CAGCGGGGCGGCGGGGAAGCGTATACCTAATCTGGGAGCCTGCAAGTGACAACA

GCCTTTGCGGTCCTTAGACAGCTTGGCCTGGAGGAGAACACATGAAAGAAAGAA

CCTCAAGAGGCTTTGTTTTCTGTGAAACAGTATTTCTATACAGTTGCTCCA

>5' FLANKING SEQUENCE FROM NATIVE PSEN1 MRNA

SEQ ID NO: 11

CATATTTGCGGTTAGAATCCCATGGATGTTTCTTCTTTGACTATAACAAAATCTGG

GGAGGACAAAGGTGATTTTCCTGTGTCCACATCTAACAAAGTCAAGATTCCCGGC

TGGACTTTTGCAGCTTCCTTCCAAGTCTTCCTGACCACCTTGCACTATTGGACTTT

GGAAGGAGGTGCCTATAGAAAACGATTTTGAACATACTTCATCGCAGTGGACTG

TGTCCCTCGGTGCAGAAACTACCAGATTTGAGGGACGAGGTCAAGGAGATATGA

TAGGCCCGGAAGTTGCTGTGCCCCATCAGCAGCTTGACGCGTGGTCACAGGACG

ATTTCACTGACACTGCGAACTCTCAGGACTACCGTTACCAAGAGGTTAGGTGAAG

TGGTTTAAACCAAACGGAACTCTTCATCTTAAACTACACGTTGAAAATCAACCCA

ATAATTCTGTATTAACTGAATTCTGAACTTTTCAGGAGGTACTGTGAGGAAGAGC

AGGCACCAGCAGCAGAATGGGGAATGGAGAGGTGGGCAGGGGTTCCAGCTTCCC

TTTGATTTTTTGCTGCAGACTCATCCTTTTTAAATGAGACTTGTTTTCCCCTCTCTT

TGAGTCAAGTCAAATATGTAGATTGCCTTTGGCAATTCTTCTTCTCAAGCACTGA

CACTCATTACCGTCTGTGATTGCCATTTCTTCCCAAGGCCAGTCTGAACCTGAGG

TTGCTTTATCCTAAAAGTTTTAACCTCAGGTTCCAAATTCAGTAAATTTTGGAAAC

AGTACAGCTATTTCTCATCAATTCTCTATCATGTTGAAGTCAAATTTGGATTTTCC

ACCAAATTCTGAATTTGTAGACATACTTGTACGCTCACTTGCCCCAGATGCCTCC

TCTGTCCTCATTCTTCTCTCCCACACAAGCAGTCTTTTTCTACAGCCAGTAAGGCA

GCTCTGTCGTGGTAGCAGATGGTCCCATTATTCTAGGGTCTTACTCTTTGTATGAT

GAAAAGAATGTGTTATGAATCGGTGCTGTCAGCCCTGCTGTCAGACCTTCTTCCA

CAGCAAATGAGATGTATGCCCAAAGACGGTAGAATTAAAGAAGAGTAAAATGG

CTGTTGAAGCACTTTCTGTCCTGGTATTTTGTTTTTGCTTTTGCCACACAGTAGCT

-continued

CAGAATTTGAACAAATAGCCAAAAGCTGGTGGTTGATGAATTATGAACTAGTTGT

ATCAACACAAAGCAAGAGTTGGGGAAAGCCATATTTAACTTGGTGAGCTGTGGG

AGAACCTGGTGGCAGAAGGAGAACCAACTGCCAAGGGGAAAGAGAAGGGGCCT

CCAGCAGCGAAGGGGATACAGTGAGCTAATGATGTCAAGGAGGAGTTTCAGGTT

ATTCTCGTCAGCTCCACAAATGGGTGCTTTGTGGTCTCTGCCCGCGTTACCTTTCC

TCTCAATGTACCTTTGTGTGAACTGGGCAGTGGAGGTGCCTGCTGCAGTTACCAT

GGAGTTCAGGCTCTGGGCAGCTCAGTCAGGCAAAACACACAAACAGCCATCAGC

CTGTGTGGGCTCAGGGCACCTCTGGACAAAGGCTTGTGGGGCATAACCTTCTTTA

CCACAGAGAGCCCTTAGCTATGCTGATCAGACCGTAAGCGTTTATGAGAAACTTA

GTTTCCTCCTGTGGCTGAGGAGGGGCCAGCTTTTTCTTCTTTTGCCTGCTGTTTTCT

CTCCCAATCTATGATATGATATGACCTGGTTTGGGGCTGTCTTTGGTGTTTAGAAT

ATTTGTTTTCTGTCCCAGGATATTTCTTATAAGAACCTAACTTCAAGAGTAGTGTG

CGAGTACTGATCTGAATTTAAATTAAAATTGGCTTATATTAGGCAGTCACAGACA

GGAAAAATAAGAGCTATGCAAAGAAAGGGGGATTTAAAGTAGTAGGTTCTATCA

TCTCAATTCATTTTTTTCCATGAAATCCCTTCTTCCAAGATTCATTCCCTCTCTCAG

ACATGTGCTAGCATGGGTATTATCATTGAGAAAGCACAGCTACAGCAAAGCCAC

CTGAATAGCAATTTGTGATTGGAAGCATTCTTGAGGGATCCCTAATCTAGAGTAA

TTTATTTGTGTAAGGATCCCAAATGTGTTGCACCTTTCATGATACATTTCTTCTCT

GAAGAGGGTACGTGGGGTGTGTGTATTTAAATCCATCCTATGTATTACTGATTGT

CCTGTGTAGAAAGATGGCAATTATTCTGTCTCTTTCTCCAAGTTTGAGCCACATCT

CAGCCACATTGTTAGACAGTGTACAGAGAACCTATCTTTCCTTTTTTTTTTTTTAA

AGGACAGGATTTTGCTGTGTTGCCCAGGCTAGACTTGAACTCCTGGGCTCAAGTA

ATCCACCTCAGCCTGAGTAGCTGAGACTACAGCCCATCTTATTTCTTTAAATCATT

CATCTCAGGCAGAGAACTTTTCCCTCAAACATTCTTTTTAGAATTAGTTCAGTCAT

TCCTAAAACATCCAAATGCTAGTCTTCCACCATGAAAAATAGATTGTCACTGGAA

AGAACAGTAGCAATTTCCATAAGGATGTGCCTTCACTCACACGGGACAGGCGGT

GGTTATAGAGTCGGGCAAAACCAGCAGTAGAGTATGACCAGCCAAGCCAATCTG

CTTAATAAAAAGATGGAAGACAGTAAGGAAGGAAAGTAGCCACTAAGAGTCTG

AGTCTGACTGGGCTACAGAATAAAGGGTATTTATGGACAGAATGTCATTACATGC

CTATGGGAATACCAATCATATTTGGAAGATTTGCAGATTTTTTTTCAGAGAGGAA

AGACTCACCTTCCTGTTTTTGGTTCTCAGTAGGTTCGTGTGTGTTCCTAGAATCAC

AGCTCTGACTCCAAATGACTCAATTTCTCAATTAGAAAAAGTAGAAGCTTTCTAA

GCAACTTGGAAGAAAACAGTCATAAGTAAGCAATTTGTTGATTTTACTACAGAA

GCAACAACTGAAGAGGCAGTGTTTTTACTTTCAGACTCCGGGATTCCCATTCTGT

AGTCTCTCTGCTTTTAAAAACCCTCCTTTTGCAATAGATGCCCAAACAGATGATG

TTTATTACTTGTTATTTACGTGGCCTCAGACAGTGTATGTATTCTCGATATAACTT

GTAGAGTGTGAAATATAAGTTTAACTACCAAATAAGGTCTCCCAGGGTTAGATG

ACTGCGGGAAGCCTTTGATCCCAACCCCCAAGGCTTTGTATATTTGATCATTTGT

GATCTAACCCTGGAAGAAAAAGAGCTCAGAAACCCACTATGAAAAAATTTGTTCA

GTGTTTTCTGTGTTCCCGTAGGTTCTGGAGTCTGAGGATGCAAAGATGAATAAGA

TAAATTCTCAGAATGTAGTTATAATCTCTTGTTTTCTGGTATATGCCATCTTTCTTT

-continued

AACTTCTCTAAAATATTGGGTATTTGTCAAATAACCACTTTTAACAGTTACCATTA
CTGAGGGCTTATACATTGGTGTTATAAAAGTGACTTGATTCAGAAATCAATCCAT
TCAGTAAAGTACTCCTTCTCTAAATTTGCTGTTATGTCTATAAGGAACAGTTTGAC
CTGCCCTTCTCCTCACCTCCTCACCTGCCTTCCAACATTGAATTTGGAAGGAGAC
GTGAAAATTGGACATTTGGTTTTGCCCTTGGGCTGGAAACTATCATATAATCATA
AGTTTGAGCCTAGAAGTGATCCTTGTGATCTTCTCACCTCTTTAAATTCCCACAAC
ACAAGAGATTAAAAACAGAGGTTTCAGCTCTTCATAGTGCGTTGTGAAATGGCTG
GCCAGAGTGTACCAACAAAGCTGTCATCGGGCTCACAGCTCAGAGACATCTGCA
TGTGATCATCTGCATAGTCCTCTCCTCTAACGGGAAACACCTCAGATTTGCATAT
AAAAAAGCACCCTGGTGCTGAAATGAACCCCTTTCTTGAACATCAAAGCTGTCTC
CCACAGCCTTGGGCAGCAGGGTGCCTCTTAGTGGATGTGCTGGGTCCACCCTGAG
CCCTGACATGTGGTGGCAGCATTGCCAGTTGGTCTGTGTGTCTGTGTAGCAGGGA
CGATTTCCCAGAAAGCAATTTTCCTTTTGAAATACGTAATTGTTGAGACTAGGCA
GTTTCAAAGTCAGCTGCATATAGTAGCAAGTACAGGACTGTCTTGTTTTTGGTGT
CCTTGGAGGTGCTGGGGTGAGGGTTTCAGTGGGATCATTTACTCTCACATGTTGT
CTGCCTTCTGCTTCTGTGGACACTGCTTTGTACTTAATTCAGACAGACTGTGAATA
CACCTTTTTTATAAATACCTTTCAAATTCTTGGTAAGATATAATTTTGATAGCTGA
TTGCAGATTTTCTGTATTTGTCAGATTAATAAAGACTGCATGAATCCA

>XP_011535274.1 human presenilin-1 isoform X1 [467 amino acids]

SEQ ID NO: 12

MTELPAPLSYFQNAQMSEDNHLSNTVRSQNDNRERQEHNDRRSLGHPEPLSNGRPQ
GNSRQVVEQDEEEDEELTLKYGAKHVIMLFVPVTLCMVVVVATIKSVSFYTRKDGQ
LIYTPFTEDTETVGQRALHSILNAAIMISVIVVMTILLVVLYKYRCYKVIHAWLIISSLL
LLFFFSFIYLGEVFKTYNVAVDYITVALLIWNFGVVGMISIHWKGPLRLQQAYLIMIS
ALMALVFIKYLPEWTAWLILAVISVYDLVAVLCPKGPLRMLVETAQERNETLFPALI
YSSTMVWLVNMAEGDPEAQRRVSKNSKYNAESTERESQDTVAENDDGGFSEEWEA
QRDSHLGPHRSTPESRAAVQELSSSILAGEDPEERGVKLGLGDFIFYSVLVGKASATA
SGDWNTTIACFVAILIGLCLTLLLLAIFKKALPALPISITFGLVFYFATDYLVQPFMDQL
AFHQFYI

>Gene (cDNA) for human PSEN1 463 amino acid isoform X2 (GenBank NM_007318.3)

SEQ ID NO: 13 atgacagagttacctgcaccgttgtcctacttccagaatgcacagatgtctgaggacaaccacctgagcaatactaatgacaatagaga
acggcaggagcacaacgacagacggagccttggccaccctgagccattatctaatggacgaccccagggtaactcccggcaggtg
gtggagcaagatgaggaagaagatgaggagctgacattgaaatatggcgccaagcatgtgatcatgctctttgtccctgtgactctctg
catggtggtggtcgtggctaccattaagtcagtcagcttttatacccggaaggatgggcagctaatctataccccattcacagaagatac
cgagactgtgggccagagagccctgcactcaattctgaatgctgccatcatgatcagtgtcattgttgtcatgactatcctcctggtggtt
ctgtataaatacaggtgctataaggtcatccatgcctggcttattatatcatctctattgttgctgttcttttttttcattcatttacttgggggaagt
gtttaaaacctataacgttgctgtggactacattactgttgcactcctgatctggaattttggtgtggtgggaatgatttccattcactggaaa
ggtccacttcgactccagcaggcatatctcattatgattagtgccctcatggccctggtgtttatcaagtacctccctgaatggactgcgtg
gctcatcttggctgtgatttcagtatatgatttagtggctgttttgtgtccgaaaggtccacttcgtatgctggttgaaacagctcaggagag
aaatgaaacgctttttccagctctcatttactcctcaacaatggtgtggttggtgaatatggcagaaggagacccggaagctcaaaggag
agtatccaaaaattccaagtataatgcagaaagcacagaaagggagtcacaagacactgttgcagagaatgatgatggcgggttcagt -continued gaggaatgggaagcccagagggacagtcatctagggcctcatcgctctacacctgagtcacgagctgctgtccaggaactttccagc agtatcctcgctggtgaagacccagaggaaaggggagtaaaacttggattgggagatttcattttctacagtgttctggttggtaaagcct cagcaacagccagtggagactggaacacaaccatagcctgtttcgtagccatattaattggtttgtgccttacattattactccttgccattt tcaagaaagcattgccagctcttccaatctccatcacctttgggcttgttttctactttgccacagattatcttgtacagccttttatggaccaa ttagcattccatcaattttatatctag >presenilin-1 isoform X2 [463 amino acids]

SEQ ID NO: 14

MTELPAPLSYFQNAQMSEDNHLSNTNDNRERQEHNDRRSLGHPEPLSNGRPQGNSR

QVVEQDEEEDEELTKYGAKHVIMLFVPVTLCMVVVVATIKSVSFYTRKDGQLIYTPF

TEDTETVGQRALHSILNAAIMISVIVVMTILLVVLYKYRCYKVIHAWLIISSLLLLFFFS

FIYLGEVFKTYNVAVDYITVALLIWNFGVVGMISIHWKGPLRLQQAYLIMISALMAL

VFIKYLPEWTAWLILAVISVYDLVAVLCPKGPLRMLVETAQERNETLFPALIYSSTMV

WLVNMAEGDPEAQRRVSKNSKYNAESTERESQDTVAENDDGGFSEEWEAQRDSHL

GPHRSTPESRAAVQELSSSILAGEDPEERGVKLGLGDFIFYSVLVGKASATASGDWNT

TIACFVAILIGLCLTLLLAIFKKALPALPISITFGLVFYFATDYLVQPFMDQLAFHQFYI

>presenelin-1 isoform X1 coding sequence with intolerant codons underlined

SEQ ID NO: 15

ATG ACA GAG TTA CCT GCA CCG TTG TCC TAC TTC CAG AAT GCA CAG ATG

TCT GAG GAC AAC CAC CTG AGC AAT ACT GTA CGT AGC CAG AAT GAC AAT

AGA GAA CGG CAG GAG CAC AAC GAC AGA CGG AGC CTT GGC CAC CCT GAG

CCA TTA TCT AAT GGA CGA CCC CAG GGT AAC TCC CGG CAG GTG GTG GAG

CAA GAT GAG GAA GAA GAT GAG GAG CTG ACA TTG AAA TAT GGC GCC AAG

CAT GTG ATC ATG CTC TTT GTC CCT GTG ACT CTC TGC ATG GTG GTG GTC GTG

GCT ACC ATT AAG TCA GTC AGC TTT TAT ACC CGG AAG GAT GGG CAG CTA

ATC TAT ACC CCA TTC ACA GAA GAT ACC GAG ACT GTG GGC CAG AGA GCC

CTG CAC TCA ATT CTG AAT GCT GCC ATC ATG ATC AGT GTC ATT GTT GTC ATG

ACT ATC CTC CTG GTG GTT CTG TAT AAA TAC AGG TGC TAT AAG GTC ATC CAT

GCC TGG CTT ATT ATA TCA TCT CTA TTG TTG CTG TTC TTT TTT TCA TTC

ATT TAC TTG GGG GAA GTG TTT AAA ACC TAT AAC GTT GCT GTG GAC TAC ATT

ACT GTT GCA CTC CTG ATC TGG AAT TTT GGT GTG GTG GGA ATG ATT TCC ATT

CAC TGG AAA GGT CCA CTT CGA CTC CAG CAG GCA TAT CTC ATT ATG ATT

AGT GCC CTC ATG GCC CTG GTG TTT ATC AAG TAC CTC CCT GAA TGG ACT

GCG TGG CTC ATC TTG GCT GTG ATT TCA GTA TAT GAT TTA GTG GCT GTT TTG

TGT CCG AAA GGT CCA CTT CGT ATG CTG GTT GAA ACA GCT CAG GAG AGA

AAT GAA ACG CTT TTT CCA GCT CTC ATT TAC TCC TCA ACA ATG GTG TGG TTG

GTG AAT ATG GCA GAA GGA GAC CCG GAA GCT CAA AGG AGA GTA TCC AAA

AAT TCC AAG TAT AAT GCA GAA AGC ACA GAA AGG GAG TCA CAA GAC ACT

GTT GCA GAG AAT GAT GAT GGC GGG TTC AGT GAG GAA TGG GAA GCC CAG

AGG GAC AGT CAT CTA GGG CCT CAT CGC TCT ACA CCT GAG TCA CGA GCT

GCT GTC CAG GAA CTT TCC AGC AGT ATC CTC GCT GGT GAA GAC CCA

GAG GAA AGG GGA GTA AAA CTT GGA TTG GGA GAT TTC ATT TTC TAC

AGT GTT CTG GTT GGT AAA GCC TCA GCA ACA GCC AGT GGA GAC TGG

AAC ACA ACC ATA GCC TGT TTC GTA GCC ATA TTA ATT GGT TTG TGC CTT ACA

-continued

TTA TTA CTC CTT GCC ATT TTC AAG AAA GCA TTG CCA GCT CTT CCA ATC TCC

ATC ACC TTT GGG CTT GTT TTC TAC TTT GCC ACA GAT TAT CTT GTA CAG CCT

TTT ATG GAC CAA TTA GCA TTC CAT CAA TTT TAT ATC TAG

Inverted terminal repeats (ITR) for single-stranded AAV2
nc_001401.2 nt 1-145 and 4535-4679
>left ITR

SEQ ID NO: 16 ttggccactc cctctctgcg cgctcgctcg ctcactgagg ccgggcgacc aaaggtcgcc cgacgcccgg gctttgcccg ggcggcctca gtgagcgagc gagcgcgcag agagggagtg gccaactcca tcactagggg ttcct >right ITR

SEQ ID NO: 17 aggaac ccctagtgat ggagttggcc actccctctc tgcgcgctcg ctcgctcact gaggccgggc gaccaaaggt cgcccgacgc ccgggctttg cccgggcggc ctcagtgagc gagcgagcgc gcagagaggg agtggccaa Inverted terminal repeats for self-complementary AAV2
>left ITR

SEQ ID NO: 18 ctgcgcgctcgctcgctcactgaggccgcccgggcaaagcccgggcgtcgggcgacctttggtcgcccggcctcagtgagcgagc gagcgcgcagagagggagtg >right ITR

SEQ ID NO: 19 aggaacccctagtgatggagttggccactccctctctgcgcgctcgctcgctcactgaggccgggcgaccaaaggtcgcccgacgc ccgggctttgcccgggcggcctcagtgagcgagcgagcgcgcag Introns
>MVM NC_001510.1 minute virus of mice intron nt 2312-2403

SEQ ID NO: 20 aagaggtaa gggtttaagg gatggttggt tggtggggta ttaatgttta attacctgtt ttacaggcct gaaatcactt ggttttaggt tgg hybrid adenovirus SD/IgG SA; ac_000008.1 adenovirus type 5 tripartite leader, nt 573-758
and nc_000078.6 mus musculus strain c57bl/6j nt 115158736-115158695

SEQ ID NO: 21 tctgccac ggaggtgtta ttaccgaaga aatggccgcc agtcttttgg accagctgat cgaagaggta ctggctgata atcttccacc tcctagccat tttgaaccac ctacccttca cgaactgta t gatttagacg tgacggcccc cgaagatccc aacgaggagg cggtttcgca gatttttc tgacatc cactttgcct ttctctccac aggtgtccac tcccaaa >hBG intron chimeric cmv promoter 601-734, cmv intron1 1263-1294, followed by the intron
ii of the beta-globin gene, the 3'end of the intron is fused to the first 20 nucleotides of exon 3
of the beta globin gene.

SEQ ID NO: 22 tcagatcgcctggagacgccatccacgctgttttgacctccatagaagacaccgggaccgatccagcctccgcggattcgaatcccg gccgggaacggtgcattggaacgcggattccccgtgccaagagtgacgtaagtaccgcctatagagtctataggcccacaaaaaatgctttc ttcttttaatatactttttttgtttatcttatttctaatactttccctaatctctttctttcagggcaataatgatacaatgtatcatgcctctttgc accattctaaagaataacagtgataatttctgggttaaggcaatagcaatatttctgcatataaatatttctgcatataaattgtaactgatgta agaggtttcatattgctaatagcagctacaatccagctaccattctgcttttattttatggttgggataaggctggattattctgagtccaagc taggccctttttgctaatcatgttcatacctcttatcttcctcccacagctcctgggcaacgtgctggtctgtgtgctggcccatcactttggc aaagaatt Promoters
>CAG lt727518.1, nt 3074 to 4750

SEQ ID NO: 23 gacattg attattgact agttattaat agtaatcaat tacggggtca ttagttcata gcccatatat ggagttccgc gttacataac ttacggtaaa tggcccgcct ggctgaccgc ccaacgaccc ccgcccattg acgtcaataa tgacgtatgt tcccatagta acgccaatag ggactttcca ttgacgtcaa tgggtggagt atttacggta aactgcccac ttggcagtac atcaagtgta tcatatgcca agtacgcccc ctattgacgt caatgacggt aaatggcccg cctggcatta tgcccagtac atgaccttat gggactttcc tacttggcag tacatctacg tattagtcat cgctattacc atggtcgagg tgagccccac gttctgcttc -continued actctcccca tctcccccccc ctccccaccc ccaattttgt atttatttat tttttaatta ttttgtgcag cgatgggggc gggggggggg gggggcccc ccccaggcgg ggcggggcgg ggcgaggggc ggggcggggc gaggcggaaa ggtgcggcgg cagccaatca gagcggcgcg ctccgaaagt ttccttttat ggcgaggcgg cggcggcggc ggccctataa aaagcgaagc gcgcggcggg cgggagtcgt tgcgcgctgc cttcccccgg tgccccgctc cgccgccgcc tcgcgccgcc cgccccggct ctgactgacc gcgttactcc cacaggtgag cgggcgggac ggcccttctc ctccgggctg taattagcgc ttggtttaat gacggcttgt ttcttttctg tggctgcgtg aaagccttga ggggctccgg gagggccctt tgtgcggggg gagcggctcg gggggtgcgt gcgtgtgtgt gtgcgtgggg agcgccgcgt gcggctccgc gctgcccggc ggctgtgagc gctgcgggcg cggcgcgggg ctttgtgcgc tccgcagtgt gcgcgagggg agcgcggccg gggcggtgc cccgcggtgc ggggggggct gcgaggggaa caaaggctgc gtgcggggtg tgtgcgtggg ggggtgagca gggggtgtgg gcgcgtcggt cgggctgcaa ccccccctgc accccccctcc ccgagttgct gagcacggcc cggcttcggg tgcggggctc cgtacggggc gtggcgcggg gctcgccgtg ccgggcgggg ggtggcggca ggtgggggtg ccgggcgggg cggggccgcc tcgggccggg gagggctcgg gggaaggggc gcggcggccc ccggagcgcc ggcggctgtc gaggcgcggc gagccgcagc cattgccttt tatggtaatc gtgcgagagg gcgcagggac ttcctttgtc ccaaatctgt gcggagccga aatctgggag gcgccgccgc acccccctcta gcgggcgcgg ggcgaagcgg tgcggcgccg gcaggaagga aatgggcggg gagggccttc gtgcgtcgcc gcgccgccgt ccccttctcc ctctccagcc tcggggctgt ccgcgggggg acggctgcct tcggggggga cggggcaggg cggggttcgg cttctggcgt gtgaccggcg gctctagagc ctctgctaac catgttcatg ccttcttctt tttcctacag >CBA nc_006273.2, nt 175625-175294 and GenBank accession no. x00182.1, nt 280-540.

SEQ ID NO: 24 cgcgtcgacattgattattgactagttattaatagtaatcaattacggggtcattagttcatagcccatatatggagttccgcgttacataact tacggtaaatggcccgcctggctgaccgcccaacgacccccgcccattgacgtcaataatgacgtatgttcccatagtaacgccaata gggactttccattgacgtcaatgggtggagtatttacggtaaactgcccacttggcagtacatcaagtgtatcatatgccaagtacgccc cctattgacgtcaatgacggtaaatggcccgcctggcattatgcccagtacatgaccttatgggactttcctacttggcagtacatctacg tattagtcatcgctattaccatgtcgaggccacgttctgcttcactctccccatctcccccccctccccacccccaattttgtatttatttattttt taattattttgtgcagcgatgggggcgggggggggggggcgcgcgccaggcggggcggggcggggcgaggggcggggcgggg cgaggcggagaggtgcggcggcagccaatcagagcggcgcgctccgaaagtttccttttatggcgaggcggcggcggcggcggc cctataaaaagcgaagcgcgcggcggg >UBC d63791 nt 3553-4729

SEQ ID NO: 25 ggtgcagcggcctccgcgccgggttttggcgcctcccgcgggcgcccccctcctcacggcgagcgctgccacgtcagacgaagg gcgcaggagcgttcctgatccttccgcccggacgctcaggacagcggcccgctgctcataagactcggccttagaaccccagtatca gcagaaggacattttaggacgggacttgggtgactctagggcactggttttctttccagagagcggaacaggcgaggaaaagtagtcc cttctcggcgattctgcggagggatctccgtggggcggtgaacgccgatgattatataaggacgcgccgggtgtggcacagctagttc cgtcgcagccgggatttgggtcgcggttcttgtttgtggatcgctgtgatcgtcacttggtgagttgcgggctgctgggctggccgggg ctttcgtggccgccgggccgctcggtgggacggaagcgtgtggagagaccgccaagggctgtagtctgggtccgcgagcaaggtt gccctgaactgggggttggggggagcgcacaaaatggcggctgttcccgagtcttgaatggaagacgcttgtaaggcgggctgtga ggtcgttgaaacaaggtgggggggcatggtgggcggcaagaacccaaggtcttgaggccttcgctaatgcgggaaagctcttattcgg gtgagatgggctggggcaccatctggggaccctgacgtgaagtttgtcactgactggagaactcgggtttgtcgtctggttgcggggg cggcagttatgcggtgccgttgggcagtgcacccgtacctttgggagcgcgcgcctcgtcgtgtcgtgacgtcacccgttctgttggct tataatgcagggtggggccacctgccggtaggtgtgcggtaggcttttctccgtcgcaggacgcagggttcgggcctagggtaggct ctcctgaatcgacaggcgccggacctctggtgaggggagggataagtgaggcgtcagtttctttggtcggttttatgtacctatcttctta agtagctgaagctccggttttgaactatgcgctcggggttggcgagtgtgttttgtgaagttttttaggcaccttttgaaatgtaatcatttgg gtcaatatgtaattttcagtgttagactagtaaa -continued >PGK nc_000086.7 106186725-106187235

SEQ ID NO: 26 ttctaccgggtaggggaggcgcttttcccaaggcagtctggagcatgcgctttagcagccccgctgggcacttggcgctacacaagtg gcctctggcctcgcacacattccacatccaccggtaggcgccaaccggctccgttctttggtggccccttcgcgccaccttctactcctc ccctagtcaggaagttcccccccgccccgcagctcgcgtcgtgcaggacgtgacaaatggaagtagcacgtctcactagtctcgtgc agatggacagcaccgctgagcaatggaagcgggtaggcctttggggcagcggccaatagcagctttgctccttcgctttctgggctca gaggctgggaaggggtgggtccgggggcgggctcaggggcgggctcaggggcggggcgggcgcccgaaggtcctccggagg cccggcattctgcacgcttcaaaagcgcacgtctgccgcgctgttctcctcttcctcatctccgggcctttcgacct >Ef1a j04617.1 nt 379-1560

SEQ ID NO: 27 gctccggtgcccgtcagtgggcagagcgcacatcgcccacagtccccgagaagttggggggaggggtcggcaattgaaccggtgc ctagagaaggtggcgcggggtaaactgggaaagtgatgtcgtgtactggctccgcctttttcccgagggtgggggagaaccgtatata agtgcagtagtcgccgtgaacgttctttttcgcaacgggtttgccgccagaacacaggtaagtgccgtgtgtggttcccgcgggcctgg cctctttacgggttatggcccttgcgtgccttgaattacttccacgcccctggctgcagtacgtgattcttgatcccgagcttcgggttgga agtgggtgggagagttcgaggccttgcgcttaaggagccccttcgcctcgtgcttgagttgaggcctggcctgggcgctggggccgc cgcgtgcgaatctggtggcaccttcgcgcctgtctcgctgctttcgataagtctctagccatttaaaatttttgatgacctgctgcgacgctt tttttctggcaagatagtcttgtaaatgcgggccaagatctgcacactggtatttcggtttttggggccgcgggcggcgacggggcccgt gcgtcccagcgcacatgttcggcgaggcggggcctgcgagcgcggccaccgagaatcggacgggggtagtctcaagctggccgg cctgctctggtgcctggcctcgcgccgccgtgtatcgccccgccctgggcggcaaggctggcccggtcggcaccagttgcgtgagc ggaaagatggccgcttcccggccctgctgcagggagctcaaaatggaggacgcggcgctcgggagagcgggcgggtgagtcacc cacacaaaggaaaagggcctttccgtcctcagccgtcgcttcatgtgactccacggagtaccgggcgccgtccaggcacctcgatta gttctcgagcttttggagtacgtcgtctttaggttggggggaggggttttatgcgatggagtttccccacactgagtgggtggagactga agttaggccagcttggcacttgatgtaattctccttggaatttgccctttttgagtttggatcttggttcattctcaagcctcagacagtggttc aaagtttttttcttccatttcaggtgtcgtga

>CMV

SEQ ID NO: 28 gtcgacattgattattgactagttattaatagtaatcaattacggggtcattagttcatagcccatatatggagttccgcgttacataacttac ggtaaatggcccgcctggctgaccgcccaacgacccccgcccattgacgtcaataatgacgtatgttcccatagtaacgccaataggg actttccattgacgtcaatgggtggagtatttacggtaaactgcccacttggcagtacatcaagtgtatcatatgccaagtacgccccctat tgacgtcaatgacggtaaatggcccgcctggcattatgcccagtacatgaccttatgggactttcctacttggcagtacatctacgtatta gtcatcgctattaccatggtgatgcggttttggcagtacatcaatgggcgtggatagcggtttgactcacggggatttccaagtctccacc ccattgacgtcaatgggagtttgttttggcaccaaaatcaacgggactttccaaaatgtcgtaacaactccgccccattgacgcaaatgg gcggtaggcgtgtacggtgggaggtctatataagcagagctctctggctaactagagaacccactgcttactggcttatcgaaattaata cgactcactatagggagacccaagctggctagcgtttaaactt >NSE similar to *Rattus norvegicus* neuron specific enolase gene ab038993.1 nt 1023-2715

SEQ ID NO: 29 agctctgagctcctcctctgctcgcccaatccttccaaccccctatggtggtatggctgacacagaaaatgtctgctcctgtatgggacat ttgcccctcttctccaaatataagacaggatgaggcctagcttttgctgctccaaagttttaaaagaacacattgcacggcatttagggact ctaaagggtggaggaggaatgagggaattgcatcatgccaaggctggtcctcatccatcactgcttccagggcccagagtggcttcca ggaagtattcttacaaaggaagcccgatctgtagctaacactcagagcccattttcctgcgttaacccctcccgacctcatatacaggag taacatgatcagtgacctgggggagctggccaaactgcgggacctgcccaagctgagggccttggtgctgctggacaacccctgtgc cgatgagactgactaccgccaggaggccctggtgcagatggcacacctagagcgcctagacaaagagtactatgaggacgaggac cgggcagaagctgaggagatccgacagaggctgaaggaggaacaggagcaagaactcgacccggaccaagacatggaaccgta cctcccgccaacttagtggctcctctagcctgcagggacagtaaaggtgatggcaggaaggcagcccccggaggtcaaaggctgg -continued gcacgcgggaggagaggccagagtcagaggctgcgggtatctcagatatgaaggaaagatgagagaggctcaggaagaggtaag aaaagacacaagagaccagagaagggagaagaattagagagggaggcagaggaccgctgtctctacagacatagctggtagaga ctgggaggaagggatgaaccctgagcgcatgaagggaaggaggtggctggtggtatatggaggatgtagctgggccagggaaaa gatcctgcactaaaaatctgaagctaaaaataacaggacacggggtggagaggcgaaaggagggcagagtgaggcagagagact gagaggcctggggatgtgggcattccggtagggcacacagttcacttgtcttctctttttccaggaggccaaagatgctgacgtcaaga actcataataccccagtggggaccaccgcattcatagccctgttacaagaagtgggagatgttcctttttgtcccagactggaaatccgtt acatcccgaggctcaggttctgtggtggtcatctctgtgtggcttgttctgtgggcctacctaaagtcctaagcacagctctcaagcagat ccgaggcgactaagatgctagtaggggttgtctggagagaagagccgaggaggtgggctgtgatggatcagttcagctttcaaataa aaaggcgtttttatattctgtgtcgagttcgtgaacccctgtggtgggcttctccatctgtctgggttagtacctgccactatactggaataa ggggacgcctgcttccctcgagttggctggacaaggttatgagcatccgtgtacttatggggttgccagcttggtcctggatcgcccgg gcccttcccccacccgttcggttccccaccaccacccgcgctcgtacgtgcgtctccgcctgcagctcttgactcatcggggcccccg ggtcacatgcgctcgctcggctctataggcgccgcccccctgcccacccccccgcccgcgctgggagccgcagccgccgccactcct gctctctctgcgccg >MeCP2 nc_000086.7 nt -677 to +56 mouse mecp2 methyl cpg binding protein 2

SEQ ID NO: 30 tgcccattataaacgtctgcaaagaccaaggtttgatatgttgattttactgtcagccttaagagtgcgacatctgctaatttagtgtaataat acaatcagtagaccctttaaaacaagtcccttggcttggaacaacgccaggctcctcaacaggcaactttgctacttctacagaaaatga taataaagaaatgctggtgaagtcaaatgcttatcacaatggtgaactactcagcagggaggctctaataggcgccaagagcctagact tccttaagcgccagagtccacaagggcccagttaatcctcaacattcaaatgctgcccacaaaaccagcccctctgtgccctagccgc ctctttttttccaagtgacagtagaactccaccaatccgcagctgaatggggtccgcctcttttccctgcctaaacagacaggaactcctgc caattgagggcgtcaccgctaaggctccgccccagcctgggctccacaaccaatgaagggtaatctcgacaaagagcaaggggtg gggcgcgggcgcgcaggtgcagcagcacacaggctggtcgggagggcggggcgcgacgtctgccgtgcggggtcccggcatc ggttgcgcgcgcgctccctcctctcggagagagggctgtggtaaaacccgtccggaaaatggccgccgctgccg ccaccgccgccgccgccgccgcgccgagcggaggaggagg >GFAP nc_000017.11 nt -1991-0 *Homo sapiens* glial fibrillary acidic protein (GFAP)

SEQ ID NO: 31 ggcaacatggcaagaccctatctctacaaaaaaagttaaaaaatcagccacgtgtggtgacacacacctgtagtcccagctattcagg aggctgaggtgaggggatcacttaaggctgggaggttgaggctgcagtgagtcgtggttgcgccactgcactccagcctgggcaac agtgagaccctgtctcaaaagacaaaaaaaaaaaaaaaaaaaaaaaagaacatatcctggtgtggagtaggggacgctgctctgacag aggctcgggggcctgagctggctctgtgagctggggaggaggcagacagccaggccttgtctgcaagcagacctggcagcattgg gctggccgcccccccagggcctcctcttcatgcccagtgaatgactcaccttggcacagacacaatgttcggggtgggcacagtgcct gcttcccgccgcaccccagccccccctcaaatgccttccgagaagcccattgagcagggggcttgcattgcaccccagcctgacagcc tggcatcttgggataaaagcagcacagccccctaggggctgcccttgctgtgtggcgccaccggcggtggagaacaaggctctattc agcctgtgcccaggaaaggggatcaggggatgcccaggcatggacagtgggtggcaggggggggagaggagggctgtctgcttcc cagaagtccaaggacacaaatgggtgaggggactgggcagggttctgaccctgtgggaccagagtggagggcgtagatggacctg aagtctccagggacaacagggcccaggtctcaggctcctagttgggcccagtggctccagcgtttccaaacccatccatccccagag gttcttcccatctctccaggctgatgtgtgggaactcgaggaaataaatctccagtgggagacggaggggtggccagggaaacgggg cgctgcaggaataaagacgagccagcacagccagctcatgtgtaacggctttgtggagctgtcaaggcctggtctctgggagagag gcacagggaggccagacaaggaaggggtgacctggagggacagatccaggggctaaagtcctgataaggcaagagagtgccgg ccccctcttgccctatcaggacctccactgccacatagaggccatgattgacccttagacaaagggctggtgtccaatcccagccccc agccccagaactccagggaatgaatgggcagagagcaggaatgtgggacatctgtgttcaagggaaggactccaggagtctgctgg gaatgaggcctagtaggaaatgaggtggcccttgagggtacagaacaggttcattcttcgccaaattcccagcaccttgcaggcactta cagctgagtgagataatgcctgggttatgaaatcaaaaagttggaaagcaggtcagaggtcatctggtacagcccttccttcccttttttt -continued tttttttttgtgagacaaggtctctctgttgcccaggctggagtggcgcaaacacagctcactgcagcctcaacctactgggctcaag caatcctccagcctcagcctcccaaagtgctgggattacaagcatgagccaccccactcagccctttccttcctttttaattgatgcataat aattgtaagtattcatcatggtccaaccaaccctttcttgacccaccttcctagagagagggtcctcttgcttcagcggtcagggccccag acccatggtctggctccaggtaccacctgcctcatgcaggagttggcgtgcccaggaagctctgcctctgggcacagtgacctcagtg gggtgaggggagctctccccatagctgggctgcggcccaaccccacccccctcaggctatgccagggggtgttgccaggggcaccc gggcatcgccagtctagcccactccttcataaagccctcgcatcccaggagcgagcagagccagagcagg Tag
>HA

SEQ ID NO: 32 tatccttatgacgtgcctgactatgcc

Polyadenylation signals
>hGH ng_011676.1 nt 6537-7013

SEQ ID NO: 33 gggtggcatccctgtgacccctccccagtgcctctcctggccctggaagttgccactccagtgcccaccagccttgtcctaataaaatta agttgcatcattttgtctgactaggtgtccttctataatattatggggtggaggggggtggtatggagcaaggggcaagttgggaagaca acctgtagggcctgcggggtctattgggaaccaagctggagtgcagtggcacaatcttggctcactgcaatctccgcctcctgggttca agcgattctcctgcctcagcctcccgagttgttgggattccaggcatgcatgaccaggctcagctaattttttgtttttttggtagagacggg gtttcaccatattggccaggctggtctccaactcctaatctcaggtgatctacccaccttggcctcccaaattgctgggattacaggcgtg aaccactgctcccttccctgtcctt >rBG ah001222.2, nt 1623-1749

SEQ ID NO: 34 gatctttttccctctgccaaaaattatggggacatcatgaagccccttgagcatctgacttctggctaataaaggaaatttattttcattgcaa tagtgtgttggaattttttgtgtctctcactcg >rBG ah001222.2, nt 1690-1745

SEQ ID NO: 35 aataaaggaaatttattttcattgcaatagtgtgttggaattttttgtgtctctca

SYNTHETIC PSEN1 CDNA with maximum number of CpG dinucleotides removed by altering only tolerant codons. Changed codon are indicated in lower case.

SEQ ID NO: 36

ATGACAGAGTTACCTGCAccaTTGTCCTACTTCCAGAATGCACAGATGTCTGAGGACAACCA

CCTGAGCAATACTGTACGTAGCCAGAATGACAATAGAGAAagaCAGGAGCACaatGACAGAC

GGAGCCTTGGCCACCCTGAGCCATTATCTAATGGAagaCCCCAGGGTAACTCCagaCAGGTG

GTGGAGCAAGATGAGGAAGAAGATGAGGAGCTGACATTGAAATATggtGCCAAGCATGTGAT

CATGCTCTTTGTCCCTGTGACTCTCTGCATGGTGGTGgttGTGGCTACCATTAAGTCAGTCA

GCTTTTATACCCGGAAGGATGGGCAGCTAATCTATACCCCATTCACAGAAGATACCGAGACT

GTGGGCCAGAGAGCCCTGCACTCAATTCTGAATGCTGCCATCATGATCAGTGTCATTGTTGT

CATGACTATCCTCCTGGTGGTTCTGTATAAATACAGGTGCTATAAGGTCATCCATGCCTGGC

TTATTATATCATCTCTATTGTTGCTGTTCTTTTTTTCATTCATTTACTTGGGGGAAGTGTTT

AAAACCTATaatGTTGCTGTGGACTACATTACTGTTGCACTCCTGATCTGGAATTTTGGTGT

GGTGGGAATGATTTCCATTCACTGGAAAGGTCCACTTagaCTCCAGCAGGCATATCTCATTA

TGATTAGTGCCCTCATGGCCCTGGTGTTTATCAAGTACCTCCCTGAATGGACTgccTGGCTC

ATCTTGGCTGTGATTTCAGTATATGATTTAGTGGCTGTTTTGTGTcccAAAGGTCCACTTCG

TATGCTGGTTGAAACAGCTCAGGAGAGAAATGAAaccCTTTTTCCAGCTCTCATTTACTCCT

CAACAATGGTGTGGTTGGTGAATATGGCAGAAGGAGACccaGAAGCTCAAAGGAGAGTATCC

AAAAATTCCAAGTATAATGCAGAAAGCACAGAAAGGGAGTCACAAGACACTGTTGCAGAGAA

TGATGATggtGGGTTCAGTGAGGAATGGGAAGCCCAGAGGGACAGTCATCTAGGGCCTCATa ggTCTACACCTGAGTCAagaGCTGCTGTCCAGGAACTTTCCAGCAGTATCctgGCTGGTGAA -continued

GACCCAGAGGAAAGGGGAGTAAAACTTGGATTGGGAGATTTCATTTTCTACAGTGTTCTGGT

TGGTAAAGCCTCAGCAACAGCCAGTGGAGACTGGAACACAACCATAGCCTGTtttGTAGCCA

TATTAATTGGTTTGTGCCTTACATTATTAGTCCTTGCCATTTTCAAGAAAGCATTGCCAGCT

CTTCCAATCTCCATCACCTTTGGGCTTGTTTTCTACTTTGCCACAGATTATCTTGTACAGCC

TTTTATGGACCAATTAGCATTCCATCAATTTTATATCTAG hPSEN1v1.5. PSEN1 with certain tolerant codons changed to highly preferred synonymous codons. Changed codons are in lower case.

SEQ ID NO: 37

ATGACAgaaTTACCTgCCCCcTTGagcTACTTCCAGAATGCACAGATGagCGAGGACAAC

CACCTGAGCAATACTGTACGTAGCCAGAATGACaacAGAGAACGGCAGgaaCACAACGAC aggCGGAGCCtgGGCCACCCTGAGCCCCtgTCTAATGGAagaCCCCAGGGTAACagcaga CAGGTGGTGgaaCAAGATGAGGAAgaggacGAGGAGCTGaccctgaagtacGGCGCCAAG cacGTGATCATGCTCttCgtgCCCGTGACTCTCTGCATGGTGGTGgtgGTGGCTacaato AAGagcGTCAGCTTTTATACCCGGAAGGATGGGCAGCTAATCTATACCCCATTCACAGAA gacACCGAGACTGTGGGCCAGAGAGCCCTGCACTCAatCCTGAATgCCGCCATCATGATC agcGTCATTGTTGTCATGACTATCCTCCTGGTGGTTCTGTATAAATACAGGTGCTATAAG GTCATCCATGCCTGGctgatcATATCATCTctgTTGctgCTGTTCTTTTTTagcTTCATT TACctgggcGAAGTGTTTAAAACCTATAACGTTgccGTGGACTACATTACTGTTgccCTC CTGATCTGGaacttcggcGTGGTGggcATGATTTCCATTCACTGGAAAggcccccctgaga CtgCAGCAGGCAtacCTCATTATGatCtCCGCCCTCATGGCCCTGGTGttcATCAAGTAC ctgcccgagTGGACTgctTGGCTCATCTTGGCTGTGatctccgtgTATGATTTAGTGGCT GTTctgTGTcctAAAGGTCCActgCGTATGCTGgtgGAAACAGCTCAGgaaAGAAATGAA acactgTTTcctGCTctgATTTAGTCCTCAACAATGGTGTGGctCGTGAATATGgccGAA GGAGACcctGAAgccCAAcggAGAgtgTCCAAAaacTCCAAGTATaacgccgagAGCACA GAAAGGGAGagccaggatacaGTTgccGAGAATgacGATGGCggcTTCAGTGAGGAATGG GAAGCCCAGAGGGACagccacctgGGGCCTcacagaagcaccCCTGAGtctagagccGCT GTCCAGGAActgTCCAGCtCCATCCtggccggCGAAGACCCCgaaGAAAGGGGAGTAAAA CTTGGActgGGAGATTTCatcTTCTACAGTGTTctcGTTggcAAAGCCagcGCAACAgct agcCGGAGACTGGAACACAacaATAGCCTGTTTCaTAGCCatcTTAATTggcctgTGCCTT ACActtctgCTCctgGCCatcTTCAAGaaggccctgCCAgcoctgcctATCagcATCACC ttcGGGcTTGTTTTCTACTTTGCCaccGATTATctggtgCAGcccttcATGGACcagctg gccTTCcaccagTTTtacATCTAG hPSEN1v2.0. PSEN1 with certain tolerant codons changed to highly preferred synonymous codons. Changed codons are in lower case.

SEQ ID NO: 38

ATGACAGAGTTACCTGCAcccTTGTCCTACTTCCAGAATGCACAGATGTCTGAGGACAAC

CACCTGAGCAATACTGTACGTAGCCAGAATGACAATAGAGAACGGCAGGAGCACAACGAC

AGACGGAGCctcGGCCACCCTGAGCCAttgTCTAATGGAcggCCCCAGGGTAACTCCCGG

CAGGTGGTGGAGCagGATGAGGAAGAAGATGAGGAGCTGACATTGAAATATGGCGCCAAG

CATGTGATCATGCTCTTTGTCCCTGTGACTCTCTGCATGGTGGTGGTCGTGGCTACCATT

AAGTCAGTCAGCTTTTATACCCGGAAGGATGGGCAGCTAATCTATACCCCATTCACAGAA

GATACCGAGACTGTGGGCCAGAGAGCCCTGCACTCAATTCTGAATGCTGCCATCATGATC

GTCATCCATGCCTGGCtCATTATATCATCTctgTTGTTGCTGTTCTTTTTTTCATTCATT

-continued

TACTTGGGGGAAGTGTTTAAAACCTATAACGTTGCTGTGGACTACATTACTGTTGCACTC

CTGATCTGGAATTTTggcGTGGTGgggATGATTTCCATTCACTGGAAAggcCCActccgg

CTCCAGCAGGCATATCTCATTATGATTAGTGCCCTCATGGCCCTGGTGTTTATCAAGTAC

CTCCCTGAATGGACTgccTGGCTCATCTTGGCTGTGATTTCAgtgTATGATTTAGTGGCT

GTTTTGTGTcccAAAGGTCCActcCGTATGCTGgtcGAAACAGCTCAGGAGAGAAATGAA accctcTTTCCAGCTCTCATTTACTCCTCAACAATGGTGTGGTTGGTGAATATGGCAGAA GGAGACcccGAAGCTCAAAGGAGAgtgTCCAAAAATTCCAAGTATAATGCAGAAAGCACA GAAAGGGAGTCAcagGACACTGTTGCAGAGAATGATGATGGCGGGTTCAGTGAGGAATGG GAAGCCCAGAGGGACAGTCATctgGGGCCTCATCGCTCTACACCTGAGTCACggGCTGCT GTCCAGGAACtcTCCAGCAGTATCCTCGCTgGCGAAGACCCAGAGGAAAGGGGAGTAAAA CTTGGATTGGGAGATTTCATTTTCTACAGTGTTCTGGTTggcAAAGCCTCAGCAACAGCC AGTGGAGACTGGAACACAACCATAGCCTGTTTCGTAGCCatcTTAATTggcTTGTGCCTT ACAttgttgCTCctcGCCATTTTCAAGAAAGCATTGCCAGCTctcCCAATCTCCATCACC TTTGGGCTTGTTTTCTACTTTGCCACAGATTATCtCgtgCAGCCTTTTATGGACcagttg

GCATTCCATCAATTTTATATCTAG hPSEN1 v3.0 PSEN1 with tolerant codons changed to highly preferred synonymous codons.
Changed codons are in lower case.

SEQ ID NO: 39

ATGACAGAGTTACCTgccccccTTGagcTACTTCCAGAATGCACAGATGagcGAGGACAACCA

CCTGAGCAATACTGTACGTAGCCAGAATGACaacAGAGAACGGCAGGAGCACAACGACAGAC

GGAGCctgGGCCACCCTGAGcccctgagcAATGGAagaCCCCAGGGTAACagcCGGCAGGTG

GTGGAGCagGATGAGGAAgaggacGAGGAGCTGaccctgaagtacGGCGCCAAGcacGTGAT

CATGCTCttcgtgcccGTGACTCTCTGCATGGTGGTGgtgGTGGCTACCatcAAGagcGTCA

GCTTTTATACCCGGAAGGATGGGCAGCTAATCTATACCCCATTCACAGAAgacACCGAGACT

GTGGGCCAGAGAGCCCTGCACTCAatcCTGAATgccGCCATCATGATCagcGTCATTGTTGT

CATGACTATCCTCCTGGTGGTTCTGTATAAATACAGGTGCTATAAGGTCATCCATGCCTGGc tgatcATATCATCTctgTTGctgCTGTTCTTTTTTagcTTCATTTACctgggcGAAGTGTTT AAAACCTATAACGTTgccGTGGACTACATTACTGTTgccCTCCTGATCTGGaacttcggcGT GGTGggcATGATTagcATTCACTGGAAAggccccctgagactgCAGCAGGCAtacCTCatcA TGatcagcGCCCTCATGGCCCT GGTGttcATCAAGTACctgcccgagTGGACTgccTGGCTCATCTTGGCTGTGatcagcgtgT ATGATTTAGTGGCTGTTCtgTGTCCCAAAGGTCCActgCGTATGCTGgtggagACAGCTCAG GAGAGTTAATGAAaccctgTTTcccGCTctgATTTACTCCTCAaccATGGTGTGGctgGTGAA TATGgccGAAGGAGACcccGAAgccCAAcggAGAgtgagcAAAaacagcAAGTATaacgccg agAGCACAGAAAGGGAGagccagGACaccGTTgccGAGAATgacGATGGCggcTTCAGTGAG gagTGGGAAGCCCAGAGGGACagccacctgGGGccccacagaagcacccccGAGagcagagc cGCTGTCCAGGAActgTCCAGCagcATCctggccggcGAAGACcccGAGGAAAGGGGAGTAa agCTTGGActgGGAGATTTCatcTTCTACAGTGTTCTGGTTggcAAAGCCagcGCAACAGCC agcGGAGACTGGAACACAACCATAGCCTGTTTCGTAGCCatCTTAATTggcctgTGCCTTac cctgctgCTCctgGCCatcTTCAAGaaggccctgCCAgccctgcccATCagcATCACCttcG GGCTTGTTTTCTACTTTGCCaccGATTATctggtgCAGcccttcATGGACcagctggccTTC caccagTTTtacATCTGA -continued CAG promoter used in pAT029, pAT024, and pAT022

SEQ ID NO: 40

GACATTGATTATTGACTAGTTATTAATAGTAATCAATTACGGGGTCATTAGTTCA

TAGCCCATATATGGAGTTCCGCGTTACATAACTTACGGTAAATGGCCCGCCTGGC

TGACCGCCCAACGACCCCCGCCCATTGACGTCAATAATGACGTATGTTCCCATAG

TAACGCCAATAGGGACTTTCCATTGACGTCAATGGGTGGACTATTTACGGTAAAC

TGCCCACTTGGCAGTACATCAAGTGTATCATATGCCAAGTACGCCCCCTATTGAC

GTCAATGACGGTAAATGGCCCGCCTGGCATTATGCCCAGTACATGACCTTATGGG

ACTTTCCTACTTGGCAGTACATCTACGTATTAGTCATCGCTATTACCATGGGTCGA

GGTGAGCCCCACGTTCTGCTTCACTCTCCCCATCTCCCCCCCCTCCCCACCCCCAA

TTTTGTATTTATTTATTTTTTAATTATTTTGTGCAGCGATGGGGGCGGGGGGGGGG

GGGGCGCGCGCCAGGCGGGGCGGGGCGGGGCGAGGGGCGGGGCGGGGCGAGGC

GGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCG

GGAGTCGCTGCGTTGCCTTCGCCCCGTGCCCCGCTCCGCGCCGCCTCGCGCCGCC

CGCCCCGGCTCTGACTGACCGCGTTACTCCCACAGGTGAGCGGGCGGGACGGCC

CTTCTCCTCCGGGCTGTAATTAGCGCTTGGTTTAATGACGGCTCGTTTCTTTTCTG

TGGCTGCGTGAAAGCCTTAAAGGGCTCCGGGAGGGCCCTTTGTGCGGGGGGGAG

CGGCTCGGGGGGTGCGTGCGTGTGTGTGTGCGTGGGGAGCGCCGCGTGCGGCCC

GCGCTGCCCGGCGGCTGTGAGCGCTGCGGGCGCGGCGCGGGGCTTTGTGCGCTC

CGCGTGTGCGCGAGGGGAGCGCGGCCGGGGGCGGTGCCCCGCGGTGCGGGGGG

GCTGCGAGGGGAACAAAGGCTGCGTGCGGGGTGTGTGCGTGGGGGGGTGAGCA

GGGGGTGTGGGCGCGGCGGTCGGGCTGTAACCCCCCCCTGCACCCCCCTCCCCG

AGTTGCTGAGCACGGCCCGGCTTCGGGTGCGGGGCTCCGTGCGGGGCGTGGCGC

GGGGCTCGCCGTGCCGGGCGGGGGGTGGCGGCAGGTGGGGGTGCCGGGCGGGG

CGGGGCCGCCTCGGGCCGGGGAGGGCTCGGGGGAGGGGCGCGGCGGCCCCGGA

GCGCCGGCGGCTGTCGAGGCGCGGCGAGCCGCAGCCATTGCCTTTTATGGTAATC

GTGCGAGAGGGCGCAGGGACTTCCTTTGTCCCAAATCTGGCGGAGCCGAAATCT

GGGAGGCGCCGCCGCACCCCCTCTAGCGGGCGCGGGCGAAGCGGTGCGGCGCCG

GCAGGAAGGAAATGGGCGGGGAGGGCCTTCGTGCGTCGCCGCGCCGCCGTCCCC

TTCTCCATCTCCAGCCTCGGGGCTGCCGCAGGGGGACGGCTGCCTTCGGGGGGG

ACGGGGCAGGGCGGGGTTCGGCTTCTGGCGTGTGACCGGCGGCTCTAGAGCCTC

TGCTAACCATGTTCATGCCTTCTTCTTTTTCCTACAG

Expression cassette for AAV production containing AAV2 ITRs (1-141, 4553-4693), Presenilin 1 promoter (underlined 237-1200), a synthetic human beta-globin intron (1221-1786), HA-tag (1866-1898), codon-optimized human presenilin 1v1.5 (uppercase SEQ ID NO: 37, 1899-3299), human growth hormone polyadenylation sequence (3330-3806) and albumin genomic sequence (3810-4522).

SEQ ID NO: 41 cctgcaggcagctgcgcgctcgctcgctcactgaggccgcccgggcaaagcccgggcgtcgggcgacctttggtcgcccggcctc agtgagcgagcgagcgcgcagagagggagtggccaactccatcactaggggttcctgcggccaattcagtcgataactataacggt cctaaggtagcgatttaaatacgcgctctcttaaggtagccccgggacgcgtcaattgagatctcgggggtggatttttaaagaaacttta gaagaatgtaacttgcccagataccatgtaccgttaatttcattttcggtttttttgaatacccatgtttgacatttctccgttcaccttgattaaat aaggtagtattcatttttttagttttagcttttggatatatgtgtaagtgtggtatgctgtctaatgaattagacattggtactgtctttaccaaaac tggacaaagagcaggcagatgcaaaaatcaagtgacccagcaaaccagacacattttctgctctcagctagcttgccacctagaaaga -continued ctggttgtcaaaggggggagtccaagaatcgcggaggatgtttaaaatgcagtttctcaggttctcgccacccaccagaagttttgattcat tgagtggtgggagagggcagagatatttgcgattttaacagcattctcttgattgtgatgcagctggttcgcaaataggtaccctaaagaa atgacaggtgttaaatttaggatggccatcgcttgtatgccgggagaagcacacgctgggcccaatttatatagggggctttcgtcctcag ctcgagcagcctcagaaccccgacaacccacgccagcgctctgggcggattccgtcaggtggggaaggccaggtggagctctggg ttctccccgcaatcgtttctccaggccggaggccccgcccccttcctcctggctcctcccctcctccgtgggccggccgccaacgacg ccagagccggaaatgacgacaacggtgagggttctcgggcggggcctgggacaggcagctccggggtccgcggtttcacatcgg aaacaaaacagcggctggtctggaaggaacctgagctacgagccgcggcggcagcggggcggcggggaagcgtatgtgcgtgat ggggagtccgggcaagccaggaaggcaccgcggacatgggcggaagcttcgtttagtgaaccgtcagatcgcctggagacgccat ccacgctgttttgacctccatagaagacaccgggaccgatccagcctccgcggattcgaatcccggccgggaacggtgcattggaac gcggattccccgtgccaagagtgacgtaagtaccgcctatagagtctataggcccacaaaaaatgctttcttcttttaatatactttttttgttt atcttatttctaatactttccctaatctctttctttcagggcaataatgatacaatgtatcatgcctctttgcaccattctaaagaataacagtgat aatttctgggttaaggcaatagcaatatttctgcatataaatatttctgcatataaattgtaactgatgtaagaggtttcatattgctaatagca gctacaatccagctaccattctgcttttattttgtggttgggataaggctggattattctgagtccaagctaggcccttttgctaatcgtgttca tacctcttatcttcctcccacagctcctgggcaacgtgctggtctgtgtgctggcccatcactttggcaaagaattaccggtctcctgggc aacgtgctggttattgtgctgtctcatcattttggcaaagaattcacgccccagagccgccaccATGgcctacccatacgatgttccag attacgctACAGAATTACCTGCCCCCTTGAGCTACTTCCAGAATGCACAGATGAGCGA

GGACAACCACCTGAGCAATACTGTACGTAGCCAGAATGACAACAGAGAACGGCA

GGAACACAACGACAGGCGGAGCCTGGGCCACCCTGAGCCCCTGTCTAATGGAAG

ACCCCAGGGTAACAGCAGACAGGTGGTGGAACAAGATGAGGAAGAGGACGAGG

AGCTGACCCTGAAGTACGGCGCCAAGCACGTGATCATGCTCTTCGTGCCCGTGAC

TCTCTGCATGGTGGTGGTGGTGGCTACAATCAAGAGCGTCAGCTTTTATACCCGG

AAGGATGGGCAGCTAATCTATACCCCATTCACAGAAGACACCGAGACTGTGGGC

CAGAGAGCCCTGCACTCAATCCTGAATGCCGCCATCATGATCAGCGTCATTGTTG

TCATGACTATCCTCCTGGTGGTTCTGTATAAATACAGGTGCTATAAGGTCATCCA

TGCCTGGCTGATCATATCATCTCTGTTGCTGCTGTTCTTTTTTAGCTTCATTTACCT

GGGCGAAGTGTTTAAAACCTATAACGTTGCCGTGGACTACATTACTGTTGCCCTC

CTGATCTGGAACTTCGGCGTGGTGGGCATGATTTCCATTCACTGGAAAGGCCCCC

TGAGACTGCAGCAGGCATACCTCATTATGATCTCCGCCCTCATGGCCCTGGTGTT

CATCAAGTACCTGCCCGAGTGGACTGCTTGGCTCATCTTGGCTGTGATCTCCGTG

TATGATTTAGTGGCTGTTCTGTGTCCTAAAGGTCCACTGCGTATGCTGGTGGAAA

CAGCTCAGGAAAGAAATGAAACACTGTTTCCTGCTCTGATTTACTCCTCAACAAT

GGTGTGGCTCGTGAATATGGCCGAAGGAGACCCTGAAGCCCAACGGAGAGTGTC

CAAAAACTCCAAGTATAACGCCGAGAGCACAGAAAGGGAGAGCCAGGATACAG

TTGCCGAGAATGACGATGGCGGCTTCAGTGAGGAATGGGAAGCCCAGAGGGACA

GCCACCTGGGGCCTCACAGAAGCACCCCTGAGTCTAGAGCCGCTGTCCAGGAAC

TGTCCAGCTCCATCCTGGCCGGCGAAGACCCCGAAGAAAGGGGAGTAAAACTTG

GACTGGGAGATTTCATCTTCTACAGTGTTCTCGTTGGCAAAGCCAGCGCAACAGC

TAGCGGAGACTGGAACACAACAATAGCCTGTTTCGTAGCCATCTTAATTGGCCTG

TGCCTTACACTTCTGCTCCTGGCCATCTTCAAGAAGGCCCTGCCAGCCCTGCCTAT

CAGCATCACCTTCGGGCTTGTTTTCTACTTTGCCACCGATTATCTGGTGCAGCCCT

-continued

TCATGGACCAGCTGGCCTTCCACCAGTTTTACATCTAGtaagcggccgccctagggagctcctcg agggggtggcatccctgtgacccctccccagtgcctctcctggccctggaagttgccactccagtgcccaccagccttgtcctaataaa attaagttgcatcattttgtctgactaggtgtccttctataatattatggggtggaggggggtggtatggagcaaggggcaaggggggaa gacaacctgtagggcctgcggggtctattgggaaccaagctggagtgcagtggcacaatcttggctcactgcaatctccgcctcctgg gttcaagcgattctcctgcctcagcctcccgagttgttgggattccaggcatgcatgaccaggctcagctaatttttgtttttttggtagaga cggggtttcaccatattggccaggctggtctcccctcctaatctcaggtgatctacccaccttggcctcccaaattgctgggattacagg cgtgaaccactgctcccttccctgtccttggcctaggtttcttgagacctctacaagaggggggagttgacacttggggtactttcttggtgt aacgaactaatagcctgaaaaaaagaagtcatgtgttttcagcaaggcaagaaactgtctaacatagtagataaaacagagaacacttg gccggaatcaactaagatgttgctatgttccattcatcatattatctccatctgcagagtagtgggttagtggagggtagaaaacattctcc tgaacaactagttaaacttggctttgagttccacctgtaccacttgcataatcttgggaaagtgagttgcctaattcagtgacattaataaatt tattaatttcttctttcaataaaacctggagagagcttcatatgtatcagcatatgctaaacttgaaagatacaagtagaaaatggaaggaa atatatctgactcaatagggatagttcaagggttaaattaaaagtagtaaagtattataattaatctgacatggtacctaatatataataatca tgtattaagaatgccagtcaccattaaaagtcaatgtatgactttaatctactcgaggaaagaaactatgtcttgttcactgttattatctctaa aatccataatcagaagagcaccatgtgtatgagccacacaataaatatctactgtataatatgtctcttcttgtttttaaccttcatagataag acttagggataacagggtaatggcgcgggccgcaggaacccctagtgatggagttggccactccctctctgcgcgctcgctcgctca ctgaggccgggcgaccaaaggtcgcccgacgcccgggctttgcccgggcggcctcagtgagcgagcgagcgcgcagctgcctg cagg Expression cassette for AAV production containing AAV2 ITRs (1-141, 4554-4694), Ubiquitin C promoter (underlined, 237-1323), a synthetic human beta-globin intron (1344-1909), HA-tag (1989-2015), codon-optimized human presenilin 1v1.5 (uppercase SEQ ID NO: 37, 1983-3416), human growth hormone polyadenylation (3447-3923) and human growth hormone genomic sequence (3924-4523).

SEQ ID NO: 42 cctgcaggcagctgcgcgctcgctcgctcactgaggccgcccgggcaaagcccgggcgtcgggcgacctttggtcgcccggcctc agtgagcgagcgagcgcgcagagagggagtggccaactccatcactaggggttcctgcggccaattcagtcgataactataacggt cctaaggtagcgatttaaatacgcgctctcttaaggtagccccgggacgcgtcaattgagatctcggtgcagcggcctccgcgccggg ttttggcgcctcccgcgggcgcccccctcctcacggcgagcgctgccacgtcagacgaagggcgcaggagcgttcctgatccttcc gcccggacgctcaggacagcggcccgctgctcataagactcggccttagaaccccagtatcagcagaaggacattttaggacggga cttgggtgactctagggcactggttttctttccagagagcggaacaggcgaggaaaagtagtcccttctcggcgattctgcggagggat ctccgtggggcggtgaacgccgatgattatataaggacgcgccgggtgtggcacagctagttccgtcgcagccgggatttgggtcgc ggttcttgtttgtggatcgctgtgatcgtcacttggtgagttgcgggctgctgggctggccggggctttcgtggccgccgggccgctcg gtgggacggaagcgtgtggagagaccgccaagggctgtagtctgggtccgcgagcaaggttgccctgaactgggggttgggggg agcgcacaaaatggcggctgttcccgagtcttgaatggaagacgcttgtaaggcgggctgtgaggtcgttgaaacaaggtgggggg catggtgggcggcaagaacccaaggtcttgaggccttcgctaatgcgggaaagctcttattcgggtgagatgggctggggcaccatc tggggaccctgacgtgaagtttgtcactgactggagaactcgggtttgtcgtctggttgcgggggcggcagttatgcggtgccgttggg cagtgcacccgtacctttgggagcgcgcgcctcgtcgtgtcgtgacgtcacccgttctgttggcttataatgcagggtggggccacctg ccggtaggtgtgcggtaggcttttctccgtcgcaggacgcagggttcgggcctagggtaggctctcctgaatcgacaggcgccggac ctctggtgaggggagggataagtgaggcgtcagtttctttggtcggttttatgtacctatcttcttaagtagctgaagctccggttttgaact atgactagtaaaaagcttcgtttagtgaaccgtcagatcgcctggagacgccatccacgctgttttgacctccatagaagacaccggga ccgatccagcctccgcggattcgaatcccggccgggaacggtgcattggaacgcggattccccgtgccaagagtgacgtaagtaccgcc tatagagtctataggcccacaaaaaatgctttcttcttttaatatactttttttgtttatcttatttctaatactttccctaatctctttctttcagg gcaataatgatacaatgtatcatgcctctttgcaccattctaaagaataacagtgataatttctgggttaaggcaatagcaatatttctgcata taaatatttctgcatataaattgtaactgatgtaagaggtttcatattgctaatagcagctacaatccagctaccattctgcttttattttgtggtt gggataaggctggattattctgagtccaagctaggcccttttgctaatcgtgttcatacctcttatcttcctcccacagctcctgggcaacgt -continued gctggtctgtgtgctggcccatcactttggcaaagaattaccggtggcaacgtgctggttattgtgctgtctcatcattttggcaaagaatt cacgccccagagccgccaccATGgcctacccatacgatgttccagattacgctACAGAATTACCTGCCCCCTTG

AGCTACTTCCAGAATGCACAGATGAGCGAGGACAACCACCTGAGCAATACTGTA

CGTAGCCAGAATGACAACAGAGAACGGCAGGAACACAACGACAGGCGGAGCCT

GGGCCACCCTGAGCCCCTGTCTAATGGAAGACCCCAGGGTAACAGCAGACAGGT

GGTGGAACAAGATGAGGAAGAGGACGAGGAGCTGACCCTGAAGTACGGCGCCA

AGCACGTGATCATGCTCTTCGTGCCCGTGACTCTCTGCATGGTGGTGGTGGTGGC

TACAATCAAGAGCGTCAGCTTTTATACCCGGAAGGATGGGCAGCTAATCTATACC

CCATTCACAGAAGACACCGAGACTGTGGGCCAGAGAGCCCTGCACTCAATCCTG

AATGCCGCCATCATGATCAGCGTCATTGTTGTCATGACTATCCTCCTGGTGGTTCT

GTATAAATACAGGTGCTATAAGGTCATCCATGCCTGGCTGATCATATCATCTCTG

TTGCTGCTGTTCTTTTTTAGCTTCATTTACCTGGGCGAAGTGTTTAAAACCTATAA

CGTTGCCGTGGACTACATTACTGTTGCCCTCCTGATCTGGAACTTCGGCGTGGTG

GGCATGATTTCCATTCACTGGAAAGGCCCCCTGAGACTGCAGCAGGCATACCTCA

TTATGATCTCCGCCCTCATGGCCCTGGTGTTCATCAAGTACCTGCCCGAGTGGAC

TGCTTGGCTCATCTTGGCTGTGATCTCCGTGTATGATTTAGTGGCTGTTCTGTGTC

CTAAAGGTCCACTGCGTATGCTGGTGGAAACAGCTCAGGAAAGAAATGAAACAC

TGTTTCCTGCTCTGATTTACTCCTCAACAATGGTGTGGCTCGTGAATATGGCCGA

AGGAGACCCTGAAGCCCAACGGAGAGTGTCCAAAAACTCCAAGTATAACGCCGA

GAGCACAGAAAGGGAGAGCCAGGATACAGTTGCCGAGAATGACGATGGCGGCT

TCAGTGAGGAATGGGAAGCCCAGAGGGACAGCCACCTGGGGCCTCACAGAAGC

ACCCCTGAGTCTAGAGCCGCTGTCCAGGAACTGTCCAGCTCCATCCTGGCCGGCG

AAGACCCCGAAGAAAGGGGAGTAAAACTTGGACTGGGAGATTTCATCTTCTACA

GTGTTCTCGTTGGCAAAGCCAGCGCAACAGCTAGCGGAGACTGGAACACAACAA

TAGCCTGTTTCGTAGCCATCTTAATTGGCCTGTGCCTTACACTTCTGCTCCTGGCC

ATCTTCAAGAAGGCCCTGCCAGCCCTGCCTATCAGCATCACCTTCGGGCTTGTTT

TCTACTTTGCCACCGATTATCTGGTGCAGCCCTTCATGGACCAGCTGGCCTTCCAC

CAGTTTTACATCTAGtaagcggccgccctagggagctcctcgagggggtggcatccctgtgacccctccccagtgcct ctcctggccctggaagttgccactccagtgcccaccagccttgtcctaataaaattaagttgcatcattttgtctgactaggtgtccttctat aatattatggggtggaggggggtggtatggagcaaggggcaagggggggaagacaacctgtagggcctgcggggtctattgggaac caagctggagtgcagtggcacaatcttggctcactgcaatctccgcctcctgggttcaagcgattctcctgcctcagcctcccgagttgt tgggattccaggcatgcatgaccaggctcagctaatttttgtttttttggtagagacggggtttcaccatattggccaggctggtctccccc tcctaatctcaggtgatctacccaccttggcctcccaaattgctgggattacaggcgtgaaccactgctcccttccctgtccttctgatttta aaataactataccagcaggaggacgtccagacacagcataggctacctggccatgcccaaccggtgggacatttgagttgcttgcttg gcactgtcctctcatgcgttgggtccactcagtagatgcctgttgaattcctgggcctagggctgtgccagctgcctcgtcccgtcaccttctgg cttcttctctccctccatatcttagctgttttcctcatgagaatgttccaaattcgaaatttctatttaaccattatatatttacttgtttgctat tatctctgcccccagtagattgttagctccagaagagaaaggatcatgtcttttgcttatctagatatgcccatctgcctggtacaatctctg gcacatgttacaggcaacaactacttgtggaattggtgaatgcatgaatagaagaatgagtgaatgaatgaatagacaataggcagaa atccagcctcaaagagcttacagtctggtaagaggaataaaatgtctgcaaatagccacaggacaggtcaaaggaaggaggggctat ttccagctgagggcaccccatcaggaaagcaccccagacttccttagggataacagggtaatggcgcgggccgcaggaacccctag -continued tgatggagttggccactccctctctgcgcgctcgctcgctcactgaggccgggcgaccaaaggtcgcccgacgcccgggctttgccc gggcggcctcagtgagcgagcgagcgcgcagctgcctgcagg Expression cassette for AAV production containing AAV2 ITRs (1-141, 4554-4694), CBA promoter (underlined, 237-890), a synthetic human beta-globin intron (911-1476), HA-tag (1556-1582), codon-optimized human presenilin 1v1.5 (uppercase SEQ ID NO: 37, 1550-2983), human growth hormone polyadenylation (3014-3490) and human growth hormone genomic sequence (3014-3491).

SEQ ID NO: 43 cctgcaggcagctgcgcgctcgctcgctcactgaggccgcccgggcaaagcccgggcgtcgggcgacctttggtcgcccggcctc agtgagcgagcgagcgcgcagagagggagtggccaactccatcactaggggttcctgcggccaattcagtcgataactataacggt cctaaggtagcgatttaaatacgcgctctcttaaggtagccccgggacgcgtcaattgagatctccgacattgattattgactagttattaa tagtaatcaattacggggtcattagttcatagcccatatatggagttccgcgttacataacttacggtaaatggcccgcctggctgaccgc ccaacgacccccgcccattgacgtcaataatgacgtatgttcccatagtaacgccaatagggactttccattgacgtcaatgggtggagt atttacggtaaactgcccacttggcagtacatcaagtgtatcatatgccaagtacgccccctattgacgtcaatgacggtaaatggcccg cctggcattatgcccagtacatgaccttatgggactttcctacttggcagtacatctacgtattagtcatcgctattaccatgtcgaggcca cgttctgcttcactctccccatctcccccccctccccacccccaattttgtatttatttattttttaattattttgtgcagcgatgggggcgggg ggggggggcgcgcgccaggcggggcggggcggggcgaggggcggggcggggcgaggcggagaggtgcggcggcagcca atcagagcggcgcgctccgaaagtttccttttatggcgaggcggcggcggcggcggccctataaaaagcgaagcgcgcggcgggc gggagcaagcttcgtttagtgaaccgtcagatcgcctggagacgccatccacgctgttttgacctccatagaagacaccgggaccgat ccagcctccgcggattcgaatcccggccgggaacggtgcattggaacgcggattccccgtgccaagagtgacgtaagtaccgcctatagag tctataggcccacaaaaaatgctttcttcttttaatatacttttttgtttatcttatttctaatactttccctaatctctttctttcagggcaata atgatacaatgtatcatgcctctttgcaccattctaaagaataacagtgataatttctgggttaaggcaatagcaatatttctgcatataaata tttctgcatataaattgtaactgatgtaagaggtttcatattgctaatagcagctacaatccagctaccattctgcttttattttgtggttgggat aaggctggattattctgagtccaagctaggcccttttgctaatcgtgttcatacctcttatcttcctcccacagctcctgggcaacgtgctgg tctgtgtgctggcccatcactttggcaaagaattaccggtggcaacgtgctggttattgtgctgtctcatcattttggcaaagaattcacgc cccagagccgccaccATGgcctacccatacgatgttccagattacgctACAGAATTACCTGCCCCCTTGAGC

TACTTCCAGAATGCACAGATGAGCGAGGACAACCACCTGAGCAATACTGTACGT

AGCCAGAATGACAACAGAGAACGGCAGGAACACAACGACAGGCGGAGCCTGGG

CCACCCTGAGCCCCTGTCTAATGGAAGACCCCAGGGTAACAGCAGACAGGTGGT

GGAACAAGATGAGGAAGAGGACGAGGAGCTGACCCTGAAGTACGGCGCCAAGC

ACGTGATCATGCTCTTCGTGCCCGTGACTCTCTGCATGGTGGTGGTGGTGGCTAC

AATCAAGAGCGTCAGCTTTTATACCCGGAAGGATGGGCAGCTAATCTATACCCC

ATTCACAGAAGACACCGAGACTGTGGGCCAGAGAGCCCTGCACTCAATCCTGAA

TGCCGCCATCATGATCAGCGTCATTGTTGTCATGACTATCCTCCTGGTGGTTCTGT

ATAAATACAGGTGCTATAAGGTCATCCATGCCTGGCTGATCATATCATCTCTGTT

GCTGCTGTTCTTTTTTAGCTTCATTTACCTGGGCGAAGTGTTTAAAACCTATAACG

TTGCCGTGGACTACATTACTGTTGCCCTCCTGATCTGGAACTTCGGCGTGGTGGG

CATGATTTCCATTCACTGGAAAGGCCCCCTGAGACTGCAGCAGGCATACCTCATT

ATGATCTCCGCCCTCATGGCCCTGGTGTTCATCAAGTACCTGCCCGAGTGGACTG

CTTGGCTCATCTTGGCTGTGATCTCCGTGTATGATTTAGTGGCTGTTCTGTGTCCT

AAAGGTCCACTGCGTATGCTGGTGGAAACAGCTCAGGAAAGAAATGAAACACTG

TTTCCTGCTCTGATTTACTCCTCAACAATGGTGTGGCTCGTGAATATGGCCGAAG

GAGACCCTGAAGCCCAACGGAGAGTGTCCAAAAACTCCAAGTATAACGCCGAGA

GCACAGAAAGGGAGAGCCAGGATACAGTTGCCGAGAATGACGATGGCGGCTTC

-continued

AGTGAGGAATGGGAAGCCCAGAGGGACAGCCACCTGGGGCCTCACAGAAGCAC

CCCTGAGTCTAGAGCCGCTGTCCAGGAACTGTCCAGCTCCATCCTGGCCGGCGAA

GACCCCGAAGAAAGGGGAGTAAAACTTGGACTGGGAGATTTCATCTTCTACAGT

GTTCTCGTTGGCAAAGCCAGCGCAACAGCTAGCGGAGACTGGAACACAACAATA

GCCTGTTTCGTAGCCATCTTAATTGGCCTGTGCCTTACACTTCTGCTCCTGGCCAT

CTTCAAGAAGGCCCTGCCAGCCCTGCCTATCAGCATCACCTTCGGGCTTGTTTTCT

ACTTTGCCACCGATTATCTGGTGCAGCCCTTCATGGACCAGCTGGCCTTCCACCA

GTTTTACATCTAGtaagcggccgccctagggagctcctcgaggggggtggcatccctgtgacccctccccagtgcctctcc tggccctggaagttgccactccagtgcccaccagccttgtcctaataaaattaagttgcatcattttgtctgactaggtgtccttctataatat tatggggtggaggggggtggtatggagcaaggggcaagggggaagacaacctgtagggcctgcggggtctattgggaaccaag ctggagtgcagtggcacaatcttggctcactgcaatctccgcctcctgggttcaagcgattctcctgcctcagcctcccgagttgttggg attccaggcatgcatgaccaggctcagctaatttttgtttttttggtagagacggggtttcaccatattggccaggctggtctcccccctccta atctcaggtgatctacccaccttggcctcccaaattgctgggattacaggcgtgaaccactgctcccttccctgtccttctgattttaaaata actataccagcaggaggacgtccagacacagcataggctacctggccatgcccaaccggtgggacatttgagttgcttgcttggcact gtcctctcatgcgttgggtccactcagtagatgcctgttgaattcctgggcctagggctgtgccagctgcctcgtcccgtcaccttctggcttctt ctctccctccatatcttagctgttttcctcatgagaatgttccaaattcgaaatttctatttaaccattatatatttacttgtttgctattatctc tgcccccagtagattgttagctccagaagagaaaggatcatgtcttttgcttatctagatatgcccatctgcctggtacaatctctggcaca tgttacaggcaacaactacttgtggaattggtgaatgcatgaatagaagaatgagtgaatgaatgaatagacaataggcagaaatccag cctcaaagagcttacagtctggtaagaggaataaaatgtctgcaaatagccacaggacaggtcaaaggaaggaggggctatttccag ctgagggcaccccatcaggaaagcaccccagacttcctacaactactagacacatctcgatgcttttcacttctctatcaatggatcgtct ccctggagaataatccccaaagtgaaattacttagcacgtccagttaggtagatccttgtgtacttcttggttgttcagagatcatcaacca gtgcaaacaatcccccccatcaatacacagcagtgcctgcccctctccccccgaggtcttccgaggcccttcctccgtgcctgaacccc ctggacatatcatatggcaaactgaagtgtccaacgagatataggaagtgaaacacgatgtacactgaaacgtgcaatacaaatatgca gcatgaagtgcctcggttcactaacccgagctacgctgggtgcttcttttctaccactttccttaatgcctatggacacctcattctgtggct gaagttccttgtgttcaatagggataacagggtaatggcgcgggccgcaggaacccctagtgatggagttggccactccctctctgcg cgctcgctcgctcactgaggccgggcgaccaaaggtcgcccgacgcccgggctttgcccgggcggcctcagtgagcgagcgagc gcgcagctgcctgcagg Expression cassette for AAV production containing AAV2 ITRs (1-141, 4500-4640), EF-1alpha promoter (underlined, 237-1415), a synthetic human beta-globin intron (1436-2001), HA-tag (2081-2107), codon-optimized human presenilin 1v1.5 (uppercase SEQ ID NO: 37, 2075-3508), human growth hormone polyadenylation (3539-4015) and human growth hormone genomic sequence (4016-4469).

SEQ ID NO: 44 cctgcaggcagctgcgcgctcgctcgctcactgaggccgcccgggcaaagcccgggcgtcgggcgacctttggtcgcccggcctc agtgagcgagcgagcgcgcagagagggagtggccaactccatcactaggggttcctgcggccaattcagtcgataactataacggt cctaaggtagcgatttaaatacgcgctctcttaaggtagccccgggacgcgtcaattgagatctcggctccggtgcccgtcagtgggc agagcgcacatcgcccacagtccccgagaagggggggggaggggtcggcaattgaaccggtccctagagaaggtggcgcgggg taaactgggaaagtgatgtcgtgtactggctccgcctttttcccgagggtgggggagaaccgtatataagtgcagtagtcgccgtgaac gttctttttcgcaacgggtttgccgccagaacacaggtaagtgccgtgtgtggttcccgcgggcctggcctctttacgggttatggccctt gcgtgccttgaattacttccacctggctgcagtacgtgattcttgatcccgagcttcgggttggaagtgggtgggagagttcgaggcctt gcgcttaaggagccccttcgcctcgtgcttgagttgaggcctggcctgggcgctggggccgccgcgtgcgaatctggtggcaccttc gcgcctgtctcgctgctttcgataagtctctagccatttaaaatttttgatgacctgctgcgacgctttttttctggcaagatagtcttgtaaat gcgggccaagatctgcacactggtatttcggtttttggggccgcgggcggcgacggggcccgtgcgtcccagcgcacatgttcggc -continued gaggcggggcctgcgagcgcggccaccgagaatcggacgggggtagtctcaagctggccggcctgctctggtgcctggtctcgcg ccgccgtgtatcgccccgccctgggcggcaaggctggcccggtcggcaccagttgcgtgagcggaaagatggccgcttcccggcc ctgctgcagggagctcaaaatggaggacgcggcgctcgggagagcgggcgggtgagtcacccacacaaaggaaaagggcctttc cgtcctcagccgtcgcttcatgtgactccacggagtaccgggcgccgtccaggcacctcgattagttctcgagcttttggagtacgtcgt ctttaggttggggggaggggttttatgcgatggagtttccccacactgagtgggtggagactgaagttaggccagcttggcacttgatgtaa ttctccttggaatttgccctttttgagtttggatcttggttcattctcaagcctcagacagtggttcaaagtttttttcttccatttcaggtgtcg tgaaagcttcgtttagtgaaccgtcagatcgcctggagacgccatccacgctgttttgacctccatagaagacaccgggaccgatccag cctccgcggattcgaatcccggccgggaacggtgcattggaacgcggattccccgtgccaagagtgacgtaagtaccgcctatagagtcta taggcccacaaaaaatgctttcttcttttaatatactttttttgtttatcttatttctaatactttccctaatctctttctttcagggcaataatg atacaatgtatcatgcctctttgcaccattctaaagaataacagtgataatttctgggttaaggcaatagcaatatttctgcatataaatatttc tgcatataaattgtaactgatgtaagaggtttcatattgctaatagcagctacaatccagctaccattctgcttttattttgtggttgggataag gctggattattctgagtccaagctaggcccttttgctaatcgtgttcatacctcttatcttcctcccacagctcctgggcaacgtgctggtct gtgtgctggcccatcactttggcaaagaattaccggtggcaacgtgctggttattgtgctgtctcatcattttggcaaagaattcacgccc cagagccgccaccATGgcctacccatacgatgttccagattacgctACAGAATTACCTGCCCCCTTGAGCT

ACTTCCAGAATGCACAGATGAGCGAGGACAACCACCTGAGCAATACTGTACGTA

GCCAGAATGACAACAGAGAACGGCAGGAACACAACGACAGGCGGAGCCTGGGC

CACCCTGAGCCCCTGTCTAATGGAAGACCCCAGGGTAACAGCAGACAGGTGGTG

GAACAAGATGAGGAAGAGGACGAGGAGCTGACCCTGAAGTACGGCGCCAAGCA

CGTGATCATGCTCTTCGTGCCCGTGACTCTCTGCATGGTGGTGGTGGTGGCTACA

ATCAAGAGCGTCAGCTTTTATACCCGGAAGGATGGGCAGCTAATCTATACCCCAT

TCACAGAAGACACCGAGACTGTGGGCCAGAGAGCCCTGCACTCAATCCTGAATG

CCGCCATCATGATCAGCGTCATTGTTGTCATGACTATCCTCCTGGTGGTTCTGTAT

AAATACAGGTGCTATAAGGTCATCCATGCCTGGCTGATCATATCATCTCTGTTGC

TGCTGTTCTTTTTTAGCTTCATTTACCTGGGCGAAGTGTTTAAAACCTATAACGTT

GCCGTGGACTACATTACTGTTGCCCTCCTGATCTGGAACTTCGGCGTGGTGGGCA

TGATTTCCATTCACTGGAAAGGCCCCCTGAGACTGCAGCAGGCATACCTCATTAT

GATCTCCGCCCTCATGGCCCTGGTGTTCATCAAGTACCTGCCCGAGTGGACTGCT

TGGCTCATCTTGGCTGTGATCTCCGTGTATGATTTAGTGGCTGTTCTGTGTCCTAA

AGGTCCACTGCGTATGCTGGTGGAAACAGCTCAGGAAAGAAATGAAACACTGTT

TCCTGCTCTGATTTACTCCTCAACAATGGTGTGGCTCGTGAATATGGCCGAAGGA

GACCCTGAAGCCCAACGGAGAGTGTCCAAAAACTCCAAGTATAACGCCGAGAGC

ACAGAAAGGGAGAGCCAGGATACAGTTGCCGAGAATGACGATGGCGGCTTCAGT

GAGGAATGGGAAGCCCAGAGGGACAGCCACCTGGGGCCTCACAGAAGCACCCC

TGAGTCTAGAGCCGCTGTCCAGGAACTGTCCAGCTCCATCCTGGCCGGCGAAGA

CCCCGAAGAAAGGGGAGTAAAACTTGGACTGGGAGATTTCATCTTCTACAGTGT

TCTCGTTGGCAAAGCCAGCGCAACAGCTAGCGGAGACTGGAACACAACAATAGC

CTGTTTCGTAGCCATCTTAATTGGCCTGTGCCTTACACTTCTGCTCCTGGCCATCT

TCAAGAAGGCCCTGCCAGCCCTGCCTATCAGCATCACCTTCGGGCTTGTTTTCTA

CTTTGCCACCGATTATCTGGTGCAGCCCTTCATGGACCAGCTGGCCTTCCACCAG

TTTTACATCTAGtaagcggccgccctagggagctcctcgagggggtggcatccctgtgacccctccccagtgcctctcctg gccctggaagttgccactccagtgcccaccagccttgtcctaataaaattaagttgcatcattttgtctgactaggtgtccttctataatatta -continued tggggtggagggggtggtatggagcaaggggcaagggggaagacaacctgtagggcctgcggggtctattgggaaccaagct ggagtgcagtggcacaatcttggctcactgcaatctccgcctcctgggttcaagcgattctcctgcctcagcctcccgagttgttgggatt ccaggcatgcatgaccaggctcagctaattttttgtttttttggtagagacggggtttcaccatattggccaggctggtctcccctcctaat ctcaggtgatctacccaccttggcctcccaaattgctgggattacaggcgtgaaccactgctcccttccctgtccttcctgggcctaggg ctgtgccagctgcctcgtcccgtcaccttctggcttcttctctccctccatatcttagctgttttcctcatgagaatgttccaaattcgaaatttc tatttaaccattatatatttacttgtttgctattatctctgcccccagtagattgttagctccagaagagaaaggatcatgtcttttgcttatctag atatgcccatctgcctggtacaatctctggcacatgttacaggcaacaactacttgtggaattggtgaatgcatgaatagaagaatgagt gaatgaatgaatagacaataggcagaaatccagcctcaaagagcttacagtctggtaagaggaataaaatgtctgcaaatagccacag gacaggtcaaaggaaggaggggctatttccagctgagggcaccccatcaggaaagcaccccagacttccttagggataacagggta atggcgcgggccgcaggaacccctagtgatggagttggccactccctctctgcgcgctcgctcgctcactgaggccgggcgaccaa aggtcgcccgacgcccgggctttgcccgggcggcctcagtgagcgagcgagcgcgcagctgcctgcagg Expression cassette for AAV production containing AAV2 ITRs (1-141, 4533-4673), PGK promoter (underlined, 237-663), a synthetic human beta-globin intron (684-1249), HA-tag (1329-1355), codon-optimized human presenilin 1v1.5 (uppercase SEQ ID NO: 37, 1323-2756), human growth hormone polyadenylation (2787-3263) and human growth hormone genomic sequence (3264-4502).

SEQ ID NO: 45 cctgcaggcagctgcgcgctcgctcgctcactgaggccgcccgggcaaagcccgggcgtcgggcgacctttggtcgcccggcctc agtgagcgagcgagcgcgcagagagggagtggccaactccatcactaggggttcctgcggccaattcagtcgataactataacggt cctaaggtagcgatttaaatacgcgctctcttaaggtagccccgggacgcgtcaattgagatctcgcctcgaattccacggggttgggg ttgcaccttttccaaggcagccctggctttgcgcagggacgcggctactctgcgcgtggttccgagaaacacagcgacgccgaccct gggtctcgcacattcttcacgtccgttcgcagcgtcacccggatcttcgccgctacccttgtgggccccccggcgacgcttcctgctcc gccccctaagtcgggaaggttccttgcggttcgcggcgtgccggacgtgacaaacggaagccgcacgtctcactagtaccctcgcag acggacagcgccagggagcaatggcagcgcgccgaccgcgatgggctgtggccaatagcggctgctcagcagggcgcgccgag agcagcggccgggaaggggcggtgcgggaggcggggtgtggggcggtagtgtgggcccaagcttcgtttagtgaaccgtcagat cgcctggagacgccatccacgctgttttgacctccatagaagacaccgggaccgatccagcctccgcggattcgaatcccggccgg gaacggtgcattggaacgcggattccccgtgccaagagtgacgtaagtaccgcctatagagtctataggcccacaaaaaatgctttcttcttttt aatatactttttttgtttatcttatttctaatactttccctaatctctttctttcagggcaataatgatacaatgtatcatgcctctttgcaccatt ctaaagaataacagtgataatttctgggttaaggcaatagcaatatttctgcatataaatatttctgcatataaattgtaactgatgtaagagg tttcatattgctaatagcagctacaatccagctaccattctgcttttattttgtggttgggataaggctggattattctgagtccaagctaggc ccttttgctaatcgtgttcatacctcttatcttcctcccacagctcctgggcaacgtgctggtctgtgtgctggcccatcactttggcaaaga attaccggtggcaacgtgctggttattgtgctgtctcatcattttggcaaagaattcacgccccagagccgccaccATGgcctaccca tacgatgttccagattacgctACAGAATTACCTGCCCCCTTGAGCTACTTCCAGAATGCACAG

ATGAGCGAGGACAACCACCTGAGCAATACTGTACGTAGCCAGAATGACAACAGA

GAACGGCAGGAACACAACGACAGGCGGAGCCTGGGCCACCCTGAGCCCCTGTCT

AATGGAAGACCCCAGGGTAACAGCAGACAGGTGGTGGAACAAGATGAGGAAGA

GGACGAGGAGCTGACCCTGAAGTACGGCGCCAAGCACGTGATCATGCTCTTCGT

GCCCGTGACTCTCTGCATGGTGGTGGTGGTGGCTACAATCAAGAGCGTCAGCTTT

TATACCCGGAAGGATGGGCAGCTAATCTATACCCCATTCACAGAAGACACCGAG

ACTGTGGGCCAGAGAGCCCTGCACTCAATCCTGAATGCCGCCATCATGATCAGC

GTCATTGTTGTCATGACTATCCTCCTGGTGGTTCTGTATAAATACAGGTGCTATAA

GGTCATCCATGCCTGGCTGATCATATCATCTCTGTTGCTGCTGTTCTTTTTTAGCTT

CATTTACCTGGGCGAAGTGTTTAAAACCTATAACGTTGCCGTGGACTACATTACT

-continued

GTTGCCCTCCTGATCTGGAACTTCGGCGTGGTGGGCATGATTTCCATTCACTGGA

AAGGCCCCCTGAGACTGCAGCAGGCATACCTCATTATGATCTCCGCCCTCATGGC

CCTGGTGTTCATCAAGTACCTGCCCGAGTGGACTGCTTGGCTCATCTTGGCTGTG

ATCTCCGTGTATGATTTAGTGGCTGTTCTGTGTCCTAAAGGTCCACTGCGTATGCT

GGTGGAAACAGCTCAGGAAAGAAATGAAACACTGTTTCCTGCTCTGATTTACTCC

TCAACAATGGTGTGGCTCGTGAATATGGCCGAAGGAGACCCTGAAGCCCAACGG

AGAGTGTCCAAAAACTCCAAGTATAACGCCGAGAGCACAGAAAGGGAGAGCCA

GGATACAGTTGCCGAGAATGACGATGGCGGCTTCAGTGAGGAATGGGAAGCCCA

GAGGGACAGCCACCTGGGGCCTCACAGAAGCACCCCTGAGTCTAGAGCCGCTGT

CCAGGAACTGTCCAGCTCCATCCTGGCCGGCGAAGACCCCGAAGAAAGGGGAGT

AAAACTTGGACTGGGAGATTTCATCTTCTACAGTGTTCTCGTTGGCAAAGCCAGC

GCAACAGCTAGCGGAGACTGGAACACAACAATAGCCTGTTTCGTAGCCATCTTA

ATTGGCCTGTGCCTTACACTTCTGCTCCTGGCCATCTTCAAGAAGGCCCTGCCAG

CCCTGCCTATCAGCATCACCTTCGGGCTTGTTTTCTACTTTGCCACCGATTATCTG

GTGCAGCCCTTCATGGACCAGCTGGCCTTCCACCAGTTTTACATCTAGtaagcggccgc cctagggagctcctcgaggggggtggcatccctgtgacccctccccagtgcctctcctggccctggaagttgccactccagtgcccacc agccttgtcctaataaaattaagttgcatcattttgtctgactaggtgtccttctataatattatggggtggaggggggtggtatggagcaa ggggcaagggggaagacaacctgtagggcctgcggggtctattgggaaccaagctggagtgcagtggcacaatcttggctcactg caatctccgcctcctgggttcaagcgattctcctgcctcagcctcccgagttgttgggattccaggcatgcatgaccaggctcagctaatt tttgtttttttggtagagacggggtttcaccatattggccaggctggtctcccccctcctaatctcaggtgatctacccaccttggcctcccaa attgctgggattacaggcgtgaaccactgctcccttccctgtccttctgattttaaaataactataccagcaggaggacgtccagacaca gcataggctacctggccatgcccaaccggtgggacatttgagttgcttgcttggcactgtcctctcatgcgttgggtccactcagtagat gcctgttgaattcctgggcctagggctgtgccagctgcctcgtcccgtcaccttctggcttcttctctccctccatatcttagctgttttcctc atgagaatgttccaaattcgaaatttctatttaaccattatatatttacttgtttgctattatctctgcccccagtagattgttagctccagaaga gaaaggatcatgtcttttgcttatctagatatgcccatctgcctggtacaatctctggcacatgttacaggcaacaactacttgtggaattgg tgaatgcatgaatagaagaatgagtgaatgaatgaatagacaataggcagaaatccagcctcaaagagcttacagtctggtaagagga ataaaatgtctgcaaatagccacaggacaggtcaaaggaaggaggggctatttccagctgagggcaccccatcaggaaagcacccc agacttcctacaactactagacacatctcgatgcttttcacttctctatcaatggatcgtctccctggagaataatccccaaagtgaaattac ttagcacgtccagttaggtagatccttgtgtacttcttggttgttcagagatcatcaaccagtgcaaacaatcccccatcaatacacagca gtgcctgcccctctcccccgaggtcttccgaggcccttcctccgtgcctgaacccccctggacatatcatatggcaaactgaagtgtcc aacgagatataggaagtgaaacacgatgtacactgaaacgtgcaatacaaatatgcagcatgaagtgcctcggttcactaacccgagc tacgctgggtgcttcttttctaccactttccttaatgcctatggacacctcattctgtggctgaagttccttgtgttcaattccccccatcttcatt gaacatcctgtgtagggacctcacccctgtcctgctagctttgcactgaggcaagttctgtccatgcctagtagtgccaccacctttacta gatgagacttctaaagagcttggcatggaaggaaagcccgggggccttggaagccatcacttagaaactgggagagctccaggcaa gccacctcatcttagggataacagggtaatggcgcgggccgcaggaacccctagtgatggagttggccactccctctctgcgcgctc gctcgctcactgaggccgggcgaccaaaggtcgcccgacgcccgggctttgcccgggcggcctcagtgagcgagcgagcgcgca gctgcctgcagg Expression cassette for AAV production containing AAV2 ITRs (1-141, 4554-4694), synapsin 1 promoter (underlined, 237-684), a synthetic human beta-globin intron (705-1270), HA-tag (1350-1376), codon-optimized human presenilin 1v1.5 (uppercase SEQ ID NO: 37, 1344-2777), human growth hormone polyadenylation (2808-3284) and human growth hormone genomic sequence (3285-4523).

SEQ ID NO: 46 cctgcaggcagctgcgcgctcgctcgctcactgaggccgcccgggcaaagcccgggcgtcgggcgacctttggtcgcccggcctc -continued agtgagcgagcgagcgcgcagagagggagtggccaactccatcactaggggttcctgcggccaattcagtcgataactataacggt cctaaggtagcgatttaaatacgcgctctcttaaggtagccccgggacgcgtcaattgagatctcagtgcaagtgggttttaggaccag gatgaggcgggctggggctacctacctgacgaccgaccccgacccactggacaagcacccaacccccattccccaaattgcgcat cccctatcagagagggggaggggaaacaggatgcggcgaggcgcgtgcgcactgccagcttcagcaccgcggacagtgccttcg cccccgcctggcggcgcgcgccaccgccgcctcagcactgaaggcgcgctgacgtcactcgccggtcccccgcaaactccccttc ccggccaccttggtcgcgtccgcgccgccgccggcccagccggaccgcaccacgcgaggcgcgagatagggggcacgggcg cgaccatctgcgctgcggcgccggcgactcagcgctgcctcagtctgcggtgggcagcggaggagtcgtgtcgtgcctgagagcg cagaagcttcgtttagtgaaccgtcagatcgcctggagacgccatccacgctgttttgacctccatagaagacaccgggaccgatcca gcctccgcggattcgaatcccggccgggaacggtgcattggaacgcggattccccgtgccaagagtgacgtaagtaccgcctatagagtc tataggcccacaaaaaatgctttcttcttttaatatactttttttgtttatcttatttctaatactttccctaatctctttctttcagggcaataat gatacaatgtatcatgcctctttgcaccattctaaagaataacagtgataatttctgggttaaggcaatagcaatatttctgcatataaatattt ctgcatataaattgtaactgatgtaagaggtttcatattgctaatagcagctacaatccagctaccattctgcttttattttgtggttgggataa ggctggattattctgagtccaagctaggcccttttgctaatcgtgttcatacctcttatcttcctcccacagctcctgggcaacgtgctggtc tgtgtgctggcccatcactttggcaaagaattaccggtggcaacgtgctggttattgtgctgtctcatcattttggcaaagaattcacgccc cagagccgccaccATGgcctacccatacgatgttccagattacgctACAGAATTACCTGCCCCCTTGAGCT

ACTTCCAGAATGCACAGATGAGCGAGGACAACCACCTGAGCAATACTGTACGTA

GCCAGAATGACAACAGAGAACGGCAGGAACACAACGACAGGCGGAGCCTGGGC

CACCCTGAGCCCCTGTCTAATGGAAGACCCCAGGGTAACAGCAGACAGGTGGTG

GAACAAGATGAGGAAGAGGACGAGGAGCTGACCCTGAAGTACGGCGCCAAGCA

CGTGATCATGCTCTTCGTGCCCGTGACTCTCTGCATGGTGGTGGTGGTGGCTACA

ATCAAGAGCGTCAGCTTTTATACCCGGAAGGATGGGCAGCTAATCTATACCCCAT

TCACAGAAGACACCGAGACTGTGGGCCAGAGAGCCCTGCACTCAATCCTGAATG

CCGCCATCATGATCAGCGTCATTGTTGTCATGACTATCCTCCTGGTGGTTCTGTAT

AAATACAGGTGCTATAAGGTCATCCATGCCTGGCTGATCATATCATCTCTGTTGC

TGCTGTTCTTTTTTAGCTTCATTTACCTGGGCGAAGTGTTTAAAACCTATAACGTT

GCCGTGGACTACATTACTGTTGCCCTCCTGATCTGGAACTTCGGCGTGGTGGGCA

TGATTTCCATTCACTGGAAAGGCCCCCTGAGACTGCAGCAGGCATACCTCATTAT

GATCTCCGCCCTCATGGCCCTGGTGTTCATCAAGTACCTGCCCGAGTGGACTGCT

TGGCTCATCTTGGCTGTGATCTCCGTGTATGATTTAGTGGCTGTTCTGTGTCCTAA

AGGTCCACTGCGTATGCTGGTGGAAACAGCTCAGGAAAGAAATGAAACACTGTT

TCCTGCTCTGATTTACTCCTCAACAATGGTGTGGCTCGTGAATATGGCCGAAGGA

GACCCTGAAGCCCAACGGAGAGTGTCCAAAAACTCCAAGTATAACGCCGAGAGC

ACAGAAAGGGAGAGCCAGGATACAGTTGCCGAGAATGACGATGGCGGCTTCAGT

GAGGAATGGGAAGCCCAGAGGGACAGCCACCTGGGGCCTCACAGAAGCACCCC

TGAGTCTAGAGCCGCTGTCCAGGAACTGTCCAGCTCCATCCTGGCCGGCGAAGA

CCCCGAAGAAAGGGGAGTAAAACTTGGACTGGGAGATTTCATCTTCTACAGTGT

TCTCGTTGGCAAAGCCAGCGCAACAGCTAGCGGAGACTGGAACACAACAATAGC

CTGTTTCGTAGCCATCTTAATTGGCCTGTGCCTTACACTTCTGCTCCTGGCCATCT

TCAAGAAGGCCCTGCCAGCCCTGCCTATCAGCATCACCTTCGGGCTTGTTTTCTA

CTTTGCCACCGATTATCTGGTGCAGCCCTTCATGGACCAGCTGGCCTTCCACCAG

-continued

TTTTACATCTAGtaagcggccgccctagggagctcctcgagggggtggcatccctgtgacccctccccagtgcctctcctg gccctggaagttgccactccagtgcccaccagccttgtcctaataaaattaagttgcatcattttgtctgactaggtgtccttctataatatta tggggtggaggggggtggtatggagcaaggggcaagggggaagacaacctgtagggcctgcggggtctattgggaaccaagct ggagtgcagtggcacaatcttggctcactgcaatctccgcctcctgggttcaagcgattctcctgcctcagcctcccgagttgttgggatt ccaggcatgcatgaccaggctcagctaattttttgtttttttggtagagacggggtttcaccatattggccaggctggtctcccctcctaat ctcaggtgatctacccaccttggcctcccaaattgctgggattacaggcgtgaaccactgctcccttccctgtccttctgattttaaaataa ctataccagcaggaggacgtccagacacagcataggctacctggccatgcccaaccggtgggacatttgagttgcttgcttggcactg tcctctcatgcgttgggtccactcagtagatgcctgttgaattcctgggcctagggctgtgccagctgcctcgtcccgtcaccttctggcttcttc tctccctccatatcttagctgttttcctcatgagaatgttccaaattcgaaatttctatttaaccattatatatttacttgtttgctattatctct gcccccagtagattgttagctccagaagagaaaggatcatgtcttttgcttatctagatatgcccatctgcctggtacaatctctggcacat gttacaggcaacaactacttgtggaattggtgaatgcatgaatagaagaatgagtgaatgaatgaatagacaataggcagaaatccag cctcaaagagcttacagtctggtaagaggaataaaatgtctgcaaatagccacaggacaggtcaaaggaaggaggggctatttccag ctgagggcaccccatcaggaaagcaccccagacttcctacaactactagacacatctcgatgcttttcacttctctatcaatggatcgtct ccctggagaataatccccaaagtgaaattacttagcacgtccagttaggtagatccttgtgtacttcttggttgttcagagatcatcaacca gtgcaaacaatcccccccatcaatacacagcagtgcctgcccctctcccccgaggtcttccgaggcccttcctccgtgcctgaacccc ctggacatatcatatggcaaactgaagtgtccaacgagatataggaagtgaaacacgatgtacactgaaacgtgcaatacaaatatgca gcatgaagtgcctcggttcactaacccgagctacgctgggtgcttcttttctaccactttccttaatgcctatggacacctcattctgtggct gaagttccttgtgttcaattcccccatcttcattgaacatcctgtgtagggacctcacccctgtcctgctagctttgcactgaggcaagttc tgtccatgcctagtagtgccaccacctttactagatgagacttctaaagagcttggcatggaaggaaagcccgggggccttggaagcc atcacttagaaactgggagagctccaggcaagccacctcatcttagggataacagggtaatggcgcgggccgcaggaacccctagt gatggagttggccactccctctctgcgcgctcgctcgctcactgaggccgggcgaccaaaggtcgcccgacgcccgggctttgccc gggcggcctcagtgagcgagcgagcgcgcagctgcctgcagg Expression cassette for production of a self-complementary AAV containing native and modified AAV2 ITRs (1-105, 2386-2526), CBA promoter (underlined, 113-766), minute virus of mice intron (776-867), HA-tag (884-910), codon-optimized human presenilin 1v1.5 (uppercase SEQ ID NO: 37, 881-2311), rabbit beta-globin polyadenylation sequence (2319-2367).

SEQ ID NO: 47 ctgcgcgctcgctcgctcactgaggccgcccgggcaaagcccgggcgtcgggcgacctttggtcgcccggcctcagtgagcgagc gagcgcgcagagagggagtgagatctccgacattgattattgactagttattaatagtaatcaattacggggtcattagttcatagcccat atatggagttccgcgttacataacttacggtaaatggcccgcctggctgaccgcccaacgacccccgcccattgacgtcaataatgac gtatgttcccatagtaacgccaatagggactttccattgacgtcaatgggtggagtatttacggtaaactgcccacttggcagtacatcaa gtgtatcatatgccaagtacgccccctattgacgtcaatgacggtaaatggcccgcctggcattatgcccagtacatgaccttatgggac tttcctacttggcagtacatctacgtattagtcatcgctattaccatgtcgaggccacgttctgcttcactctccccatctcccccccctcccc acccccaattttgtatttatttattttttaattattttgtgcagcgatgggggcgggggggggggggcgcgcgccaggcggggcggggcg gggcgaggggcggggcggggcgaggcggagaggtgcggcggcagccaatcagagcggcgcgctccgaaagtttccttttatgg cgaggcggcggcggcggcggccctataaaaagcgaagcgcgcggcgggcgggagcaagcttcgtaagaggtaagggtttaagg gatggttggttggtggggtattaatgtttaattacctgttttacaggcctgaaatcacttggttttaggttgggctagccgccaccATGta cccatacgatgttccagattacgctACAGAATTACCTGCCCCCTTGAGCTACTTCCAGAATGCAC

AGATGAGCGAGGACAACCACCTGAGCAATACTGTACGTAGCCAGAATGACAACA

GAGAACGGCAGGAACACAACGACAGGCGGAGCCTGGGCCACCCTGAGCCCCTGT

CTAATGGAAGACCCCAGGGTAACAGCAGACAGGTGGTGGAACAAGATGAGGAA

GAGGACGAGGAGCTGACCCTGAAGTACGGCGCCAAGCACGTGATCATGCTCTTC

GTGCCCGTGACTCTCTGCATGGTGGTGGTGGTGGCTACAATCAAGAGCGTCAGCT

-continued

TTTATACCCGGAAGGATGGGCAGCTAATCTATACCCCATTCACAGAAGACACCG

AGACTGTGGGCCAGAGAGCCCTGCACTCAATCCTGAATGCCGCCATCATGATCA

GCGTCATTGTTGTCATGACTATCCTCCTGGTGGTTCTGTATAAATACAGGTGCTAT

AAGGTCATCCATGCCTGGCTGATCATATCATCTCTGTTGCTGCTGTTCTTTTTTAG

CTTCATTTACCTGGGCGAAGTGTTTAAAACCTATAACGTTGCCGTGGACTACATT

ACTGTTGCCCTCCTGATCTGGAACTTCGGCGTGGTGGGCATGATTTCCATTCACT

GGAAAGGCCCCCTGAGACTGCAGCAGGCATACCTCATTATGATCTCCGCCCTCAT

GGCCCTGGTGTTCATCAAGTACCTGCCCGAGTGGACTGCTTGGCTCATCTTGGCT

GTGATCTCCGTGTATGATTTAGTGGCTGTTCTGTGTCCTAAAGGTCCACTGCGTAT

GCTGGTGGAAACAGCTCAGGAAAGAAATGAAACACTGTTTCCTGCTCTGATTTAC

TCCTCAACAATGGTGTGGCTCGTGAATATGGCCGAAGGAGACCCTGAAGCCCAA

CGGAGAGTGTCCAAAAACTCCAAGTATAACGCCGAGAGCACAGAAAGGGAGAG

CCAGGATACAGTTGCCGAGAATGACGATGGCGGCTTCAGTGAGGAATGGGAAGC

CCAGAGGGACAGCCACCTGGGGCCTCACAGAAGCACCCCTGAGTCTAGAGCCGC

TGTCCAGGAACTGTCCAGCTCCATCCTGGCCGGCGAAGACCCCGAAGAAAGGGG

AGTAAAACTTGGACTGGGAGATTTCATCTTCTACAGTGTTCTCGTTGGCAAAGCC

AGCGCAACAGCTAGCGGAGACTGGAACACAACAATAGCCTGTTTCGTAGCCATC

TTAATTGGCCTGTGCCTTACACTTCTGCTCCTGGCCATCTTCAAGAAGGCCCTGCC

AGCCCTGCCTATCAGCATCACCTTCGGGCTTGTTTTCTACTTTGCCACCGATTATC

TGGTGCAGCCCTTCATGGACCAGCTGGCCTTCCACCAGTTTTACATCTAGgcggccga ataaaagatctttattttcattagatctgtgtgttggttttttgtgtgtagggataacagggtaataggaacccctagtgatggagttggccac tccctctctgcgcgctcgctcgctcactgaggccgggcgaccaaaggtcgcccgacgcccgggctttgcccgggcggcctcagtga gcgagcgagcgcgcagctgcctgcagg Any and all references and citations to other documents, such as patents, patent applications, patent publications, journals, books, papers, web contents, that have been made throughout this disclosure are hereby incorporated herein by reference in their entirety for all purposes.

Although the present invention has been described with reference to specific details of certain embodiments thereof in the above examples, it will be understood that modifications and variations are encompassed within the spirit and scope of the invention. Accordingly, the invention is limited only by the following claims.

What is claimed:

1. An isolated polynucleotide set forth in SEQ ID NO: 37 or SEQ ID NO: 39, wherein the polynucleotide is not naturally occurring.

2. The isolated polynucleotide of claim 1, having the nucleotide sequence set forth in SEQ ID NO: 37.

3. The isolated polynucleotide of claim 1, having the nucleotide sequence set forth in SEQ ID NO: 39.

4. A nucleic acid expression cassette comprising:

(I) a polynucleotide encoding presenilin 1, wherein the polynucleotide comprises:

(a) a polynucleotide set forth in SEQ ID NO: 37 or SEQ ID NO: 39; and (II) one or more regulatory elements operably linked to the polynucleotide encoding presenilin 1.

5. The nucleic acid expression cassette of claim 4, wherein one of the regulatory elements is a Kozak translation initiation signal.

6. The nucleic acid expression cassette of claim 5, wherein the Kozak translation initiation signal comprises a polynucleotide set forth in SEQ ID NO: 5.

7. The nucleic acid expression cassette of claim 4, wherein one of the regulatory elements is a chromatin insulator sequence.

8. The nucleic acid expression cassette of claim 7, wherein the chromatin insulator sequence comprises a polynucleotide set forth in SEQ ID NO: 4.

9. The nucleic acid expression cassette of claim 4, wherein one of the regulatory elements is a neuron-specific promoter.

10. The nucleic acid expression cassette of claim 9, wherein the neuron-specific promoter comprises (i) a polynucleotide set forth in SEQ ID NO: 2; or (ii) a polynucleotide set forth in SEQ ID NO: 3.

11. The nucleic acid expression cassette of claim 4, wherein one or more of the regulatory elements is independently selected from a mRNA stability element.

12. The nucleic acid expression cassette of claim 11, wherein the mRNA stability element comprises a polynucleotide set forth in SEQ ID NO: 9, SEQ ID NO: 10, or SEQ ID NO: 11.

13. The nucleic acid expression cassette of claim 11, wherein the mRNA stability element is located 3' of an open reading frame of the polynucleotide encoding presenilin 1 or 5' of a polyadenylation signal.

14. The nucleic acid expression cassette of claim 13 comprising a first and a second mRNA stability element, wherein the first mRNA stability element is located 3' of an open reading frame of the polynucleotide encoding presenilin 1; and the second mRNA stability element is located 5' of a polyadenylation signal.

15. A vector comprising the nucleic acid expression cassette of claim 4.

16. The vector of claim 15, wherein the vector is a viral vector.

17. The vector of claim 16, wherein the viral vector is an adeno-associated virus (AAV) vector, a retroviral vector, a lentiviral vector, or an adenoviral vector.

18. The vector of claim 17, wherein the AAV vector is AAV1, AAV2, AAV3, AAV4, AAV5, AAV6, AAV7, AAV8, AAV9, AAVDJ, AAVrh10, AAV11, AAV12, AAV2/1, AAV2/5, AAV2/6, AAV2/7, AAV2/8, AAV2/9, AAV2/rh10, AAV2/11, or AAV2/12.

19. The vector of claim 17, wherein the vector comprises:

a. a promoter selected from a CAG promoter, a presenilin-1 promoter, a ubiquitin C promoter, a CBA promoter, a synapsin-1 promoter, a PGK promoter, and an EF1α promoter, operatively linked to:

b. a presenilin-1 coding sequence selected from SEQ ID NO: 37 or SEQ ID NO: 39; and c. a polyadenylation sequence selected from a human growth hormone polyadenylation sequence and a rabbit β-globin polyadenylation sequence.

20. The vector of claim 19 additionally comprising an intron selected from a human beta globin intron or a minute virus of mice intron, wherein the intron is located in between the promoter and the presenilin-1 coding sequence.

21. The vector of claim 20, wherein the vector comprises:

a. nucleotides 1-141 of SEQ ID NO: 41, nucleotides 237-1200 of SEQ ID NO: 41, nucleotides 1221-1786 of SEQ ID NO: 41, nucleotides 1899-3299 of SEQ ID NO: 41, nucleotides 3330-3806 of SEQ ID NO: 41, and nucleotides 4553-4693 of SEQ ID NO: 41;

b. Nucleotides 1-141 of SEQ ID NO: 42, nucleotides 237-1323 of SEQ ID NO: 42, nucleotides 1344-1909 of SEQ ID NO: 42, nucleotides 1983-3416 of SEQ ID NO: 42, nucleotides 3447-3923 of SEQ ID NO: 42, and nucleotides 4554-4694 of SEQ ID NO: 42;

c. Nucleotides 1-141 of SEQ ID NO: 43, nucleotides 237-890 of SEQ ID NO: 43, nucleotides 911-1476 of SEQ ID NO: 43, nucleotides 1550-2983 of SEQ ID NO: 43, nucleotides 3014-3490 of SEQ ID NO: 43, and nucleotides 4553-4694 of SEQ ID NO: 43;

d. Nucleotides 1-141, nucleotides 237-1415 of SEQ ID NO: 44, nucleotides 1436-2001 of SEQ ID NO: 44, nucleotides 2075-3508 of SEQ ID NO: 44, nucleotides 3539-4015 of SEQ ID NO: 44, and nucleotides 4500-4640 of SEQ ID NO: 44;

e. Nucleotides 1-141 of SEQ ID NO: 45, nucleotides 237-664 of SEQ ID NO: 45, nucleotides 684-1249 of SEQ ID NO: 45, nucleotides 1323-2756 of SEQ ID NO: 45, 2787-3263 of SEQ ID NO: 45, and nucleotides 4533-4673 of SEQ ID NO: 45;

f. Nucleotides 1-141 of SEQ ID NO: 46, nucleotides 237-684 of SEQ ID NO: 46, nucleotides 705-1270 of SEQ ID NO: 46, nucleotides 1344-2777 of SEQ ID NO: 46, nucleotides 2808-3284 of SEQ ID NO: 46, and nucleotides 4554-4695 of SEQ ID NO: 46; or g. Nucleotides 1-105 of SEQ ID NO: 47, nucleotides 113-766 of SEQ ID NO: 47, nucleotides 776-867 of SEQ ID NO: 47, nucleotides 881-2311 of SEQ ID NO: 47, nucleotides 2319-2367 of SEQ ID NO: 47, and nucleotides 2386-2526 of SEQ ID NO: 47.

22. The vector of claim 21, wherein the vector comprises a nucleotide sequence of any one of SEQ ID NOs: 41-47.

23. The nucleic acid expression cassette of claim 4, wherein the regulatory elements operably linked to the polynucleotide encoding presenilin 1 comprise:

(i) a Kozak translation initiation signal;

(ii) a neuron-specific promoter;

(iii) a chromatin insulator sequence;

(iv) a mRNA stability element located 3' of an open reading frame of the polynucleotide encoding presenilin 1; and (v) a mRNA stability element located 5' of a polyadenylation signal.

24. The nucleic acid expression cassette of claim 23, wherein:

the Kozak translation initiation signal comprises a polynucleotide set forth in SEQ ID NO: 5;

the chromatin insulator sequence comprises a polynucleotide set forth in SEQ ID NO: 4;

the mRNA stability element located 3' of the open reading frame of the polynucleotide encoding presenilin 1 comprises a polynucleotide set forth in SEQ ID NO: 9, or SEQ ID NO: 10;

the at least one mRNA stability element located 5' of a polyadenylation signal comprises a polynucleotide set forth in SEQ ID NO: 11; and the neuron-specific promoter comprises a polynucleotide set forth in SEQ ID NO: 2 or SEQ ID NO: 3.

25. The nucleic acid expression cassette of claim 4, wherein the promoter operably linked to the polynucleotide encoding presenilin 1 is a ubiquitous promoter.

26. A method of treating a neurodegenerative disease, disorder, or condition comprising administering to a subject in need thereof the vector of claim 15.

27. The method of claim 26, wherein the neurodegenerative disease, disorder, or condition is Alzheimer's disease, Familial Alzheimer's Disease (FAD), presenilin 1 (PSEN-1) mediated FAD, frontotemporal dementia, frontotemporal lobar degeneration, Pick's disease, Lewy body dementia, memory loss, cognitive impairment, or mild cognitive impairment.

28. A method of treating Familial Alzheimer's Disease (FAD) or presenilin 1 (PSEN-1) mediated FAD comprising administering to a subject in need thereof the vector of claim 15.

29. A method of producing presenilin 1 protein comprising:

transforming a host cell with a vector comprising an optimized polynucleotide set forth in SEQ ID NO: 37 or SEQ ID NO: 39; and culturing the cell under conditions and for a time that allow expression of the presenilin 1 protein, wherein the expression of the presenilin 1 protein encoded by the optimized polynucleotide in the host cell is greater than a level of expression of presenilin 1 protein encoded by a wilt-type polynucleotide in a host cell, thereby producing presenilin 1 protein.

* * * * *

SEQUENCE LISTING

```
<160> NUMBER OF SEQ ID NOS: 47

<210> SEQ ID NO 1
<211> LENGTH: 6018
<212> TYPE: DNA
<213> ORGANISM: Homo sapiens
<220> FEATURE:
<221> NAME/KEY: misc_feature
<223> OTHER INFORMATION: presenilin 1 (PSEN1), transcript variant 1
<220> FEATURE:
<221> NAME/KEY: misc_feature
<223> OTHER INFORMATION: presenilin 1 (PSEN1) transcript variant 1

<400> SEQUENCE: 1

ggaaacaaaa cagcggctgg tctggaagga acctgagcta cgagccgcgg cggcagcggg      60

gcggcgggga agcgtatacc taatctggga gcctgcaagt gacaacagcc tttgcggtcc     120

ttagacagct tggcctggag gagaacacat gaaagaaaga acctcaagag gctttgtttt     180
```

```
ctgtgaaaca gtatttctat acagttgctc caatgacaga gttacctgca ccgttgtcct    240
acttccagaa tgcacagatg tctgaggaca accacctgag caatactgta cgtagccaga    300
atgacaatag agaacggcag gagcacaacg acagacggag ccttggccac cctgagccat    360
tatctaatgg acgaccccag ggtaactccc ggcaggtggt ggagcaagat gaggaagaag    420
atgaggagct gacattgaaa tatggcgcca agcatgtgat catgctcttt gtccctgtga    480
ctctctgcat ggtggtggtc gtggctacca ttaagtcagt cagcttttat acccggaagg    540
atgggcagct aatctatacc ccattcacag aagataccga gactgtgggc cagagagccc    600
tgcactcaat tctgaatgct gccatcatga tcagtgtcat tgttgtcatg actatcctcc    660
tggtggttct gtataaatac aggtgctata aggtcatcca tgcctggctt attatatcat    720
ctctattgtt gctgttcttt ttttcattca tttacttggg ggaagtgttt aaaacctata    780
acgttgctgt ggactacatt actgttgcac tcctgatctg gaattttggt gtggtgggaa    840
tgatttccat tcactggaaa ggtccacttc gactccagca ggcatatctc attatgatta    900
gtgccctcat ggccctggtg tttatcaagt acctccctga atggactgcg tggctcatct    960
tggctgtgat ttcagtatat gatttagtgg ctgttttgtg tccgaaaggt ccacttcgta   1020
tgctggttga aacagctcag gagagaaatg aaacgctttt tccagctctc atttactcct   1080
caacaatggt gtggttggtg aatatggcag aaggagaccc ggaagctcaa aggagagtat   1140
ccaaaaattc caagtataat gcagaaagca cagaaaggga gtcacaagac actgttgcag   1200
agaatgatga tggcgggttc agtgaggaat gggaagccca gagggacagt catctagggc   1260
ctcatcgctc tacacctgag tcacgagctg ctgtccagga actttccagc agtatcctcg   1320
ctggtgaaga cccagaggaa aggggagtaa aacttggatt gggagatttc attttctaca   1380
gtgttctggt tggtaaagcc tcagcaacag ccagtggaga ctggaacaca accatagcct   1440
gtttcgtagc catattaatt ggtttgtgcc ttacattatt actccttgcc attttcaaga   1500
aagcattgcc agctcttcca atctccatca cctttgggct tgttttctac tttgccacag   1560
attatcttgt acagcctttt atggaccaat tagcattcca tcaattttat atctagcata   1620
tttgcggtta gaatcccatg gatgtttctt ctttgactat aacaaaatct ggggaggaca   1680
aaggtgattt tcctgtgtcc acatctaaca aagtcaagat tcccggctgg acttttgcag   1740
cttccttcca agtcttcctg accaccttgc actattggac tttggaagga ggtgcctata   1800
gaaaacgatt ttgaacatac ttcatcgcag tggactgtgt ccctcggtgc agaaactacc   1860
agatttgagg gacgaggtca aggagatatg ataggcccgg aagttgctgt gccccatcag   1920
cagcttgacg cgtggtcaca ggacgatttc actgacactg cgaactctca ggactaccgt   1980
taccaagagg ttaggtgaag tggtttaaac caaacggaac tcttcatctt aaactacacg   2040
ttgaaaatca acccaataat tctgtattaa ctgaattctg aacttttcag gaggtactgt   2100
gaggaagagc aggcaccagc agcagaatgg ggaatggaga ggtgggcagg ggttccagct   2160
tccctttgat tttttgctgc agactcatcc tttttaaatg agacttgttt tcccctctct   2220
ttgagtcaag tcaaatatgt agattgcctt tggcaattct tcttctcaag cactgacact   2280
cattaccgtc tgtgattgcc atttcttccc aaggccagtc tgaacctgag gttgctttat   2340
cctaaaagtt ttaacctcag gttccaaatt cagtaaattt tggaaacagt acagctattt   2400
ctcatcaatt ctctatcatg ttgaagtcaa atttggattt tccaccaaat tctgaatttg   2460
tagacatact tgtacgctca cttgccccag atgcctcctc tgtcctcatt cttctctccc   2520
```

```
acacaagcag tctttttcta cagccagtaa ggcagctctg tcgtggtagc agatggtccc   2580
attattctag ggtcttactc tttgtatgat gaaaagaatg tgttatgaat cggtgctgtc   2640
agccctgctg tcagaccttc ttccacagca aatgagatgt atgcccaaag acggtagaat   2700
taaagaagag taaaatggct gttgaagcac tttctgtcct ggtattttgt ttttgctttt   2760
gccacacagt agctcagaat ttgaacaaat agccaaaagc tggtggttga tgaattatga   2820
actagttgta tcaacacaaa gcaagagttg ggaaagccca tatttaactt ggtgagctgt   2880
gggagaacct ggtggcagaa ggagaaccaa ctgccaaggg gaaagagaag gggcctccag   2940
cagcgaaggg gatacagtga gctaatgatg tcaaggagga gtttcaggtt attctcgtca   3000
gctccacaaa tgggtgcttt gtggtctctg cccgcgttac ctttcctctc aatgtacctt   3060
tgtgtgaact gggcagtgga ggtgcctgct gcagttacca tggagttcag gctctgggca   3120
gctcagtcag gcaaaacaca caaacagcca tcagcctgtg tgggctcagg gcacctctgg   3180
acaaaggctt gtggggcata accttcttta ccacagagag cccttagcta tgctgatcag   3240
accgtaagcg tttatgagaa acttagtttc ctcctgtggc tgaggagggg ccagcttttt   3300
cttcttttgc ctgctgtttt ctctcccaat ctatgatatg atatgacctg gtttggggct   3360
gtctttggtg tttagaatat ttgttttctg tcccaggata tttcttataa gaacctaact   3420
tcaagagtag tgtgcgagta ctgatctgaa tttaaattaa aattggctta tattaggcag   3480
tcacagacag gaaaaataag agctatgcaa agaaaggggg atttaaagta gtaggttcta   3540
tcatctcaat tcattttttt ccatgaaatc ccttcttcca agattcattc cctctctcag   3600
acatgtgcta gcatgggtat tatcattgag aaagcacagc tacagcaaag ccacctgaat   3660
agcaatttgt gattggaagc attcttgagg gatccctaat ctagagtaat ttatttgtgt   3720
aaggatccca aatgtgttgc acctttcatg atacatttct tctctgaaga gggtacgtgg   3780
ggtgtgtgta tttaaatcca tcctatgtat tactgattgt cctgtgtaga aagatggcaa   3840
ttattctgtc tctttctcca agtttgagcc acatctcagc cacattgtta gacagtgtac   3900
agagaaccta tctttccttt tttttttttt aaaggacagg atttgctgt gttgcccagg   3960
ctagacttga actcctgggc tcaagtaatc cacctcagcc tgagtagctg agactacagc   4020
ccatcttatt tctttaaatc attcatctca ggcagagaac ttttccctca aacattcttt   4080
ttagaattag ttcagtcatt cctaaaacat ccaaatgcta gtcttccacc atgaaaaata   4140
gattgtcact ggaaagaaca gtagcaattt ccataaggat gtgccttcac tcacacggga   4200
caggcggtgg ttatagagtc gggcaaaacc agcagtagag tatgaccagc caagccaatc   4260
tgcttaataa aaagatggaa gacagtaagg aaggaaagta gccactaaga gtctgagtct   4320
gactgggcta cagaataaag ggtatttatg gacagaatgt cattacatgc ctatgggaat   4380
accaatcata tttggaagat ttgcagattt tttttcagag aggaaagact caccttcctg   4440
tttttggttc tcagtaggtt cgtgtgtgtt cctagaatca cagctctgac tccaaatgac   4500
tcaatttctc aattagaaaa agtagaagct ttctaagcaa cttggaagaa aacagtcata   4560
agtaagcaat ttgttgattt tactacagaa gcaacaactg aagaggcagt gtttttactt   4620
tcagactccg ggattcccat tctgtagtct ctctgctttt aaaaaccctc cttttgcaat   4680
agatgcccaa acagatgatg tttattactt gttatttacg tggcctcaga cagtgtatgt   4740
attctcgata taacttgtag agtgtgaaat ataagtttaa ctaccaaata aggtctccca   4800
gggttagatg actgcgggaa gcctttgatc ccaacccca aggctttgta tatttgatca   4860
tttgtgatct aaccctggaa gaaaaagagc tcagaaacca ctatgaaaaa atttgttcag   4920
```

tgttttctgt gttcccgtag gttctggagt ctgaggatgc aaagatgaat aagataaatt 4980
ctcagaatgt agttataatc tcttgttttc tggtatatgc catctttctt taacttctct 5040
aaaatattgg gtatttgtca aataaccact tttaacagtt accattactg agggcttata 5100
cattggtgtt ataaaagtga cttgattcag aaatcaatcc attcagtaaa gtactccttc 5160
tctaaatttg ctgttatgtc tataaggaac agtttgacct gcccttctcc tcacctcctc 5220
acctgccttc caacattgaa tttggaagga gacgtgaaaa ttggacattt ggttttgccc 5280
ttgggctgga aactatcata taatcataag tttgagccta gaagtgatcc ttgtgatctt 5340
ctcacctctt taaattccca caacacaaga gattaaaaac agaggtttca gctcttcata 5400
gtgcgttgtg aaatggctgg ccagagtgta ccaacaaagc tgtcatcggg ctcacagctc 5460
agagacatct gcatgtgatc atctgcatag tcctctcctc taacgggaaa cacctcagat 5520
ttgcatataa aaaagcaccc tggtgctgaa atgaacccct ttcttgaaca tcaaagctgt 5580
ctcccacagc cttgggcagc agggtgcctc ttagtggatg tgctgggtcc accctgagcc 5640
ctgacatgtg gtggcagcat tgccagttgg tctgtgtgtc tgtgtagcag ggacgatttc 5700
ccagaaagca attttccttt tgaaatacgt aattgttgag actaggcagt ttcaaagtca 5760
gctgcatata gtagcaagta caggactgtc ttgtttttgg tgtccttgga ggtgctgggg 5820
tgagggtttc agtgggatca tttactctca catgttgtct gccttctgct tctgtggaca 5880
ctgctttgta cttaattcag acagactgtg aatacacctt ttttataaat acctttcaaa 5940
ttcttggtaa gatataattt tgatagctga ttgcagattt tctgtatttg tcagattaat 6000
aaagactgca tgaatcca 6018

<210> SEQ ID NO 2
<211> LENGTH: 480
<212> TYPE: DNA
<213> ORGANISM: Homo sapiens
<220> FEATURE:
<221> NAME/KEY: misc_feature
<223> OTHER INFORMATION: SST promoter

<400> SEQUENCE: 2
acactaaaat gttagagtat gatgacagat ggagttgtct gggtacattt gtgtgcattt 60
aagggtgata gtgtatttgc tctttaagag ctgagtgttt gagcctctgt ttgtgtgtaa 120
ttgagtgtgc atgtgtggga gtgaaattgt ggaatgtgta tgctcatagc actgagtgaa 180
aataaaagat tgtataaatc gtggggcatg tggaattgtg tgtgcctgtg cgtgtgcagt 240
attttttttt ttttaagtaa gccactttag atcttgtcac ctcccctgtc ttctgtgatt 300
gattttgcga ggctaatggt gcgtaaaagg gctggtgaga tctgggggcg cctcctagcc 360
tgacgtcaga gagagagttt aaaacagagg gagacggttg agagcacaca agccgcttta 420
ggagcgaggt tcggagccat cgctgctgcc tgctgatccg cgcctagagt ttgaccagcc 480

<210> SEQ ID NO 3
<211> LENGTH: 1000
<212> TYPE: DNA
<213> ORGANISM: Homo sapiens
<220> FEATURE:
<221> NAME/KEY: misc_feature
<223> OTHER INFORMATION: NPY promoter

<400> SEQUENCE: 3
ttttggccag gggatgtggc ttggactgga gagaaaggag ataaggatgt aaacacatgt 60
agggcatatc accccctatt ttttattctc tgaatcctta accctcagaa taagttctta 120
ttcttgagaa tcaatgacat tatcttaagc taaattaatc aagcctccac agtgttcttc 180
tctcaatagt ggtgtgggcc ttcctagaag taatttttcc caaattcagt gatacatttt 240
aagttcagat tttaattgat atgaatctgt gatacactct aaaataagat tattttattg 300
aaaagtggac tgtaactttc cctttatcta ggaagagctc taagttagaa gatgttttgc 360
acttttaccg aaggctgtgt cttgtaagca cccccgagca actctgagag ccttgatttt 420
tgtgtcctca gcatatgttt gtgtaataca gaaagagaag cagttgccaa gtgaaaggga 480
tgttggtctc caaaattata gtttgatccc acaaacacac aaacacatac atgcaaagga 540
ttgtttgctt cacggttttt gatatttaat tcaatgctgt tggaacagca caaaaactaa 600
gtgtcagttt aacagaatca cttgtccttt tagcattaaa ataacatgga acttaatgct 660
ttaatttccc aacatgcctt tttatttaga aagattcaga cttttatttc atttagaaat 720
aaaatgccat tttatttaga aagatacagg agcattcatt cacggaactt tcagatctca 780
gtccactgca taaaatcttg atcctgtaat aatagtttct gtatcttgca tattcattca 840
acaggtttaa cgcgatgagc aaattaatgt tcatcgtttt taacatgttt cgtcttaatc 900
agaacccaca ttctcaacgt taattgaacg tacataggac tatacaaggg ttagtaaata 960
agacagaaac tgttgctcat ttaaccaccg tcactttgga 1000

<210> SEQ ID NO 4
<211> LENGTH: 250
<212> TYPE: DNA
<213> ORGANISM: Homo sapiens
<220> FEATURE:
<221> NAME/KEY: misc_feature
<223> OTHER INFORMATION: Chromatin insulator

<400> SEQUENCE: 4
cagcctaaag ctttttcccc gtatccccca ggtgtctgca ggctcaaaga gcagcgagaa 60
gcgttcagag gaaagcgatc ccgtgccacc ttccccgtgc ccgggctgtc cccgcacgct 120
gccggctcgg ggatgcgggg ggagcgccgg accggagcgg agccccgggc ggctcgctgc 180
tgccccctag cgggggaggg acgtaattac atccctgggg gctttggggg ggggctgtcc 240
ccgtgagctc 250

<210> SEQ ID NO 5
<211> LENGTH: 5
<212> TYPE: DNA
<213> ORGANISM: Homo sapiens
<220> FEATURE:
<221> NAME/KEY: misc_feature
<223> OTHER INFORMATION: Kozak consensus sequence

<400> SEQUENCE: 5 ccacc 5

<210> SEQ ID NO 6
<211> LENGTH: 1404
<212> TYPE: DNA
<213> ORGANISM: Homo sapiens

<400> SEQUENCE: 6
atgacagagt tacctgcacc tttgtcctac ttccagaatg cacagatgtc tgaggacaac 60
cacctgagca atactgtacg tagccagaat gacaatagag aacggcagga gcacaacgac 120
agacggagcc tgggccaccc tgagccactg tctaatggaa gaccccaggg taactcccgg 180

```
caggtggtgg agcaggatga ggaagaagat gaggagctga cactgaaata tggcgccaag    240
cacgtgatca tgctctttgt ccctgtgact ctctgcatgg tggtggtcgt ggctaccatt    300
aagtcagtca gcttttatac ccggaaggat gggcagctaa tctatacccc attcacagaa    360
gataccgaga ctgtgggcca gagagccctg cactcaattc tgaatgctgc catcatgatc    420
agtgtcattg ttgtcatgac tatcctcctg gtggttctgt ataaatacag gtgctataag    480
gtcatccatg cctggctgat tatatcatct ctgttgctgc tgttcttttt ttcattcatt    540
tacctggggg aagtgtttaa aacctataac gttgctgtgg actacattac tgttgcactc    600
ctgatctgga attttggcgt ggtgggaatg atttccattc actggaaagg cccactgaga    660
ctccagcagg catatctcat tatgattagt gccctcatgg ccctggtgtt tatcaagtac    720
ctccctgaat ggactgcctg gctcatcttg gctgtgattt cagtgtatga tttagtggct    780
gttctgtgtc ctaaaggtcc actgcgtatg ctggtggaaa cagctcagga gagaaatgaa    840
accctgtttc cagctctcat ttactcctca acaatggtgt ggctggtgaa tatggcagaa    900
ggagaccctg aagctcaaag gagagtgtcc aaaaattcca agtataatgc agaaagcaca    960
gaaagggagt cacaggacac tgttgcagag aatgatgatg gcgggttcag tgaggaatgg   1020
gaagcccaga gggacagtca cctggggcct caccgctcta cacctgagtc aagagctgct   1080
gtccaggaac tgtccagcag tatcctcgct ggcgaagacc cagaggaaag gggagtaaaa   1140
cttggattgg gagatttcat tttctacagt gttctggttg gcaaagcctc agcaacagcc   1200
agtggagact ggaacacaac catagcctgt ttcgtagcca tcttaattgg cctgtgcctt   1260
acactgctgc tcctggccat tttcaagaaa gcactgccag ctctgccaat ctccatcacc   1320
tttgggcttg ttttctactt tgccacagat tatctggtgc agccttttat ggaccagctg   1380
gcattccacc agttttatat ctaa                                          1404
```

<210> SEQ ID NO 7
<211> LENGTH: 1404
<212> TYPE: DNA
<213> ORGANISM: Artificial Sequence
<220> FEATURE:
<223> OTHER INFORMATION: Synthetic

<400> SEQUENCE: 7

```
atgacagagt tacctgcacc attgtcctac ttccagaatg cacagatgtc tgaggacaac     60
cacctgagca atactgtaag aagccagaat gacaatagag aaagacagga gcacaatgac    120
agaagaagcc ttggccaccc tgagccatta tctaatggaa gaccccaggg taactccaga    180
caggtggtgg agcaagatga ggaagaagat gaggagctga cattgaaata tggtgccaag    240
catgtgatca tgctctttgt ccctgtgact ctctgcatgg tggtggttgt ggctaccatt    300
aagtcagtca gcttttatac cagaaaggat gggcagctaa tctatacccc attcacagaa    360
gatactgaga ctgtgggcca gagagccctg cactcaattc tgaatgctgc catcatgatc    420
agtgtcattg ttgtcatgac tatcctcctg gtggttctgt ataaatacag gtgctataag    480
gtcatccatg cctggcttat tatatcatct ctattgttgc tgttcttctt ttcattcatt    540
tacttggggg aagtgtttaa aacctataat gttgctgtgg actacattac tgttgcactc    600
ctgatctgga attttggtgt ggtgggaatg atttccattc actggaaagg tccacttaga    660
ctccagcagg catatctcat tatgattagt gccctcatgg ccctggtgtt tatcaagtac    720
ctccctgaat ggactgcctg gctcatcttg gctgtgattt cagtatatga tttagtggct    780
```

gttttgtgtc ccaaaggtcc acttagaatg ctggttgaaa cagctcagga gagaaatgaa 840 acccttttc cagctctcat ttactcctca acaatggtgt ggttggtgaa tatggcagaa 900
ggagacccag aagctcaaag gagagtatcc aaaaattcca agtataatgc agaaagcaca 960
gaaagggagt cacaagacac tgttgcagag aatgatgatg gtgggttcag tgaggaatgg 1020
gaagcccaga gggacagtca tctagggcct cataggtcta cacctgagtc aagagctgct 1080
gtccaggaac tttccagcag tatcctggct ggtgaagacc cagaggaaag gggagtaaaa 1140
cttggattgg gagatttcat tttctacagt gttctggttg gtaaagcctc agcaacagcc 1200
agtggagact ggaacacaac catagcctgt tttgtagcca tattaattgg tttgtgcctt 1260
acattattac tccttgccat tttcaagaaa gcattgccag ctcttccaat ctccatcacc 1320
tttgggcttg ttttctactt tgccacagat tatcttgtac agccttttat ggaccaatta 1380
gcattccatc aattttatat ctag 1404

<210> SEQ ID NO 8
<211> LENGTH: 2032
<212> TYPE: DNA
<213> ORGANISM: Homo sapiens

<400> SEQUENCE: 8
cccagatctg acaacagcct ttgcggtcct tagacagctt ggcctggagg agaacacatg 60
aaagaaaggt ttgtttctgc ttaatgtaat ctatgaaagt gttttttata acagtataat 120
tgtagtgcac aaagttctgt ttttctttcc cttttcagaa cctcaagagg ctttgttttc 180
tgtgaaacag tatttctata cagttgccac catgacagag ttacctgcac cgttgtccta 240
cttccagaat gcacagatgt ctgaggacaa ccacctgagc aatactgtac gtagccaggt 300
acagtgtcag tctctgaaac tgcctttgcc agactggatt cacttatcat ctcccctcac 360
ctctgagaaa tgctgagggg gctaggcagg ctttctctac tttttagaac tcatagtgac 420
gggtctgttg ttaatcccag gtctaaccgt taccttgatt ctgctgagaa tctgatttac 480
tgaaaatgtt tttcttgtgc ttatagaatg acaatagaga acggcaggag cacaacgaca 540
gacggagcct tggccaccct gagccattat ctaatggacg accccagggt aactcccggc 600
aggtggtgga gcaagatgag gaagaagatg aggagctgac attgaaatat ggcgccaagc 660
atgtgatcat gctctttgtc cctgtgactc tctgcatggt ggtggtcgtg gctaccatta 720
agtcagtcag cttttatacc cggaaggatg ggcagctgta cgtatgagtt ttgttttatt 780
attctcaaag ccagtgtggc ttttctttac agcatgtcat catcaccttg aaggcctctg 840
cattgaaggg gcatgacttg aattaagaaa aagaaaattc tgtgttggag gtggtaatgt 900
ggttggtgat ctccattaac actgacctag ggcttttgtg tttgttttat tgtagaatct 960
ataccccatt cacagaagat accgagactg tgggccagag agccctgcac tcaattctga 1020
atgctgccat catgatcagt gtcattgttg tcatgactat cctcctggtg gttctgtata 1080
aatacaggtg ctataaggtc atccatgcct ggcttattat atcatctcta ttgttgctgt 1140 tcttttttc attcatttac ttgggggaag tgtttaaaac ctataacgtt gctgtggact 1200
acattactgt tgcactcctg atctggaatt ttggtgtggt gggaatgatt tccattcact 1260
ggaaaggtcc acttcgactc cagcaggcat atctcattat gattagtgcc ctcatggccc 1320
tggtgtttat caagtacctc cctgaatgga ctgcgtggct catcttggct gtgatttcag 1380
tatatgattt agtggctgtt ttgtgtccga aaggtccact tcgtatgctg gttgaaacag 1440
ctcaggagag aaatgaaacg ctttttccag ctctcattta ctcctcaaca atggtgtggt 1500
tggtgaatat ggcagaagga gacccggaag ctcaaaggag agtatccaaa aattccaagt 1560
ataatgcaga aagcacagaa agggagtcac aagacactgt tgcagagaat gatgatggcg 1620
ggttcagtga ggaatgggaa gcccagaggg acagtcatct agggcctcat cgctctacac 1680
ctgagtcacg agctgctgtc caggaacttt ccagcagtat cctcgctggt gaagacccag 1740
aggaaagggg agtaaaactt ggattgggag atttcatttt ctacagtgtt ctggttggta 1800
aagcctcagc aacagccagt ggagactgga acacaaccat agcctgtttc gtagccatat 1860
taattggttt gtgccttaca ttattactcc ttgccatttt caagaaagca ttgccagctc 1920
ttccaatctc catcaccttt gggcttgttt tctactttgc cacagattat cttgtacagc 1980
cttttatgga ccaattagca ttccatcaat tttatatcta gcatagtcga cc 2032

<210> SEQ ID NO 9
<211> LENGTH: 171
<212> TYPE: DNA
<213> ORGANISM: Homo sapiens
<220> FEATURE:
<221> NAME/KEY: misc_feature
<223> OTHER INFORMATION: MALAT1 MRNA stability element

<400> SEQUENCE: 9
tagggtcatg aaggtttttc ttttcctgag aaaacaacac gtattgtttt ctcaggtttt 60
gctttttggc ctttttctag cttaaaaaaa aaaaaagcaa aagatgctgg tggttggcac 120
tcctggtttc caggacgggg ttcaaatccc tgcggcgtct ttgctttgac t 171

<210> SEQ ID NO 10
<211> LENGTH: 212
<212> TYPE: DNA
<213> ORGANISM: Homo sapiens
<220> FEATURE:
<221> NAME/KEY: misc_feature
<223> OTHER INFORMATION: 3' flanking sequence from native PSEN1 RNA

<400> SEQUENCE: 10
ggaaacaaaa cagcggctgg tctggaagga acctgagcta cgagccgcgg cggcagcggg 60
gcggcgggga agcgtatacc taatctggga gcctgcaagt gacaacagcc tttgcggtcc 120
ttagacagct tggcctggag gagaacacat gaaagaaaga acctcaagag gctttgtttt 180
ctgtgaaaca gtatttctat acagttgctc ca 212

<210> SEQ ID NO 11
<211> LENGTH: 4402
<212> TYPE: DNA
<213> ORGANISM: Homo sapiens
<220> FEATURE:
<221> NAME/KEY: misc_feature
<223> OTHER INFORMATION: 5' flanking sequence from native PSEN1 MRNA

<400> SEQUENCE: 11
catatttgcg gttagaatcc catggatgtt tcttctttga ctataacaaa atctggggag 60
gacaaaggtg attttcctgt gtccacatct aacaaagtca agattcccgg ctggactttt 120
gcagcttcct tccaagtctt cctgaccacc ttgcactatt ggactttgga aggaggtgcc 180
tatagaaaac gattttgaac atacttcatc gcagtggact gtgtccctcg gtgcagaaac 240
taccagattt gagggacgag gtcaaggaga tatgataggc ccggaagttg ctgtgcccca 300
tcagcagctt gacgcgtggt cacaggacga tttcactgac actgcgaact ctcaggacta 360
ccgttaccaa gaggttaggt gaagtggttt aaaccaaacg gaactcttca tcttaaacta 420

```
cacgttgaaa atcaacccaa taattctgta ttaactgaat tctgaacttt tcaggaggta    480
ctgtgaggaa gagcaggcac cagcagcaga atggggaatg gagaggtggg caggggttcc    540
agcttccctt tgatttttg ctgcagactc atccttttta aatgagactt gttttcccct    600
ctctttgagt caagtcaaat atgtagattg cctttggcaa ttcttcttct caagcactga    660
cactcattac cgtctgtgat tgccatttct tcccaaggcc agtctgaacc tgaggttgct    720
ttatcctaaa agttttaacc tcaggttcca aattcagtaa attttggaaa cagtacagct    780
atttctcatc aattctctat catgttgaag tcaaatttgg attttccacc aaattctgaa    840
tttgtagaca tacttgtacg ctcacttgcc ccagatgcct cctctgtcct cattcttctc    900
tcccacacaa gcagtctttt tctacagcca gtaaggcagc tctgtcgtgg tagcagatgg    960
tcccattatt ctagggtctt actctttgta tgatgaaaag aatgtgttat gaatcggtgc   1020
tgtcagccct gctgtcagac cttcttccac agcaaatgag atgtatgccc aaagacggta   1080
gaattaaaga agagtaaaat ggctgttgaa gcactttctg tcctggtatt ttgtttttgc   1140
ttttgccaca cagtagctca gaatttgaac aaatagccaa aagctggtgg ttgatgaatt   1200
atgaactagt tgtatcaaca caaagcaaga gttggggaaa gccatattta acttggtgag   1260
ctgtgggaga acctggtggc agaaggagaa ccaactgcca aggggaaaga gaaggggcct   1320
ccagcagcga aggggataca gtgagctaat gatgtcaagg aggagtttca ggttattctc   1380
gtcagctcca caaatgggtg ctttgtggtc tctgcccgcg ttacctttcc tctcaatgta   1440
cctttgtgtg aactgggcag tggaggtgcc tgctgcagtt accatggagt tcaggctctg   1500
ggcagctcag tcaggcaaaa cacacaaaca gccatcagcc tgtgtgggct cagggcacct   1560
ctggacaaag gcttgtgggg cataaccttc tttaccacag agagccctta gctatgctga   1620
tcagaccgta agcgtttatg agaaacttag tttcctcctg tggctgagga ggggccagct   1680
ttttcttctt ttgcctgctg ttttctctcc caatctatga tatgatatga cctggtttgg   1740
ggctgtcttt ggtgtttaga atatttgttt tctgtcccag gatatttctt ataagaacct   1800
aacttcaaga gtagtgtgcg agtactgatc tgaatttaaa ttaaaattgg cttatattag   1860
gcagtcacag acaggaaaaa taagagctat gcaaagaaag ggggatttaa agtagtaggt   1920
tctatcatct caattcattt ttttccatga aatcccttct tccaagattc attccctctc   1980
tcagacatgt gctagcatgg gtattatcat tgagaaagca cagctacagc aaagccacct   2040
gaatagcaat ttgtgattgg aagcattctt gagggatccc taatctagag taatttattt   2100
gtgtaaggat cccaaatgtg ttgcaccttt catgatacat ttcttctctg aagagggtac   2160
gtggggtgtg tgtatttaaa tccatcctat gtattactga ttgtcctgtg tagaaagatg   2220
gcaattattc tgtctctttc tccaagtttg agccacatct cagccacatt gttagacagt   2280
gtacagagaa cctatctttc cttttttttt ttttaaagga caggattttg ctgtgttgcc   2340
caggctagac ttgaactcct gggctcaagt aatccacctc agcctgagta gctgagacta   2400
cagcccatct tatttcttta aatcattcat ctcaggcaga gaacttttcc ctcaaacatt   2460
ctttttagaa ttagttcagt cattcctaaa acatccaaat gctagtcttc caccatgaaa   2520
aatagattgt cactggaaag aacagtagca atttccataa ggatgtgcct tcactcacac   2580
gggacaggcg gtggttatag agtcgggcaa aaccagcagt agagtatgac cagccaagcc   2640
aatctgctta ataaaaagat ggaagacagt aaggaaggaa agtagccact aagagtctga   2700
gtctgactgg gctacagaat aaagggtatt tatggacaga atgtcattac atgcctatgg   2760
```

gaataccaat catatttgga agatttgcag attttttttc agagaggaaa gactcacctt 2820
cctgtttttg gttctcagta ggttcgtgtg tgttcctaga atcacagctc tgactccaaa 2880
tgactcaatt tctcaattag aaaaagtaga agctttctaa gcaacttgga agaaaacagt 2940
cataagtaag caatttgttg attttactac agaagcaaca actgaagagg cagtgttttt 3000
actttcagac tccgggattc ccattctgta gtctctctgc ttttaaaaac cctccttttg 3060
caatagatgc ccaaacagat gatgtttatt acttgttatt tacgtggcct cagacagtgt 3120
atgtattctc gatataactt gtagagtgtg aaatataagt ttaactacca aataaggtct 3180
cccagggtta gatgactgcg ggaagccttt gatcccaacc cccaaggctt tgtatatttg 3240
atcatttgtg atctaaccct ggaagaaaaa gagctcagaa accactatga aaaaatttgt 3300
tcagtgtttt ctgtgttccc gtaggttctg gagtctgagg atgcaaagat gaataagata 3360
aattctcaga atgtagttat aatctcttgt tttctggtat atgccatctt tctttaactt 3420
ctctaaaata ttgggtattt gtcaaataac cacttttaac agttaccatt actgagggct 3480
tatacattgg tgttataaaa gtgacttgat tcagaaatca atccattcag taaagtactc 3540
cttctctaaa tttgctgtta tgtctataag gaacagtttg acctgccctt ctcctcacct 3600
cctcacctgc cttccaacat tgaatttgga aggagacgtg aaaattggac atttggtttt 3660
gcccttgggc tggaaactat catataatca taagtttgag cctagaagtg atccttgtga 3720
tcttctcacc tctttaaatt cccacaacac aagagattaa aaacagaggt ttcagctctt 3780
catagtgcgt tgtgaaatgg ctggccagag tgtaccaaca aagctgtcat cgggctcaca 3840
gctcagagac atctgcatgt gatcatctgc atagtcctct cctctaacgg gaaacacctc 3900
agatttgcat ataaaaaagc accctggtgc tgaaatgaac ccctttcttg aacatcaaag 3960
ctgtctccca cagccttggg cagcagggtg cctcttagtg gatgtgctgg gtccaccctg 4020
agccctgaca tgtggtggca gcattgccag ttggtctgtg tgtctgtgta gcagggacga 4080
tttcccagaa agcaattttc cttttgaaat acgtaattgt tgagactagg cagtttcaaa 4140
gtcagctgca tatagtagca agtacaggac tgtcttgttt ttggtgtcct tggaggtgct 4200
ggggtgaggg tttcagtggg atcatttact ctcacatgtt gtctgccttc tgcttctgtg 4260
gacactgctt tgtacttaat tcagacagac tgtgaataca ccttttttat aaataccttt 4320
caaattcttg gtaagatata attttgatag ctgattgcag attttctgta tttgtcagat 4380
taataaagac tgcatgaatc ca 4402

<210> SEQ ID NO 12
<211> LENGTH: 420
<212> TYPE: PRT
<213> ORGANISM: Homo sapiens
<220> FEATURE:
<221> NAME/KEY: misc_feature
<223> OTHER INFORMATION: presenilin-1 isoform X1

<400> SEQUENCE: 12

Met Thr Glu Leu Pro Ala Pro Leu Ser Tyr Phe Gln Asn Ala Gln Met
1 5 10 15

Ser Glu Asp Asn His Leu Ser Asn Thr Val Arg Ser Gln Asn Asp Asn
20 25 30

Arg Glu Arg Gln Glu His Asn Asp Arg Arg Ser Leu Gly His Pro Glu
35 40 45

Pro Leu Ser Asn Gly Arg Pro Gln Gly Asn Ser Arg Gln Val Val Glu
50 55 60

Gln Asp Glu Glu Glu Asp Glu Glu Leu Thr Leu Lys Tyr Gly Ala Lys
65 70 75 80

His Val Ile Met Leu Phe Val Pro Val Thr Leu Cys Met Val Val Val
85 90 95

Val Ala Thr Ile Lys Ser Val Ser Phe Tyr Thr Arg Lys Asp Gly Gln
100 105 110

Leu Ile Tyr Thr Pro Phe Thr Glu Asp Thr Glu Thr Val Gly Gln Arg
115 120 125

Ala Leu His Ser Ile Leu Asn Ala Ala Ile Met Ile Ser Val Ile Val
130 135 140

Val Met Thr Ile Leu Leu Val Val Leu Tyr Lys Tyr Arg Cys Tyr Lys
145 150 155 160

Val Ile His Ala Trp Leu Ile Ile Ser Ser Leu Leu Leu Leu Phe Phe
165 170 175

Phe Ser Phe Ile Tyr Leu Gly Glu Val Phe Lys Thr Tyr Asn Val Ala
180 185 190

Val Asp Tyr Ile Thr Val Ala Leu Leu Ile Trp Asn Phe Gly Val Val
195 200 205

Gly Met Ile Ser Ile His Trp Lys Gly Pro Leu Arg Leu Gln Gln Ala
210 215 220

Tyr Leu Ile Met Ile Ser Ala Leu Met Ala Leu Val Phe Ile Lys Tyr
225 230 235 240

Leu Pro Glu Trp Thr Ala Trp Leu Ile Leu Ala Val Ile Ser Val Tyr
245 250 255

Asp Leu Val Ala Val Leu Cys Pro Lys Gly Pro Leu Arg Met Leu Val
260 265 270

Glu Thr Ala Gln Glu Arg Asn Glu Thr Leu Phe Pro Ala Leu Ile Tyr
275 280 285

Ser Ser Thr Met Val Trp Leu Val Asn Met Ala Glu Gly Asp Pro Glu
290 295 300

Ala Gln Arg Arg Val Ser Lys Asn Ser Lys Tyr Asn Ala Glu Ser Thr
305 310 315 320

Glu Arg Glu Ser Gln Asp Thr Val Ala Glu Asn Asp Asp Gly Gly Phe
325 330 335

Ser Glu Glu Trp Glu Ala Gln Arg Asp Ser His Leu Gly Pro His Arg
340 345 350

Ser Thr Pro Glu Ser Arg Ala Ala Val Gln Glu Leu Ser Ser Ser Ile
355 360 365

Leu Ala Gly Glu Asp Pro Glu Glu Arg Gly Val Lys Leu Gly Leu Gly
370 375 380

Asp Phe Ile Phe Tyr Ser Val Leu Val Gly Lys Ala Ser Ala Thr Ala
385 390 395 400

Ser Gly Asp Trp Asn Thr Thr Ile Ala Cys Phe Val Ala Ile Leu Ile
405 410 415

Gly Leu Cys Leu
420

<210> SEQ ID NO 13
<211> LENGTH: 1392
<212> TYPE: DNA
<213> ORGANISM: Homo sapiens

<400> SEQUENCE: 13
atgacagagt tacctgcacc gttgtcctac ttccagaatg cacagatgtc tgaggacaac 60

```
cacctgagca atactaatga caatagagaa cggcaggagc acaacgacag acggagcctt    120

ggccaccctg agccattatc taatggacga ccccagggta actcccggca ggtggtggag    180

caagatgagg aagaagatga ggagctgaca ttgaaatatg gcgccaagca tgtgatcatg    240

ctctttgtcc ctgtgactct ctgcatggtg gtggtcgtgg ctaccattaa gtcagtcagc    300

ttttataccc ggaaggatgg gcagctaatc tataccccat tcacagaaga taccgagact    360

gtgggccaga gagccctgca ctcaattctg aatgctgcca tcatgatcag tgtcattgtt    420

gtcatgacta tcctcctggt ggttctgtat aaatacaggt gctataaggt catccatgcc    480

tggcttatta tatcatctct attgttgctg ttcttttttt cattcattta cttgggggaa    540

gtgtttaaaa cctataacgt tgctgtggac tacattactg ttgcactcct gatctggaat    600

tttggtgtgg tgggaatgat ttccattcac tggaaaggtc cacttcgact ccagcaggca    660

tatctcatta tgattagtgc cctcatggcc ctggtgttta tcaagtacct ccctgaatgg    720

actgcgtggc tcatcttggc tgtgatttca gtatatgatt tagtggctgt tttgtgtccg    780

aaaggtccac ttcgtatgct ggttgaaaca gctcaggaga gaaatgaaac gctttttcca    840

gctctcattt actcctcaac aatggtgtgg ttggtgaata tggcagaagg agacccggaa    900

gctcaaagga gagtatccaa aaattccaag tataatgcag aaagcacaga aagggagtca    960

caagacactg ttgcagagaa tgatgatggc gggttcagtg aggaatggga agcccagagg   1020

gacagtcatc tagggcctca tcgctctaca cctgagtcac gagctgctgt ccaggaactt   1080

tccagcagta tcctcgctgg tgaagaccca gaggaaaggg gagtaaaact tggattggga   1140

gatttcattt tctacagtgt tctggttggt aaagcctcag caacagccag tggagactgg   1200

aacacaacca tagcctgttt cgtagccata ttaattggtt tgtgccttac attattactc   1260

cttgccattt tcaagaaagc attgccagct cttccaatct ccatcacctt tgggcttgtt   1320

ttctactttg ccacagatta tcttgtacag ccttttatgg accaattagc attccatcaa   1380

ttttatatct ag                                                         1392
```

<210> SEQ ID NO 14
<211> LENGTH: 462
<212> TYPE: PRT
<213> ORGANISM: Homo sapiens
<220> FEATURE:
<221> NAME/KEY: misc_feature
<223> OTHER INFORMATION: presenilin-1 isoform X2

<400> SEQUENCE: 14

```
Met Thr Glu Leu Pro Ala Pro Leu Ser Tyr Phe Gln Asn Ala Gln Met
1               5                   10                  15

Ser Glu Asp Asn His Leu Ser Asn Thr Asn Asp Asn Arg Glu Arg Gln
            20                  25                  30

Glu His Asn Asp Arg Arg Ser Leu Gly His Pro Glu Pro Leu Ser Asn
        35                  40                  45

Gly Arg Pro Gln Gly Asn Ser Arg Gln Val Val Glu Gln Asp Glu Glu
    50                  55                  60

Glu Asp Glu Glu Leu Thr Lys Tyr Gly Ala Lys His Val Ile Met Leu
65                  70                  75                  80

Phe Val Pro Val Thr Leu Cys Met Val Val Val Val Ala Thr Ile Lys
                85                  90                  95

Ser Val Ser Phe Tyr Thr Arg Lys Asp Gly Gln Leu Ile Tyr Thr Pro
            100                 105                 110

Phe Thr Glu Asp Thr Glu Thr Val Gly Gln Arg Ala Leu His Ser Ile
```

```
        115                 120                 125

Leu Asn Ala Ala Ile Met Ile Ser Val Ile Val Val Met Thr Ile Leu
    130                 135                 140

Leu Val Val Leu Tyr Lys Tyr Arg Cys Tyr Lys Val Ile His Ala Trp
145                 150                 155                 160

Leu Ile Ile Ser Ser Leu Leu Leu Leu Phe Phe Phe Ser Phe Ile Tyr
                165                 170                 175

Leu Gly Glu Val Phe Lys Thr Tyr Asn Val Ala Val Asp Tyr Ile Thr
            180                 185                 190

Val Ala Leu Leu Ile Trp Asn Phe Gly Val Val Gly Met Ile Ser Ile
        195                 200                 205

His Trp Lys Gly Pro Leu Arg Leu Gln Gln Ala Tyr Leu Ile Met Ile
    210                 215                 220

Ser Ala Leu Met Ala Leu Val Phe Ile Lys Tyr Leu Pro Glu Trp Thr
225                 230                 235                 240

Ala Trp Leu Ile Leu Ala Val Ile Ser Val Tyr Asp Leu Val Ala Val
                245                 250                 255

Leu Cys Pro Lys Gly Pro Leu Arg Met Leu Val Glu Thr Ala Gln Glu
            260                 265                 270

Arg Asn Glu Thr Leu Phe Pro Ala Leu Ile Tyr Ser Ser Thr Met Val
        275                 280                 285

Trp Leu Val Asn Met Ala Glu Gly Asp Pro Glu Ala Gln Arg Arg Val
    290                 295                 300

Ser Lys Asn Ser Lys Tyr Asn Ala Glu Ser Thr Glu Arg Glu Ser Gln
305                 310                 315                 320

Asp Thr Val Ala Glu Asn Asp Asp Gly Gly Phe Ser Glu Glu Trp Glu
                325                 330                 335

Ala Gln Arg Asp Ser His Leu Gly Pro His Arg Ser Thr Pro Glu Ser
            340                 345                 350

Arg Ala Ala Val Gln Glu Leu Ser Ser Ser Ile Leu Ala Gly Glu Asp
        355                 360                 365

Pro Glu Glu Arg Gly Val Lys Leu Gly Leu Gly Asp Phe Ile Phe Tyr
    370                 375                 380

Ser Val Leu Val Gly Lys Ala Ser Ala Thr Ala Ser Gly Asp Trp Asn
385                 390                 395                 400

Thr Thr Ile Ala Cys Phe Val Ala Ile Leu Ile Gly Leu Cys Leu Thr
                405                 410                 415

Leu Leu Leu Leu Ala Ile Phe Lys Lys Ala Leu Pro Ala Leu Pro Ile
            420                 425                 430

Ser Ile Thr Phe Gly Leu Val Phe Tyr Phe Ala Thr Asp Tyr Leu Val
        435                 440                 445

Gln Pro Phe Met Asp Gln Leu Ala Phe His Gln Phe Tyr Ile
    450                 455                 460


<210> SEQ ID NO 15
<211> LENGTH: 1404
<212> TYPE: DNA
<213> ORGANISM: Homo sapiens
<220> FEATURE:
<221> NAME/KEY: misc_feature
<223> OTHER INFORMATION: presenelin-1 isoform X1 coding sequence

<400> SEQUENCE: 15

atgacagagt tacctgcacc gttgtcctac ttccagaatg cacagatgtc tgaggacaac      60

cacctgagca atactgtacg tagccagaat gacaatagag aacggcagga gcacaacgac     120
```

```
agacggagcc ttggccaccc tgagccatta tctaatggac gaccccaggg taactcccgg    180

caggtggtgg agcaagatga ggaagaagat gaggagctga cattgaaata tggcgccaag    240

catgtgatca tgctctttgt ccctgtgact ctctgcatgg tggtggtcgt ggctaccatt    300

aagtcagtca gcttttatac ccggaaggat gggcagctaa tctatacccc attcacagaa    360

gataccgaga ctgtgggcca gagagccctg cactcaattc tgaatgctgc catcatgatc    420

agtgtcattg ttgtcatgac tatcctcctg gtggttctgt ataaatacag gtgctataag    480

gtcatccatg cctggcttat tatatcatct ctattgttgc tgttcttttt ttcattcatt    540

tacttggggg aagtgtttaa aacctataac gttgctgtgg actacattac tgttgcactc    600

ctgatctgga attttggtgt ggtgggaatg atttccattc actggaaagg tccacttcga    660

ctccagcagg catatctcat tatgattagt gccctcatgg ccctggtgtt tatcaagtac    720

ctccctgaat ggactgcgtg gctcatcttg gctgtgattt cagtatatga tttagtggct    780

gttttgtgtc cgaaaggtcc acttcgtatg ctggttgaaa cagctcagga gagaaatgaa    840

acgctttttc cagctctcat ttactcctca acaatggtgt ggttggtgaa tatggcagaa    900

ggagacccgg aagctcaaag gagagtatcc aaaaattcca agtataatgc agaaagcaca    960

gaaagggagt cacaagacac tgttgcagag aatgatgatg gcgggttcag tgaggaatgg   1020

gaagcccaga gggacagtca tctagggcct catcgctcta cacctgagtc acgagctgct   1080

gtccaggaac tttccagcag tatcctcgct ggtgaagacc cagaggaaag gggagtaaaa   1140

cttggattgg gagatttcat tttctacagt gttctggttg gtaaagcctc agcaacagcc   1200

agtggagact ggaacacaac catagcctgt ttcgtagcca tattaattgg tttgtgcctt   1260

acattattac tccttgccat tttcaagaaa gcattgccag ctcttccaat ctccatcacc   1320

tttgggcttg ttttctactt tgccacagat tatcttgtac agccttttat ggaccaatta   1380

gcattccatc aattttatat ctag                                          1404
```

<210> SEQ ID NO 16
<211> LENGTH: 145
<212> TYPE: DNA
<213> ORGANISM: Homo sapiens
<220> FEATURE:
<221> NAME/KEY: misc_feature
<223> OTHER INFORMATION: Inverted terminal repeats (ITR) for single-stranded AAV2
<220> FEATURE:
<221> NAME/KEY: misc_feature
<223> OTHER INFORMATION: left ITR

<400> SEQUENCE: 16

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcct                                          145
```

<210> SEQ ID NO 17
<211> LENGTH: 145
<212> TYPE: DNA
<213> ORGANISM: Homo sapiens
<220> FEATURE:
<221> NAME/KEY: misc_feature
<223> OTHER INFORMATION: Inverted terminal repeats (ITR) for single-stranded AAV2
<220> FEATURE:
<221> NAME/KEY: misc_feature
<223> OTHER INFORMATION: right ITR

<400> SEQUENCE: 17
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag agagggagtg gccaa 145

<210> SEQ ID NO 18
<211> LENGTH: 105
<212> TYPE: DNA
<213> ORGANISM: Homo sapiens
<220> FEATURE:
<221> NAME/KEY: misc_feature
<223> OTHER INFORMATION: Inverted terminal repeats for self-complementary AAV2
<220> FEATURE:
<221> NAME/KEY: misc_feature
<223> OTHER INFORMATION: left ITR

<400> SEQUENCE: 18
ctgcgcgctc gctcgctcac tgaggccgcc cgggcaaagc ccgggcgtcg ggcgaccttt 60
ggtcgcccgg cctcagtgag cgagcgagcg cgcagagagg gagtg 105

<210> SEQ ID NO 19
<211> LENGTH: 130
<212> TYPE: DNA
<213> ORGANISM: Homo sapiens
<220> FEATURE:
<221> NAME/KEY: misc_feature
<223> OTHER INFORMATION: right ITR

<400> SEQUENCE: 19
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag 130

<210> SEQ ID NO 20
<211> LENGTH: 92
<212> TYPE: DNA
<213> ORGANISM: Minute virus of mice

<400> SEQUENCE: 20
aagaggtaag ggtttaaggg atggttggtt ggtggggtat taatgtttaa ttacctgttt 60
tacaggcctg aaatcacttg gttttaggtt gg 92

<210> SEQ ID NO 21
<211> LENGTH: 230
<212> TYPE: DNA
<213> ORGANISM: Artificial Sequence
<220> FEATURE:
<223> OTHER INFORMATION: Synthetic

<400> SEQUENCE: 21
tctgccacgg aggtgttatt accgaagaaa tggccgccag tcttttggac cagctgatcg 60
aagaggtact ggctgataat cttccacctc ctagccattt tgaaccacct acccttcacg 120
aactgtatga tttagacgtg acggcccccg aagatcccaa cgaggaggcg gtttcgcaga 180
tttttctgac atccactttg cctttctctc cacaggtgtc cactcccaaa 230

<210> SEQ ID NO 22
<211> LENGTH: 566
<212> TYPE: DNA
<213> ORGANISM: Homo sapiens

<400> SEQUENCE: 22
tcagatcgcc tggagacgcc atccacgctg ttttgacctc catagaagac accgggaccg 60
atccagcctc cgcggattcg aatcccggcc gggaacggtg cattggaacg cggattcccc 120
gtgccaagag tgacgtaagt accgcctata gagtctatag gcccacaaaa aatgctttct 180
tcttttaata tacttttttg tttatcttat ttctaatact ttccctaatc tctttcttc 240 agggcaataa tgatacaatg tatcatgcct ctttgcacca ttctaaagaa taacagtgat 300
aatttctggg ttaaggcaat agcaatattt ctgcatataa atatttctgc atataaattg 360
taactgatgt aagaggtttc atattgctaa tagcagctac aatccagcta ccattctgct 420
tttattttat ggttgggata aggctggatt attctgagtc caagctaggc ccttttgcta 480
atcatgttca tacctcttat cttcctccca cagctcctgg gcaacgtgct ggtctgtgtg 540
ctggcccatc actttggcaa agaatt 566

<210> SEQ ID NO 23
<211> LENGTH: 1677
<212> TYPE: DNA
<213> ORGANISM: Homo sapiens
<220> FEATURE:
<221> NAME/KEY: misc_feature
<223> OTHER INFORMATION: Promotor

<400> SEQUENCE: 23
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggagtatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg gtcgaggtga gccccacgtt ctgcttcact ctccccatct 420 ccccccccctc cccaccccca attttgtatt tatttatttt ttaattattt tgtgcagcga 480
tgggggcggg gggggggggg gggcccccccc caggcggggc ggggcggggc gaggggcggg 540
gcggggcgag gcggaaaggt gcggcggcag ccaatcagag cggcgcgctc cgaaagtttc 600
cttttatggc gaggcggcgg cggcggcggc cctataaaaa gcgaagcgcg cggcgggcgg 660
gagtcgttgc gcgctgcctt cgccccgtgc cccgctccgc cgccgcctcg cgccgcccgc 720
cccggctctg actgaccgcg ttactcccac aggtgagcgg gcgggacggc ccttctcctc 780
cgggctgtaa ttagcgcttg gtttaatgac ggcttgtttc ttttctgtgg ctgcgtgaaa 840
gccttgaggg gctccgggag ggccctttgt gcggggggag cggctcgggg ggtgcgtgcg 900
tgtgtgtgtg cgtggggagc gccgcgtgcg gctccgcgct gcccggcggc tgtgagcgct 960
gcgggcgcgg cgcggggctt tgtgcgctcc gcagtgtgcg cgaggggagc gcggccgggg 1020
gcggtgcccc gcggtgcggg gggggctgcg aggggaacaa aggctgcgtg cggggtgtgt 1080
gcgtgggggg gtgagcaggg ggtgtgggcg cgtcggtcgg gctgcaaccc cccctgcacc 1140
cccctccccg agttgctgag cacggcccgg cttcgggtgc ggggctccgt acggggcgtg 1200
gcgcggggct cgccgtgccg ggcggggggt ggcggcaggt gggggtgccg ggcggggcgg 1260
ggccgcctcg ggccggggag ggctcggggg aaggggcgcg gcggcccccg gagcgccggc 1320
ggctgtcgag gcgcggcgag ccgcagccat tgccttttat ggtaatcgtg cgagagggcg 1380
cagggacttc ctttgtccca aatctgtgcg gagccgaaat ctgggaggcg ccgccgcacc 1440
ccctctagcg ggcgcggggc gaagcggtgc ggcgccggca ggaaggaaat gggcggggag 1500
ggccttcgtg cgtcgccgcg ccgccgtccc cttctccctc tccagcctcg gggctgtccg 1560
cggggggacg gctgccttcg ggggggacgg ggcagggcgg ggttcggctt ctggcgtgtg 1620
accggcggct ctagagcctc tgctaaccat gttcatgcct tcttcttttt cctacag 1677

<210> SEQ ID NO 24
<211> LENGTH: 652
<212> TYPE: DNA
<213> ORGANISM: Homo sapiens

<400> SEQUENCE: 24
cgcgtcgaca ttgattattg actagttatt aatagtaatc aattacgggg tcattagttc 60
atagcccata tatggagttc cgcgttacat aacttacggt aaatggcccg cctggctgac 120
cgcccaacga cccccgccca ttgacgtcaa taatgacgta tgttcccata gtaacgccaa 180
tagggacttt ccattgacgt caatgggtgg agtatttacg gtaaactgcc cacttggcag 240
tacatcaagt gtatcatatg ccaagtacgc cccctattga cgtcaatgac ggtaaatggc 300
ccgcctggca ttatgcccag tacatgacct tatgggactt tcctacttgg cagtacatct 360
acgtattagt catcgctatt accatgtcga ggccacgttc tgcttcactc tccccatctc 420
ccccccctcc ccacccccaa ttttgtattt atttattttt taattatttt gtgcagcgat 480
gggggcgggg gggggggcg cgcgccaggc ggggcggggc ggggcgaggg gcggggcggg 540
gcgaggcgga gaggtgcggc ggcagccaat cagagcggcg cgctccgaaa gtttcctttt 600
atggcgaggc ggcggcggcg gcggccctat aaaaagcgaa gcgcgcggcg gg 652

<210> SEQ ID NO 25
<211> LENGTH: 1177
<212> TYPE: DNA
<213> ORGANISM: Homo sapiens

<400> SEQUENCE: 25
ggtgcagcgg cctccgcgcc gggttttggc gcctcccgcg ggcgcccccc tcctcacggc 60
gagcgctgcc acgtcagacg aagggcgcag gagcgttcct gatccttccg cccggacgct 120
caggacagcg gcccgctgct cataagactc ggccttagaa ccccagtatc agcagaagga 180
cattttagga cgggacttgg gtgactctag ggcactggtt ttctttccag agagcggaac 240
aggcgaggaa aagtagtccc ttctcggcga ttctgcggag ggatctccgt ggggcggtga 300
acgccgatga ttatataagg acgcgccggg tgtggcacag ctagttccgt cgcagccggg 360
atttgggtcg cggttcttgt ttgtggatcg ctgtgatcgt cacttggtga gttgcgggct 420
gctgggctgg ccggggcttt cgtggccgcc gggccgctcg gtgggacgga agcgtgtgga 480
gagaccgcca agggctgtag tctgggtccg cgagcaaggt tgccctgaac tgggggttgg 540
ggggagcgca caaaatggcg gctgttcccg agtcttgaat ggaagacgct tgtaaggcgg 600
gctgtgaggt cgttgaaaca aggtgggggg catggtgggc ggcaagaacc caaggtcttg 660
aggccttcgc taatgcggga aagctcttat tcgggtgaga tgggctgggg caccatctgg 720
ggaccctgac gtgaagtttg tcactgactg gagaactcgg gtttgtcgtc tggttgcggg 780
ggcggcagtt atgcggtgcc gttgggcagt gcacccgtac ctttgggagc gcgcgcctcg 840
tcgtgtcgtg acgtcacccg ttctgttggc ttataatgca gggtggggcc acctgccggt 900
aggtgtgcgg taggcttttc tccgtcgcag gacgcagggt tcgggcctag ggtaggctct 960
cctgaatcga caggcgccgg acctctggtg aggggaggga taagtgaggc gtcagtttct 1020
ttggtcggtt ttatgtacct atcttcttaa gtagctgaag ctccggtttt gaactatgcg 1080
ctcggggttg gcgagtgtgt tttgtgaagt tttttaggca ccttttgaaa tgtaatcatt 1140
tgggtcaata tgtaatttc agtgttagac tagtaaa 1177

<210> SEQ ID NO 26
<211> LENGTH: 511
<212> TYPE: DNA
<213> ORGANISM: Homo sapiens

<400> SEQUENCE: 26
ttctaccggg taggggaggc gcttttccca aggcagtctg gagcatgcgc tttagcagcc 60
ccgctgggca cttggcgcta cacaagtggc ctctggcctc gcacacattc cacatccacc 120
ggtaggcgcc aaccggctcc gttctttggt ggccccttcg cgccaccttc tactcctccc 180
ctagtcagga agttcccccc cgcccgcag ctcgcgtcgt gcaggacgtg acaaatggaa 240
gtagcacgtc tcactagtct cgtgcagatg gacagcaccg ctgagcaatg gaagcgggta 300
ggcctttggg gcagcggcca atagcagctt tgctccttcg ctttctgggc tcagaggctg 360
ggaaggggtg ggtccggggg cgggctcagg ggcgggctca ggggcggggc gggcgcccga 420
aggtcctccg gaggcccggc attctgcacg cttcaaaagc gcacgtctgc cgcgctgttc 480
tcctcttcct catctccggg cctttcgacc t 511

<210> SEQ ID NO 27
<211> LENGTH: 1182
<212> TYPE: DNA
<213> ORGANISM: Homo sapiens

<400> SEQUENCE: 27
gctccggtgc ccgtcagtgg gcagagcgca catcgcccac agtccccgag aagttggggg 60
gaggggtcgg caattgaacc ggtgcctaga gaaggtggcg cggggtaaac tgggaaagtg 120
atgtcgtgta ctggctccgc ctttttcccg agggtggggg agaaccgtat ataagtgcag 180
tagtcgccgt gaacgttctt tttcgcaacg ggtttgccgc cagaacacag gtaagtgccg 240
tgtgtggttc ccgcgggcct ggcctcttta cgggttatgg cccttgcgtg ccttgaatta 300
cttccacgcc cctggctgca gtacgtgatt cttgatcccg agcttcgggt tggaagtggg 360
tgggagagtt cgaggccttg cgcttaagga gccccttcgc ctcgtgcttg agttgaggcc 420
tggcctgggc gctggggccg ccgcgtgcga atctggtggc accttcgcgc ctgtctcgct 480
gctttcgata agtctctagc catttaaaat ttttgatgac ctgctgcgac gcttttttc 540 tggcaagata gtcttgtaaa tgcgggccaa gatctgcaca ctggtatttc ggtttttggg 600
gccgcgggcg gcgacggggc ccgtgcgtcc cagcgcacat gttcggcgag gcggggcctg 660
cgagcgcggc caccgagaat cggacggggg tagtctcaag ctggccggcc tgctctggtg 720
cctggcctcg cgccgccgtg tatcgccccg ccctgggcgg caaggctggc ccggtcggca 780
ccagttgcgt gagcggaaag atggccgctt cccggccctg ctgcagggag ctcaaaatgg 840
aggacgcggc gctcgggaga gcgggcgggt gagtcaccca cacaaaggaa aagggccttt 900
ccgtcctcag ccgtcgcttc atgtgactcc acggagtacc gggcgccgtc caggcacctc 960
gattagttct cgagcttttg gagtacgtcg tctttaggtt ggggggaggg gttttatgcg 1020
atggagtttc cccacactga gtgggtggag actgaagtta ggccagcttg gcacttgatg 1080
taattctcct tggaatttgc ccttttttgag tttggatctt ggttcattct caagcctcag 1140
acagtggttc aaagtttttt tcttccattt caggtgtcgt ga 1182

<210> SEQ ID NO 28
<211> LENGTH: 679
<212> TYPE: DNA
<213> ORGANISM: Homo sapiens

<400> SEQUENCE: 28
gtcgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600
gagaacccac tgcttactgg cttatcgaaa ttaatacgac tcactatagg gagacccaag 660
ctggctagcg tttaaactt 679

<210> SEQ ID NO 29
<211> LENGTH: 1765
<212> TYPE: DNA
<213> ORGANISM: Artificial Sequence
<220> FEATURE:
<223> OTHER INFORMATION: Synthetic

<400> SEQUENCE: 29
agctctgagc tcctcctctg ctcgcccaat ccttccaacc ccctatggtg gtatggctga 60
cacagaaaat gtctgctcct gtatgggaca tttgcccctc ttctccaaat ataagacagg 120
atgaggccta gcttttgctg ctccaaagtt ttaaaagaac acattgcacg gcatttaggg 180
actctaaagg gtggaggagg aatgagggaa ttgcatcatg ccaaggctgg tcctcatcca 240
tcactgcttc cagggcccag agtggcttcc aggaagtatt cttacaaagg aagcccgatc 300
tgtagctaac actcagagcc cattttcctg cgttaacccc tcccgacctc atatacagga 360
gtaacatgat cagtgacctg ggggagctgg ccaaactgcg ggacctgccc aagctgaggg 420
ccttggtgct gctggacaac ccctgtgccg atgagactga ctaccgccag gaggccctgg 480
tgcagatggc acacctagag cgcctagaca aagagtacta tgaggacgag gaccgggcag 540
aagctgagga gatccgacag aggctgaagg aggaacagga gcaagaactc gacccggacc 600
aagacatgga accgtacctc ccgccaactt agtggctcct ctagcctgca gggacagtaa 660
aggtgatggc aggaaggcag cccccggagg tcaaaggctg ggcacgcggg aggagaggcc 720
agagtcagag gctgcgggta tctcagatat gaaggaaaga tgagagaggc tcaggaagag 780
gtaagaaaag acacaagaga ccagagaagg gagaagaatt agagagggag gcagaggacc 840
gctgtctcta cagacatagc tggtagagac tgggaggaag ggatgaaccc tgagcgcatg 900
aagggaagga ggtggctggt ggtatatgga ggatgtagct gggccaggga aaagatcctg 960
cactaaaaat ctgaagctaa aaataacagg acacggggtg gagaggcgaa aggagggcag 1020
agtgaggcag agagactgag aggcctgggg atgtgggcat tccggtaggg cacacagttc 1080
acttgtcttc tctttttcca ggaggccaaa gatgctgacg tcaagaactc ataatacccc 1140
agtggggacc accgcattca tagccctgtt acaagaagtg ggagatgttc ctttttgtcc 1200
cagactggaa atccgttaca tcccgaggct caggttctgt ggtggtcatc tctgtgtggc 1260
ttgttctgtg ggcctaccta aagtcctaag cacagctctc aagcagatcc gaggcgacta 1320
agatgctagt aggggttgtc tggagagaag agccgaggag gtgggctgtg atggatcagt 1380
tcagctttca aataaaaagg cgtttttata ttctgtgtcg agttcgtgaa cccctgtggt 1440
gggcttctcc atctgtctgg gttagtacct gccactatac tggaataagg ggacgcctgc 1500
ttccctcgag ttggctggac aaggttatga gcatccgtgt acttatgggg ttgccagctt 1560
ggtcctggat cgcccgggcc cttcccccac ccgttcggtt ccccaccacc acccgcgctc 1620
gtacgtgcgt ctccgcctgc agctcttgac tcatcggggc ccccgggtca catgcgctcg 1680
ctcggctcta taggcgccgc cccctgccca ccccccgccc gcgctgggag ccgcagccgc 1740
cgccactcct gctctctctg cgccg 1765

<210> SEQ ID NO 30
<211> LENGTH: 733
<212> TYPE: DNA
<213> ORGANISM: Homo sapiens

<400> SEQUENCE: 30
tgcccattat aaacgtctgc aaagaccaag gtttgatatg ttgattttac tgtcagcctt 60
aagagtgcga catctgctaa tttagtgtaa taatacaatc agtagaccct ttaaaacaag 120
tcccttggct tggaacaacg ccaggctcct caacaggcaa ctttgctact tctacagaaa 180
atgataataa agaaatgctg gtgaagtcaa atgcttatca caatggtgaa ctactcagca 240
gggaggctct aataggcgcc aagagcctag acttccttaa gcgccagagt ccacaagggc 300
ccagttaatc ctcaacattc aaatgctgcc cacaaaacca gcccctctgt gccctagccg 360
cctctttttt ccaagtgaca gtagaactcc accaatccgc agctgaatgg ggtccgcctc 420
ttttccctgc ctaaacagac aggaactcct gccaattgag ggcgtcaccg ctaaggctcc 480
gccccagcct gggctccaca accaatgaag ggtaatctcg acaaagagca aggggtgggg 540
cgcgggcgcg caggtgcagc agcacacagg ctggtcggga gggcggggcg cgacgtctgc 600
cgtgcggggt cccggcatcg gttgcgcgcg cgctccctcc tctcggagag agggctgtgg 660
taaaacccgt ccggaaaatg gccgccgctg ccgccaccgc cgccgccgcc gccgcgccga 720
gcggaggagg agg 733

<210> SEQ ID NO 31
<211> LENGTH: 1991
<212> TYPE: DNA
<213> ORGANISM: Homo sapiens

<400> SEQUENCE: 31
ggcaacatgg caagacccta tctctacaaa aaaagttaaa aaatcagcca cgtgtggtga 60
cacacacctg tagtcccagc tattcaggag gctgaggtga ggggatcact taaggctggg 120
aggttgaggc tgcagtgagt cgtggttgcg ccactgcact ccagcctggg caacagtgag 180
accctgtctc aaaagacaaa aaaaaaaaaa aaaaaaaaaa gaacatatcc tggtgtggag 240
taggggacgc tgctctgaca gaggctcggg ggcctgagct ggctctgtga gctggggagg 300
aggcagacag ccaggccttg tctgcaagca gacctggcag cattgggctg gccgcccccc 360
agggcctcct cttcatgccc agtgaatgac tcaccttggc acagacacaa tgttcggggt 420
gggcacagtg cctgcttccc gccgcacccc agcccccctc aaatgccttc cgagaagccc 480
attgagcagg gggcttgcat tgcaccccag cctgacagcc tggcatcttg ggataaaagc 540
agcacagccc cctaggggct gcccttgctg tgtggcgcca ccggcggtgg agaacaaggc 600
tctattcagc ctgtgcccag gaaaggggat caggggatgc ccaggcatgg acagtgggtg 660
gcaggggggg agaggagggc tgtctgcttc ccagaagtcc aaggacacaa atgggtgagg 720
ggactgggca gggttctgac cctgtgggac cagagtggag ggcgtagatg gacctgaagt 780
ctccagggac aacagggccc aggtctcagg ctcctagttg ggcccagtgg ctccagcgtt 840
tccaaaccca tccatcccca gaggttcttc ccatctctcc aggctgatgt gtgggaactc 900
gaggaaataa atctccagtg ggagacggag gggtggccag ggaaacgggg cgctgcagga 960
ataaagacga gccagcacag ccagctcatg tgtaacggct ttgtggagct gtcaaggcct 1020
ggtctctggg agagaggcac agggaggcca gacaaggaag gggtgacctg gagggacaga 1080
tccaggggct aaagtcctga taaggcaaga gagtgccggc cccctcttgc cctatcagga 1140
cctccactgc cacatagagg ccatgattga cccttagaca aagggctggt gtccaatccc 1200
agcccccagc cccagaactc cagggaatga atgggcagag agcaggaatg tgggacatct 1260
gtgttcaagg gaaggactcc aggagtctgc tgggaatgag gcctagtagg aaatgaggtg 1320
gcccttgagg gtacagaaca ggttcattct tcgccaaatt cccagcacct tgcaggcact 1380
tacagctgag tgagataatg cctgggttat gaaatcaaaa agttggaaag caggtcagag 1440
gtcatctggt acagcccttc cttccctttt tttttttttt ttttgtgaga caaggtctct 1500
ctctgttgcc caggctggag tggcgcaaac acagctcact gcagcctcaa cctactgggc 1560
tcaagcaatc ctccagcctc agcctcccaa agtgctggga ttacaagcat gagccacccc 1620
actcagccct ttccttcctt tttaattgat gcataataat tgtaagtatt catcatggtc 1680
caaccaaccc tttcttgacc caccttccta gagagagggt cctcttgctt cagcggtcag 1740
ggccccagac ccatggtctg gctccaggta ccacctgcct catgcaggag ttggcgtgcc 1800
caggaagctc tgcctctggg cacagtgacc tcagtggggt gaggggagct ctccccatag 1860
ctgggctgcg gcccaacccc acccccctcag gctatgccag gggtgttgc cagggggcacc 1920 cgggcatcgc cagtctagcc cactccttca taaagccctc gcatcccagg agcgagcaga 1980
gccagagcag g 1991

<210> SEQ ID NO 32
<211> LENGTH: 27
<212> TYPE: DNA
<213> ORGANISM: Homo sapiens

<400> SEQUENCE: 32
tatccttatg acgtgcctga ctatgcc 27

<210> SEQ ID NO 33
<211> LENGTH: 477
<212> TYPE: DNA
<213> ORGANISM: Homo sapiens

<400> SEQUENCE: 33
gggtggcatc cctgtgaccc ctccccagtg cctctcctgg ccctggaagt tgccactcca 60
gtgcccacca gccttgtcct aataaaatta agttgcatca ttttgtctga ctaggtgtcc 120
ttctataata ttatggggtg gaggggggtg gtatggagca aggggcaagt tgggaagaca 180
acctgtaggg cctgcggggt ctattgggaa ccaagctgga gtgcagtggc acaatcttgg 240
ctcactgcaa tctccgcctc ctgggttcaa gcgattctcc tgcctcagcc tcccgagttg 300
ttgggattcc aggcatgcat gaccaggctc agctaatttt tgttttttttg gtagagacgg 360 ggtttcacca tattggccag gctggtctcc aactcctaat ctcaggtgat ctacccacct 420
tggcctccca aattgctggg attacaggcg tgaaccactg ctcccttccc tgtcctt 477

<210> SEQ ID NO 34
<211> LENGTH: 127
<212> TYPE: DNA
<213> ORGANISM: Homo sapiens

<400> SEQUENCE: 34
gatctttttc cctctgccaa aaattatggg gacatcatga agccccttga gcatctgact 60
tctggctaat aaaggaaatt tattttcatt gcaatagtgt gttggaattt tttgtgtctc 120
tcactcg 127

<210> SEQ ID NO 35
<211> LENGTH: 56
<212> TYPE: DNA
<213> ORGANISM: Homo sapiens

<400> SEQUENCE: 35
aataaaggaa atttattttc attgcaatag tgtgttggaa tttttttgtgt ctctca 56

<210> SEQ ID NO 36
<211> LENGTH: 1404
<212> TYPE: DNA
<213> ORGANISM: Artificial Sequence
<220> FEATURE:
<223> OTHER INFORMATION: Synthetic

<400> SEQUENCE: 36
atgacagagt tacctgcacc attgtcctac ttccagaatg cacagatgtc tgaggacaac 60
cacctgagca atactgtacg tagccagaat gacaatagag aaagacagga gcacaatgac 120
agacggagcc ttggccaccc tgagccatta tctaatggaa gaccccaggg taactccaga 180
caggtggtgg agcaagatga ggaagaagat gaggagctga cattgaaata tggtgccaag 240
catgtgatca tgctctttgt ccctgtgact ctctgcatgg tggtggttgt ggctaccatt 300
aagtcagtca gcttttatac ccggaaggat gggcagctaa tctatacccc attcacagaa 360
gataccgaga ctgtgggcca gagagccctg cactcaattc tgaatgctgc catcatgatc 420
agtgtcattg ttgtcatgac tatcctcctg gtggttctgt ataaatacag gtgctataag 480
gtcatccatg cctggcttat tatatcatct ctattgttgc tgttcttttt ttcattcatt 540
tacttggggg aagtgtttaa aacctataat gttgctgtgg actacattac tgttgcactc 600
ctgatctgga attttggtgt ggtgggaatg atttccattc actggaaagg tccacttaga 660
ctccagcagg catatctcat tatgattagt gccctcatgg ccctggtgtt tatcaagtac 720
ctccctgaat ggactgcctg gctcatcttg gctgtgattt cagtatatga tttagtggct 780
gttttgtgtc ccaaaggtcc acttcgtatg ctggttgaaa cagctcagga gagaaatgaa 840 acccttttttc cagctctcat ttactcctca acaatggtgt ggttggtgaa tatggcagaa 900
ggagacccag aagctcaaag gagagtatcc aaaaattcca agtataatgc agaaagcaca 960

```
gaaagggagt cacaagacac tgttgcagag aatgatgatg gtgggttcag tgaggaatgg   1020

gaagcccaga gggacagtca tctagggcct cataggtcta cacctgagtc aagagctgct   1080

gtccaggaac tttccagcag tatcctggct ggtgaagacc cagaggaaag gggagtaaaa   1140

cttggattgg gagatttcat tttctacagt gttctggttg gtaaagcctc agcaacagcc   1200

agtggagact ggaacacaac catagcctgt tttgtagcca tattaattgg tttgtgcctt   1260

acattattac tccttgccat tttcaagaaa gcattgccag ctcttccaat ctccatcacc   1320

tttgggcttg ttttctactt tgccacagat tatcttgtac agccttttat ggaccaatta   1380

gcattccatc aattttatat ctag                                          1404
```

<210> SEQ ID NO 37
<211> LENGTH: 1404
<212> TYPE: DNA
<213> ORGANISM: Homo sapiens

<400> SEQUENCE: 37

```
atgacagaat tacctgcccc cttgagctac ttccagaatg cacagatgag cgaggacaac     60

cacctgagca atactgtacg tagccagaat gacaacagag aacggcagga acacaacgac    120

aggcggagcc tgggccaccc tgagcccctg tctaatggaa gaccccaggg taacagcaga    180

caggtggtgg aacaagatga ggaagaggac gaggagctga ccctgaagta cggcgccaag    240

cacgtgatca tgctcttcgt gcccgtgact ctctgcatgg tggtggtggt ggctacaatc    300

aagagcgtca gcttttatac ccggaaggat gggcagctaa tctatacccc attcacagaa    360

gacaccgaga ctgtgggcca gagagccctg cactcaatcc tgaatgccgc catcatgatc    420

agcgtcattg ttgtcatgac tatcctcctg gtggttctgt ataaatacag gtgctataag    480

gtcatccatg cctggctgat catatcatct ctgttgctgc tgttcttttt tagcttcatt    540

tacctgggcg aagtgtttaa aacctataac gttgccgtgg actacattac tgttgccctc    600

ctgatctgga acttcggcgt ggtgggcatg atttccattc actggaaagg ccccctgaga    660

ctgcagcagg catacctcat tatgatctcc gccctcatgg ccctggtgtt catcaagtac    720

ctgcccgagt ggactgcttg gctcatcttg gctgtgatct ccgtgtatga tttagtggct    780

gttctgtgtc ctaaaggtcc actgcgtatg ctggtggaaa cagctcagga aagaaatgaa    840

acactgtttc ctgctctgat ttactcctca acaatggtgt ggctcgtgaa tatggccgaa    900

ggagaccctg aagcccaacg gagagtgtcc aaaaactcca agtataacgc cgagagcaca    960

gaaagggaga gccaggatac agttgccgag aatgacgatg gcggcttcag tgaggaatgg   1020

gaagcccaga gggacagcca cctggggcct cacagaagca cccctgagtc tagagccgct   1080

gtccaggaac tgtccagctc catcctggcc ggcgaagacc ccgaagaaag gggagtaaaa   1140

cttggactgg gagatttcat cttctacagt gttctcgttg gcaaagccag cgcaacagct   1200

agcggagact ggaacacaac aatagcctgt ttcgtagcca tcttaattgg cctgtgcctt   1260

acacttctgc tcctggccat cttcaagaag gccctgccag ccctgcctat cagcatcacc   1320

ttcgggcttg ttttctactt tgccaccgat tatctggtgc agcccttcat ggaccagctg   1380

gccttccacc agttttacat ctag                                          1404
```

<210> SEQ ID NO 38
<211> LENGTH: 1344
<212> TYPE: DNA
<213> ORGANISM: Homo sapiens

<400> SEQUENCE: 38
atgacagagt tacctgcacc cttgtcctac ttccagaatg cacagatgtc tgaggacaac 60
cacctgagca atactgtacg tagccagaat gacaatagag aacggcagga gcacaacgac 120
agacggagcc tcggccaccc tgagccattg tctaatggac ggccccaggg taactcccgg 180
caggtggtgg agcaggatga ggaagaagat gaggagctga cattgaaata tggcgccaag 240
catgtgatca tgctctttgt ccctgtgact ctctgcatgg tggtggtcgt ggctaccatt 300
aagtcagtca gcttttatac ccggaaggat gggcagctaa tctatacccc attcacagaa 360
gataccgaga ctgtgggcca gagagccctg cactcaattc tgaatgctgc catcatgatc 420
gtcatccatg cctggctcat tatatcatct ctgttgttgc tgttcttttt ttcattcatt 480
tacttggggg aagtgtttaa aacctataac gttgctgtgg actacattac tgttgcactc 540
ctgatctgga attttggcgt ggtggggatg atttccattc actggaaagg cccactccgg 600
ctccagcagg catatctcat tatgattagt gccctcatgg ccctggtgtt tatcaagtac 660
ctccctgaat ggactgcctg gctcatcttg gctgtgattt cagtgtatga tttagtggct 720
gttttgtgtc ccaaaggtcc actccgtatg ctggtcgaaa cagctcagga gagaaatgaa 780
accctctttc cagctctcat ttactcctca acaatggtgt ggttggtgaa tatggcagaa 840
ggagaccccg aagctcaaag gagagtgtcc aaaaattcca agtataatgc agaaagcaca 900
gaaagggagt cacaggacac tgttgcagag aatgatgatg gcgggttcag tgaggaatgg 960
gaagcccaga gggacagtca tctggggcct catcgctcta cacctgagtc acgggctgct 1020
gtccaggaac tctccagcag tatcctcgct ggcgaagacc cagaggaaag gggagtaaaa 1080
cttggattgg gagatttcat tttctacagt gttctggttg gcaaagcctc agcaacagcc 1140
agtggagact ggaacacaac catagcctgt ttcgtagcca tcttaattgg cttgtgcctt 1200
acattgttgc tcctcgccat tttcaagaaa gcattgccag ctctcccaat ctccatcacc 1260
tttgggcttg ttttctactt tgccacagat tatctcgtgc agccttttat ggaccagttg 1320
gcattccatc aattttatat ctag 1344

<210> SEQ ID NO 39
<211> LENGTH: 1404
<212> TYPE: DNA
<213> ORGANISM: Homo sapiens

<400> SEQUENCE: 39
atgacagagt tacctgcccc cttgagctac ttccagaatg cacagatgag cgaggacaac 60
cacctgagca atactgtacg tagccagaat gacaacagag aacggcagga gcacaacgac 120
agacggagcc tgggccaccc tgagcccctg agcaatggaa gaccccaggg taacagccgg 180
caggtggtgg agcaggatga ggaagaggac gaggagctga ccctgaagta cggcgccaag 240
cacgtgatca tgctcttcgt gcccgtgact ctctgcatgg tggtggtggt ggctaccatc 300
aagagcgtca gcttttatac ccggaaggat gggcagctaa tctatacccc attcacagaa 360
gacaccgaga ctgtgggcca gagagccctg cactcaatcc tgaatgccgc catcatgatc 420
agcgtcattg ttgtcatgac tatcctcctg gtggttctgt ataaatacag gtgctataag 480
gtcatccatg cctggctgat catatcatct ctgttgctgc tgttcttttt tagcttcatt 540
tacctgggcg aagtgtttaa aacctataac gttgccgtgg actacattac tgttgccctc 600
ctgatctgga acttcggcgt ggtgggcatg attagcattc actggaaagg ccccctgaga 660
ctgcagcagg catacctcat catgatcagc gccctcatgg ccctggtgtt catcaagtac 720
ctgcccgagt ggactgcctg gctcatcttg gctgtgatca gcgtgtatga tttagtggct 780
gttctgtgtc ccaaaggtcc actgcgtatg ctggtggaga cagctcagga gagaaatgaa 840
accctgtttc ccgctctgat ttactcctca accatggtgt ggctggtgaa tatggccgaa 900
ggagaccccg aagcccaacg gagagtgagc aaaaacagca agtataacgc cgagagcaca 960
gaaagggaga gccaggacac cgttgccgag aatgacgatg gcggcttcag tgaggagtgg 1020
gaagcccaga gggacagcca cctggggccc cacagaagca cccccgagag cagagccgct 1080
gtccaggaac tgtccagcag catcctggcc ggcgaagacc ccgaggaaag gggagtaaag 1140
cttggactgg gagatttcat cttctacagt gttctggttg gcaaagccag cgcaacagcc 1200
agcggagact ggaacacaac catagcctgt ttcgtagcca tcttaattgg cctgtgcctt 1260
accctgctgc tcctggccat cttcaagaag gccctgccag ccctgcccat cagcatcacc 1320
ttcgggcttg ttttctactt tgccaccgat tatctggtgc agcccttcat ggaccagctg 1380
gccttccacc agttttacat ctga 1404

<210> SEQ ID NO 40
<211> LENGTH: 1667
<212> TYPE: DNA
<213> ORGANISM: Homo sapiens
<220> FEATURE:
<221> NAME/KEY: misc_feature
<223> OTHER INFORMATION: CAG promoter used in pAT029, pAT024, and pAT022

<400> SEQUENCE: 40
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggactatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg ggtcgaggtg agccccacgt tctgcttcac tctccccatc 420
tcccccccct ccccaccccc aattttgtat ttatttattt tttaattatt ttgtgcagcg 480
atgggggcgg gggggggggg ggcgcgcgcc aggcggggcg gggcggggcg aggggcgggg 540
cggggcgagg cggagaggtg cggcggcagc caatcagagc ggcgcgctcc gaaagtttcc 600
ttttatggcg aggcggcggc ggcggcggcc ctataaaaag cgaagcgcgc ggcgggcggg 660
agtcgctgcg ttgccttcgc cccgtgcccc gctccgcgcc gcctcgcgcc gcccgccccg 720
gctctgactg accgcgttac tcccacaggt gagcgggcgg gacggccctt ctcctccggg 780
ctgtaattag cgcttggttt aatgacggct cgtttctttt ctgtggctgc gtgaaagcct 840
taaagggctc cgggagggcc ctttgtgcgg ggggagcgg ctcgggggt gcgtgcgtgt 900 gtgtgtgcgt ggggagcgcc gcgtgcggcc cgcgctgccc ggcggctgtg agcgctgcgg 960
gcgcggcgcg gggctttgtg cgctccgcgt gtgcgcgagg ggagcgcggc cgggggcggt 1020
gccccgcggt gcgggggggc tgcgagggga acaaaggctg cgtgcggggt gtgtgcgtgg 1080
gggggtgagc agggggtgtg ggcgcggcgg tcgggctgta acccccccct gcaccccccct 1140 ccccgagttg ctgagcacgg cccggcttcg ggtgcggggc tccgtgcggg gcgtggcgcg 1200
gggctcgccg tgccgggcgg ggggtggcgg caggtggggg tgccgggcgg ggcggggccg 1260
cctcgggccg ggagggctc gggggagggg cgcggcggcc ccggagcgcc ggcggctgtc 1320

```
gaggcgcggc gagccgcagc cattgccttt tatggtaatc gtgcgagagg gcgcagggac   1380

ttcctttgtc ccaaatctgg cggagccgaa atctgggagg cgccgccgca ccccctctag   1440

cgggcgcggg cgaagcggtg cggcgccggc aggaaggaaa tgggcgggga gggccttcgt   1500

gcgtcgccgc gccgccgtcc ccttctccat ctccagcctc ggggctgccg caggggggacg   1560

gctgccttcg ggggggacgg ggcagggcgg ggttcggctt ctggcgtgtg accggcggct   1620

ctagagcctc tgctaaccat gttcatgcct tcttcttttt cctacag                 1667
```

<210> SEQ ID NO 41
<211> LENGTH: 4693
<212> TYPE: DNA
<213> ORGANISM: Artificial Sequence
<220> FEATURE:
<223> OTHER INFORMATION: Synthetic

<400> SEQUENCE: 41

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccaat tcagtcgata actataacgg tcctaaggta    180

gcgatttaaa tacgcgctct cttaaggtag ccccgggacg cgtcaattga gatctcgggg    240

gtggattttt aaagaaactt tagaagaatg taacttgccc agataccatg taccgttaat    300

ttcattttcg gtttttgaa tacccatgtt tgacatttct ccgttcacct tgattaaata    360

aggtagtatt catttttag ttttagcttt tggatatatg tgtaagtgtg gtatgctgtc    420

taatgaatta gacattggta ctgtctttac caaaactgga caaagagcag gcagatgcaa    480

aaatcaagtg acccagcaaa ccagacacat tttctgctct cagctagctt gccacctaga    540

aagactggtt gtcaaagggg gagtccaaga atcgcggagg atgtttaaaa tgcagtttct    600

caggttctcg ccacccacca gaagttttga ttcattgagt ggtgggagag ggcagagata    660

tttgcgattt taacagcatt ctcttgattg tgatgcagct ggttcgcaaa taggtaccct    720

aaagaaatga caggtgttaa atttaggatg gccatcgctt gtatgccggg agaagcacac    780

gctgggccca atttatatag ggctttcgt cctcagctcg agcagcctca gaaccccgac    840

aacccacgcc agcgctctgg gcggattccg tcaggtgggg aaggccaggt ggagctctgg    900

gttctccccg caatcgtttc tccaggccgg aggccccgcc cccttcctcc tggctcctcc    960

cctcctccgt gggccggccg ccaacgacgc cagagccgga aatgacgaca acggtgaggg   1020

ttctcgggcg gggcctggga caggcagctc cggggtccgc ggtttcacat cggaaacaaa   1080

acagcggctg gtctggaagg aacctgagct acgagccgcg gcggcagcgg ggcggcgggg   1140

aagcgtatgt gcgtgatggg gagtccgggc aagccaggaa ggcaccgcgg acatgggcgg   1200

aagcttcgtt tagtgaaccg tcagatcgcc tggagacgcc atccacgctg ttttgacctc   1260

catagaagac accgggaccg atccagcctc cgcggattcg aatcccggcc gggaacggtg   1320

cattggaacg cggattcccc gtgccaagag tgacgtaagt accgcctata gagtctatag   1380

gcccacaaaa aatgctttct tcttttaata tactttttg tttatcttat ttctaatact   1440

ttccctaatc tctttctttc agggcaataa tgatacaatg tatcatgcct ctttgcacca   1500

ttctaaagaa taacagtgat aatttctggg ttaaggcaat agcaatattt ctgcatataa   1560

atatttctgc atataaattg taactgatgt aagaggtttc atattgctaa tagcagctac   1620

aatccagcta ccattctgct tttattttgt ggttgggata aggctggatt attctgagtc   1680
```

caagctaggc cctttttgcta atcgtgttca tacctcttat cttcctccca cagctcctgg 1740
gcaacgtgct ggtctgtgtg ctggcccatc actttggcaa agaattaccg gtctcctggg 1800
caacgtgctg gttattgtgc tgtctcatca ttttggcaaa gaattcacgc cccagagccg 1860
ccaccatggc ctacccatac gatgttccag attacgctac agaattacct gccccccttga 1920
gctacttcca gaatgcacag atgagcgagg acaaccacct gagcaatact gtacgtagcc 1980
agaatgacaa cagagaacgg caggaacaca acgacaggcg gagcctgggc caccctgagc 2040
ccctgtctaa tggaagaccc cagggtaaca gcagacaggt ggtggaacaa gatgaggaag 2100
aggacgagga gctgaccctg aagtacggcg ccaagcacgt gatcatgctc ttcgtgcccg 2160
tgactctctg catggtggtg gtggtggcta caatcaagag cgtcagcttt tatacccgga 2220
aggatgggca gctaatctat accccattca cagaagacac cgagactgtg ggccagagag 2280
ccctgcactc aatcctgaat gccgccatca tgatcagcgt cattgttgtc atgactatcc 2340
tcctggtggt tctgtataaa tacaggtgct ataaggtcat ccatgcctgg ctgatcatat 2400
catctctgtt gctgctgttc ttttttagct tcatttacct gggcgaagtg tttaaaacct 2460
ataacgttgc cgtggactac attactgttg ccctcctgat ctggaacttc ggcgtggtgg 2520
gcatgatttc cattcactgg aaaggccccc tgagactgca gcaggcatac ctcattatga 2580
tctccgccct catggccctg gtgttcatca agtacctgcc cgagtggact gcttggctca 2640
tcttggctgt gatctccgtg tatgatttag tggctgttct gtgtcctaaa ggtccactgc 2700
gtatgctggt ggaaacagct caggaaagaa atgaaacact gtttcctgct ctgatttact 2760
cctcaacaat ggtgtggctc gtgaatatgg ccgaaggaga ccctgaagcc caacggagag 2820
tgtccaaaaa ctccaagtat aacgccgaga gcacagaaag ggagagccag gatacagttg 2880
ccgagaatga cgatggcggc ttcagtgagg aatgggaagc ccagagggac agccacctgg 2940
ggcctcacag aagcacccct gagtctagag ccgctgtcca ggaactgtcc agctccatcc 3000
tggccggcga agaccccgaa gaaaggggag taaaacttgg actgggagat ttcatcttct 3060
acagtgttct cgttggcaaa gccagcgcaa cagctagcgg agactggaac acaacaatag 3120
cctgtttcgt agccatctta attggcctgt gccttacact tctgctcctg gccatcttca 3180
agaaggccct gccagccctg cctatcagca tcaccttcgg gcttgttttc tactttgcca 3240
ccgattatct ggtgcagccc ttcatggacc agctggcctt ccaccagttt tacatctagt 3300
aagcggccgc cctagggagc tcctcgaggg ggtggcatcc ctgtgacccc tccccagtgc 3360
ctctcctggc cctggaagtt gccactccag tgcccaccag ccttgtccta ataaaattaa 3420
gttgcatcat tttgtctgac taggtgtcct tctataatat tatggggtgg agggggggtgg 3480
tatggagcaa ggggcaaggg ggggaagacaa cctgtagggc ctgcggggtc tattgggaac 3540
caagctggag tgcagtggca caatcttggc tcactgcaat ctccgcctcc tgggttcaag 3600
cgattctcct gcctcagcct cccgagttgt tgggattcca ggcatgcatg accaggctca 3660
gctaattttt gttttttttgg tagagacggg gtttcaccat attggccagg ctggtctccc 3720
cctcctaatc tcaggtgatc tacccacctt ggcctcccaa attgctggga ttacaggcgt 3780
gaaccactgc tcccttccct gtccttggcc taggtttctt gagacctcta caagaggggg 3840
agttgacact tggggtactt tcttggtgta acgaactaat agcctgaaaa aaagaagtca 3900
tgtgttttca gcaaggcaag aaactgtcta acatagtaga taaaacagag aacacttggc 3960
cggaatcaac taagatgttg ctatgttcca ttcatcatat tatctccatc tgcagagtag 4020
tgggttagtg gagggtagaa aacattctcc tgaacaacta gttaaacttg gctttgagtt 4080
ccacctgtac cacttgcata atcttgggaa agtgagttgc ctaattcagt gacattaata 4140
aatttattaa tttcttcttt caataaaacc tggagagagc ttcatatgta tcagcatatg 4200
ctaaacttga aagatacaag tagaaaatgg aaggaaatat atctgactca atagggatag 4260
ttcaagggtt aaattaaaag tagtaaagta ttataattaa tctgacatgg tacctaatat 4320
ataataatca tgtattaaga atgccagtca ccattaaaag tcaatgtatg actttaatct 4380
actcgaggaa agaaactatg tcttgttcac tgttattatc tctaaaatcc ataatcagaa 4440
gagcaccatg tgtatgagcc acacaataaa tatctactgt ataatatgtc tcttcttgtt 4500
tttaaccttc atagataaga cttagggata acagggtaat ggcgcgggcc gcaggaaccc 4560
ctagtgatgg agttggccac tccctctctg cgcgctcgct cgctcactga ggccgggcga 4620
ccaaaggtcg cccgacgccc gggctttgcc cgggcggcct cagtgagcga gcgagcgcgc 4680
agctgcctgc agg 4693

<210> SEQ ID NO 42
<211> LENGTH: 4694
<212> TYPE: DNA
<213> ORGANISM: Artificial Sequence
<220> FEATURE:
<223> OTHER INFORMATION: Synthetic

<400> SEQUENCE: 42
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtcgata actataacgg tcctaaggta 180
gcgatttaaa tacgcgctct cttaaggtag ccccgggacg cgtcaattga gatctcggtg 240
cagcggcctc cgcgccgggt tttggcgcct cccgcgggcg ccccccctcct cacggcgagc 300 gctgccacgt cagacgaagg gcgcaggagc gttcctgatc cttccgcccg gacgctcagg 360
acagcggccc gctgctcata agactcggcc ttagaacccc agtatcagca gaaggacatt 420
ttaggacggg acttgggtga ctctagggca ctggttttct ttccagagag cggaacaggc 480
gaggaaaagt agtcccttct cggcgattct gcggagggat ctccgtgggg cggtgaacgc 540
cgatgattat ataaggacgc gccgggtgtg gcacagctag ttccgtcgca gccgggattt 600
gggtcgcggt tcttgtttgt ggatcgctgt gatcgtcact tggtgagttg cgggctgctg 660
ggctggccgg ggctttcgtg gccgccgggc cgctcggtgg gacggaagcg tgtggagaga 720
ccgccaaggg ctgtagtctg ggtccgcgag caaggttgcc ctgaactggg ggttgggggg 780
agcgcacaaa atggcggctg ttcccgagtc ttgaatggaa gacgcttgta aggcgggctg 840
tgaggtcgtt gaaacaaggt ggggggcatg gtgggcggca agaacccaag gtcttgaggc 900
cttcgctaat gcgggaaagc tcttattcgg gtgagatggg ctggggcacc atctggggac 960
cctgacgtga agtttgtcac tgactggaga actcgggttt gtcgtctggt tgcgggggcg 1020
gcagttatgc ggtgccgttg ggcagtgcac ccgtaccttt gggagcgcgc gcctcgtcgt 1080
gtcgtgacgt cacccgttct gttggcttat aatgcagggt ggggccacct gccggtaggt 1140
gtgcggtagg cttttctccg tcgcaggacg cagggttcgg gcctagggta ggctctcctg 1200
aatcgacagg cgccggacct ctggtgaggg gagggataag tgaggcgtca gtttctttgg 1260
tcggttttat gtacctatct tcttaagtag ctgaagctcc ggttttgaac tatgactagt 1320
aaaaagcttc gtttagtgaa ccgtcagatc gcctggagac gccatccacg ctgttttgac 1380

-continued

```
ctccatagaa gacaccggga ccgatccagc ctccgcggat tcgaatcccg gccgggaacg   1440
gtgcattgga acgcggattc cccgtgccaa gagtgacgta agtaccgcct atagagtcta   1500
taggcccaca aaaaatgctt tcttctttta atatactttt ttgtttatct tatttctaat   1560
actttcccta atctctttct ttcagggcaa taatgataca atgtatcatg cctctttgca   1620
ccattctaaa gaataacagt gataatttct gggttaaggc aatagcaata tttctgcata   1680
taaatatttc tgcatataaa ttgtaactga tgtaagaggt ttcatattgc taatagcagc   1740
tacaatccag ctaccattct gcttttattt tgtggttggg ataaggctgg attattctga   1800
gtccaagcta ggcccttttg ctaatcgtgt tcatacctct tatcttcctc ccacagctcc   1860
tgggcaacgt gctggtctgt gtgctggccc atcactttgg caaagaatta ccggtggcaa   1920
cgtgctggtt attgtgctgt ctcatcattt tggcaaagaa ttcacgcccc agagccgcca   1980
ccatggccta cccatacgat gttccagatt acgctacaga attacctgcc cccttgagct   2040
acttccagaa tgcacagatg agcgaggaca accacctgag caatactgta cgtagccaga   2100
atgacaacag agaacggcag gaacacaacg acaggcggag cctgggccac cctgagcccc   2160
tgtctaatgg aagaccccag ggtaacagca gacaggtggt ggaacaagat gaggaagagg   2220
acgaggagct gaccctgaag tacggcgcca agcacgtgat catgctcttc gtgcccgtga   2280
ctctctgcat ggtggtggtg gtggctacaa tcaagagcgt cagcttttat acccggaagg   2340
atgggcagct aatctatacc ccattcacag aagacaccga gactgtgggc cagagagccc   2400
tgcactcaat cctgaatgcc gccatcatga tcagcgtcat tgttgtcatg actatcctcc   2460
tggtggttct gtataaatac aggtgctata aggtcatcca tgcctggctg atcatatcat   2520
ctctgttgct gctgttcttt tttagcttca tttacctggg cgaagtgttt aaaacctata   2580
acgttgccgt ggactacatt actgttgccc tcctgatctg gaacttcggc gtggtgggca   2640
tgatttccat tcactggaaa ggcccccctga gactgcagca ggcatacctc attatgatct   2700
ccgccctcat ggccctggtg ttcatcaagt acctgcccga gtggactgct tggctcatct   2760
tggctgtgat ctccgtgtat gatttagtgg ctgttctgtg tcctaaaggt ccactgcgta   2820
tgctggtgga aacagctcag gaaagaaatg aaacactgtt tcctgctctg atttactcct   2880
caacaatggt gtggctcgtg aatatggccg aaggagaccc tgaagcccaa cggagagtgt   2940
ccaaaaactc caagtataac gccgagagca cagaaaggga gagccaggat acagttgccg   3000
agaatgacga tggcggcttc agtgaggaat gggaagccca gagggacagc cacctggggc   3060
ctcacagaag caccccctgag tctagagccg ctgtccagga actgtccagc tccatcctgg   3120
ccggcgaaga ccccgaagaa aggggagtaa aacttggact gggagatttc atcttctaca   3180
gtgttctcgt tggcaaagcc agcgcaacag ctagcggaga ctggaacaca acaatagcct   3240
gtttcgtagc catcttaatt ggcctgtgcc ttacacttct gctcctggcc atcttcaaga   3300
aggccctgcc agccctgcct atcagcatca ccttcgggct tgttttctac tttgccaccg   3360
attatctggt gcagcccttc atggaccagc tggccttcca ccagttttac atctagtaag   3420
cggccgccct agggagctcc tcgagggggt ggcatccctg tgacccctcc ccagtgcctc   3480
tcctggccct ggaagttgcc actccagtgc ccaccagcct tgtcctaata aaattaagtt   3540
gcatcatttt gtctgactag gtgtccttct ataatattat ggggtggagg ggggtggtat   3600
ggagcaaggg gcaagggggg aagacaacct gtagggcctg cggggtctat tgggaaccaa   3660
gctggagtgc agtggcacaa tcttggctca ctgcaatctc cgcctcctgg gttcaagcga   3720
ttctcctgcc tcagcctccc gagttgttgg gattccaggc atgcatgacc aggctcagct   3780
```

aatttttgtt tttttggtag agacggggtt tcaccatatt ggccaggctg gtctcccccct 3840 cctaatctca ggtgatctac ccaccttggc ctcccaaatt gctgggatta caggcgtgaa 3900
ccactgctcc cttccctgtc cttctgattt taaaataact ataccagcag gaggacgtcc 3960
agacacagca taggctacct ggccatgccc aaccggtggg acatttgagt tgcttgcttg 4020
gcactgtcct ctcatgcgtt gggtccactc agtagatgcc tgttgaattc ctgggcctag 4080
ggctgtgcca gctgcctcgt cccgtcacct tctggcttct tctctccctc catatcttag 4140
ctgttttcct catgagaatg ttccaaattc gaaatttcta tttaaccatt atatatttac 4200
ttgtttgcta ttatctctgc ccccagtaga ttgttagctc cagaagagaa aggatcatgt 4260
cttttgctta tctagatatg cccatctgcc tggtacaatc tctggcacat gttacaggca 4320
acaactactt gtggaattgg tgaatgcatg aatagaagaa tgagtgaatg aatgaataga 4380
caataggcag aaatccagcc tcaaagagct tacagtctgg taagaggaat aaaatgtctg 4440
caaatagcca caggacaggt caaaggaagg aggggctatt tccagctgag ggcaccccat 4500
caggaaagca ccccagactt ccttagggat aacagggtaa tggcgcgggc cgcaggaacc 4560
cctagtgatg gagttggcca ctccctctct gcgcgctcgc tcgctcactg aggccgggcg 4620
accaaaggtc gcccgacgcc cgggctttgc ccgggcggcc tcagtgagcg agcgagcgcg 4680
cagctgcctg cagg 4694

<210> SEQ ID NO 43
<211> LENGTH: 4694
<212> TYPE: DNA
<213> ORGANISM: Artificial Sequence
<220> FEATURE:
<223> OTHER INFORMATION: Synthetic

<400> SEQUENCE: 43
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtcgata actataacgg tcctaaggta 180
gcgatttaaa tacgcgctct cttaaggtag ccccgggacg cgtcaattga gatctccgac 240
attgattatt gactagttat taatagtaat caattacggg gtcattagtt catagcccat 300
atatggagtt ccgcgttaca taacttacgg taaatggccc gcctggctga ccgcccaacg 360
acccccgccc attgacgtca ataatgacgt atgttcccat agtaacgcca atagggactt 420
tccattgacg tcaatgggtg gagtatttac ggtaaactgc ccacttggca gtacatcaag 480
tgtatcatat gccaagtacg ccccctattg acgtcaatga cggtaaatgg cccgcctggc 540
attatgccca gtacatgacc ttatgggact ttcctacttg gcagtacatc tacgtattag 600
tcatcgctat taccatgtcg aggccacgtt ctgcttcact ctccccatct cccccccctc 660
cccaccccca attttgtatt tatttatttt ttaattattt tgtgcagcga tgggggcggg 720
gggggggggc gcgcgccagg cggggcgggg cggggcgagg ggcggggcgg ggcgaggcgg 780
agaggtgcgg cggcagccaa tcagagcggc gcgctccgaa agtttccttt tatggcgagg 840
cggcggcggc ggcggcccta taaaaagcga agcgcgcggc gggcgggagc aagcttcgtt 900
tagtgaaccg tcagatcgcc tggagacgcc atccacgctg ttttgacctc catagaagac 960
accgggaccg atccagcctc cgcggattcg aatcccggcc gggaacggtg cattggaacg 1020
cggattcccc gtgccaagag tgacgtaagt accgcctata gagtctatag gcccacaaaa 1080

```
aatgctttct tcttttaata tacttttttg tttatcttat ttctaatact ttccctaatc   1140
tctttctttc agggcaataa tgatacaatg tatcatgcct ctttgcacca ttctaaagaa   1200
taacagtgat aatttctggg ttaaggcaat agcaatattt ctgcatataa atatttctgc   1260
atataaattg taactgatgt aagaggtttc atattgctaa tagcagctac aatccagcta   1320
ccattctgct tttattttgt ggttgggata aggctggatt attctgagtc caagctaggc   1380
ccttttgcta atcgtgttca tacctcttat cttcctccca cagctcctgg gcaacgtgct   1440
ggtctgtgtg ctggcccatc actttggcaa agaattaccg gtggcaacgt gctggttatt   1500
gtgctgtctc atcatttgg caaagaattc acgccccaga gccgccacca tggcctaccc   1560
atacgatgtt ccagattacg ctacagaatt acctgccccc ttgagctact tccagaatgc   1620
acagatgagc gaggacaacc acctgagcaa tactgtacgt agccagaatg acaacagaga   1680
acggcaggaa cacaacgaca ggcggagcct gggccaccct gagcccctgt ctaatggaag   1740
accccagggt aacagcagac aggtggtgga acaagatgag gaagaggacg aggagctgac   1800
cctgaagtac ggcgccaagc acgtgatcat gctcttcgtg cccgtgactc tctgcatggt   1860
ggtggtggtg gctacaatca agagcgtcag cttttatacc cggaaggatg ggcagctaat   1920
ctatacccca ttcacagaag acaccgagac tgtgggccag agagccctgc actcaatcct   1980
gaatgccgcc atcatgatca gcgtcattgt tgtcatgact atcctcctgg tggttctgta   2040
taaatacagg tgctataagg tcatccatgc ctggctgatc atatcatctc tgttgctgct   2100
gttctttttt agcttcattt acctgggcga agtgtttaaa acctataacg ttgccgtgga   2160
ctacattact gttgccctcc tgatctggaa cttcggcgtg gtgggcatga tttccattca   2220
ctggaaaggc cccctgagac tgcagcaggc atacctcatt atgatctccg ccctcatggc   2280
cctggtgttc atcaagtacc tgcccgagtg gactgcttgg ctcatcttgg ctgtgatctc   2340
cgtgtatgat ttagtggctg ttctgtgtcc taaaggtcca ctgcgtatgc tggtggaaac   2400
agctcaggaa agaaatgaaa cactgtttcc tgctctgatt tactcctcaa caatggtgtg   2460
gctcgtgaat atggccgaag gagaccctga agcccaacgg agagtgtcca aaaactccaa   2520
gtataacgcc gagagcacag aaagggagag ccaggataca gttgccgaga atgacgatgg   2580
cggcttcagt gaggaatggg aagcccagag ggacagccac ctggggcctc acagaagcac   2640
ccctgagtct agagccgctg tccaggaact gtccagctcc atcctggccg gcgaagaccc   2700
cgaagaaagg ggagtaaaac ttggactggg agatttcatc ttctacagtg ttctcgttgg   2760
caaagccagc gcaacagcta gcggagactg gaacacaaca atagcctgtt tcgtagccat   2820
cttaattggc ctgtgcctta cacttctgct cctggccatc ttcaagaagg ccctgccagc   2880
cctgcctatc agcatcacct tcgggcttgt tttctacttt gccaccgatt atctggtgca   2940
gcccttcatg gaccagctgg ccttccacca gttttacatc tagtaagcgg ccgccctagg   3000
gagctcctcg agggggtggc atccctgtga cccctcccca gtgcctctcc tggccctgga   3060
agttgccact ccagtgccca ccagccttgt cctaataaaa ttaagttgca tcattttgtc   3120
tgactaggtg tccttctata atattatggg gtggaggggg gtggtatgga gcaaggggca   3180
aggggggaag acaacctgta gggcctgcgg ggtctattgg gaaccaagct ggagtgcagt   3240
ggcacaatct tggctcactg caatctccgc ctcctgggtt caagcgattc tcctgcctca   3300
gcctcccgag ttgttgggat tccaggcatg catgaccagg ctcagctaat ttttgttttt   3360
ttggtagaga cggggtttca ccatattggc caggctggtc tcccctcct aatctcaggt   3420
gatctaccca ccttggcctc ccaaattgct gggattacag gcgtgaacca ctgctccctt   3480
```

cccctgtcctt ctgattttaa aataactata ccagcaggag gacgtccaga cacagcatag 3540
gctacctggc catgcccaac cggtgggaca tttgagttgc ttgcttggca ctgtcctctc 3600
atgcgttggg tccactcagt agatgcctgt tgaattcctg ggcctagggc tgtgccagct 3660
gcctcgtccc gtcaccttct ggcttcttct ctccctccat atcttagctg ttttcctcat 3720
gagaatgttc caaattcgaa atttctattt aaccattata tatttacttg tttgctatta 3780
tctctgcccc cagtagattg ttagctccag aagagaaagg atcatgtctt ttgcttatct 3840
agatatgccc atctgcctgg tacaatctct ggcacatgtt acaggcaaca actacttgtg 3900
gaattggtga atgcatgaat agaagaatga gtgaatgaat gaatagacaa taggcagaaa 3960
tccagcctca aagagcttac agtctggtaa gaggaataaa atgtctgcaa atagccacag 4020
gacaggtcaa aggaaggagg ggctatttcc agctgagggc accccatcag gaaagcaccc 4080
cagacttcct acaactacta gacacatctc gatgcttttc acttctctat caatggatcg 4140
tctccctgga gaataatccc caaagtgaaa ttacttagca cgtccagtta ggtagatcct 4200
tgtgtacttc ttggttgttc agagatcatc aaccagtgca aacaatcccc ccatcaatac 4260
acagcagtgc ctgcccctct ccccccgagg tcttccgagg cccttcctcc gtgcctgaac 4320
cccctggaca tatcatatgg caaactgaag tgtccaacga gatataggaa gtgaaacacg 4380
atgtacactg aaacgtgcaa tacaaatatg cagcatgaag tgcctcggtt cactaacccg 4440
agctacgctg ggtgcttctt ttctaccact ttccttaatg cctatggaca cctcattctg 4500
tggctgaagt tccttgtgtt caatagggat aacagggtaa tggcgcgggc cgcaggaacc 4560
cctagtgatg gagttggcca ctccctctct gcgcgctcgc tcgctcactg aggccgggcg 4620
accaaaggtc gcccgacgcc cgggctttgc ccgggcggcc tcagtgagcg agcgagcgcg 4680
cagctgcctg cagg 4694

<210> SEQ ID NO 44
<211> LENGTH: 4640
<212> TYPE: DNA
<213> ORGANISM: Artificial Sequence
<220> FEATURE:
<223> OTHER INFORMATION: Synthetic

<400> SEQUENCE: 44
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtcgata actataacgg tcctaaggta 180
gcgatttaaa tacgcgctct cttaaggtag ccccgggacg cgtcaattga gatctcggct 240
ccggtgcccg tcagtgggca gagcgcacat cgcccacagt ccccgagaag gggggggag 300 gggtcggcaa ttgaaccggt gcctagagaa ggtggcgcgg ggtaaactgg gaaagtgatg 360
tcgtgtactg gctccgcctt tttcccgagg gtgggggaga accgtatata agtgcagtag 420
tcgccgtgaa cgttcttttt cgcaacgggt ttgccgccag aacacaggta agtgccgtgt 480
gtggttcccg cgggcctggc ctctttacgg gttatggccc ttgcgtgcct tgaattactt 540
ccacctggct gcagtacgtg attcttgatc ccgagcttcg ggttggaagt gggtgggaga 600
gttcgaggcc ttgcgcttaa ggagcccctt cgcctcgtgc ttgagttgag gcctggcctg 660
ggcgctgggg ccgccgcgtg cgaatctggt ggcaccttcg cgcctgtctc gctgctttcg 720
ataagtctct agccatttaa aatttttgat gacctgctgc gacgcttttt ttctggcaag 780

-continued

```
atagtcttgt aaatgcgggc caagatctgc acactggtat ttcggttttt ggggccgcgg    840
gcggcgacgg ggcccgtgcg tcccagcgca catgttcggc gaggcggggc ctgcgagcgc    900
ggccaccgag aatcggacgg gggtagtctc aagctggccg gcctgctctg gtgcctggtc    960
tcgcgccgcc gtgtatcgcc ccgccctggg cggcaaggct ggcccggtcg gcaccagttg   1020
cgtgagcgga aagatggccg cttcccggcc ctgctgcagg gagctcaaaa tggaggacgc   1080
ggcgctcggg agagcgggcg ggtgagtcac ccacacaaag gaaaagggcc tttccgtcct   1140
cagccgtcgc ttcatgtgac tccacggagt accgggcgcc gtccaggcac ctcgattagt   1200
tctcgagctt ttggagtacg tcgtctttag gttgggggga ggggttttat gcgatggagt   1260
ttccccacac tgagtgggtg gagactgaag ttaggccagc ttggcacttg atgtaattct   1320
ccttggaatt tgcccttttt gagtttggat cttggttcat tctcaagcct cagacagtgg   1380
ttcaaagttt ttttcttcca tttcaggtgt cgtgaaagct tcgtttagtg aaccgtcaga   1440
tcgcctggag acgccatcca cgctgttttg acctccatag aagacaccgg gaccgatcca   1500
gcctccgcgg attcgaatcc cggccgggaa cggtgcattg gaacgcggat tccccgtgcc   1560
aagagtgacg taagtaccgc ctatagagtc tataggccca caaaaaatgc tttcttcttt   1620
taatatactt ttttgtttat cttatttcta atactttccc taatctcttt ctttcagggc   1680
aataatgata caatgtatca tgcctctttg caccattcta aagaataaca gtgataattt   1740
ctgggttaag gcaatagcaa tatttctgca tataaatatt tctgcatata aattgtaact   1800
gatgtaagag gtttcatatt gctaatagca gctacaatcc agctaccatt ctgcttttat   1860
tttgtggttg ggataaggct ggattattct gagtccaagc taggcccttt tgctaatcgt   1920
gttcatacct cttatcttcc tcccacagct cctgggcaac gtgctggtct gtgtgctggc   1980
ccatcacttt ggcaaagaat taccggtggc aacgtgctgg ttattgtgct gtctcatcat   2040
tttggcaaag aattcacgcc ccagagccgc caccatggcc tacccatacg atgttccaga   2100
ttacgctaca gaattacctg ccccccttgag ctacttccag aatgcacaga tgagcgagga   2160
caaccacctg agcaatactg tacgtagcca gaatgacaac agagaacggc aggaacacaa   2220
cgacaggcgg agcctgggcc accctgagcc cctgtctaat ggaagacccc agggtaacag   2280
cagacaggtg gtggaacaag atgaggaaga ggacgaggag ctgaccctga agtacggcgc   2340
caagcacgtg atcatgctct tcgtgcccgt gactctctgc atggtggtgg tggtggctac   2400
aatcaagagc gtcagctttt atacccggaa ggatgggcag ctaatctata ccccattcac   2460
agaagacacc gagactgtgg gccagagagc cctgcactca atcctgaatg ccgccatcat   2520
gatcagcgtc attgttgtca tgactatcct cctggtggtt ctgtataaat acaggtgcta   2580
taaggtcatc catgcctggc tgatcatatc atctctgttg ctgctgttct tttttagctt   2640
catttacctg ggcgaagtgt ttaaaaccta taacgttgcc gtggactaca ttactgttgc   2700
cctcctgatc tggaacttcg gcgtggtggg catgatttcc attcactgga aaggcccccct   2760
gagactgcag caggcatacc tcattatgat ctccgccctc atggccctgg tgttcatcaa   2820
gtacctgccc gagtggactg cttggctcat cttggctgtg atctccgtgt atgatttagt   2880
ggctgttctg tgtcctaaag gtccactgcg tatgctggtg gaaacagctc aggaaagaaa   2940
tgaaacactg tttcctgctc tgatttactc ctcaacaatg gtgtggctcg tgaatatggc   3000
cgaaggagac cctgaagccc aacggagagt gtccaaaaac tccaagtata acgccgagag   3060
cacagaaagg gagagccagg atacagttgc cgagaatgac gatggcggct tcagtgagga   3120
atgggaagcc cagagggaca gccacctggg gcctcacaga agcacccctg agtctagagc   3180
```

cgctgtccag gaactgtcca gctccatcct ggccggcgaa gaccccgaag aaaggggagt 3240
aaaacttgga ctgggagatt tcatcttcta cagtgttctc gttggcaaag ccagcgcaac 3300
agctagcgga gactggaaca caacaatagc ctgtttcgta gccatcttaa ttggcctgtg 3360
ccttacactt ctgctcctgg ccatcttcaa gaaggccctg ccagccctgc ctatcagcat 3420
caccttcggg cttgttttct actttgccac cgattatctg gtgcagccct tcatggacca 3480
gctggccttc caccagtttt acatctagta agcggccgcc ctagggagct cctcgagggg 3540
gtggcatccc tgtgacccct ccccagtgcc tctcctggcc ctggaagttg ccactccagt 3600
gcccaccagc cttgtcctaa taaaattaag ttgcatcatt ttgtctgact aggtgtcctt 3660
ctataatatt atggggtgga ggggggtggt atggagcaag gggcaagggg ggaagacaac 3720
ctgtagggcc tgcggggtct attgggaacc aagctggagt gcagtggcac aatcttggct 3780
cactgcaatc tccgcctcct gggttcaagc gattctcctg cctcagcctc ccgagttgtt 3840
gggattccag gcatgcatga ccaggctcag ctaatttttg tttttttggt agagacgggg 3900
tttcaccata ttggccaggc tggtctcccc ctcctaatct caggtgatct acccaccttg 3960
gcctcccaaa ttgctgggat tacaggcgtg aaccactgct cccttccctg tccttcctgg 4020
gcctagggct gtgccagctg cctcgtcccg tcaccttctg gcttcttctc tccctccata 4080
tcttagctgt tttcctcatg agaatgttcc aaattcgaaa tttctattta accattatat 4140
atttacttgt ttgctattat ctctgccccc agtagattgt tagctccaga agagaaagga 4200
tcatgtcttt tgcttatcta gatatgccca tctgcctggt acaatctctg gcacatgtta 4260
caggcaacaa ctacttgtgg aattggtgaa tgcatgaata gaagaatgag tgaatgaatg 4320
aatagacaat aggcagaaat ccagcctcaa agagcttaca gtctggtaag aggaataaaa 4380
tgtctgcaaa tagccacagg acaggtcaaa ggaaggaggg gctatttcca gctgagggca 4440
ccccatcagg aaagcacccc agacttcctt agggataaca gggtaatggc gcgggccgca 4500
ggaaccccta gtgatggagt tggccactcc ctctctgcgc gctcgctcgc tcactgaggc 4560
cgggcgacca aaggtcgccc gacgcccggg ctttgcccgg gcggcctcag tgagcgagcg 4620
agcgcgcagc tgcctgcagg 4640

<210> SEQ ID NO 45
<211> LENGTH: 4673
<212> TYPE: DNA
<213> ORGANISM: Artificial Sequence
<220> FEATURE:
<223> OTHER INFORMATION: Synthetic

<400> SEQUENCE: 45
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtcgata actataacgg tcctaaggta 180
gcgatttaaa tacgcgctct cttaaggtag ccccgggacg cgtcaattga gatctcgcct 240
cgaattccac ggggttgggg ttgcgccttt tccaaggcag ccctgggttt gcgcagggac 300
gcggctgctc tgggcgtggt tccgggaaac gcagcggcgc cgaccctggg tctcgcacat 360
tcttcacgtc cgttcgcagc gtcacccgga tcttcgccgc taccctttgtg ggccccccgg 420 cgacgcttcc tgctccgccc ctaagtcggg aaggttcctt gcggttcgcg gcgtgccgga 480
cgtgacaaac ggaagccgca cgtctcacta gtaccctcgc agacggacag cgccagggag 540

```
caatggcagc gcgccgaccg cgatgggctg tggccaatag cggctgctca gcagggcgcg    600
ccgagagcag cggccgggaa ggggcggtgc gggaggcggg gtgtggggcg gtagtgtggg    660
cccaagcttc gtttagtgaa ccgtcagatc gcctggagac gccatccacg ctgttttgac    720
ctccatagaa gacaccggga ccgatccagc ctccgcggat tcgaatcccg gccgggaacg    780
gtgcattgga acgcggattc cccgtgccaa gagtgacgta agtaccgcct atagagtcta    840
taggcccaca aaaaatgctt tcttctttta atatactttt ttgtttatct tatttctaat    900
actttcccta atctctttct ttcagggcaa taatgataca atgtatcatg cctctttgca    960
ccattctaaa gaataacagt gataatttct gggttaaggc aatagcaata tttctgcata   1020
taaatatttc tgcatataaa ttgtaactga tgtaagaggt ttcatattgc taatagcagc   1080
tacaatccag ctaccattct gcttttattt tgtggttggg ataaggctgg attattctga   1140
gtccaagcta ggcccttttg ctaatcgtgt tcatacctct tatcttcctc ccacagctcc   1200
tgggcaacgt gctggtctgt gtgctggccc atcactttgg caaagaatta ccggtggcaa   1260
cgtgctggtt attgtgctgt ctcatcattt tggcaaagaa ttcacgcccc agagccgcca   1320
ccatggccta cccatacgat gttccagatt acgctacaga attacctgcc cccttgagct   1380
acttccagaa tgcacagatg agcgaggaca accacctgag caatactgta cgtagccaga   1440
atgacaacag agaacggcag gaacacaacg acaggcggag cctgggccac cctgagcccc   1500
tgtctaatgg aagaccccag ggtaacagca gacaggtggt ggaacaagat gaggaagagg   1560
acgaggagct gaccctgaag tacggcgcca agcacgtgat catgctcttc gtgcccgtga   1620
ctctctgcat ggtggtggtg gtggctacaa tcaagagcgt cagcttttat acccggaagg   1680
atgggcagct aatctatacc ccattcacag aagacaccga gactgtgggc cagagagccc   1740
tgcactcaat cctgaatgcc gccatcatga tcagcgtcat tgttgtcatg actatcctcc   1800
tggtggttct gtataaatac aggtgctata aggtcatcca tgcctggctg atcatatcat   1860
ctctgttgct gctgttcttt tttagcttca tttacctggg cgaagtgttt aaaacctata   1920
acgttgccgt ggactacatt actgttgccc tcctgatctg gaacttcggc gtggtgggca   1980
tgatttccat tcactggaaa ggcccccctga gactgcagca ggcatacctc attatgatct   2040
ccgccctcat ggccctggtg ttcatcaagt acctgcccga gtggactgct tggctcatct   2100
tggctgtgat ctccgtgtat gatttagtgg ctgttctgtg tcctaaaggt ccactgcgta   2160
tgctggtgga aacagctcag gaaagaaatg aaacactgtt tcctgctctg atttactcct   2220
caacaatggt gtggctcgtg aatatggccg aaggagaccc tgaagcccaa cggagagtgt   2280
ccaaaaactc caagtataac gccgagagca cagaaaggga gagccaggat acagttgccg   2340
agaatgacga tggcggcttc agtgaggaat gggaagccca gagggacagc cacctggggc   2400
ctcacagaag cacccctgag tctagagccg ctgtccagga actgtccagc tccatcctgg   2460
ccggcgaaga ccccgaagaa aggggagtaa aacttggact gggagatttc atcttctaca   2520
gtgttctcgt tggcaaagcc agcgcaacag ctagcggaga ctggaacaca acaatagcct   2580
gtttcgtagc catcttaatt ggcctgtgcc ttacacttct gctcctggcc atcttcaaga   2640
aggccctgcc agccctgcct atcagcatca ccttcgggct tgttttctac tttgccaccg   2700
attatctggt gcagcccttc atggaccagc tggccttcca ccagttttac atctagtaag   2760
cggccgccct agggagctcc tcgagggggt ggcatccctg tgacccctcc ccagtgcctc   2820
tcctggccct ggaagttgcc actccagtgc ccaccagcct tgtcctaata aaattaagtt   2880
gcatcatttt gtctgactag gtgtccttct ataatattat ggggtggagg ggggtggtat   2940
```

ggagcaaggg gcaagggggg aagacaacct gtagggcctg cggggtctat tgggaaccaa 3000
gctggagtgc agtggcacaa tcttggctca ctgcaatctc cgcctcctgg gttcaagcga 3060
ttctcctgcc tcagcctccc gagttgttgg gattccaggc atgcatgacc aggctcagct 3120
aatttttgtt tttttggtag agacggggtt tcaccatatt ggccaggctg gtctccccct 3180
cctaatctca ggtgatctac ccaccttggc ctcccaaatt gctgggatta caggcgtgaa 3240
ccactgctcc cttccctgtc cttctgattt taaaataact ataccagcag gaggacgtcc 3300
agacacagca taggctacct ggccatgccc aaccggtggg acatttgagt tgcttgcttg 3360
gcactgtcct ctcatgcgtt gggtccactc agtagatgcc tgttgaattc ctgggcctag 3420
ggctgtgcca gctgcctcgt cccgtcacct tctggcttct tctctccctc catatcttag 3480
ctgttttcct catgagaatg ttccaaattc gaaatttcta tttaaccatt atatatttac 3540
ttgtttgcta ttatctctgc ccccagtaga ttgttagctc cagaagagaa aggatcatgt 3600
cttttgctta tctagatatg cccatctgcc tggtacaatc tctggcacat gttacaggca 3660
acaactactt gtggaattgg tgaatgcatg aatagaagaa tgagtgaatg aatgaataga 3720
caataggcag aaatccagcc tcaaagagct tacagtctgg taagaggaat aaaatgtctg 3780
caaatagcca caggacaggt caaaggaagg aggggctatt tccagctgag ggcaccccat 3840
caggaaagca ccccagactt cctacaacta ctagacacat ctcgatgctt ttcacttctc 3900
tatcaatgga tcgtctccct ggagaataat ccccaaagtg aaattactta gcacgtccag 3960
ttaggtagat ccttgtgtac ttcttggttg ttcagagatc atcaaccagt gcaaacaatc 4020
cccccatcaa tacacagcag tgcctgcccc tctccccccg aggtcttccg aggcccttcc 4080
tccgtgcctg aaccccctgg acatatcata tggcaaactg aagtgtccaa cgagatatag 4140
gaagtgaaac acgatgtaca ctgaaacgtg caatacaaat atgcagcatg aagtgcctcg 4200
gttcactaac ccgagctacg ctgggtgctt cttttctacc actttcctta atgcctatgg 4260
acacctcatt ctgtggctga agttccttgt gttcaattcc ccccatcttc attgaacatc 4320
ctgtgtaggg acctcacccc tgtcctgcta gctttgcact gaggcaagtt ctgtccatgc 4380
ctagtagtgc caccaccttt actagatgag acttctaaag agcttggcat ggaaggaaag 4440
cccgggggcc ttggaagcca tcacttagaa actgggagag ctccaggcaa gccacctcat 4500
cttagggata acagggtaat ggcgcgggcc gcaggaaccc ctagtgatgg agttggccac 4560
tccctctctg cgcgctcgct cgctcactga ggccgggcga ccaaaggtcg cccgacgccc 4620
gggctttgcc cgggcggcct cagtgagcga gcgagcgcgc agctgcctgc agg 4673

<210> SEQ ID NO 46
<211> LENGTH: 4694
<212> TYPE: DNA
<213> ORGANISM: Artificial Sequence
<220> FEATURE:
<223> OTHER INFORMATION: Synthetic

<400> SEQUENCE: 46
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtcgata actataacgg tcctaaggta 180
gcgatttaaa tacgcgctct cttaaggtag ccccgggacg cgtcaattga gatctcagtg 240
caagtgggtt ttaggaccag gatgaggcgg ggtgggggtg cctacctgac gaccgacccc 300
gacccactgg acaagcaccc aacccccatt ccccaaattg cgcatcccct atcagagagg 360
gggaggggaa acaggatgcg gcgaggcgcg tgcgcactgc cagcttcagc accgcggaca 420
gtgccttcgc ccccgcctgg cggcgcgcgc caccgccgcc tcagcactga aggcgcgctg 480
acgtcactcg ccggtccccc gcaaactccc cttcccggcc accttggtcg cgtccgcgcc 540
gccgccggcc cagccggacc gcaccacgcg aggcgcgaga taggggggca cgggcgcgac 600
catctgcgct gcggcgccgg cgactcagcg ctgcctcagt ctgcggtggg cagcggagga 660
gtcgtgtcgt gcctgagagc gcagaagctt cgtttagtga accgtcagat cgcctggaga 720
cgccatccac gctgttttga cctccataga agacaccggg accgatccag cctccgcgga 780
ttcgaatccc ggccgggaac ggtgcattgg aacgcggatt ccccgtgcca agagtgacgt 840
aagtaccgcc tatagagtct ataggcccac aaaaaatgct ttcttctttt aatatacttt 900
tttgtttatc ttatttctaa tactttccct aatctctttc tttcagggca ataatgatac 960
aatgtatcat gcctctttgc accattctaa agaataacag tgataatttc tgggttaagg 1020
caatagcaat atttctgcat ataaatattt ctgcatataa attgtaactg atgtaagagg 1080
tttcatattg ctaatagcag ctacaatcca gctaccattc tgcttttatt ttgtggttgg 1140
gataaggctg gattattctg agtccaagct aggccctttt gctaatcgtg ttcatacctc 1200
ttatcttcct cccacagctc ctgggcaacg tgctggtctg tgtgctggcc catcactttg 1260
gcaaagaatt accggtggca acgtgctggt tattgtgctg tctcatcatt ttggcaaaga 1320
attcacgccc cagagccgcc accatggcct acccatacga tgttccagat tacgctacag 1380
aattacctgc cccccttgagc tacttccaga atgcacagat gagcgaggac aaccacctga 1440
gcaatactgt acgtagccag aatgacaaca gagaacggca ggaacacaac gacaggcgga 1500
gcctgggcca ccctgagccc ctgtctaatg gaagacccca gggtaacagc agacaggtgg 1560
tggaacaaga tgaggaagag gacgaggagc tgaccctgaa gtacggcgcc aagcacgtga 1620
tcatgctctt cgtgcccgtg actctctgca tggtggtggt ggtggctaca atcaagagcg 1680
tcagctttta tacccggaag gatgggcagc taatctatac cccattcaca gaagacaccg 1740
agactgtggg ccagagagcc ctgcactcaa tcctgaatgc cgccatcatg atcagcgtca 1800
ttgttgtcat gactatcctc ctggtggttc tgtataaata caggtgctat aaggtcatcc 1860
atgcctggct gatcatatca tctctgttgc tgctgttctt ttttagcttc atttacctgg 1920
gcgaagtgtt taaaacctat aacgttgccg tggactacat tactgttgcc ctcctgatct 1980
ggaacttcgg cgtggtgggc atgatttcca ttcactggaa aggcccccctg agactgcagc 2040 aggcatacct cattatgatc tccgccctca tggccctggt gttcatcaag tacctgcccg 2100
agtggactgc ttggctcatc ttggctgtga tctccgtgta tgatttagtg gctgttctgt 2160
gtcctaaagg tccactgcgt atgctggtgg aaacagctca ggaaagaaat gaaacactgt 2220
ttcctgctct gatttactcc tcaacaatgg tgtggctcgt gaatatggcc gaaggagacc 2280
ctgaagccca acggagagtg tccaaaaact ccaagtataa cgccgagagc acagaaaggg 2340
agagccagga tacagttgcc gagaatgacg atggcggctt cagtgaggaa tgggaagccc 2400
agagggacag ccacctgggg cctcacagaa gcacccctga gtctagagcc gctgtccagg 2460
aactgtccag ctccatcctg gccggcgaag accccgaaga aaggggagta aaacttggac 2520
tgggagattt catcttctac agtgttctcg ttggcaaagc cagcgcaaca gctagcggag 2580
actggaacac aacaatagcc tgtttcgtag ccatcttaat tggcctgtgc cttacacttc 2640
tgctcctggc catcttcaag aaggccctgc cagccctgcc tatcagcatc accttcgggc 2700

```
ttgttttcta ctttgccacc gattatctgg tgcagccctt catggaccag ctggccttcc   2760
accagtttta catctagtaa gcggccgccc tagggagctc ctcgaggggg tggcatccct   2820
gtgacccctc cccagtgcct ctcctggccc tggaagttgc cactccagtg cccaccagcc   2880
ttgtcctaat aaaattaagt tgcatcattt tgtctgacta ggtgtccttc tataatatta   2940
tggggtggag gggggtggta tggagcaagg ggcaaggggg gaagacaacc tgtagggcct   3000
gcggggtcta ttgggaacca agctggagtg cagtggcaca atcttggctc actgcaatct   3060
ccgcctcctg ggttcaagcg attctcctgc ctcagcctcc cgagttgttg ggattccagg   3120
catgcatgac caggctcagc taatttttgt ttttttggta gagacggggt ttcaccatat   3180
tggccaggct ggtctccccc tcctaatctc aggtgatcta cccaccttgg cctcccaaat   3240
tgctgggatt acaggcgtga accactgctc ccttccctgt ccttctgatt ttaaaataac   3300
tataccagca ggaggacgtc cagacacagc ataggctacc tggccatgcc caaccggtgg   3360
gacatttgag ttgcttgctt ggcactgtcc tctcatgcgt tgggtccact cagtagatgc   3420
ctgttgaatt cctgggccta gggctgtgcc agctgcctcg tcccgtcacc ttctggcttc   3480
ttctctccct ccatatctta gctgttttcc tcatgagaat gttccaaatt cgaaatttct   3540
atttaaccat tatatattta cttgtttgct attatctctg cccccagtag attgttagct   3600
ccagaagaga aaggatcatg tcttttgctt atctagatat gcccatctgc ctggtacaat   3660
ctctggcaca tgttacaggc aacaactact tgtggaattg gtgaatgcat gaatagaaga   3720
atgagtgaat gaatgaatag acaataggca gaaatccagc ctcaaagagc ttacagtctg   3780
gtaagaggaa taaaatgtct gcaaatagcc acaggacagg tcaaaggaag gaggggctat   3840
ttccagctga gggcacccca tcaggaaagc accccagact tcctacaact actagacaca   3900
tctcgatgct tttcacttct ctatcaatgg atcgtctccc tggagaataa tccccaaagt   3960
gaaattactt agcacgtcca gttaggtaga tccttgtgta cttcttggtt gttcagagat   4020
catcaaccag tgcaaacaat ccccccatca atacacagca gtgcctgccc ctctcccccc   4080
gaggtcttcc gaggcccttc ctccgtgcct gaacccccctg gacatatcat atggcaaact   4140
gaagtgtcca acgagatata ggaagtgaaa cacgatgtac actgaaacgt gcaatacaaa   4200
tatgcagcat gaagtgcctc ggttcactaa cccgagctac gctgggtgct tcttttctac   4260
cactttcctt aatgcctatg gacacctcat tctgtggctg aagttccttg tgttcaattc   4320
cccccatctt cattgaacat cctgtgtagg gacctcaccc ctgtcctgct agctttgcac   4380
tgaggcaagt tctgtccatg cctagtagtg ccaccacctt tactagatga gacttctaaa   4440
gagcttggca tggaaggaaa gcccgggggc cttggaagcc atcacttaga aactgggaga   4500
gctccaggca agccacctca tcttagggat aacagggtaa tggcgcgggc cgcaggaacc   4560
cctagtgatg gagttggcca ctccctctct gcgcgctcgc tcgctcactg aggccgggcg   4620
accaaaggtc gcccgacgcc cgggctttgc ccgggcggcc tcagtgagcg agcgagcgcg   4680
cagctgcctg cagg                                                    4694
```

```
<210> SEQ ID NO 47
<211> LENGTH: 2526
<212> TYPE: DNA
<213> ORGANISM: Artificial Sequence
<220> FEATURE:
<223> OTHER INFORMATION: Synthetic

<400> SEQUENCE: 47
```

```
ctgcgcgctc gctcgctcac tgaggccgcc cgggcaaagc ccgggcgtcg ggcgaccttt     60
ggtcgcccgg cctcagtgag cgagcgagcg cgcagagagg gagtgagatc tccgacattg    120
attattgact agttattaat agtaatcaat tacggggtca ttagttcata gcccatatat    180
ggagttccgc gttacataac ttacggtaaa tggcccgcct ggctgaccgc ccaacgaccc    240
ccgcccattg acgtcaataa tgacgtatgt tcccatagta acgccaatag ggactttcca    300
ttgacgtcaa tgggtggagt atttacggta aactgcccac ttggcagtac atcaagtgta    360
tcatatgcca agtacgcccc ctattgacgt caatgacggt aaatggcccg cctggcatta    420
tgcccagtac atgaccttat gggactttcc tacttggcag tacatctacg tattagtcat    480
cgctattacc atgtcgaggc cacgttctgc ttcactctcc ccatctcccc cccctcccca    540
cccccaattt tgtatttatt tattttttaa ttattttgtg cagcgatggg ggcggggggg    600
gggggcgcgc gccaggcggg gcggggcggg gcgaggggcg gggcggggcg aggcggagag    660
gtgcggcggc agccaatcag agcggcgcgc tccgaaagtt tccttttatg gcgaggcggc    720
ggcggcggcg gccctataaa aagcgaagcg cgcggcgggc gggagcaagc ttcgtaagag    780
gtaagggttt aagggatggt tggttggtgg ggtattaatg tttaattacc tgttttacag    840
gcctgaaatc acttggtttt aggttgggct agccgccacc atgtacccat acgatgttcc    900
agattacgct acagaattac ctgccccctt gagctacttc cagaatgcac agatgagcga    960
ggacaaccac ctgagcaata ctgtacgtag ccagaatgac aacagagaac ggcaggaaca   1020
caacgacagg cggagcctgg gccaccctga gcccctgtct aatggaagac cccagggtaa   1080
cagcagacag gtggtggaac aagatgagga agaggacgag gagctgaccc tgaagtacgg   1140
cgccaagcac gtgatcatgc tcttcgtgcc cgtgactctc tgcatggtgg tggtggtggc   1200
tacaatcaag agcgtcagct tttatacccg gaaggatggg cagctaatct ataccccatt   1260
cacagaagac accgagactg tgggccagag agccctgcac tcaatcctga atgccgccat   1320
catgatcagc gtcattgttg tcatgactat cctcctggtg gttctgtata aatacaggtg   1380
ctataaggtc atccatgcct ggctgatcat atcatctctg ttgctgctgt tctttttttag   1440
cttcatttac ctgggcgaag tgtttaaaac ctataacgtt gccgtggact acattactgt   1500
tgccctcctg atctggaact tcggcgtggt gggcatgatt tccattcact ggaaaggccc   1560
cctgagactg cagcaggcat acctcattat gatctccgcc ctcatggccc tggtgttcat   1620
caagtacctg cccgagtgga ctgcttggct catcttggct gtgatctccg tgtatgattt   1680
agtggctgtt ctgtgtccta aaggtccact gcgtatgctg gtggaaacag ctcaggaaag   1740
aaatgaaaca ctgtttcctg ctctgattta ctcctcaaca atggtgtggc tcgtgaatat   1800
ggccgaagga gaccctgaag cccaacggag agtgtccaaa aactccaagt ataacgccga   1860
gagcacagaa agggagagcc aggatacagt tgccgagaat gacgatggcg gcttcagtga   1920
ggaatgggaa gcccagaggg acagccacct ggggcctcac agaagcaccc ctgagtctag   1980
agccgctgtc caggaactgt ccagctccat cctggccggc gaagaccccg aagaaagggg   2040
agtaaaactt ggactgggag atttcatctt ctacagtgtt ctcgttggca aagccagcgc   2100
aacagctagc ggagactgga acacaacaat agcctgtttc gtagccatct taattggcct   2160
gtgccttaca cttctgctcc tggccatctt caagaaggcc ctgccagccc tgcctatcag   2220
catcaccttc gggcttgttt tctactttgc caccgattat ctggtgcagc ccttcatgga   2280
ccagctggcc ttccaccagt tttacatcta ggcggccgaa taaaagatct ttattttcat   2340
tagatctgtg tgttggtttt ttgtgtgtag ggataacagg gtaataggaa cccctagtga   2400
```

```
tggagttggc cactccctct ctgcgcgctc gctcgctcac tgaggccggg cgaccaaagg   2460
tcgcccgacg cccgggcttt gcccgggcgg cctcagtgag cgagcgagcg cgcagctgcc   2520
tgcagg                                                              2526
```